(12) United States Patent
Xiang et al.

(10) Patent No.: US 12,343,343 B2
(45) Date of Patent: Jul. 1, 2025

(54) FIVE-MEMBERED RING-FUSED SIX-MEMBERED RING COMPOUND, PREPARATION METHOD THEREFOR, AND PHARMACEUTICAL COMPOSITION AND USE THEREOF

(71) Applicant: HANGZHOU POLYMED BIOPHARMACEUTICALS, INC., Zhejiang (CN)

(72) Inventors: Jason Shaoyun Xiang, Hangzhou (CN); Lei Wu, Hangzhou (CN); Bing Zhang, Hangzhou (CN); Qiang Zhang, Hangzhou (CN); Gang Yang, Hangzhou (CN); Rui Xu, Hangzhou (CN); Shuai Yang, Hangzhou (CN); Yue Wu, Hangzhou (CN); Suyue Wang, Hangzhou (CN); Rui Yang, Hangzhou (CN)

(73) Assignee: Hangzhou Polymed Biopharmaceuticals, Inc., Hangzhou (CN)

( * ) Notice: Subject to any disclaimer, the term of this patent is extended or adjusted under 35 U.S.C. 154(b) by 0 days.

(21) Appl. No.: 18/651,214

(22) Filed: Apr. 30, 2024

(65) Prior Publication Data
US 2024/0423977 A1  Dec. 26, 2024

Related U.S. Application Data

(63) Continuation of application No. PCT/CN2023/100361, filed on Jun. 15, 2023.

(51) Int. Cl.
| | |
|---|---|
| *A61K 31/496* | (2006.01) |
| *A61K 31/4545* | (2006.01) |
| *A61K 31/519* | (2006.01) |
| *A61K 31/5377* | (2006.01) |
| *A61K 31/5386* | (2006.01) |
| *C07D 401/14* | (2006.01) |
| *C07D 413/14* | (2006.01) |
| *C07D 417/14* | (2006.01) |
| *C07D 487/04* | (2006.01) |
| *C07D 498/08* | (2006.01) |
| *C07D 519/00* | (2006.01) |

(52) U.S. Cl.
CPC ........ *A61K 31/496* (2013.01); *A61K 31/4545* (2013.01); *A61K 31/519* (2013.01); *A61K 31/5377* (2013.01); *A61K 31/5386* (2013.01); *C07D 401/14* (2013.01); *C07D 413/14* (2013.01); *C07D 417/14* (2013.01); *C07D 487/04* (2013.01); *C07D 498/08* (2013.01); *C07D 519/00* (2013.01)

(58) Field of Classification Search
CPC .............. A61K 31/496; A61K 31/4545; A61K 31/519; A61K 31/5377; A61K 31/5386; C07D 401/14; C07D 413/14; C07D 417/14; C07D 487/04; C07D 498/08; C07D 519/00
See application file for complete search history.

(56) References Cited

U.S. PATENT DOCUMENTS

2020/0276176 A1  9/2020  Dominguez et al.

FOREIGN PATENT DOCUMENTS

| CN | 112912376 A | 6/2021 | |
|---|---|---|---|
| CN | 113423427 A | 9/2021 | |
| CN | 114437035 A | 5/2022 | |
| CN | 114502158 A | 5/2022 | |
| WO | WO-2015104662 A1 * | 7/2015 | .......... A61K 31/416 |
| WO | WO 2019099926 A1 | 5/2019 | |
| WO | WO 2020/176424 A1 | 9/2020 | |
| WO | WO 2021/194878 A1 | 9/2021 | |
| WO | WO 2022/086937 A1 | 4/2022 | |
| WO | WO 2022/088551 A1 | 5/2022 | |
| WO | WO 2022/147465 A1 | 7/2022 | |
| WO | WO 2022/266258 A1 | 12/2022 | |

OTHER PUBLICATIONS

International Search Report (with English translation) received in corresponding Application No. PCT/CN2023/100361, 8 pages.

* cited by examiner

*Primary Examiner* — Clinton A Brooks
*Assistant Examiner* — Josmalen M. Ramos-Lewis
(74) *Attorney, Agent, or Firm* — Proskauer Rose LLP

(57) ABSTRACT

Disclosed in the present invention are a five-membered ring-fused six-membered ring compound, a preparation method therefor, and a pharmaceutical composition and the use thereof. Provided in the present invention is a compound as represented by formula (I), or a pharmaceutically acceptable salt or an isotope compound thereof. The compound of the present invention has an inhibition and/or degradation effect on IRAK4.

3 Claims, No Drawings

FIVE-MEMBERED RING-FUSED SIX-MEMBERED RING COMPOUND, PREPARATION METHOD THEREFOR, AND PHARMACEUTICAL COMPOSITION AND USE THEREOF

The application is a continuation of International Patent Application No. PCT/CN2023/100361, filed Jun. 15, 2023, which claims the priorities of Chinese patent application No. 202210675599.3, filed on Jun. 15, 2022, Chinese patent application No. 202211627919.4, filed on Dec. 16, 2022, and Chinese patent application No. 202310658843.X, filed on Jun. 5, 2023, the entire disclosure of each of which is incorporated herein by reference for all purposes.

FIELD OF THE DISCLOSURE

The present disclosure relates to a five-membered ring-fused six-membered ring compound, preparation method therefor, and pharmaceutical composition and use thereof.

BACKGROUND OF THE DISCLOSURE

Kinases have always been important therapeutic targets for the development of anti-inflammatory drugs (Current Opinion in Cell Biology 2009 21, 1-8). Interleukin-1 receptor-associated kinases (IRAKs) are serine/threonine protein kinases that belong to tyrosine-like kinase (TLK) family. IRAKs are located downstream of toll-like receptors and IL-1R pathways, and IRAK1 and IRAK4 have kinase activity. IRAK4 acts upstream of the IRAKs family kinase activation pathway and plays an important role in innate immune signaling (Science 1996, 271(5252): 1128-31). Stimulation of TLR can recruit myeloid differentiation primary response 88 (MYD88) and activate receptors to form a complex Myddosome, which then forms a complex with IRAK4 to activate IRAK1. Subsequently, TRAF6 is activated by IRAK1, leading to the activation of NF-κB and AMPK signaling pathways, ultimately leading to the expression of inflammatory cytokines (Molecules 2016, 21, 1529, J Biol Chem. 2018 Sep. 28; 293(39): 15195-15207, Eur J. Immunol. 2008. 38:614-618).

As a very important property, IRAK4 has two functions of scaffolding and kinase phosphorylation in the TLR and IL-1R signaling pathways. The kinase domain (KD) provides the kinase function, and the death domain (DD) provides the scaffolding function for Myddosome (Molecules 2016, 21(11), 1529). Myddosomes are related to a variety of diseases, not only to autoimmune and inflammatory diseases but also to cancer. For example, 39% of patients with active B-cell-like diffuse large B-cell lymphoma (ABC DLBCL) and 86%-100% of patients with several other types of B-cell malignancies and primary central nervous system lymphomas have MYD88 mutations (Cell Chemical Biology 27, 1-10, Dec. 17, 2020).

IRAK4 gene knockout mice and clinical pathology studies have shown that IRAK4 deficiency itself is nonlethal, and individuals with IRAK4 mutations are also been protected from chronic lung disease and inflammatory bowel disease (Eur. J. Immunol. 2008. 38: 614-618). IRAK4 inhibitors have been considered as targets for the treatment of immune diseases such as autoimmune diseases rheumatoid arthritis (RA), systemic lupus erythematosus (SLE) and psoriasis (Expert Opinion on Therapeutic Patents Volume 29, 2019-Issue 4). Meanwhile, IRAK4 is also a popular target for treating tumors, and there are currently several IRAK4 kinase inhibitors entering the clinical stage. However, these drugs under development in clinical stages are all inhibitors having IRAK4 kinase function to kinase domain (KD) and have no direct inhibitory effect on the scaffolding function of IRAK4. Protein degraders (PROTACs) targeting IRAK4 are expected to simultaneously eliminate its kinase activity and scaffolding functions, resulting in a better and broader efficacy (Nature Biotechnology 2020, volume 38, pages 1221-1223, ACS Med Chem Lett. 2019 Jul. 11; 10(7): 1081-1085).

DESCRIPTION OF THE DISCLOSURE

The present disclosure provides a five-membered ring-fused six-membered ring compound, preparation method therefor, and pharmaceutical composition and use thereof. The compound of the present disclosure has an inhibitory or/and degradative effect on IRAK4, has potential clinical application value, and is expected to improve the prognosis of patients and reduce the possibility of drug resistance.

The present disclosure provides a compound of formula I, a pharmaceutically acceptable salt or an isotope compound thereof:

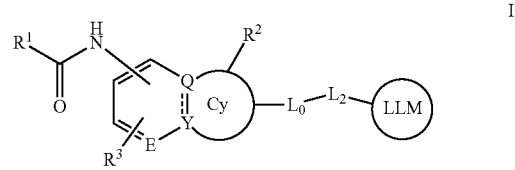

Ring Cy is a 5-membered heterocycle or a 5-membered heteroaromatic ring; the heteroatoms of the 5-membered heterocycle are selected from one or two of N, S and O, and the number of heteroatoms is 1 or 2; the heteroatoms of the 5-membered heteroaromatic ring are selected from one or more of N, S and O, and the number of heteroatoms is 1, 2 or 3;

$\overset{\shortmid}{\underset{\shortmid}{\parallel}}$ is | or ∥;

Q is C or N;

E is CH or N;

Y is C or N;

$R^1$ is a 5- to 10-membered heteroaryl that is unsubstituted or substituted by one or more $R^{1-1}$, or a 6- to 10-membered aryl that is unsubstituted or substituted by one or more $R^{1-2}$; the heteroatoms of the 5- to 10-membered heteroaryl are selected from one or more of N, S and O, and the number of heteroatoms is 1, 2 or 3;

Each $R_{1-1}$ and $R^{1-2}$ are independently halogen, hydroxyl,

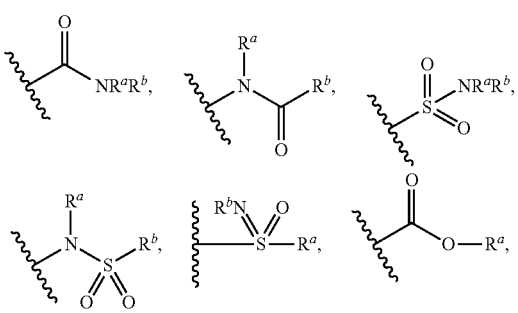

-continued

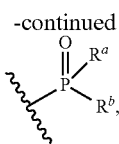

—SO$_2$—R$^a$, —SO—R$^a$, cyano, nitro, a 3- to 11-membered heterocycloalkyl that is unsubstituted or substituted by one or more R$^{1-1-1}$, C$_1$-C$_6$ alkoxy that is unsubstituted or substituted by one or more R$^{1-1-3}$, C$_1$-C$_6$ alkyl that is unsubstituted or substituted by one or more R$^{1-1-4}$,

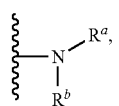

a 3- to 10-membered cycloalkyl that is unsubstituted or substituted by one or more R$^{1-1-5}$, a 6- to 10-membered aryl that is unsubstituted or substituted by one or more R$^{1-1-8}$, or a 5- to 10-membered heteroaryl that is unsubstituted or substituted by one or more R$^{1-1-7}$; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

Each R$^{1-1-1}$, R$^{1-1-3}$, R$_{1-1-4}$, R$^{1-1-5}$, R$_{1-1-7}$ and R$^{1-1-8}$ are independently deuterium, halogen, oxo, hydroxyl,

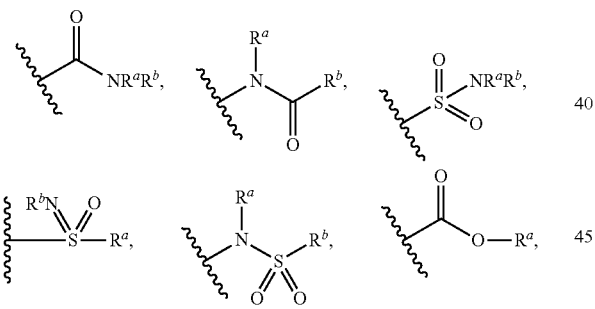

—SO$_2$—R$^a$, —SO—R$^a$, C$_1$-C$_6$ alkoxy that is unsubstituted or substituted by one or more halogens, cyano, nitro, a 3- to 11-membered heterocycloalkyl that is unsubstituted or substituted by one or more R$^{1-1-1}$, C$_1$-C$_6$ alkyl that is unsubstituted or substituted by one or more halogens or deuterium, a 3- to 10-membered cycloalkyl, a 6- to 10-membered aryl that is unsubstituted or substituted by one or more R$^{1-1-1-2}$, or a 5- to 10-membered heteroaryl that is unsubstituted or substituted by one or more R$_{1-1-1-3}$; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

Each R$^{1-1-1-1}$, R$^{1-1-1-2}$, and R$^{1-1-1-3}$ are independently halogen, oxo, hydroxyl, C$_1$-C$_6$ alkoxy or C$_1$-C$_6$ alkyl;

R$^2$ is hydrogen, hydroxyl, cyano, halogen, C$_1$-C$_6$ alkyl that is unsubstituted or substituted by one or more R$^{2-3}$, C$_1$-C$_6$ alkoxy that is unsubstituted or substituted by one or more R$^{2-2}$

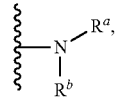

a 5- to 10-membered heteroaryl that is unsubstituted or substituted by one or more R$^{2-1}$ or a 4- to 10-membered heterocycloalkyl that is unsubstituted or substituted by one or more R$^{2-4}$; the heteroatoms of the 5- to 10-membered heteroaryl are selected from one or more of N, S and O, and the number of heteroatoms is 1, 2 or 3; the heteroatoms of the 4- to 10-membered heterocycloalkyl are selected from one or more N, S and O, and the number of heteroatoms is 1, 2 or 3;

Each R$^{2-1}$, R$^{2-2}$, R$^{2-3}$ and R$^{2-4}$ are independently halogen, hydroxyl, cyano, nitro, C$_1$-C$_6$ alkyl that is unsubstituted or substituted by one or more halogens,

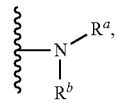

or C$_1$-C$_6$ alkoxy that is unsubstituted or substituted by one or more halogens;

R$^3$ is hydrogen, deuterium, halogen, cyano, hydroxyl, nitro,

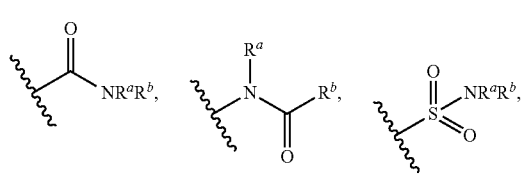

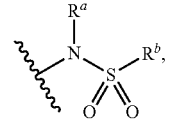

—SO$_2$—R$^a$, —SO—R$^a$,

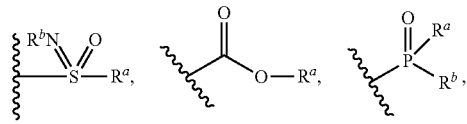

a 3- to 11-membered heterocycloalkyl that is unsubstituted or substituted by one or more R$^{3-1}$, a 3- to 10-membered cycloalkyl that is unsubstituted or substituted by one or more R$^{3-2}$,

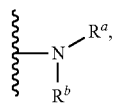

$C_1$-$C_6$ alkyl that is unsubstituted or substituted by one or more $R^{3-4}$, a 6- to 10-membered aryl that is unsubstituted or substituted by one or more $R^{3-5}$, a 5- to 10-membered heteroaryl that is unsubstituted or substituted by one or more $R^{3-6}$, a hydroxyl substituted by $R^{3-8}$, $C_1$-$C_6$ alkoxy that is unsubstituted or substituted by one or more $R^{3-7}$ or —O—COR$^a$; the heteroatoms of the 3- to 11-membered heterocycloalkyl are selected from one or more of N, S and O, and the number of the heteroatoms is 1, 2 or 3; the heteroatoms of the 5- to 10-membered heteroaryl are selected from one or more of N, S and O, and the number of heteroatoms is 1, 2 or 3;

Each $R^{3-1}$, $R^{3-2}$, $R^{3-4}$, $R^{3-5}$, $R^{3-6}$ and $R^{3-7}$ are independently deuterium, halogen, oxo, hydroxyl, a 3- to 11-membered heterocycloalkyl that is unsubstituted or substituted by one or more $R^{3-1-1}$,

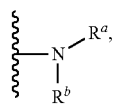

cyano, alkoxy that is unsubstituted or substituted by one or more $R^{3-1-3}$,

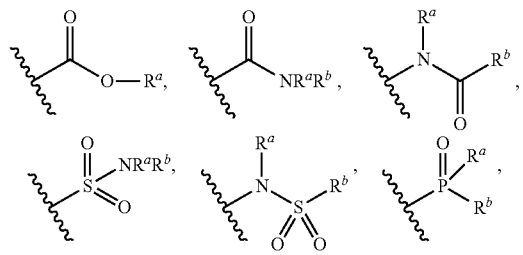

$C_1$-$C_6$ alkyl that is unsubstituted or substituted by one or more $R^{3-4-1}$, a 3- to 10-membered cycloalkyl that is unsubstituted or substituted by one or more $R^{3-1-5}$, —SO$_2$—R$^a$, —SO—R$^a$,

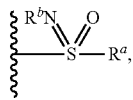

a 6- to 10-membered aryl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

$R^{3-8}$ is a 3- to 10-membered cycloalkyl, a 6- to 10-membered aryl, a 3- to 11-membered heterocycloalkyl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

Each $R^{3-1-1}$, $R^{3-1-3}$, $R^{3-1-4}$ and $R^{3-1-5}$ are independently $C_1$-$C_6$ alkyl that is unsubstituted or substituted by one or more halogens, halogen, oxo or hydroxyl;

Each $R^a$ and each $R^b$ are independently H, $C_1$-$C_6$ alkyl that is unsubstituted or substituted by one or more $R^{a-1}$, a 3- to 10-membered cycloalkyl that is unsubstituted or substituted by one or more $R^{a-2}$, a 3- to 11-membered heterocycloalkyl that is unsubstituted or substituted by one or more $R^{a-3}$, a 6- to 10-membered aryl that is unsubstituted or substituted by one or more $R^{a-4}$, or a 5- to 10-membered heteroaryl that is unsubstituted or substituted by one or more $R^{a-5}$;

Or, $R^a$ and $R^b$ and the atoms connected thereto together form a 3- to 11-membered heterocycle; the heteroatoms of the 3- to 11-membered heterocycle are selected from one or more of N, S and O, and the number of heteroatoms is 1, 2 or 3;

Each $R^{a-1}$, $R^{a-2}$, $R^{a-3}$, $R^{a-4}$ and $R^{a-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5- to 10-membered heteroaryl; the heteroatoms of the 3 to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

$L_0$ is a 5- to 12-membered cycloalkylene group that is unsubstituted or substituted by one or more $L_0^{-2}$, or a 5- to 12-membered heterocycloalkylene group that is unsubstituted or substituted by one or more $L_0^{-3}$; the 5- to 12-membered cycloalkylene group is bicyclic or polycyclic; the 5- to 12-membered heterocycloalkylene group is a monocyclic, bicyclic or polycyclic compound; the heteroatoms of the 5- to 12-membered cycloalkylene group are selected from one or more of N, S and O, and the number of heteroatoms is 1, 2 or 3; each $L_0^{-2}$ is independently deuterium, hydroxyl, halogen, $C_1$-$C_6$ alkoxy that is unsubstituted or substituted by one or more halogens or deuterium,

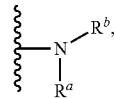

or $C_1$-$C_6$ alkyl that is unsubstituted or substituted by one or more halogens or deuterium; each $L_0^{-3}$ is independently deuterium, hydroxyl, halogen, $C_1$-$C_6$ alkoxy that is unsubstituted or substituted by one or more halogens or deuterium,

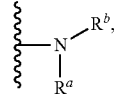

or $C_1$-$C_6$ alkyl that is unsubstituted or substituted by one or more halogens or deuterium;

$L_2$ is linker unit (connecting LLM to $L_0$);

When $L_0$ is

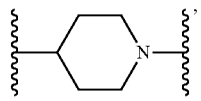 [SMILES: *C1CCN(*)CC1]

$L_2$ comprises at least one or more of the following fragments:

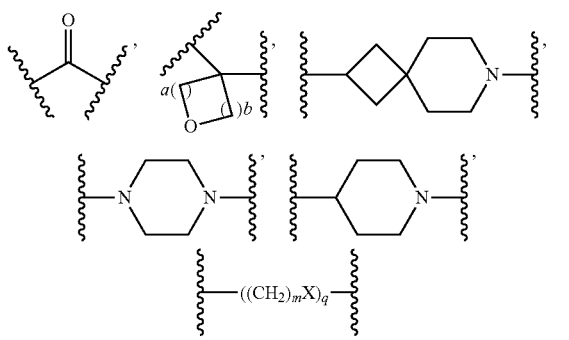

that is unsubstituted or substituted by one or more $L_2^{1-1}$, or

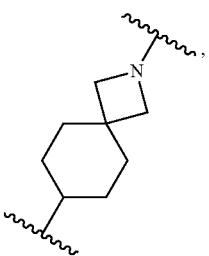 [SMILES: *C1CCC2(CC1)CN(*)C2]

a and b are independently 1 or 2, m is an integer from 1 to 4, q is an integer from 1 to 6, X is O; $L_2^{1-1}$ is halogen, $C_1$-$C_6$ alkyl that is unsubstituted or substituted by one or more halogens, $C_1$-$C_6$ alkoxy that is unsubstituted or substituted by one or more halogens,

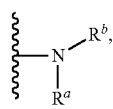

hydroxyl, oxo or;

Each $R^c$ is independently H, $C_1$-$C_6$ alkyl that is unsubstituted or substituted by one or more $R^{c-1}$, a 3- to 10-membered cycloalkyl that is unsubstituted or substituted by one or more $R^{c-2}$, a 3- to 11-membered heterocycloalkyl that is unsubstituted or substituted by one or more $R^{c-3}$, a 6- to 10-membered aryl that is unsubstituted or substituted by one or more $R^{c-4}$, or a 5- to 10-membered heteroaryl that is unsubstituted or substituted by one or more $R^{c-5}$;

Each $R^{c-1}$, $R^{c-2}$, $R^{c-3}$, $R^{c-4}$ and $R^{c-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3; LLM is

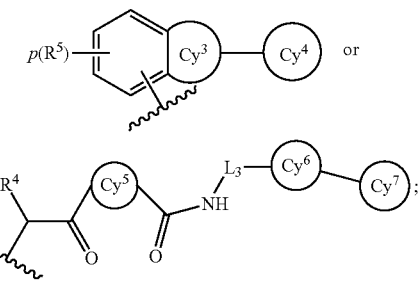

Ring $Cy^3$ is a 5- to 12-membered heterocycle that is unsubstituted or substituted by one or more $Cy^{3-1}$, the heteroatoms of the 5- to 12-membered heterocycle are selected from one or more of N, S and O, and the number of heteroatoms is 1, 2 or 3; $Cy^{3-1}$ is independently $C_1$-$C_6$ alkyl, halogen, hydroxyl or oxo;

Ring $Cy^4$ is a 5- to 12-membered heterocycloalkyl that is unsubstituted or substituted by one or more $Cy^{4-1}$, the heteroatoms of the 5- to 12-membered heterocycloalkyl are selected from one or more of N, S and O, and the number of heteroatoms is 1, 2 or 3; $Cy^{4-1}$ is independently $C_1$-$C_6$ alkyl, halogen, hydroxyl or oxo;

Ring $Cy^5$ is a 5- to 12-membered heterocycle that is unsubstituted or substituted by one or more $Cy^{5-1}$, the heteroatoms of the 5- to 12-membered heterocycle are selected from one or more of N, S and O, and the number of heteroatoms is 1, 2 or 3; $Cy^{5-1}$ is independently $C_1$-$C_6$ alkyl, hydroxyl or oxo;

Ring $Cy^6$ is a 6- to 10-membered aromatic ring that is unsubstituted or substituted by one or more $Cy^{6-1}$; $Cy^{6-1}$ is independently $C_1$-$C_6$ alkyl, hydroxyl or halogen;

Ring $Cy^7$ is a 5- to 9-membered heteroaromatic ring that is unsubstituted or substituted by one or more $Cy^{7-1}$, the heteroatoms of the 5- to 9-membered heteroaromatic ring are selected from one or more of N, S and O, and the number of heteroatoms is 1, 2 or 3; $Cy^{7-1}$ is independently $C_1$-$C_6$ alkyl, hydroxyl or halogen;

$R^4$ is independently hydrogen, halogen, hydroxyl or $C_1$-$C_6$ alkyl that is unsubstituted or substituted by one or more halogens;

P is 0, 1, 2 or 3;

Each $R^5$ is independently halogen;

$L_3$ is

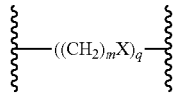

that is unsubstituted or substituted by one or more $L_3^{-1}$; where m is an integer from 1 to 4, q is an integer from 1 to 6, and X is absent or O; $L_3^{-1}$ is independently halogen, or $C_1$-$C_6$ alkyl that is unsubstituted or substituted by one or more halogens.

The present disclosure provides a compound of formula I, a pharmaceutically acceptable salt or an isotope compound thereof:

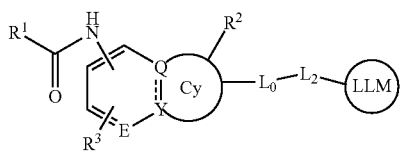

Ring Cy is a 5-membered heterocycle or a 5-membered heteroaromatic ring; the heteroatoms of the 5-membered heterocycle are selected from one or two of N, S and O, and the number of heteroatoms is 1 or 2; the heteroatoms of the 5-membered heteroaromatic ring are selected from one or more of N, S and O, and the number of heteroatoms is 1, 2 or 3;

⁞ is | or ‖;
Q is C or N;
E is CH or N;
Y is C or N;
$R^1$ is a 5- to 10-membered heteroaryl that is unsubstituted or substituted by one or more $R^{1-2}$, or a 6- to 10-membered aryl that is unsubstituted or substituted by one or more $R^{1-2}$; the heteroatoms of the 5- to 10-membered heteroaryl are selected from one or more of N, S and O, and the number of heteroatoms is 1, 2 or 3;
Each $R^{1-1}$ and $R^{1-2}$ are independently halogen, hydroxyl,

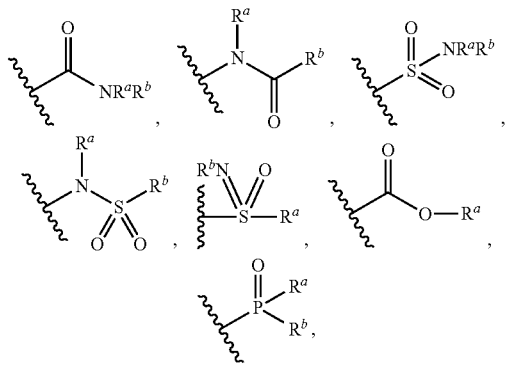

—$SO_2$—$R^a$, —SO—$R^a$, cyano, nitro, a 3- to 11-membered heterocycloalkyl that is unsubstituted or substituted by one or more $R^{1-1-1}$, $C_1$-$C_6$ alkoxy that is unsubstituted or substituted by one or more $R^{1-1-3}$, $C_1$-$C_6$ alkyl that is unsubstituted or substituted by one or more $R^{1-1-4}$,

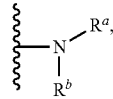

a 3- to 10-membered cycloalkyl that is unsubstituted or substituted by one or more $R^{1-1-5}$, a 6- to 10-membered aryl that is unsubstituted or substituted by one or more $R^{1-1-8}$, or a 5- to 10-membered heteroaryl that is unsubstituted or substituted by one or more $R^{1-1-7}$; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;
Each $R^{1-1-1}$, $R^{1-1-3}$, $R^{1-1-4}$, $R^{1-1-5}$, $R^{1-1-7}$ and $R^{1-1-8}$ are independently halogen, oxo, hydroxyl,

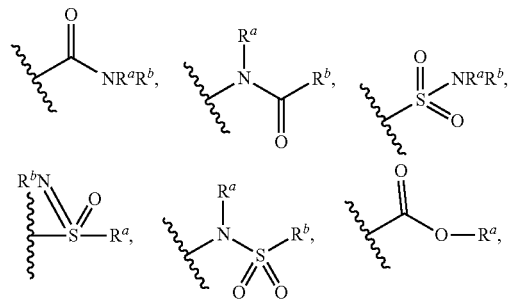

—$SO_2$—$R^a$, —SO—$R^a$, $C_1$-$C_6$ alkoxy that is unsubstituted or substituted by one or more halogens, cyano, nitro, a 3- to 11-membered heterocycloalkyl that is unsubstituted or substituted by one or more $R^{1-1-1-1}$, $C_1$-$C_6$ alkyl that is unsubstituted or substituted by one or more halogens, a 3- to 10-membered cycloalkyl, a 6- to 10-membered aryl that is unsubstituted or substituted by one or more $R^{1-1-1-2}$, or a 5- to 10-membered heteroaryl that is unsubstituted or substituted by one or more $R^{1-1-1-3}$; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;
Each $R^{1-1-1-1}$, $R^{1-1-1-2}$, and $R^{1-1-1-3}$ are independently halogen, oxo, hydroxyl, $C_1$-$C_6$ alkoxy or $C_1$-$C_6$ alkyl;
$R^2$ is hydrogen, hydroxyl, cyano, halogen, $C_1$-$C_6$ alkyl that is unsubstituted or substituted by one or more $R^{2-3}$, $C_1$-$C_6$ alkoxy that is unsubstituted or substituted by one or more $R^{2-2}$,

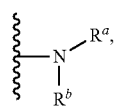

a 5- to 10-membered heteroaryl that is unsubstituted or substituted by one or more $R^{2-1}$ or a 4- to 10-membered heterocycloalkyl that is unsubstituted or substituted by one or more $R^{2-4}$; the heteroatoms of the 5- to 10-membered heteroaryl are selected from one or more of N, S and O, and the number of heteroatoms is 1, 2 or 3; the heteroatoms of the 4- to 10-membered heterocycloalkyl are selected from one or more N, S and O, and the number of heteroatoms is 1, 2 or 3;

Each $R^{2-1}$, $R^{2-2}$, $R^{2-3}$ and $R^{2-4}$ are independently halogen, hydroxyl, cyano, nitro, $C_1$-$C_6$ alkyl that is unsubstituted or substituted by one or more halogens,

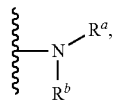

or $C_1$-$C_6$ alkoxy that is unsubstituted or substituted by one or more halogens;

$R^3$ is hydrogen, deuterium, halogen, cyano, hydroxyl, nitro,

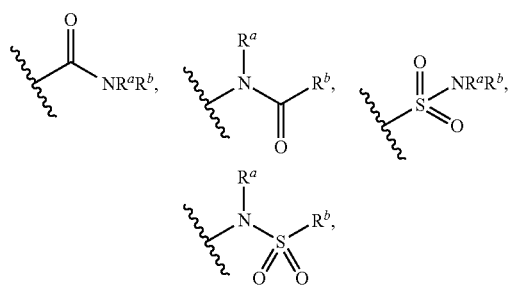

—$SO_2$—$R^a$, —SO—$R^a$,

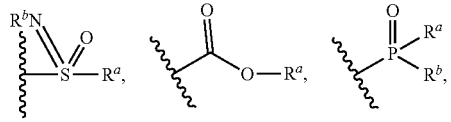

a 3- to 11-membered heterocycloalkyl that is unsubstituted or substituted by one or more $R^{3-1}$, a 3- to 10-membered cycloalkyl that is unsubstituted or substituted by one or more $R^{3-2}$,

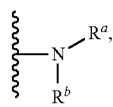

$C_1$-$C_6$ alkyl that is unsubstituted or substituted by one or more $R^{3-4}$, a 6- to 10-membered aryl that is unsubstituted or substituted by one or more $R^{3-4}$, a 5- to 10-membered heteroaryl that is unsubstituted or substituted by one or more $R^{3-6}$, a hydroxyl substituted by $R^{3-8}$, $C_1$-$C_6$ alkoxy that is unsubstituted or substituted by one or more $R^{3-7}$ or —O—$COR^a$; the heteroatoms of the 3- to 11-membered heterocycloalkyl are selected from one or more of N, S and O, and the number of the heteroatoms is 1, 2 or 3; the heteroatoms of the 5- to 10-membered heteroaryl are selected from one or more of N, S and O, and the number of heteroatoms is 1, 2 or 3;

Each $R^{3-1}$, $R^{3-2}$, $R^{3-4}$, $R^{3-5}$, $R^{3-6}$ and $R^{3-7}$ are independently deuterium, halogen, oxo, hydroxyl, a 3- to 11-membered heterocycloalkyl that is unsubstituted or substituted by one or more $R^{3-1-1}$,

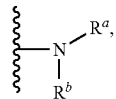

cyano, alkoxy that is unsubstituted or substituted by one or more $R^{3-1-3}$

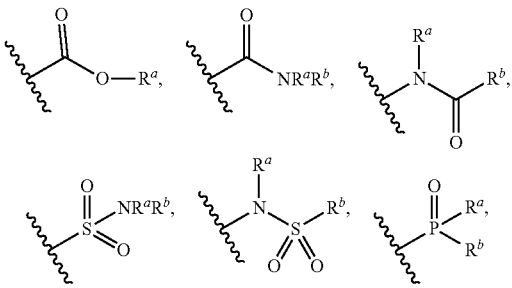

$C_1$-$C_6$ alkyl that is unsubstituted or substituted by one or more $R^{3-1-4}$, a 3- to 10-membered cycloalkyl that is unsubstituted or substituted by one or more $R^{3-1-5}$, —$SO_2$—$R^a$, —SO—$R^a$,

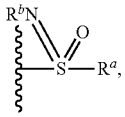

a 6- to 10-membered aryl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

$R^{3-8}$ is a 3- to 10-membered cycloalkyl, a 6- to 10-membered aryl, a 3- to 11-membered heterocycloalkyl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more N, S and O, and the number of heteroatoms is 1, 2 or 3;

Each $R^{3-1-1}$, $R^{3-1-3}$, $R^{3-1-4}$ and $R^{3-1-5}$ are independently $C_1$-$C_6$ alkyl that is unsubstituted or substituted by one or more halogens, halogen, oxo or hydroxyl;

Each $R^a$ and each $R^b$ are independently H, $C_1$-$C_6$ alkyl that is unsubstituted or substituted by one or more $R^{a-1}$, a 3- to 10-membered cycloalkyl that is unsubstituted or substituted by one or more $R^{a-2}$, a 3- to 11-membered heterocycloalkyl that is unsubstituted or substituted by one or more $R^{a-3}$, a 6- to 10-membered aryl that is unsubstituted or substituted by one or more $R^{a-4}$, or a 5- to 10-membered heteroaryl that is unsubstituted or substituted by one or more $R^{a-5}$;

Or, $R^a$ and $R^b$ and the atoms connected thereto together form a 3- to 11-membered heterocycle; the heteroatoms of the 3- to 11-membered heterocycle are selected from one or more of N, S and O, and the number of heteroatoms is 1, 2 or 3;

Each $R^{a-1}$, $R^{a-2}$, $R^{a-3}$, $R^{a-4}$ and $R^{a-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5- to 10-membered heteroaryl; the heteroatoms of the 3 to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

$L_0$ is a 5- to 12-membered cycloalkylene group that is unsubstituted or substituted by one or more $L_0^{-2}$, or a 5- to 12-membered heterocycloalkylene group that is unsubstituted or substituted by one or more $L_0^{-3}$; the 5- to 12-membered cycloalkylene group is bicyclic or polycyclic; the 5- to 12-membered heterocycloalkylene group is a monocyclic, bicyclic or polycyclic compound; the heteroatoms of the 5- to 12-membered cycloalkylene group are selected from one or more of N, S and O, and the number of heteroatoms is 1, 2 or 3; each $L_0^{-2}$ is independently hydroxyl, halogen, $C_1$-$C_6$ alkoxy that is unsubstituted or substituted by one or more halogens,

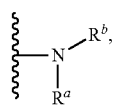

or $C_1$-$C_6$ alkyl that is unsubstituted or substituted by one or more halogens; each $L_0^{-3}$ is independently hydroxyl, halogen, $C_1$-$C_6$ alkoxy that is unsubstituted or substituted by one or more halogens,

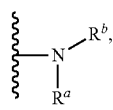

or $C_1$-$C_6$ alkyl that is unsubstituted or substituted by one or more halogens;

$L_2$ is linker unit (connecting LLM to $L_0$);

When $L_0$ is

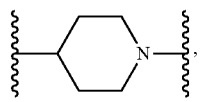

$L_2$ comprises at least one or more of the following fragments:

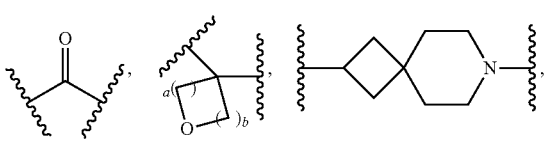

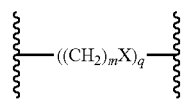

that is unsubstituted or substituted by one or more $L_2^{1-1}$, or

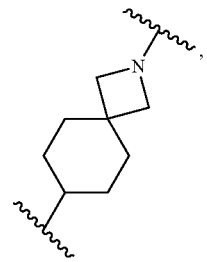 [SMILES: *C1CCC2(CC1)CN(*)C2]

a and b are independently 1 or 2, m is an integer from 1 to 4, q is an integer from 1 to 6, X is O; $L_2^{1-1}$ is halogen, $C_1$-$C_6$ alkyl that is unsubstituted or substituted by one or more halogens, $C_1$-$C_6$ alkoxy that is unsubstituted or substituted by one or more halogens,

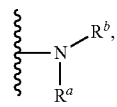

hydroxyl, oxo or

Each $R^c$ is independently H, $C_1$-$C_6$ alkyl that is unsubstituted or substituted by one or more $R^{c-1}$, a 3- to 10-membered cycloalkyl that is unsubstituted or substituted by one or more $R^{c-2}$, a 3- to 11-membered heterocycloalkyl that is unsubstituted or substituted by one or more $R^{c-3}$, a 6- to 10-membered aryl that is unsubstituted or substituted by one or more $R^{c-4}$, or a 5- to 10-membered heteroaryl that is unsubstituted or substituted by one or more $R^{c-5}$;

Each $R^{c-1}$, $R^{c-2}$, $R^{c-3}$, $R^{c-4}$ and $R^{c-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5 to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

LLM is

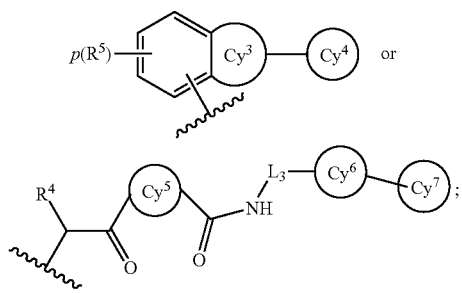

Ring $Cy^3$ is a 5- to 12-membered heterocycle that is unsubstituted or substituted by one or more $Cy^{3-1}$, the heteroatoms of the 5- to 12-membered heterocycle are selected from one or more of N, S and O, and the number of heteroatoms is 1, 2 or 3; $Cy^{3-1}$ is independently $C_1$-$C_6$ alkyl, halogen, hydroxyl or oxo;

Ring $Cy^4$ is a 5- to 12-membered heterocycloalkyl that is unsubstituted or substituted by one or more $Cy^{4-1}$, the heteroatoms of the 5- to 12-membered heterocycloalkyl are selected from one or more of N, S and O, and the number of heteroatoms is 1, 2 or 3; $Cy^{4-1}$ is independently $C_1$-$C_6$ alkyl, halogen, hydroxyl or oxo;

Ring $Cy^5$ is a 5- to 12-membered heterocycle that is unsubstituted or substituted by one or more $Cy^{5-1}$, the heteroatoms of the 5- to 12-membered heterocycle are selected from one or more of N, S and O, and the number of heteroatoms is 1, 2 or 3; $Cy^{5-1}$ is independently $C_1$-$C_6$ alkyl, hydroxyl or oxo;

Ring $Cy^6$ is a 6- to 10-membered aromatic ring that is unsubstituted or substituted by one or more $Cy^{6-1}$; $Cy^{6-1}$ is independently $C_1$-$C_6$ alkyl, hydroxyl or halogen;

Ring $Cy^7$ is a 5- to 9-membered heteroaromatic ring that is unsubstituted or substituted by one or more $Cy^{7-1}$, the heteroatoms of the 5- to 9-membered heteroaromatic ring are selected from one or more of N, S and O, and the number of heteroatoms is 1, 2 or 3; $Cy^{7-1}$ is independently $C_1$-$C_6$ alkyl, hydroxyl or halogen;

$R^4$ is independently hydrogen, halogen, hydroxyl or $C_1$-$C_6$ alkyl that is unsubstituted or substituted by one or more halogens;

P is 0, 1, 2 or 3;

Each $R^5$ is independently halogen;

$L_3$ is

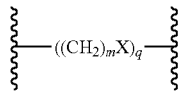

that is unsubstituted or substituted by one or more $L_3^{-1}$; where m is an integer from 1 to 4, q is an integer from 1 to 6, and X is absent or O; $L_3^{-1}$ is independently halogen, or $C_1$-$C_6$ alkyl that is unsubstituted or substituted by one or more halogens.

In a preferred embodiment, in the five-membered ring-fused six-membered ring compound as shown in Formula 1, the pharmaceutically acceptable salt or isotope compound thereof; the definitions of some groups can be as follows, and the definitions of other groups can be as described in any one of the above embodiments (hereinafter referred to as "in a certain embodiment"): LLM is a group that binds to a ligase; and the ligase can be an E3 ligase, preferably VHL, CRBN, MDM2, cIAP, Cereblon, XIAP, E3A, APC, UBR5 (EDDI), SOCS/BC-box/eloBC/CUL5/RING, LNXp80, CBX4, CBLL1, HACEI, HECTD1, HECTD2, HECTD3, HECW1, HECW2, HERC1, HERC2, HERC3, HERC4, HUWEI, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, WWP2, Parkin, A20/TNFAIP3, AMFR/gp78, ARA54, β-TrCPI/BTRC, BRCA1, CBL, CHIP/STUB1, E6, E6AP/UBE3A, F-box protein 15/FBXO15, FBXW7/Cdc4, GRAIL/RNF128, HOIP/RNF31, cIAP-1/HIAP-2, cIAP-2/HIAP-1, cIAP(pan), ITCH/AIP4, KAP1, MARCH8, Mind Bomb 1/MIB1, Mind Bomb 2/MIB2, MuRFI/TRIM63, NDFIP1, NEDD4, N1eL, Parkin, RNF2, RNF4, RNF8, RNF168, RNF43, SART1, Skp2, SMURF2, TRAF-1, TRAF-2, TRAF-3, TRAF-4, TRAF-5, TRAF-6, TRIM5, TRIM21, TRIM32, UBR5 or ZNRF3, more preferably VHL, CRBN, MDM2 or cIAP.

In a preferred embodiment, the linker unit can be a conventional linker unit in the art.

Preferably, $L_2$ is $-L_2^{-1}-L_2^{-2}-L_2^{-3}-L_2^{-4}-$; $L_2^{-1}$, $L_2^{-2}$, $L_2^{-3}$ and $L_2^{-4}$ are independently absent,

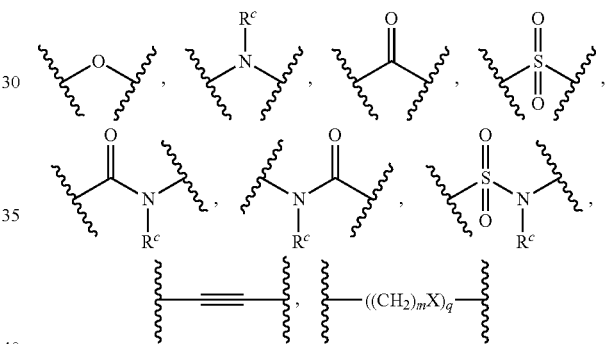

that is unsubstituted or substituted by one or more $L_2^{1-1}$,

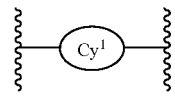

that is unsubstituted or substituted by one or more $L_2^{1-2}$, or

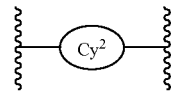

that is unsubstituted or substituted by one or more $L_2^{1-3}$, m is an integer from 1 to 4, q is an integer from 1 to 6, X is absent or O; Ring $Cy^1$ is a 4- to 12-membered heterocycle or 3- to 12-membered cycloalkyl; ring $Cy^2$ is a 5- to 10-membered heteroaromatic ring or a 6- to 10-membered aromatic ring; the heteroatoms of the 4- to 12-membered heterocycle are selected from one or more of N, S and O, and the number of heteroatoms is 1, 2 or 3; the heteroatoms of the 5- to 10-membered heteroaromatic ring are selected from one or more of N, S and O, and the number of heteroatoms is 1, 2 or 3;

$L_2^{1-1}$ and $L_2^{1-2}$ are independently halogen, $C_1$-$C_6$ alkyl that is unsubstituted or substituted by one or more halogens, $C_1$-$C_6$ alkoxy that is unsubstituted or substituted by one or more halogens,

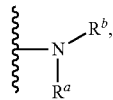

hydroxyl, oxo, or

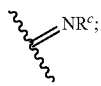

$L_2^{1-3}$ is independently halogen, $C_1$-$C_6$ alkyl that is unsubstituted or substituted by one or more halogens, $C_1$-$C_6$ alkoxy that is unsubstituted or substituted by one or more halogens, cyano,

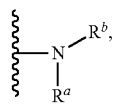

a 3- to 10-membered cycloalkyl that is unsubstituted or substituted by one or more $L_2^{1-3-1}$, a 3- to 11-membered heterocycloalkyl that is unsubstituted or substituted by one or more $L_2^{1-3-2}$,

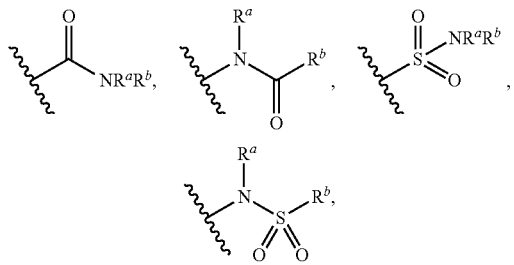

—SO$_2$—R$^a$, —SO—R$^a$,

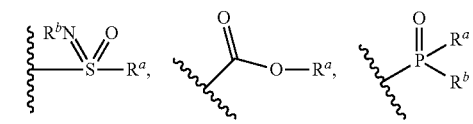

or hydroxyl; the heteroatoms of the 3- to 11-membered heterocycloalkyl are selected from one or more of N, S and O, and the number of heteroatoms is 1, 2 one or 3;

$L_2^{1-3-1}$ and $L_2^{1-3-2}$ are independently halogen, $C_1$-$C_6$ alkyl that is unsubstituted or substituted by one or more halogens, $C_1$-$C_6$ alkoxy that is unsubstituted or substituted by one or more halogens, hydroxyl, oxo, or

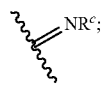

Each $R^c$ is independently H, $C_1$-$C_6$ alkyl that is unsubstituted or substituted by one or more $R^{c-1}$, a 3- to 10-membered cycloalkyl that is unsubstituted or substituted by one or more $R^{c-2}$, a 3- to 11-membered heterocycloalkyl that is unsubstituted or substituted by one or more $R^{c-3}$, a 6- to 10-membered aryl that is unsubstituted or substituted by one or more $R^{c-4}$, or a 5- to 10-membered heteroaryl that is unsubstituted or substituted by one or more $R^{c-5}$;

Each $R^{c-1}$, $R^{c-2}$, $R^{c-3}$, $R^{c-4}$ and $R^{c-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5- to 10-membered heteroaryl; the heteroatoms of the 3- to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3;

Each $R^a$ and each $R^b$ are independently H, $C_1$-$C_6$ alkyl that is unsubstituted or substituted by one or more $R^{a-1}$, a 3- to 10-membered cycloalkyl that is unsubstituted or substituted by one or more $R^{a-2}$, a 3- to 11-membered heterocycloalkyl that is unsubstituted or substituted by one or more $R^{a-3}$, a 6- to 10-membered aryl that is unsubstituted or substituted by one or more $R^{a-4}$, or a 5- to 10-membered heteroaryl that is unsubstituted or substituted by one or more $R^{a-5}$;

Each $R^{a-1}$, $R^{a-2}$, $R^{a-3}$, $R^{a-4}$ and $R^{a-5}$ are independently halogen, cyano, hydroxyl, nitro, $C_1$-$C_6$ alkyl, $C_1$-$C_6$ alkoxy, a 3- to 10-membered cycloalkyl, a 3- to 11-membered heterocycloalkyl, a 6- to 10-membered aryl, or a 5- to 10-membered heteroaryl; the heteroatoms of the 3 to 11-membered heterocycloalkyl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3.

In a preferred embodiment, when ring Cy is a 5-membered heterocycle, the heteroatom of the 5-membered heterocycle is O and the number is 1. The 5-membered heterocycle is preferably a tetrahydrofuran ring.

In a preferred embodiment, when ring Cy is a 5-membered heteroaromatic ring, the heteroatoms of the 5-membered heteroaromatic ring are selected from one or two of N, S and O, and the number of heteroatoms is 1 or 2. The 5-membered heteroaromatic ring is preferably a pyrrole ring, pyrazole ring, thiazole ring, oxazole ring or imidazole ring.

In a preferred embodiment, when $R^1$ is a 5- to 10-membered heteroaryl that is unsubstituted or substituted by one or more $R^{1-1}$, the heteroatoms of the 5- to 10-membered heteroaryl are selected from one or two of N, O and S, and the number of heteroatoms is 1, 2 or 3; the 5- to 10-membered heteroaryl can be oxazolyl, pyrazolyl, thiazolyl, imidazolyl, pyridyl, pyridazinyl, pyrazinyl, pyrimidinyl, triazinyl or pyrazolopyrimidinyl, such as pyridyl, oxazolyl, pyrazolyl or

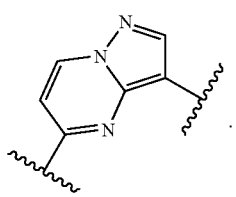 [SMILES: *c1ccn2ncc(*)c2n1]

In a preferred embodiment, when $R^1$ is a 6- to 10-membered aryl that is unsubstituted or substituted by one or more $R^{1-2}$, the 6- to 10-membered aryl group is preferably phenyl or naphthyl.

In a preferred embodiment, when each $R^{1-1}$ and $R^{1-2}$ are independently a halogen, the halogen can be fluorine, chlorine, bromine or iodine, such as fluorine.

In a preferred embodiment, when each $R^{1-1}$ and $R^{1-2}$ are independently a 3- to 11-membered heterocycloalkyl that is unsubstituted or substituted by one or more $R^{1-1-1}$, the 3- to 11-membered heterocycloalkyl may be 4- to 8-membered heterocycloalkyl, the heteroatoms of the 3- to 11-membered heterocycloalkyl are selected from one or two of N, S and O, and the number of heteroatoms is 1 or 2; preferably, the heteroatom of the 3- to 11-membered heterocycloalkyl is N, S or O, and the number of heteroatoms is 1 or 2; preferably, each $R^{1-1-1}$ is independently halogen, hydroxyl, oxo, $C_1$-$C_6$ alkoxy that is unsubstituted or substituted by one or more halogens, or $C_1$-$C_6$ alkyl that is unsubstituted or substituted by one or more halogens; the 3- to 11-membered heterocycloalkyl is preferably pyridazinyl, piperazinyl, piperidinyl, tetrahydropyrrolyl, oxacyclobutyl, azabicyclo[2.2.2]octyl, azabicyclo[3.2.1]octyl, azaspiro[3.3]heptyl or azabicyclo[2.2.1]heptyl, such as

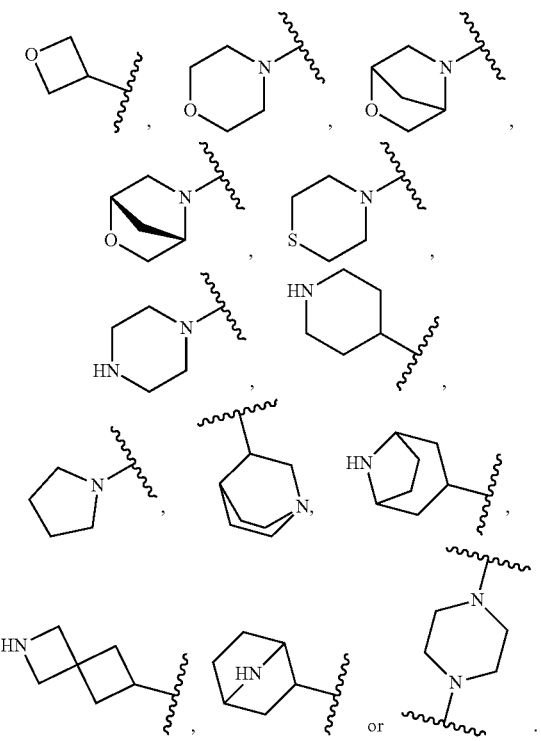

In a preferred embodiment, when each $R^{1-1}$ and $R^{1-2}$ are independently $C_1$-$C_6$ alkoxy that is unsubstituted or substituted by one or more $R^{1-1-3}$, the $C_1$-$C_6$ alkoxy can be $C_1$-$C_4$ alkoxy, such as methoxy, ethoxy, n-propoxy, isopropoxy, n-butoxy, isobutoxy, sec-butoxy or tert-butoxy; preferably, each $R^{1-1-3}$ is independently halogen, hydroxyl, $C_1$-$C_6$ alkoxy that is unsubstituted or substituted by one or more halogens or $C_1$-$C_6$ alkyl that is unsubstituted or substituted by one or more halogens.

In a preferred embodiment, when each $R^{1-1}$ and $R^{1-2}$ are independently $C_1$-$C_6$ alkyl that is unsubstituted or substituted by one or more $R^{1-1-4}$, the $C_1$-$C_6$ alkyl can be $C_1$-$C_4$ alkyl, such as methyl, ethyl, n-propyl, isopropyl, n-butyl, isobutyl, sec-butyl or tert-butyl; preferably, each $R^{1-1-4}$ is independently halogen, hydroxyl, $C_1$-$C_6$ alkoxy that is unsubstituted or substituted by one or more halogens or $C_1$-$C_6$ alkyl that is unsubstituted or substituted by one or more halogens.

In a preferred embodiment, when each $R^{1-1}$ and $R^{1-2}$ are independently a 3- to 10-membered cycloalkyl that is unsubstituted or substituted by one or more $R^{1-1-5}$, the 3- to 10-membered cycloalkyl can be a 3- to 6-membered cycloalkyl, such as cyclopropyl, cyclobutyl, cyclopentyl or cyclohexyl; preferably, each $R^{1-1-5}$ is independently halogen, hydroxyl, $C_1$-$C_6$ alkoxy that is unsubstituted or substituted by one or more halogens or $C_1$-$C_6$ alkyl that is unsubstituted or substituted by one or more halogens.

In a preferred embodiment, when each $R^{1-1}$ and $R^{1-2}$ are independently a 5- to 10-membered heteroaryl that is unsubstituted or substituted by one or more $R^{1-1-7}$, the heteroatom of the 5- to 10-membered heteroaryl is N, and the number of heteroatoms is 1, 2 or 3; preferably, each $R^{1-1-7}$ is independently halogen, hydroxyl, $C_1$-$C_6$ alkoxy that is unsubstituted or substituted by one or more halogens or $C_1$-$C_6$ alkyl that is unsubstituted or substituted by one or more halogens; the 5- to 10-membered heteroaryl may be pyridyl, pyridylene, pyridazinyl, pyrazinyl, pyrimidinyl or triazinyl, such as pyridyl or pyridylene.

In a preferred embodiment, when each $R^{1-1}$ and $R^{1-2}$ are independently a 6- to 10-membered aryl that is unsubstituted or substituted by one or more $R^{1-1-8}$, the 6- to 10-membered aryl is preferably phenyl or naphthyl; preferably, each $R^{1-1-8}$ is independently halogen, hydroxyl, $C_1$-$C_6$ alkoxy that is unsubstituted or substituted by one or more halogens or $C_1$-$C_6$ alkyl that is unsubstituted or substituted by one or more halogens.

In a preferred embodiment, when each $R^{1-1-1}$ and $R^{1-1-7}$ are independently $C_1$-$C_6$ alkyl that is unsubstituted or substituted by one or more halogens, the $C_1$-$C_6$ alkyl can be $C_1$-$C_4$ alkyl, such as methyl, ethyl, n-propyl, isopropyl, n-butyl, isobutyl, sec-butyl or tert-butyl.

In a preferred embodiment, when each $R^{1-1-4}$ is independently halogen, the halogen can be fluorine, chlorine, bromine or iodine, such as fluorine.

In a preferred embodiment, when $R^2$ is halogen, the halogen can be fluorine, chlorine, bromine or iodine, such as fluorine or chlorine.

In a preferred embodiment, when $R^2$ is a 5- to 10-membered heteroaryl that is unsubstituted or substituted by one or more $R^{2-1}$, the heteroatom of the 5- to 10-membered heteroaryl is N, and the number of heteroatoms is 1, 2 or 3; the 5- to 10-membered heteroaryl is preferably pyridyl, pyridazinyl, pyrazinyl, pyrimidinyl or triazinyl, such as pyridyl.

In a preferred embodiment, when $R^2$ is $C_1$-$C_6$ alkoxy that is unsubstituted or substituted by one or more $R^{2-2}$, the $C_1$-$C_6$ alkoxy can be $C_1$-$C_4$ alkoxy, such as methoxy, ethoxy, n-propoxy, isopropoxy, n-butoxy, isobutoxy, sec-butoxy or tert-butoxy.

In a preferred embodiment, when $R^2$ is $C_1$-$C_6$ alkyl that is unsubstituted or substituted by one or more $R^{2-3}$, the $C_1$-$C_6$ alkyl can be $C_1$-$C_4$ alkyl, such as methyl, ethyl, n-propyl, isopropyl, n-butyl, isobutyl, sec-butyl or tert-butyl.

In a preferred embodiment, when $R^2$ is independently a 4- to 10-membered heterocycloalkyl that is unsubstituted or substituted by one or more $R^{2-4}$, the 4- to 10-membered heterocycloalkyl may be 5- to 8-membered heterocycloalkyl, the heteroatoms of the 4- to 10-membered heterocycloalkyl are selected from one or two of N, S and O, and the number of heteroatoms is 1 or 2; preferably, the heteroatom of the 4- to 10-membered heterocycloalkyl is N, S or O, and the number of heteroatoms is 1 or 2; the 4- to 10-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl or azabicyclo[2.2.1]heptyl, such as

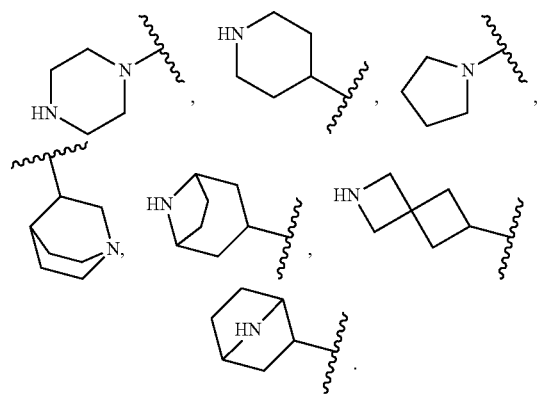

In a preferred embodiment, when each $R^{2-1}$, $R^{2-2}$, $R^{2-3}$ and $R^{2-4}$ are independently halogen, the halogen can be fluorine, chlorine, bromine or iodine; such as fluorine.

In a preferred embodiment, when each $R^{2-1}$, $R^{2-2}$, $R^{2-3}$ and $R^{2-4}$ are independently $C_1$-$C_6$ alkyl that is unsubstituted or substituted by one or more halogens, the $C_1$-$C_6$ alkyl can be $C_1$-$C_4$ alkyl, such as methyl, ethyl, n-propyl, isopropyl, n-butyl, isobutyl, sec-butyl or tert-butyl; and the halogen can be fluorine, chlorine, bromine or iodine; such as fluorine.

In a preferred embodiment, when each $R^{2-1}$, $R^{2-2}$, $R^{2-3}$ and $R^{2-4}$ are independently $C_1$-$C_6$ alkoxy, the $C_1$-$C_6$ alkoxy can be $C_1$-$C_4$ alkoxy, such as methoxy, ethoxy, n-propoxy, isopropoxy, n-butoxy, isobutoxy, sec-butoxy or tert-butoxy, further such as methoxy; and the halogen can be fluorine, chlorine, bromine or iodine; such as fluorine.

In a preferred embodiment, when $R^3$ is halogen, the halogen can be fluorine, chlorine, bromine or iodine; such as fluorine.

In a preferred embodiment, when $R^3$ is a 3- to 11-membered heterocycloalkyl that is unsubstituted or substituted by one or more $R^{3-1}$, the 3- to 11-membered heterocycloalkyl may be 3- to 8-membered heterocycloalkyl, the heteroatoms of the 3- to 11-membered heterocycloalkyl are preferably N and/or O, and the number of heteroatoms is 1 or 2; the 3- to 11-membered heterocycloalkyl is preferably piperidinyl, tetrahydropyrrolyl, tetrahydropyrrolidene, 2-azaspiro[3.3]heptyl, 2-oxaspiro[3.3]heptyl, morpholinyl, tetrahydropyranyl, oxa cyclobutyl, azabicyclo[2.2.1]heptyl or diazabicyclo[2.2.1]heptyl; preferably, each $R^{3-1}$ is independently halogen, oxo or hydroxyl, such as hydroxyl; the 3- to 8-membered heterocycloalkyl that is unsubstituted or substituted by one or more $R^{3-1}$ is preferably

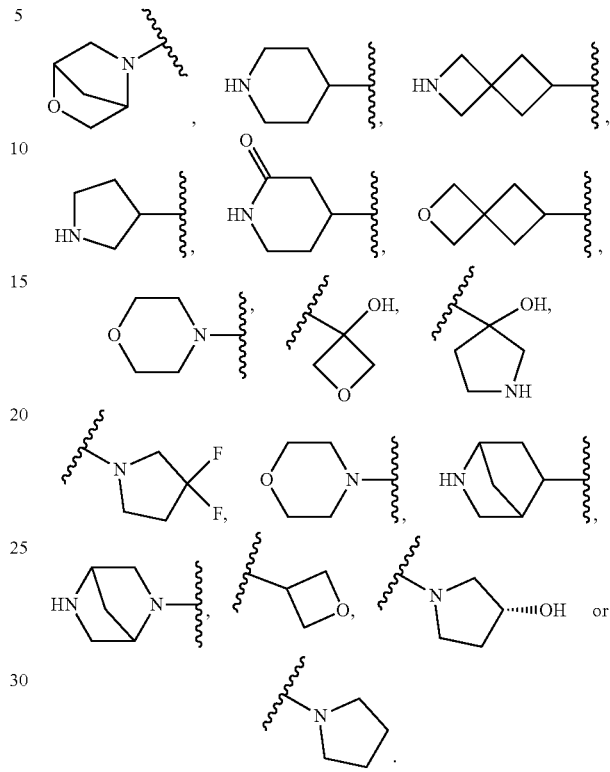

In a preferred embodiment, when $R^3$ is a 3- to 10-membered cycloalkyl that is unsubstituted or substituted by one or more $R^{3-2}$, the 3- to 10-membered cycloalkyl may be $C_3$-$C_6$ cycloalkyl, can also be cyclopropyl, cyclobutyl, cyclopentyl or cyclohexyl, such as cyclopropyl, cyclobutyl or cyclohexyl; preferably, each $R^{3-2}$ is independently halogen or hydroxyl; the 3- to 10-membered cycloalkyl that is unsubstituted or substituted by one or more $R^{3-2}$ is preferably

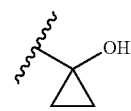

In a preferred embodiment, when $R^3$ is $C_1$-$C_6$ alkyl that is unsubstituted or substituted by one or more $R^{3-4}$, the $C_1$-$C_6$ alkyl can be methyl, ethyl, n-propyl, isopropyl, n-butyl, isobutyl, primary butyl, sec-butyl, tert-butyl, n-pentyl, isopentyl, primary pentyl, see-pentyl, tert-pentyl or neopentyl, preferably can be methyl, ethyl, propyl, isopropyl or isopentyl; preferably, each $R^{3-4}$ is independently halogen, hydroxyl, —$SO_2$—$R^a$ or

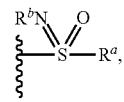

wherein $R^a$ is $C_1$-$C_6$ alkyl and $R^b$ is hydrogen; and the $C_1$-$C_6$ alkyl that is unsubstituted or substituted by one or more $R^{3-4}$ can be

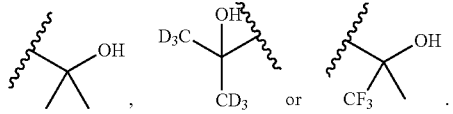

In a preferred embodiment, when $R^3$ is $C_1$-$C_6$ alkyl that is unsubstituted or substituted by one or more $R^{3-4}$, the $C_1$-$C_6$ alkyl can be methyl, ethyl, n-propyl, isopropyl, n-butyl, isobutyl, primary butyl, sec-butyl, tert-butyl, n-pentyl, isopentyl, primary pentyl, sec-pentyl, tert-pentyl or neopentyl, and can also be methyl, ethyl, propyl, isopropyl or isopentyl; preferably, each $R^{3-4}$ is independently deuterium, halogen, hydroxyl, —$SO_2$—$R^a$ or

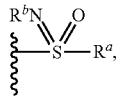

$R^a$ is $C_1$-$C_6$ alkyl and $R^b$ is hydrogen; and the $C_1$-$C_6$ alkyl that is unsubstituted or substituted by one or more $R^{3-4}$ can be

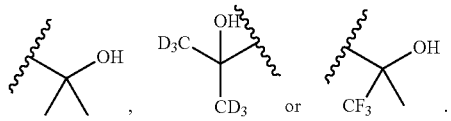

In a preferred embodiment, when $R^3$ is $C_1$-$C_6$ alkoxy that is unsubstituted or substituted by one or more $R^{3-7}$, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; preferably can be methoxy, ethoxy or isopropoxy; preferably, each $R^{3-7}$ is independently halogen, the $C_1$-$C_6$ alkoxy that is unsubstituted or substituted by one or more $R^{3-7}$ is preferably methoxy,

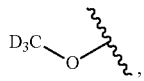

isopropoxy or trifluoromethoxy.

In a preferred embodiment, when $R^3$ is $C_1$-$C_6$ alkoxy that is unsubstituted or substituted by one or more $R^{3-7}$, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; preferably can be methoxy, ethoxy or isopropoxy; preferably, each $R^{3-7}$ is independently deuterium or halogen, the $C_1$-$C_6$ alkoxy that is unsubstituted or substituted by one or more $R^{3-7}$ is preferably methoxy,

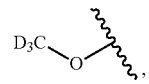

isopropoxy or trifluoromethoxy.

In a preferred embodiment, when $R^3$ is a hydroxyl group substituted by $R^{3-8}$, $R^{3-8}$ can be a 3- to 6-membered cycloalkyl or a 3- to 6-membered heterocycloalkyl, the heteroatom of the 3- to 6-membered heterocycloalkyl is oxygen, and the number of heteroatoms is 1; the hydroxyl group substituted by $R^{3-8}$ is preferably

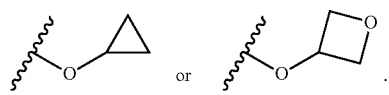

In a preferred embodiment, when $R^3$ is

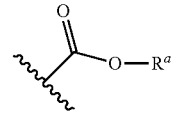

$R^a$ can be H.

In a preferred embodiment, when each $R^{3-1}$, $R^{3-2}$, $R^{3-4}$, $R^{3-5}$, $R^{3-6}$ and $R^{3-7}$ are independently a halogen, the halogen can be fluorine, chlorine, bromine or iodine, such as fluorine.

In a preferred embodiment, when each $R^{3-1}$, $R^{3-2}$, $R^{3-4}$, $R^{3-5}$, $R^{3-6}$ and $R^{3-7}$ are independently a 3- to 11-membered heterocycloalkyl that is unsubstituted or substituted by one or more $R^{3-1-1}$, the 3- to 11-membered heterocycloalkyl may be 5 to 8-membered heterocycloalkyl, the heteroatoms of the 3- to 11-membered heterocycloalkyl are preferably N and/or O, and the number of heteroatoms is 1 or 2; the 3- to 11-membered heterocycloalkyl that is unsubstituted or substituted by one or more $R^{3-1-1}$ is preferably tetrahydropyrrolyl, oxacyclobutyl or contains one oxygen and/or one azospiroheptyl group, such as

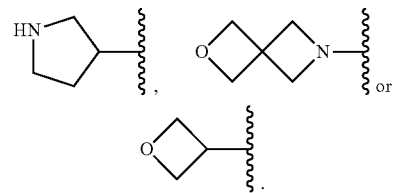

In a preferred embodiment, when each $R^{3-1-1}$, $R^{3-1-3}$, $R^{3-1-4}$ and $R^{3-1-5}$ are independently $C_1$-$C_6$ alkyl that is unsubstituted or substituted by one or more halogens, the $C_1$-$C_6$ alkyl can be $C_1$-$C_4$ alkyl, and can be methyl, ethyl, n-propyl, isopropyl, n-butyl, isobutyl, primary butyl, sec-butyl, or tert-butyl, preferably can be methyl or ethyl.

In a preferred embodiment, when each $R^{3-1-1}$, $R^{3-1-3}$, $R^{3-1-4}$ and $R^{3-1-5}$ are independently halogen, the halogen can be fluorine, chlorine, bromine or iodine, such as fluorine.

In a preferred embodiment, when $L_0$ is a 5- to 12-membered cycloalkylene group that is unsubstituted or substituted by one or more $L_0^{-2}$, the 5- to 12-membered cycloalkylene group can be subspiro ring, subbridged ring or subfused ring, preferably can be

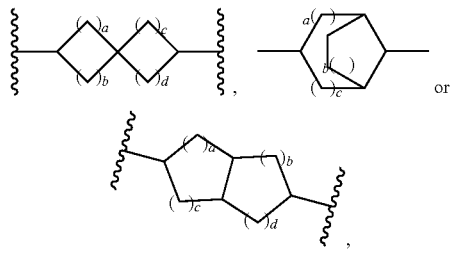

wherein a, b, c and d are independently 0, 1 or 2; such as

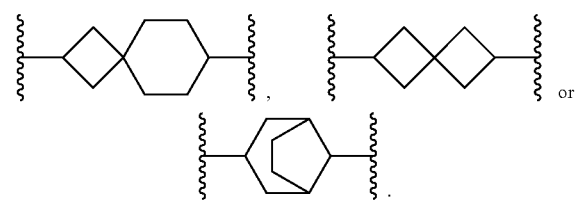

In a preferred embodiment, when $L_0$ is a 5- to 12-membered cycloalkylene group that is unsubstituted or substituted by one or more $L_0^{-2}$, the 5- to 12-membered cycloalkylene group can be subspiro ring, subbridged ring or subfused ring, preferably can be

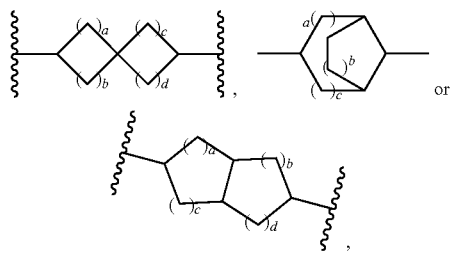

wherein a, b, c and d are independently 0, 1, or 2; such as

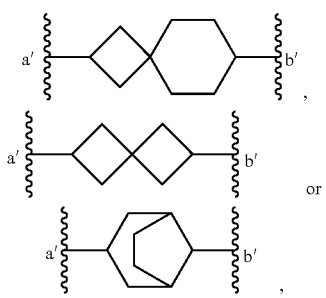

wherein the a' end is connected to ring Cy, and the b' end is connected to $L^2$.

In a preferred embodiment, when $L_0$ is a 5- to 12-membered heterocycloalkylene group that is unsubstituted or substituted by one or more $L_0^{-3}$, the 5- to 12-membered heterocycloalkylene group can be a single ring, subspiro ring, subbridged ring or subfused ring, preferably can be

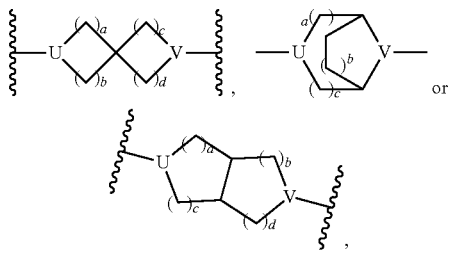

wherein U and V are independently CH or N, and at least one of U and V is N, a, b, c and d are independently 0, 1 or 2; such as

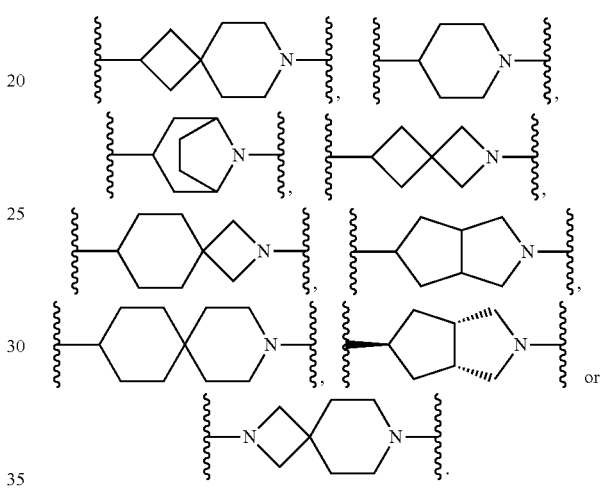

In a preferred embodiment, when $L_0$ is a 5- to 12-membered heterocycloalkylene group that is unsubstituted or substituted by one or more $L_0^{-3}$, the 5- to 12-membered heterocycloalkylene group can be a single ring, subspiro ring, subbridged ring or subfused ring, preferably can be

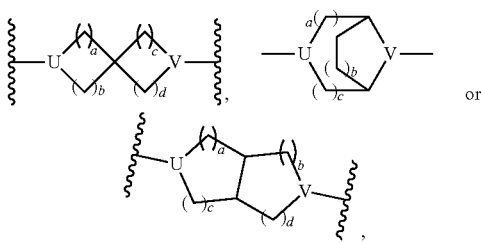

wherein U and V are independently CH or N, and at least one of U and V is N, a, b, c and d are independently 0, 1 or 2; such as

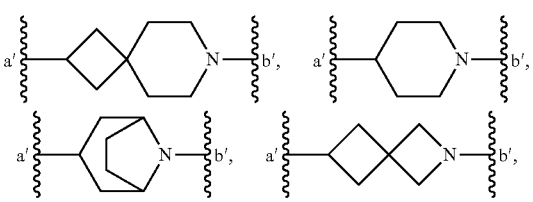

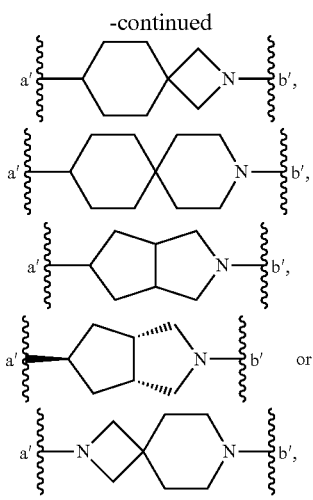

wherein the a' end is connected to ring Cy, and the b' end is connected to $L^2$.

In a preferred embodiment, when each $L_0^{-2}$ is independently $C_1$-$C_6$ alkyl that is unsubstituted or substituted by one or more halogens, the $C_1$-$C_6$ alkyl can be $C_1$-$C_4$ alkyl, preferably, can be methyl, ethyl, n-propyl, isopropyl, n-butyl, isobutyl, primary butyl, sec-butyl or tert-butyl, and preferably methyl, ethyl or isopropyl; and the halogen can be fluorine, chlorine, bromine or iodine, such as fluorine.

In a preferred embodiment, when each $L_0^{-2}$ is independently halogen, the halogen can be fluorine, chlorine, bromine or iodine, such as fluorine.

In a preferred embodiment, when each $L_0^{-2}$ is independently $C_1$-$C_6$ alkoxy that is unsubstituted or substituted by one or more halogens, the halogen can be fluorine, chlorine, bromine or iodine, such as fluorine.

In a preferred embodiment, when each $L_0^{-2}$ is independently $C_1$-$C_6$ alkoxy that is unsubstituted or substituted by one or more halogens, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; preferably methoxy, ethoxy or isopropoxy.

In a preferred embodiment, when each $L_0^{-3}$ is independently $C_1$-$C_6$ alkyl that is unsubstituted or substituted by one or more halogens, the $C_1$-$C_6$ alkyl can be $C_1$-$C_4$ alkyl, preferably, can be methyl, ethyl, n-propyl, isopropyl, n-butyl, isobutyl, primary butyl, sec-butyl or tert-butyl, and preferably methyl, ethyl or isopropyl; and the halogen can be fluorine, chlorine, bromine or iodine, such as fluorine.

In a preferred embodiment, when each $L_0^{-3}$ is independently halogen, the halogen can be fluorine, chlorine, bromine or iodine, such as fluorine.

In a preferred embodiment, when each $L_0^{-3}$ is independently $C_1$-$C_6$ alkoxy that is unsubstituted or substituted by one or more halogens, the halogen can be fluorine, chlorine, bromine or iodine, such as fluorine.

In a preferred embodiment, when each $L_0^{-3}$ is independently $C_1$-$C_6$ alkoxy that is unsubstituted or substituted by one or more halogens, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; preferably methoxy, ethoxy or isopropoxy.

In a preferred embodiment, when each $R^a$ and each $R^b$ are independently $C_1$-$C_6$ alkyl that is unsubstituted or substituted by one or more $R^{a-1}$, the $C_1$-$C_6$ alkyl can be $C_1$-$C_4$ alkyl, preferably, can be methyl, ethyl, n-propyl, isopropyl, n-butyl, isobutyl, primary butyl, sec-butyl or tert-butyl, and preferably methyl, ethyl or isopropyl.

In a preferred embodiment, when each $R^a$ and each $R^b$ are independently a 3- to 10-membered cycloalkyl that is unsubstituted or substituted by one or more $R^{a-2}$, the 3- to 10-membered cycloalkyl can be a 3- to 6-membered cycloalkyl, such as cyclopropyl, cyclobutyl, cyclopentyl or cyclohexyl.

In a preferred embodiment, when each $R^a$ and each $R^b$ are independently a 3- to 11-membered heterocycloalkyl that is unsubstituted or substituted by one or more $R^{a-3}$, the 3- to 11-membered heterocycloalkyl may be a 5 to 8-membered heterocycloalkyl, the heteroatoms of the 3- to 11-membered heterocycloalkyl are selected from one or two of N, S and O, and the number of heteroatoms is 1 or 2; preferably, the heteroatom of the 3- to 11-membered heterocycloalkyl is N, S or O, and the number of heteroatoms is 1 or 2; the 3- to 11-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl or azabicyclo[2.2.1]heptyl, such as

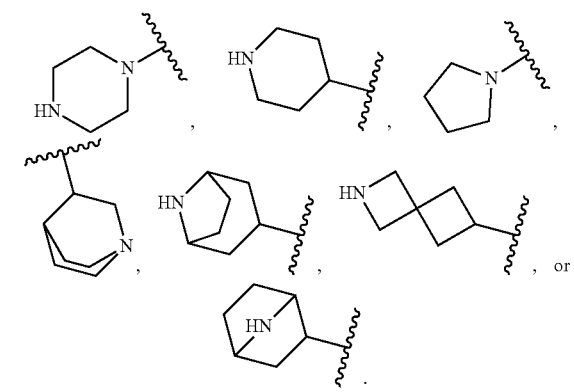

In a preferred embodiment, when each $R^a$ and each $R^b$ are independently a 3- to 11-membered heterocycloalkyl that is unsubstituted or substituted by one or more $R^{a-3}$, the 3- to 11-membered heterocycloalkyl may be a 5 to 8-membered heterocycloalkyl, the heteroatoms of the 3- to 11-membered heterocycloalkyl are selected from one or two of N, S and O, and the number of heteroatoms is 1 or 2; preferably, the heteroatom of the 3- to 11-membered heterocycloalkyl is N, S or O, and the number of heteroatoms is 1 or 2; the 3- to 11-membered heterocycloalkyl is preferably piperazinyl, piperidinyl, tetrahydropyrrolyl, azabicyclo[2.2.2]octyl, azabicyclo[3.2.1]octyl, azaspiro[3.3]heptyl or azabicyclo[2.2.1]heptyl.

In a preferred embodiment, when each $R^a$ and each $R^b$ are independently a 6- to 10-membered aryl that is unsubstituted or substituted by one or more $R^{a-4}$, the 6- to 10-membered aryl can be benzene ring or naphthalene ring.

In a preferred embodiment, when each $R^a$ and each $R^b$ are independently a 5- to 10-membered heteroaryl that is unsubstituted or substituted by one or more $R^{a-5}$; the 5- to 10-membered heteroaryl can be a 5-membered heteroaryl or a 6-membered heteroaryl; the 6-membered heteroaryl group is preferably pyridyl, pyridazinyl, pyrazinyl, pyrimidinyl or triazinyl; and the 5-membered heteroaryl group is preferably pyrazolyl, thiazolyl or imidazolyl.

In a preferred embodiment, in ring $Cy^3$, the 5- to 12-membered heterocycle may be a 5 to 6-membered heterocycle, and the heteroatom of the 5- to 12-membered heterocycle is preferably N, S or O, and the number of the heteroatom is 1 or 2; the 5- to 12-membered heterocycle may be a tetrahydropyrrole ring, a piperidine ring, a tetrahydrofuran ring or a tetrahydrothiophene ring, such as a tetrahydropyrrole ring.

In a preferred embodiment, in $Cy^{3-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in ring $Cy^4$, the 5- to 12-membered heterocycle may be a 5 to 6-membered heterocycle, and the heteroatom of the 5- to 6-membered heterocycle is preferably N, S or O, and the number of the heteroatom is 1 or 2; the 5- to 12-membered heterocycle may be a tetrahydropyrrole ring, a piperidine ring, a tetrahydrofuran ring or a tetrahydrothiophene ring, such as a piperidine ring.

In a preferred embodiment, in $Cy^{4-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in ring $Cy^5$, the 5- to 12-membered heterocycle may be a 5 to 6-membered heterocycle, and the heteroatom of the 5- to 12-membered heterocycle is preferably N, S or O, and the number of the heteroatom is 1 or 2; the 5- to 12-membered heterocycle may be a tetrahydropyrrole ring, a piperidine ring, a tetrahydrofuran ring or a tetrahydrothiophene ring, such as a tetrahydropyrrole ring.

In a preferred embodiment, in $Cy^{5-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in ring $Cy^6$, the 6- to 10-membered aromatic ring can be a benzene ring or a naphthalene ring.

In a preferred embodiment, in $Cy^{6-1}$, the halogen can be fluorine, chlorine, bromine or iodine, such as fluorine or chlorine.

In a preferred embodiment, in $Cy^{6-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in ring $Cy^7$, the 5- to 9-membered heteroaromatic ring may be a 5-membered heteroaromatic ring or a 6-membered heteroaromatic ring; the 6-membered heteroaromatic ring is preferably a pyridine ring, a pyridazine ring, a pyrazine ring, a pyrimidine ring or a triazine ring; and the 5-membered heteroaromatic ring is preferably a pyrazole ring, an oxazole ring, a thiazole ring or an imidazole ring, such as

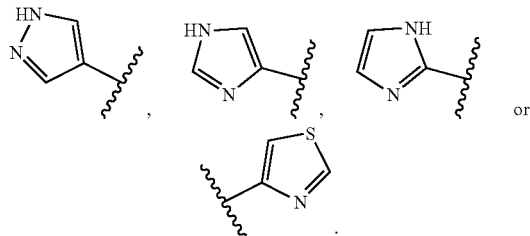

In a preferred embodiment, in $Cy^{7-1}$, the halogen can be fluorine, chlorine, bromine or iodine, such as fluorine or chlorine.

In a preferred embodiment, in $Cy^{7-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl.

In a preferred embodiment, in $R^4$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be tert-butyl.

In a preferred embodiment, in $R^4$, the halogen can be fluorine, chlorine, bromine or iodine, such as fluorine or chlorine.

In a preferred embodiment, in $R^5$, the halogen can be fluorine, chlorine, bromine or iodine, such as fluorine or chlorine.

In a preferred embodiment, in $L_3^{-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; such as methyl.

In a preferred embodiment, when the ring $Cy^1$ is a 5- to 12-membered heterocycle, the heteroatom of the 5- to 12-membered heterocycle is N, S or O, and the number of heteroatoms is 1 or 2; the 5- to 12-membered heterocycle can be oxacyclobutyl ring, diazaspiro[3.3]heptane, tetrahydrofuran ring, piperidine ring, piperazine ring, diazaspiro[3.5]nonane, azaspiro[3.3]heptane, diazaspiro[5.5]undecane, azaspiro[3.5]nonane or azaspiro[5.5]undecane.

In a preferred embodiment, when the ring $Cy^1$ is a 3- to 12-membered cycloalkyl, the 3- to 12-membered cycloalkyl may be a 3- to 6-membered cycloalkyl, such as cyclohexyl.

In a preferred embodiment, when ring $Cy^2$ is a 5- to 10-membered heteroaromatic ring, the heteroatoms of the 5- to 10-membered heteroaromatic ring are selected from one or two of N, S and O, and the number of the heteroatoms is 1 or 2; the 5- to 10-membered heteroaromatic ring is preferably a 5 or 6-membered heteroaromatic ring; the 6-membered heteroaromatic ring is preferably a pyridine ring, a pyridazine ring, a pyrazine ring, a pyrimidine ring or a triazine ring; and the 5-membered heteroaromatic ring is preferably a pyrazole ring, a thiazole ring or an imidazole ring.

In a preferred embodiment, in $L_2^{1-1}$ and $L_2^{1-2}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in $L_2^{1-1}$ and $L_2^{1-2}$, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; and can also be methoxy, ethoxy, or isopropoxy.

In a preferred embodiment, in $L_2^{1-1}$ and $L_2^{1-2}$, the halogen can be fluorine, chlorine, bromine or iodine, such as fluorine.

In a preferred embodiment, in $L_2^{1-3}$, the halogen can be fluorine, chlorine, bromine or iodine, such as fluorine or chlorine.

In a preferred embodiment, in $L_2^{1-3}$, in the $C_1$-$C_6$ alkyl that is unsubstituted or substituted by one or more halogens, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl; and the halogen is preferably fluorine, chlorine, bromine or iodine, such as fluorine or chlorine.

In a preferred embodiment, in $L_2^{1-3}$, in the $C_1$-$C_6$ alkoxy that is unsubstituted or substituted by one or more halogens, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; and can also be methoxy, ethoxy, or isopropoxy; and the halogen is preferably fluorine, chlorine, bromine or iodine, such as fluorine or chlorine.

In a preferred embodiment, in $L_2^{1-3}$, in the 3- to 10-membered cycloalkyl that is unsubstituted or substituted by one or more $L_2^{1-3-1}$, the 3- to 10-membered cycloalkyl can be $C_3$-$C_6$ cycloalkyl, can also be cyclopropyl, cyclobutyl, cyclopentyl or cyclohexyl, such as cyclopropyl, cyclobutyl or cyclohexyl; and preferably, each $L_2^{1-3-1}$ is independently halogen or hydroxyl.

In a preferred embodiment, in $L_2^{1-3}$, in the 3- to 11-membered heterocycloalkyl that is unsubstituted or substituted by one or more $L_2^{1-3-2}$, the 3- to 11-membered heterocycloalkyl can be 4 to 9-membered heterocycloalkyl, the heteroatoms of the 4 to 9-membered heterocycloalkyl are preferably selected from one or more of N, S and O, and the number of heteroatoms is 1 or 2; the 3- to 11-membered heterocycloalkyl may be a tetrahydropyrrole ring, a piperidine ring, a tetrahydrofuran ring or a tetrahydrothiophene ring, such as a piperidine ring.

In a preferred embodiment, in $L_2^{1-3-1}$ and $L_2^{1-3-2}$, the $C_1$-$C_6$ alkoxy can be $C_1$-$C_4$ alkoxy, such as methoxy, ethoxy, n-propoxy, isopropoxy, n-butoxy, isobutoxy, primary butoxy, sec-butoxy or tert-butoxy; and can also be methoxy, ethoxy, or isopropoxy.

In a preferred embodiment, when $R^c$ is $C_1$-$C_6$ alkyl that is unsubstituted or substituted by one or more $R^{c-1}$, the $C_1$-$C_6$ alkyl can be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In a preferred embodiment, in LLM, p is 0 or 1.
In a preferred embodiment, in $L_2$, m is 1 or 2.
In a preferred embodiment, in $L_2$, q is 1 or 2.
In a preferred embodiment, in $L_3$, m is 1 or 2.
In a preferred embodiment, in $L_3$, q is 1 or 2.

In the present disclosure, in $R^c$, $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the 6- to 10-membered aryl may independently be phenyl or naphthyl.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the $C_1$-$C_6$ alkoxy can independently be $C_1$-$C_4$ alkoxy, such as methoxy, ethoxy, n-propoxy, isopropoxy, n-butoxy, isobutoxy, sec-butoxy or tert-butoxy; also such as methoxy.

In the present disclosure, in $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the halogen can independently be fluorine, chlorine, bromine or iodine, such as fluorine or chlorine.

In the present disclosure, in $R^c$, $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the $C_1$-$C_6$ alkyl can independently be $C_1$-$C_4$ alkyl, such as methyl, ethyl, n-propyl, isopropyl, n-butyl, isobutyl, primary butyl, sec-butyl or tert-butyl; and can also be methyl, ethyl or isopropyl.

In the present disclosure, in $R^c$, $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the 3- to 11-membered heterocycloalkyl can be independently a 6-membered heterocycloalkyl, a 5-membered heterocycloalkyl, an 8-membered heterocycloalkyl or a 7-membered heterocycloalkyl. The heteroatoms of the 3- to 11-membered heterocycloalkyl are selected from one or two of N and O, and the number of heteroatoms is 1 or 2; the 6-membered heterocycloalkyl is preferably piperazinyl, morpholinyl or piperidinyl, such as

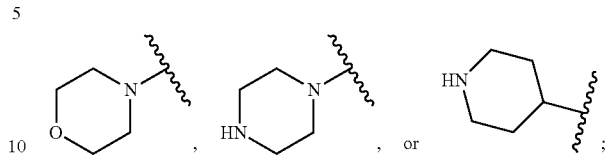

the 5-membered heterocycloalkyl is preferably tetrahydropyrrolyl, such as

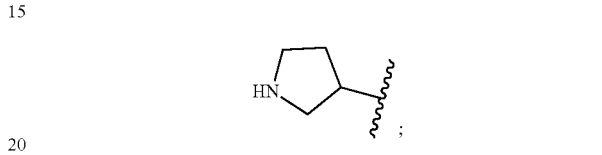

the 8-membered heterocycloalkyl is preferably azabicyclo[2.2.2]octyl or azabicyclo[3.2.1]octyl, such as

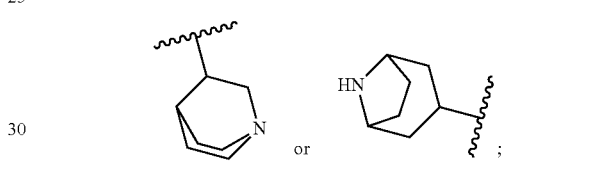

the 7-membered heterocycloalkyl is preferably azaspiro[3.3]heptyl or azabicyclo[2.2.1]heptyl, such as

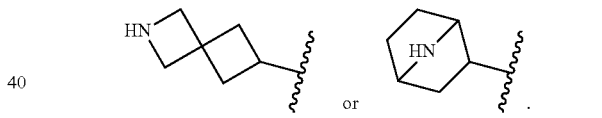

In the present disclosure, in $R^c$, $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the 3- to 10-membered cycloalkyl can be independently a 3- to 6-membered cycloalkyl, such as cyclopropyl, cyclobutyl, cyclopentyl or cyclohexyl.

In the present disclosure, in $R^c$, $R^{1-1-1}$, $R^{1-1-3}$, $R^{1-1-4}$, $R^{1-1-5}$, $R^{3-1-1}$, $R^{3-1-4}$, $R^{3-1-5}$, $R^{1-1-1-1}$, $R^{1-1-1-2}$, $R^{1-1-1-3}$, $R^{a-1}$, $R^{a-2}$, $R^{a-3}$, $R^{a-4}$, $R^{a-5}$, $R^{c-1}$, $R^{c-2}$, $R^{c-3}$, $R^{c-4}$ and $R^{c-5}$, the 5- to 10-membered heteroaryl can be independently a 5-membered heteroaryl, a 6-membered heteroaryl, a 5-membered-fused 5-membered heteroaryl; the 6-membered heteroaryl is preferably a pyridyl, a pyridazinyl, a pyrazinyl, a pyrimidinyl or a triazinyl; and the 5-membered heteroaryl ring is preferably pyrazolyl, oxazolyl, thiazolyl or imidazolyl, such as

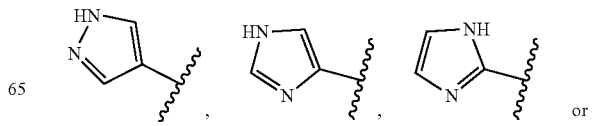

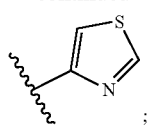

the 5- to 10-membered heteroaryl is preferably pyrazolyl, thiazolyl, imidazolyl, tetrahydropyrrolothiazolyl or tetrahydropyrrolopyrazolyl, such as

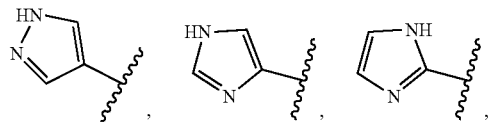,

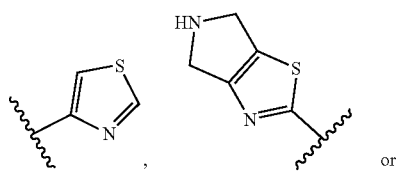 or

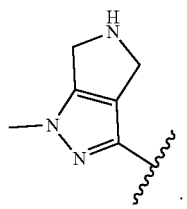

In a preferred embodiment, $R^1$ is a 5- to 10-membered heteroaryl that is unsubstituted or substituted by one or more $R^{1-1}$ or a 6- to 10-membered aryl that is unsubstituted or substituted by one or more $R^{1-2}$; the heteroatoms of the 5- to 10-membered heteroaryl are selected from one or two of N, S and O, and the number of heteroatoms is 1 or 2. $R^1$ is preferably a 5- to 6-membered heteroaryl that is unsubstituted or substituted by one or more $R^{1-1}$ or a 6- to 10-membered aryl that is unsubstituted or substituted by one or more $R^{1-2}$; the heteroatoms of the 5- to 6-membered heteroaryl are selected from one or two of N, S and O, and the number of heteroatoms is 1 or 2.

In a preferred embodiment, $R^1$ is a 5- to 10-membered heteroaryl that is unsubstituted or substituted by one or more $R^{1-1}$ or a 6- to 10-membered aryl that is unsubstituted or substituted by one or more $R^{1-2}$; the heteroatoms of the 5- to 10-membered heteroaryl are selected from one or two of N, S and O, and the number of heteroatoms is 1, 2 or 3. $R^1$ is preferably a 5- to 9-membered heteroaryl that is unsubstituted or substituted by one or more $R^{1-1}$ or a 6- to 10-membered aryl that is unsubstituted or substituted by one or more $R^{1-2}$ the heteroatoms of the 5- to 9-membered heteroaryl are selected from one or two of N, S and O, and the number of heteroatoms is 1, 2 or 3. $R^1$ is preferably a 5- to 9-membered heteroaryl that is unsubstituted or substituted by one or more $R^{1-1}$, the 5- to 9-membered heteroaryl is pyridyl, oxazolyl, pyrazolyl or

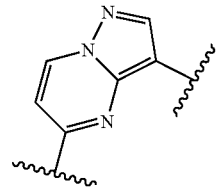

$R^1$ is preferably pyridyl substituted by one or more $R^{1-1}$, or

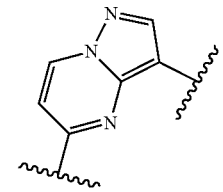 [SMILES: *c1ccn2ncc(*)c2n1]

substituted by one or more $R^{1-1}$.

In a preferred embodiment, each $R^{1-1}$ and $R^{1-2}$ are independently halogen, hydroxyl,

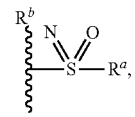

—$SO_2$—$R^a$, —SO—$R^a$, $C_1$-$C_6$ alkyl that is unsubstituted or substituted by one or more $R^{1-1-4}$, or a 5- to 10-membered heteroaryl that is unsubstituted or substituted by one or more $R^{1-1-7}$; the heteroatoms of the 5- to 10-membered heteroaryl are selected from one or more of N, S and O, and the number of heteroatoms is 1 or 2. Each $R_{1-1}$ and $R^{1-2}$ are independently halogen, a 5- to 6-membered heteroaryl that is unsubstituted or substituted by one or more $R^{1-1-7}$ or $C_1$-$C_6$ alkyl that is unsubstituted or substituted by one or more $R^{1-1-4}$, the heteroatoms of the 5- to 6-membered heteroaryl are selected from one or more of N, S and O, and the number of heteroatoms is 1 or 2.

In a preferred embodiment, each $R^{1-1}$ is $C_1$-$C_6$ alkyl that is unsubstituted or substituted by one or more $R^{1-1-4}$, a 3- to 11-membered heterocycloalkyl that is unsubstituted or substituted by one or more $R^{1-11}$ or a 5- to 10-membered heteroaryl that is unsubstituted or substituted by one or more $R^{1-1-7}$; the heteroatoms of the 5- to 10-membered heteroaryl are selected from one or more of N, S and O, and the number of heteroatoms is 1 or 2; the heteroatoms of the 3- to 11-membered heterocycloalkyl are selected from one or more of N, S and O, and the number of heteroatoms is 1, 2 or 3.

In a preferred embodiment, each $R^{1-1-4}$ is independently halogen.

In a preferred embodiment, each $R^{1-1-4}$ is independently halogen or $C_1$-$C_6$ alkyl that is unsubstituted or substituted by one or more halogens.

In a preferred embodiment, each $R^{1-1-7}$ is independently halogen, hydroxy, $C_1$-$C_6$ alkoxy that is unsubstituted or substituted by one or more halogens, cyano, nitro, $C_1$-$C_6$ alkyl that is unsubstituted or substituted by one or more halogens, a 6- to 10-membered aryl that is unsubstituted or substituted by one or more $R^{1-1-1-2}$, or a 5- to 10-membered heteroaryl that is unsubstituted or substituted by one or more $R^{1-1-1-3}$; the heteroatoms of the 3- to 11-membered heteroaryl are selected from one or more of N, S and O, and the number of heteroatoms is 1, 2 or 3; the heteroatoms of the 5- to 10-membered heteroaryl are selected from one or more of N, S and O, and the number of heteroatoms is 1, 2 or 3. Preferably, each $R^{1-1-7}$ is independently $C_1$-$C_6$ alkyl that is unsubstituted or substituted by one or more halogens.

In a preferred embodiment, preferably, each $R^{1-1-7}$ is independently halogen or $C_1$-$C_6$ alkyl that is unsubstituted or substituted by one or more halogens.

In a preferred embodiment, each $R^{1-1-1}$ is independently halogen or $C_1$-$C_6$ alkyl that is unsubstituted or substituted by one or more halogens. Preferably, each $R^{1-1-1}$ is independently $C_1$-$C_6$ alkyl that is unsubstituted or substituted by one or more halogens.

In a preferred embodiment, each $R^{1-1-1-1}$, $R^{1-1-1-2}$ and $R^{1-1-1-3}$ are independently halogen or $C_1$-$C_6$ alkyl.

In a preferred embodiment, $R^2$ is hydrogen.

In a preferred embodiment, $R^3$ is hydrogen, hydroxy, halogen, cyano, a 3- to 10-membered heterocycloalkyl that is unsubstituted or substituted by one or more $R^{3-1}$, a 3- to 8-membered cycloalkyl that is unsubstituted or substituted by one or more $R^{3-2}$, $C_1$-$C_6$ alkyl that is unsubstituted or substituted by one or more $R^{3-4}$, $C_1$-$C_6$ alkoxy that is unsubstituted or substituted by one or more $R^{3-7}$ or hydroxyl substituted by $R^{3-8}$; the heteroatoms of the 3- to 10-membered heterocycloalkyl are selected from one or two of N and O, and the number of heteroatoms is 1, 2 or 3. $R^3$ is preferably a 3- to 6-membered heterocycloalkyl that is unsubstituted or substituted by one or more $R^{3-1}$, $C_3$-$C_6$ cycloalkyl that is unsubstituted or substituted by one or more $R^{3-2}$, $C_1$-$C_6$ alkoxy that is unsubstituted or substituted by one or more $R^{3-7}$, $C_1$-$C_6$ alkyl that is unsubstituted or substituted by one or more $R^{3-4}$, or hydroxyl substituted by $R^{3-8}$; the heteroatoms of the 3- to 6-membered heterocycloalkyl are selected from one or two of N and O, and the number of heteroatoms is 1 or 2.

In a preferred embodiment, $R^3$ is hydrogen, hydroxy, halogen, cyano,

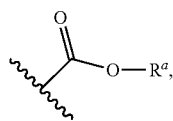

a 3- to 10-membered heterocycloalkyl that is unsubstituted or substituted by one or more $R^{3-1}$, a 3- to 8-membered cycloalkyl that is unsubstituted or substituted by one or more $R^{3-2}$, $C_1$-$C_6$ alkyl that is unsubstituted or substituted by one or more $R^{3-4}$, $C_1$-$C_6$ alkoxy that is unsubstituted or substituted by one or more $R^{3-7}$ or hydroxyl substituted by $R^{3-8}$; the heteroatoms of the 3- to 10-membered heterocycloalkyl are selected from one or two of N and O, and the number of heteroatoms is 1, 2 or 3. $R^3$ is preferably halogen,

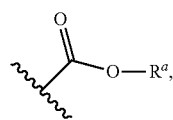

a 3- to 6-membered heterocycloalkyl that is unsubstituted or substituted by one or more $R^{3-1}$, $C_3$-$C_6$ cycloalkyl that is unsubstituted or substituted by one or more $R^{3-2}$, $C_1$-$C_6$ alkoxy that is unsubstituted or substituted by one or more $R^{3-7}$, $C_1$-$C_6$ alkyl that is unsubstituted or substituted by one or more $R^{3-4}$, or hydroxyl substituted by $R^{3-8}$; the heteroatoms of the 3- to 6-membered heterocycloalkyl are selected from one or two of N and O, and the number of heteroatoms is 1 or 2. $R^3$ is preferably $C_1$-$C_6$ alkyl that is unsubstituted or substituted by one or more $R^{3-4}$, or $C_1$-$C_6$ alkoxy that is unsubstituted or substituted by one or more $R^{3-7}$.

$R^3$ is preferably $C_1$-$C_6$ alkyl that is unsubstituted or substituted by one or more $R^{3-4}$, $C_1$-$C_6$ alkoxy that is unsubstituted or substituted by one or more $R^{3-7}$ or tetrahydropyrrolyl that is unsubstituted or substituted by one or more $R^3$.

In a preferred embodiment, each $R^{3-1}$, $R^{3-2}$, $R^{3-4}$ and $R^{3-7}$ are independently oxo, hydroxyl, halogen, a 3- to 6-membered cycloalkyl, a 3- to 6-membered heterocycloalkyl or $C_1$-$C_6$ alkoxy that is unsubstituted or substituted by one or more halogens; the heteroatoms of the 3- to 6-membered heterocycloalkyl are selected from one or two of N, S and O, and the number of heteroatoms is 1 or 2. Each $R^{3-1}$ is independently preferably hydroxyl or halogen. Each $R^{3-2}$ is independently preferably hydroxyl. Each $R^{3-4}$ is independently preferably hydroxyl; and each $R^{3-7}$ is independently preferably halogen.

In a preferred embodiment, each $R^{3-1}$, $R^{3-2}$, $R^{3-4}$ and $R^{3-7}$ are independently deuterium, oxo, hydroxyl, halogen, a 3- to 6-membered cycloalkyl, a 3- to 6-membered heterocycloalkyl or $C_1$-$C_6$ alkoxy that is unsubstituted or substituted by one or more halogens; the heteroatoms of the 3- to 6-membered heterocycloalkyl are selected from one or two of N, S and O, and the number of heteroatoms is 1 or 2. Each $R^{3-1}$ is independently preferably hydroxyl or halogen. Each $R^{3-2}$ is independently preferably hydroxyl. Each $R^{3-4}$ is independently preferably deuterium, halogen or hydroxyl; and each $R^{3-7}$ is independently preferably deuterium or halogen.

In a preferred embodiment, each $R^{3-1}$ is independently deuterium, hydroxyl or halogen.

In a preferred embodiment, each $R^{3-4}$ is independently deuterium, halogen or hydroxyl.

In a preferred embodiment, each $R^{3-7}$ is independently deuterium or hydroxyl.

In a preferred embodiment, when $R^3$ is $C_1$-$C_6$ alkyl substituted by multiple $R^{3-4}$, at least one $R^{3-4}$ is hydroxyl, deuterium and hydroxyl, or halogen and hydroxyl.

In a preferred embodiment, $R^{3-8}$ is a 3- to 6-membered cycloalkyl or a 3- to 6-membered heterocycloalkyl; the heteroatoms of the 3- to 6-membered heterocycloalkyl are selected from one or two of N, S and O, and the number of heteroatoms is 1, 2 or 3. $R^{3-8}$ is preferably a 3- to 6-membered cycloalkyl or a 3- to 6-membered heterocycloalkyl; the heteroatoms of the 3- to 6-membered heterocycloalkyl are selected from one or two of N and O, and the number of heteroatoms is 1.

In a preferred embodiment, each $R^a$ and each $R^b$ are independently H or $C_1$-$C_6$ alkyl that is unsubstituted or substituted by one or more $R^{a-1}$. Preferably, each $R^a$ and each $R^b$ are independently H.

In a preferred embodiment, $L_0$ is a 5- to 12-membered cycloalkylene group that is unsubstituted or substituted by one or more $L_0^{-2}$, or a 5- to 12-membered heterocycloalkylene group that is unsubstituted or substituted by one or more $L_0^{-3}$; the 5- to 12-membered cycloalkylene group is a spiro ring, a fused ring or a bridged ring; and the 5- to 12-membered heterocycloalkylene group is a monocyclic, a spiro ring, a fused ring or a bridged ring; the heteroatoms of the 5- to 12-membered heterocycloalkylene group are selected from one or more of N, S and O, and the number of heteroatoms is 1, 2 or 3; each $L_0^{-2}$ is independently halogen, hydroxyl, or $C_1$-$C_6$ alkyl that is unsubstituted or substituted by one or more halogens; and each $L_0^{-3}$ is independently halogen, hydroxyl, or $C_1$-$C_6$ alkyl that is unsubstituted or substituted by one or more halogens.

In a preferred embodiment, $L_0$ is a 5- to 12-membered cycloalkylene group that is unsubstituted or substituted by one or more $L_0^{-2}$, or a 5- to 12-membered heterocycloalkylene group that is unsubstituted or substituted by one or more $L_0^{-3}$; the 5- to 12-membered cycloalkylene group is a spiro ring, a fused ring or a bridged ring; and the 5- to 12-membered heterocycloalkylene group is a monocyclic, a spiro ring, a fused ring or a bridged ring; the heteroatoms of the 5- to 12-membered heterocycloalkylene group are selected from one or more of N, S and O, and the number of heteroatoms is 1, 2 or 3; each $L_0^{-2}$ is independently deuterium, halogen, hydroxyl, or $C_1$-$C_6$ alkyl that is unsubstituted or substituted by one or more halogens; and each $L_0^{-3}$ is independently deuterium, halogen, hydroxyl, or $C_1$-$C_6$ alkyl that is unsubstituted or substituted by one or more halogens.

In a preferred embodiment, $L_0$ is a 7- to 11-membered cycloalkylene group that is unsubstituted or substituted by one or more $L_0^{-2}$, or a 7- to 11-membered heterocycloalkylene group that is unsubstituted or substituted by one or more $L_0^{-3}$; the 7- to 11-membered cycloalkylene group is a spiro ring; and the 7- to 11-membered heterocycloalkylene group is a spiro ring; the heteroatom of the 7- to 11-membered heterocycloalkylene group is N, and the number of heteroatoms is 1 or 2; each $L_0^{-2}$ is independently halogen, hydroxyl, or $C_1$-$C_6$ alkyl that is unsubstituted or substituted by one or more halogens; and each $L_0^{-3}$ is independently halogen, hydroxyl, or $C_1$-$C_6$ alkyl that is unsubstituted or substituted by one or more halogens.

In a preferred embodiment, $L_0$ is a 7- to 11-membered cycloalkylene group that is unsubstituted or substituted by one or more $L_0^{-2}$, or a 7- to 11-membered heterocycloalkylene group that is unsubstituted or substituted by one or more $L_0^{-3}$; the 7- to 11-membered cycloalkylene group is a spiro ring; and the 7- to 11-membered heterocycloalkylene group is a spiro ring or a fused ring; the heteroatom of the 7- to 11-membered heterocycloalkylene group is N, and the number of heteroatoms is 1 or 2; each $L_0^{-2}$ is independently deuterium, halogen, hydroxyl, or $C_1$-$C_6$ alkyl that is unsubstituted or substituted by one or more halogens; and each $L_0^{-3}$ is independently deuterium, halogen, hydroxyl, or $C_1$-$C_6$ alkyl that is unsubstituted or substituted by one or more halogens. In a preferred embodiment, $L_0$ is a 7- to 11-membered cycloalkylene group or a 7- to 11-membered heterocycloalkylene group, the 7- to 11-membered cycloalkylene group is a spiro ring, the 7- to 11-membered heterocycloalkylene group is a spiro ring, the heteroatom of the 7- to 11-membered heterocycloalkylene group is N, and the number of heteroatoms is 1.

In a preferred embodiment, $L_0$ is a 7- to 11-membered cycloalkylene group or a 7- to 11-membered heterocycloalkylene group, the 7- to 11-membered cycloalkylene group is a spiro ring, the 7- to 11-membered heterocycloalkylene group is a spiro ring or a fused ring, the heteroatom of the 7- to 11-membered heterocycloalkylene group is N, and the number of heteroatoms is 1 or 2.

In a preferred embodiment, $L_0$ is a 8- to 11-membered cycloalkylene group or a 8- to 11-membered heterocycloalkylene group, the 8- to 11-membered cycloalkylene group is a spiro ring, the 8- to 11-membered heterocycloalkylene group is a spiro ring or a fused ring, the heteroatom of the 8- to 11-membered heterocycloalkylene group is N, and the number of heteroatoms is 1. Preferably, the 8- to 11-membered cycloalkylene group can be

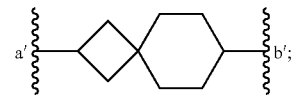 [SMILES: *C1CCC2(CC1)CC(*)C2]

and the 8- to 11-membered heterocycloalkylene group can be

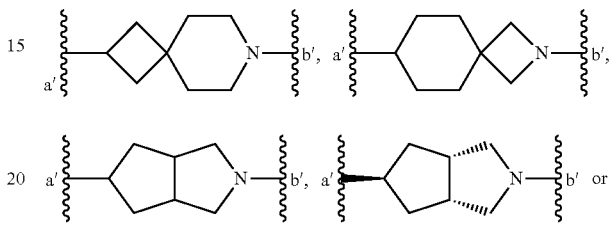

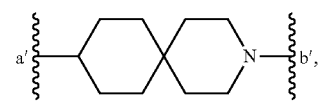

wherein the a' end is connected to ring Cy, and the b' end is connected to $L^2$.

In a preferred embodiment, $L_0$ is a 9- to 11-membered heterospirylene group; the heteroatom of the 9- to 11-membered heterospirylene group is N, and the number of heteroatoms is 1. Preferably, the 9- to 11-membered heterospirylene group is

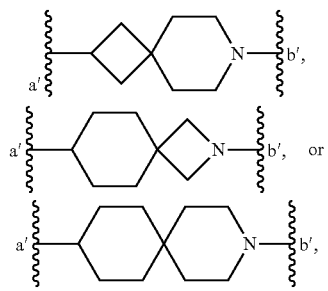

wherein the a' end is connected to ring Cy, and the b' end is connected to $L^2$.

In a preferred embodiment, $L_2^{-1}$, $L_2^{-2}$, $L_2^{-3}$ and $L_2^{-4}$ are independently absent,

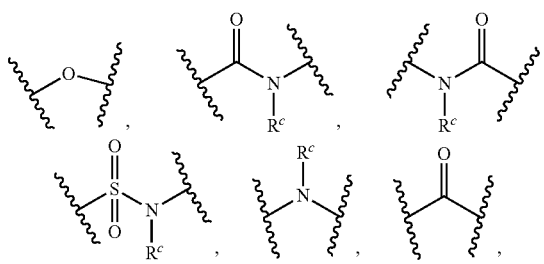

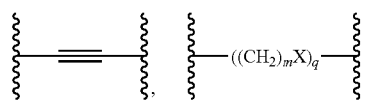

unsubstituted or substituted by one or more $L_2^{1-1}$,

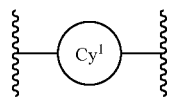

that is unsubstituted or substituted by one or more $L_2^{1-2}$, or

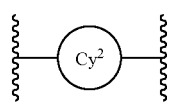

that is unsubstituted or substituted by one or more $L_2^{1-3}$, m is an integer from 1 to 4, q is an integer from 1 to 6, and X is absent or O; Ring $Cy^1$ is a 4- to 11-membered heterocycle or 4- to 11-membered cycloalkyl; ring $Cy^2$ is a 5- to 10-membered heteroaromatic ring or a 6- to 10-membered aromatic ring; the heteroatoms of the 4- to 11-membered heterocycle are selected from one or more of N, S and O, and the number of heteroatoms is 1, 2 or 3; the heteroatoms of the 5- to 10-membered heteroaromatic ring are selected from one or more of N, S and O, and the number of heteroatoms is 1, 2 or 3.

In a preferred embodiment, $L_2^{-1}$, $L_2^{-2}$, $L_2^{-3}$ and $L_2^{-4}$ are independently absent,

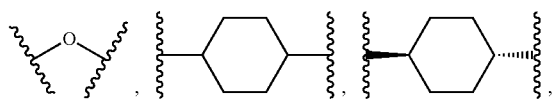

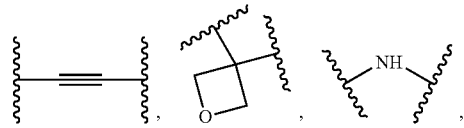

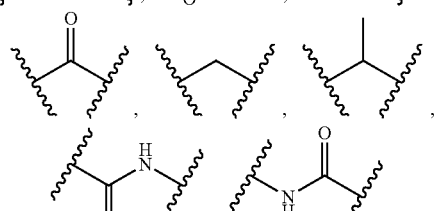

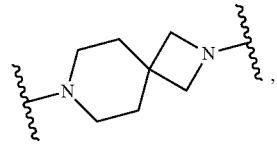

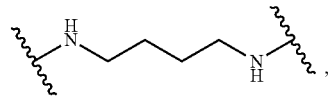

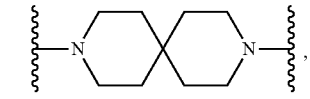

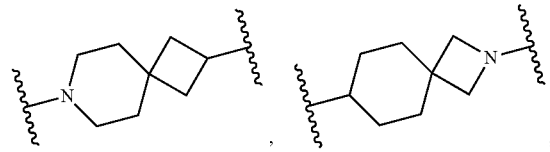

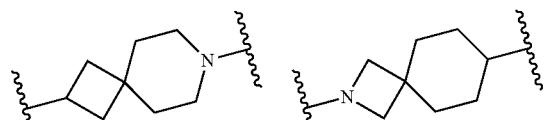

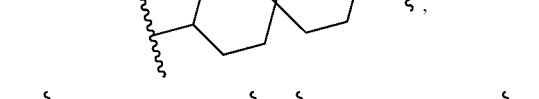

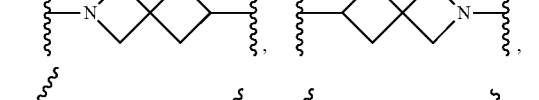

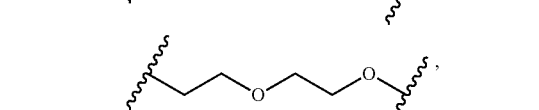

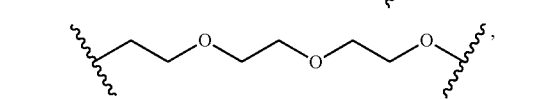

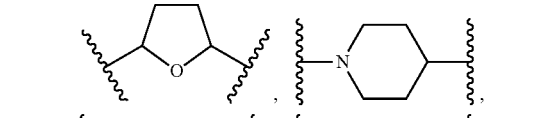

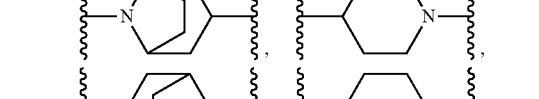

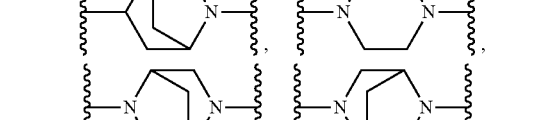

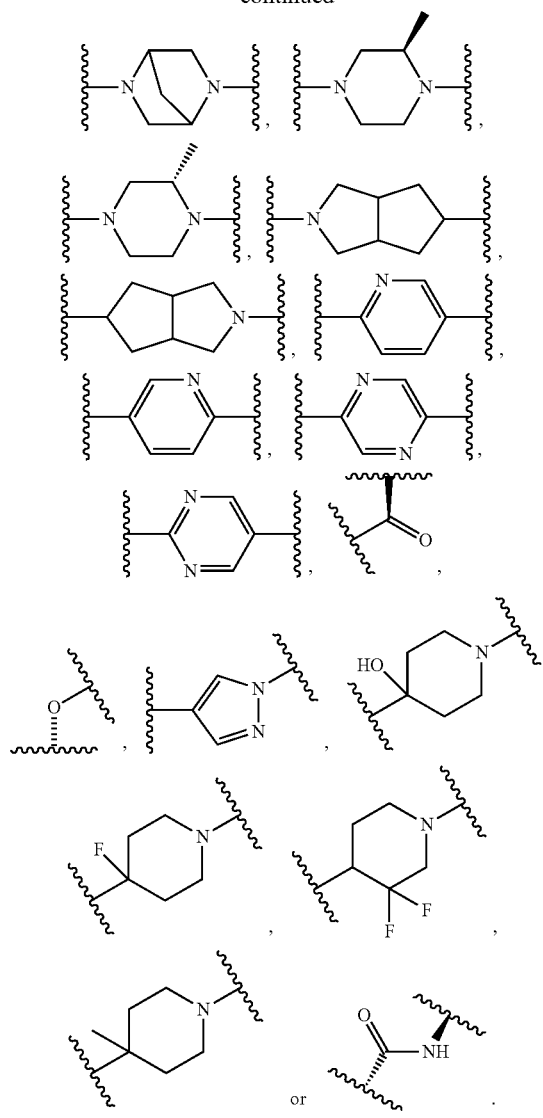
In a preferred embodiment, preferably, $L_2^{-1}$, $L_2^{-2}$, $L_2^{-3}$ and $L_2^{-4}$ are independently absent,
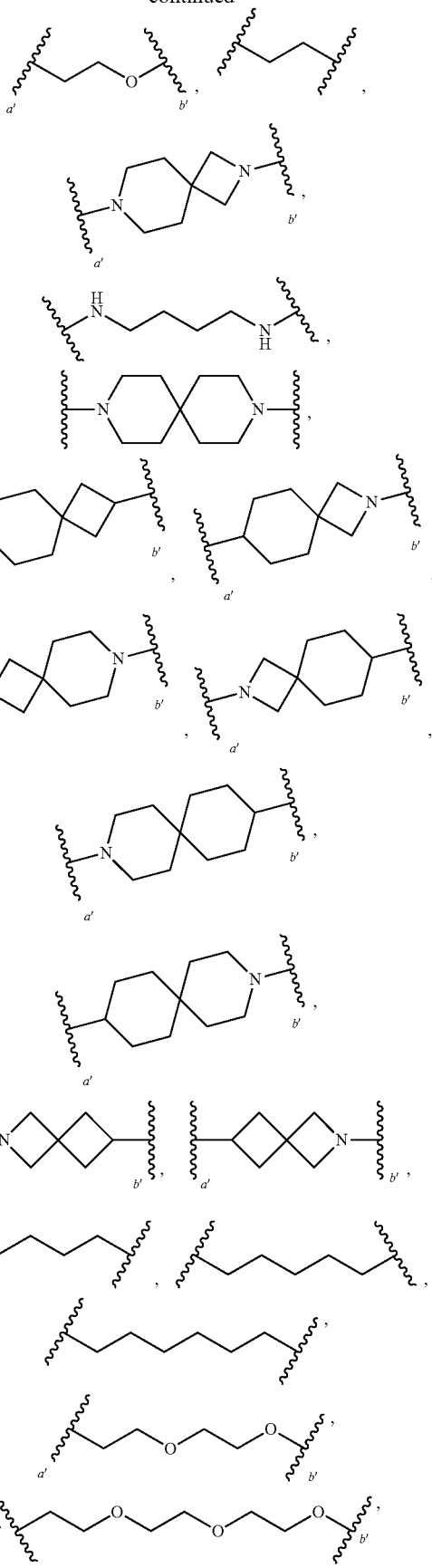

-continued

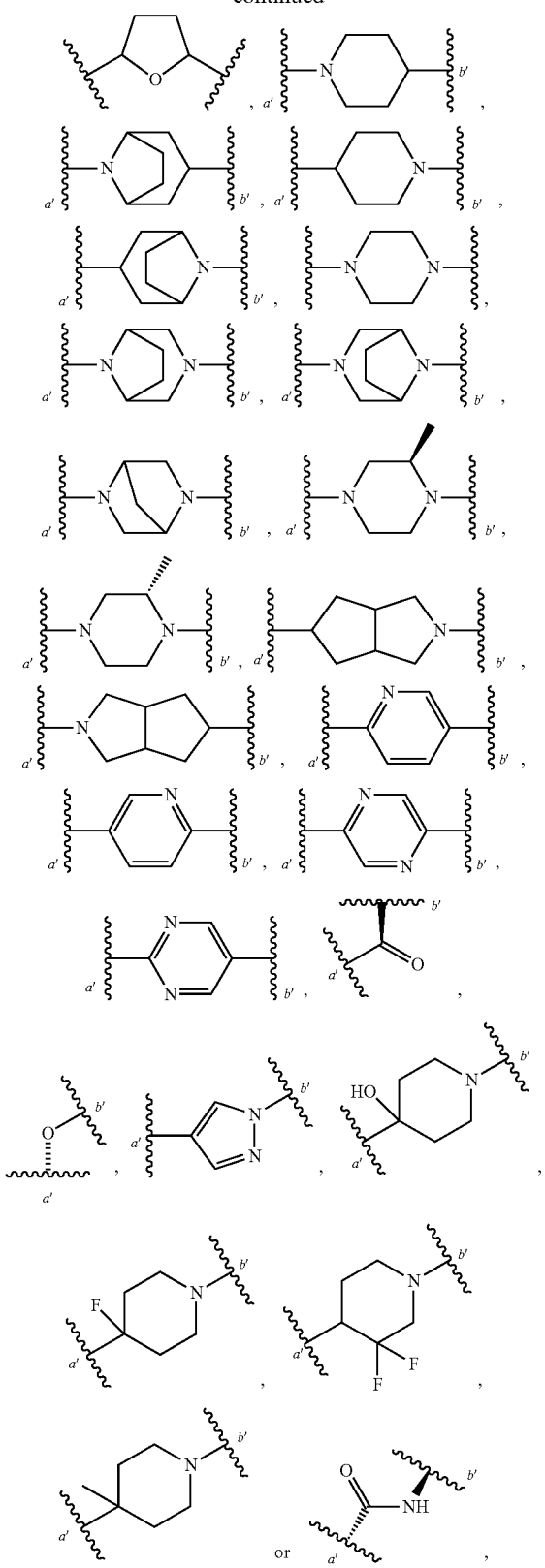

wherein the a' end towards $L_0$ and the b' end towards LLM.

In a preferred embodiment, $L_2^{-1}$, $L_2^{-2}$, $L_2^{-3}$ and $L_2^{-4}$ are independently absent,

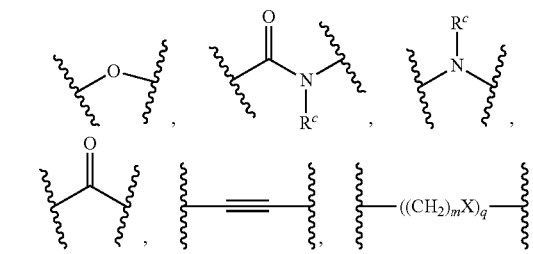

that is unsubstituted or substituted by one or more $L_2^{1-1}$, or

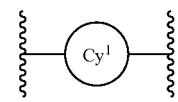

that is unsubstituted or substituted by one or more $L_2^{1-2}$, m is 1 or 2, q is 1 or 2, and X is absent or O; Ring $Cy^1$ is a 4- to 11-membered heterocycle or 4- to 6-membered cycloalkyl; the heteroatoms of the 4- to 11-membered heterocycle are N and/or O, and the number of heteroatoms is 1 or 2; the 4- to 11-membered heteroaromatic ring is a monocyclic ring, a bridged ring or a spiro ring.

In a preferred embodiment, $L_2^{-1}$, $L_2^{-2}$, $L_2^{-3}$ and $L_2^{-4}$ are independently absent,

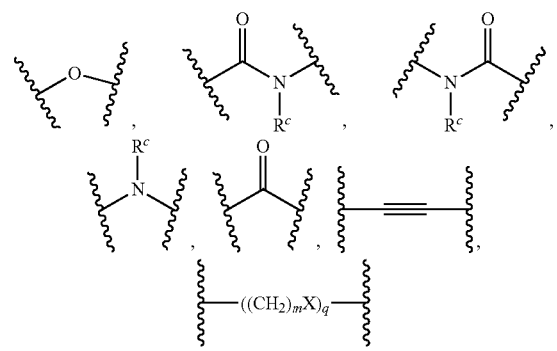

that is unsubstituted or substituted by one or more $L_2^{1-1}$,

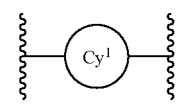

that is unsubstituted or substituted by one or more $L_2^{1-2}$, or

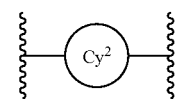

that is unsubstituted or substituted by one or more $L_2^{1-3}$, m is 1 or 2, q is 1 or 2, and X is absent or O; Ring $Cy^1$ is a 4- to 11-membered heterocycle or 4- to 6-membered cycloalkyl; the heteroatoms of the 4- to 11-membered heterocycle are N and/or O, and the number of heteroatoms is 1 or 2; the 4- to 11-membered heterocycle is a monocyclic ring, a bridged ring or a spiro ring; and the 4- to 6-membered cycloalkyl is a monocyclic ring. Ring $Cy^2$ is a 5- to 6-membered heteroaromatic ring; the heteroatoms of the 5- to 6-membered heteroaromatic ring are N and/or O, and the number of heteroatoms is 1 or 2. In a preferred embodiment, when the 4- to 11-membered heterocycle is a monocyclic ring, the 4- to 11-membered heterocycle is a 3- to 6-membered heterocycle, the heteroatom of the 4- to 11-membered heterocycle is N or O, and the number of heteroatoms is 1 or 2.

In a preferred embodiment, when the 4- to 11-membered heterocycle is a spiro ring, the 4- to 11-membered heterocycle is a 4,6-azaspirocycle, a 6,6-azaspirocycle or a 4,4-azaspirocycle.

In a preferred embodiment, $L_2^{-1}$, $L_2^{-2}$, $L_2^{-3}$ and $L_2^{-4}$ are independently absent,

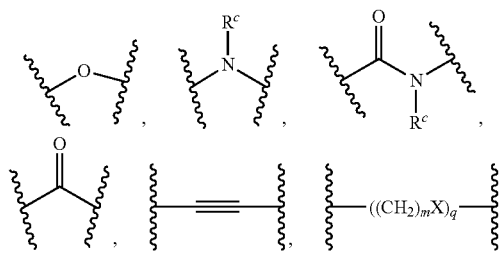

that is unsubstituted or substituted by one or more $L_2^{1-1}$, or

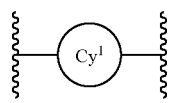

that is unsubstituted or substituted by one or more $L_2^{1-2}$, m is 1 or 2, q is 1, and X is absent or O; Ring $Cy^1$ is a 4- to 10-membered heterocycle or 4- to 6-membered cycloalkyl; the heteroatoms of the 4- to 10-membered heterocycle are N, and the number of heteroatoms is 1 or 2; the 4 to 10-membered heterocycle is a 6-membered monocyclic ring or 4,6-azaspirocycle; and $R^c$ is H.

In a preferred embodiment, $L_2^{-1}$, $L_2^{-2}$, $L_2^{-3}$ and $L_2^{-4}$ are independently absent,

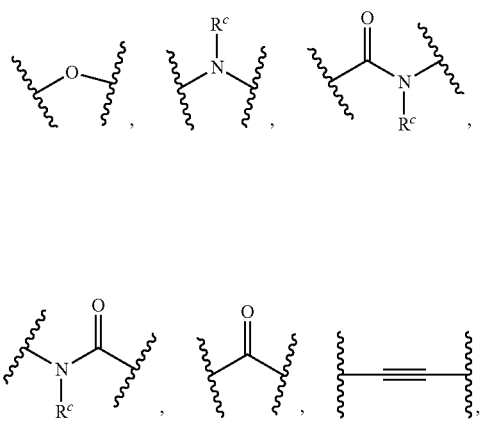

that is unsubstituted or substituted by one or more $L_2^{1-1}$,

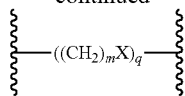

that is unsubstituted or substituted by one or more $L_2^{1-2}$, or

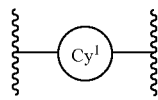

that is unsubstituted or substituted by one or more $L_2^{1-3}$, m is 1 or 2, q is 1, and X is absent or O; Ring $Cy^1$ is a 4- to 10-membered heterocycle or 4- to 6-membered cycloalkyl; the heteroatoms of the 4- to 10-membered heterocycle are N, and the number of heteroatoms is 1 or 2; the 4 to 10-membered heterocycle is a 6-membered monocyclic ring, 4,4-azaspirocycle or 4,6-azaspirocycle; $R^c$ is H, ring $Cy^2$ is a 5-membered heteroaromatic ring; the heteroatoms of the 5-membered heteroaromatic ring are N, and the number of heteroatoms is 2, the 5-membered heteroaromatic ring is preferably a pyrazole ring.

In a preferred embodiment, $L_2^{-1}$, $L_2^{-2}$, $L_2^{-3}$ and $L_2^{-4}$ are independently absent,

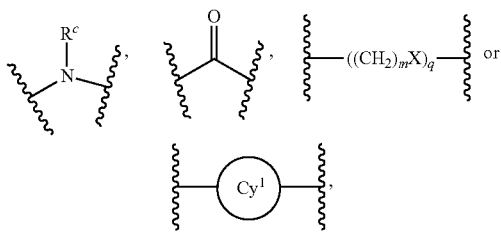

m is 1 or 2, q is 1 and X is absent; Ring $Cy^1$ is a 4- to 6-membered heterocycle or 4- to 6-membered cycloalkyl; the heteroatoms of the 4- to 10-membered heterocycle are N, and the number of heteroatoms is 1 or 2; the 4- to 6-membered cycloalkyl is a 6-membered monocyclic; $R^c$ is H.

In a preferred embodiment, $L_2^{-1}$, $L_2^{-2}$, $L_2^{-3}$ and $L_2^{-4}$ are independently absent,

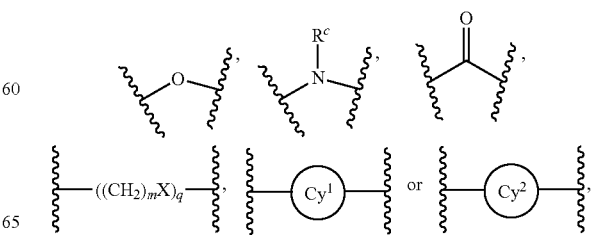

m is 1 or 2, q is 1 and X is absent; Ring $Cy^1$ is a 4- to 10-membered heterocycle or 4- to 6-membered cycloalkyl; the heteroatoms of the 4- to 10-membered heterocycle are N, and the number of heteroatoms is 1 or 2; the 4- to 6-membered cycloalkyl is a 6-membered monocyclic; $R^c$ is H, Ring $Cy^2$ is 5-membered heteroaromatic ring, the heteroatoms of the 5-membered heteroaromatic ring are N, and the number of heteroatoms is 2, such as a pyrazole ring.

In a preferred embodiment, $L_2$ is $-L_2^{-1}-L_2^{-2}-L_2^{-3}-L_2^{-4}-$; $L_2^{-1}$ and $L_2^{-2}$ are absent, $L_2^{-3}$ is

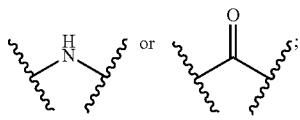

$L_2^{-4}$ is

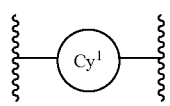

that is unsubstituted or substituted by one or more $L_2^{1-2}$; and ring $Cy^1$ is piperidinyl or piperazinyl. Preferably, $L_2$ is $-L_2^{-1}-L_2^{-2}-L_2^{-3}-L_2^{-4}-$; $L_2^{-1}$ and $L_2^{-2}$ are absent, $L_2^{-3}$ is

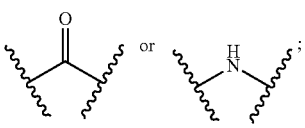

$L_2^{-4}$ is unsubstituted ring $Cy^1$, and the ring $Cy^1$ is piperidinyl or piperazinyl.

In a preferred embodiment, $L_2$ is $-L_2^{-1}-L_2^{-2}-L_2^{-3}-L_2^{-4}-$; $L_2^{-1}$ is absent, $L_2^{-2}$, $L_2^{-3}$ and $L_2^{-4}$ are independently

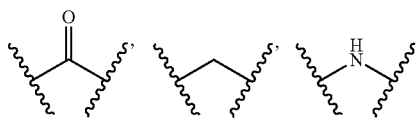

or ring $Cy^1$ that is unsubstituted or substituted by one or more $L_2^{1-2}$, and the ring $Cy^1$ is cyclohexyl, piperidinyl or piperazinyl.

In a preferred embodiment, $L_2$ is $-L_2^{-1}-L_2^{-2}-L_2^{-3}-L_2^{-4}-$; $L_2^{-1}$, $L_2^{-2}$, $L_2^{-3}$ and $L_2^{-4}$ are independently

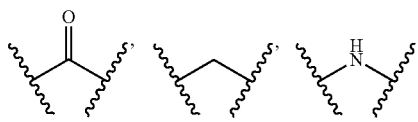

or ring $Cy^1$ that is unsubstituted or substituted by one or more $L_2^{1-2}$, and the ring $Cy^1$ is cyclohexyl, piperidinyl or piperazinyl.

In a preferred embodiment, each $L_2^{1-2}$ is independently halogen or hydroxyl.

In a preferred embodiment, $L_2$ is $-L_2^{-1}-L_2^{-2}-L_2^{-3}-L_2^{-4}-$ or

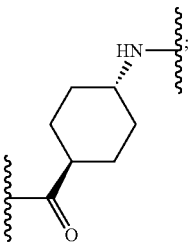 [SMILES: *N[C@H]1CC[C@H](C(*)=O)CC1]

$L_2^{-1}$ is

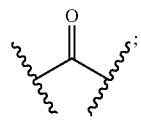 [SMILES: *C(*)=O]

$L_2^{-2}$, $L_2^{-3}$ and $L_2^{-4}$ are independently absent,

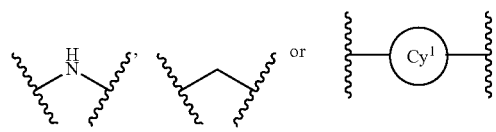

that is unsubstituted or substituted by one or more $L_2^{1-2}$; the ring $Cy^1$ is a 4- to 6-membered heterocycle; the heteroatom of the 4- to 6-membered heterocycle is N, and the number of heteroatoms is 1; and the 4- to 6-membered heterocycle is a monocyclic ring.

In a preferred embodiment, in $L_2$, $R^c$ is H or a $C_1$-$C_6$ alkyl that is unsubstituted or substituted by one or more halogens, and is more preferably H.

In a preferred embodiment, ring $Cy^3$ is a 5- to 6-membered heterocycle that is unsubstituted or substituted by one or more $Cy^{3-1}$; the heteroatom of the 5- to 6-membered heterocycle is N, S or O, and the number is 1. Ring $Cy^3$ is preferably a 5- to 6-membered heterocycle that is unsubstituted or substituted by multiple $Cy^{3-1}$, the heteroatom of the 5- to 6-membered heterocycle is N, and the number is 1.

In a preferred embodiment, each $Cy^{3-1}$ is independently oxo.

In a preferred embodiment, Ring $Cy^4$ is a 5- to 8-membered heterocycloalkyl that is unsubstituted or substituted by one or more $Cy^{4-1}$, the heteroatoms of the 5- to 8-membered heterocycle are selected from one or more of N, S and O, and the number of heteroatoms is 1, 2 or 3. Ring $Cy^4$ is a 5- to 8-membered heterocycloalkyl that is unsubstituted or substituted by one or more $Cy^{4-1}$; the heteroatom of the 5- to 8-membered heterocycle is N, S or O, and the number of heteroatoms is 1.

In a preferred embodiment, each $Cy^{4-1}$ is independently $C_1$-$C_6$ alkyl, hydroxyl or oxo, preferably oxo.

In a preferred embodiment, the five-membered ring-fused six-membered ring compound represented by formula I is a compound represented by formula I-a, I-b, I-d, I-g, I-h or I-i:

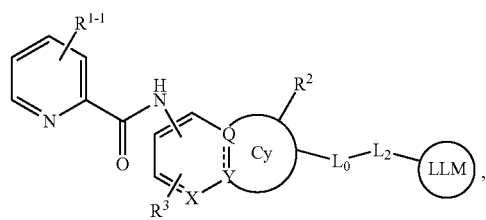
I-a
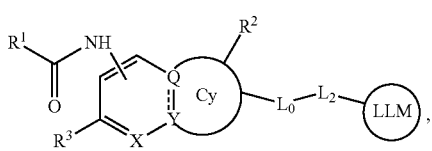
I-b
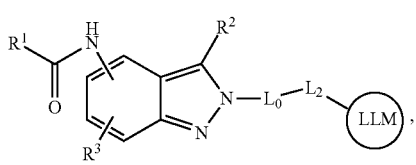
I-d
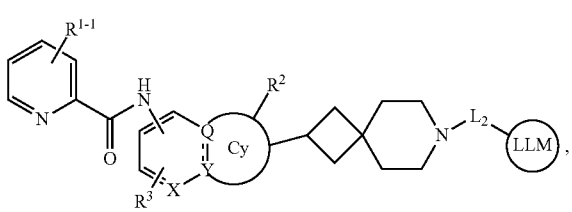
I-g
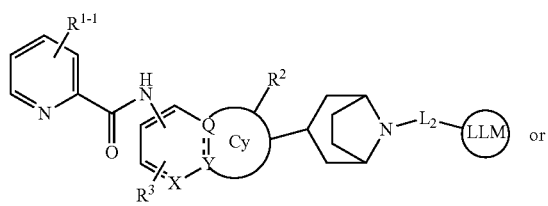
I-h
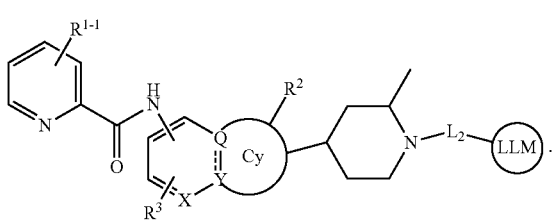
I-i
In a preferred embodiment, the five-membered ring-fused six-membered ring compound represented by formula I is a compound represented by formula I-a, I-b, I-d, I-g, I-h, I-i, I-k, I-m or I-n:
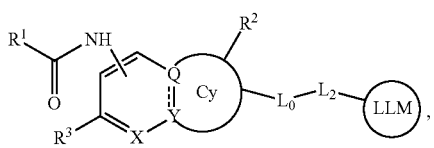
I-b
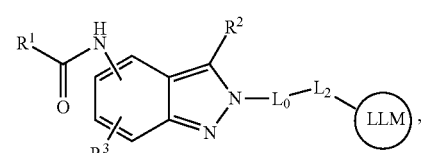
I-d
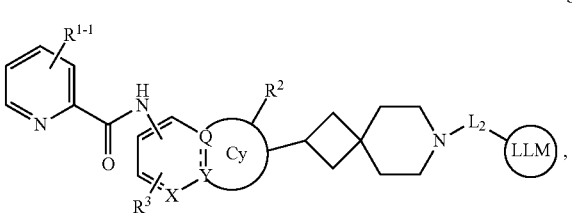
I-g
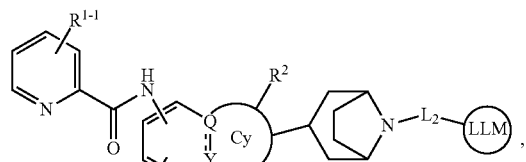
I-h
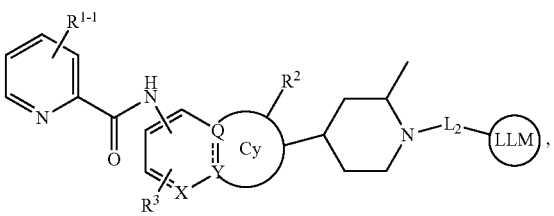
I-i
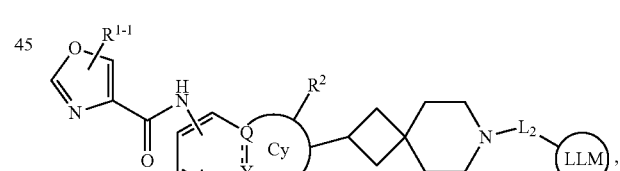
I-k
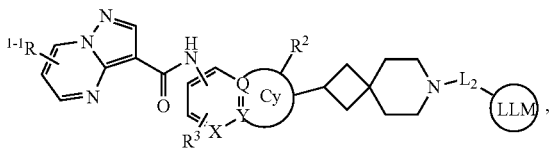
I-m
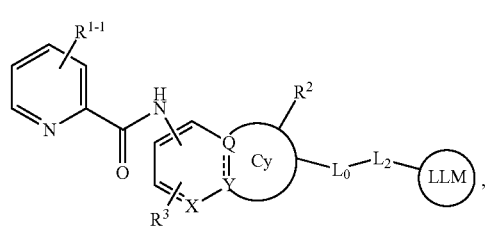
I-a
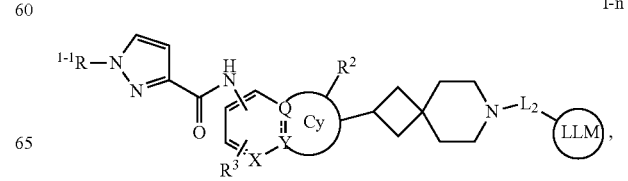
I-n -continued
I-o
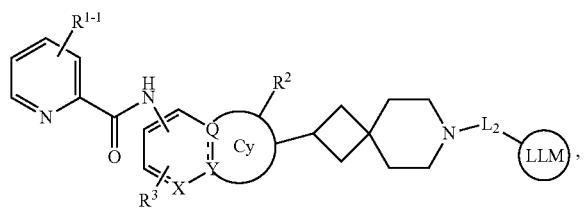
I-p
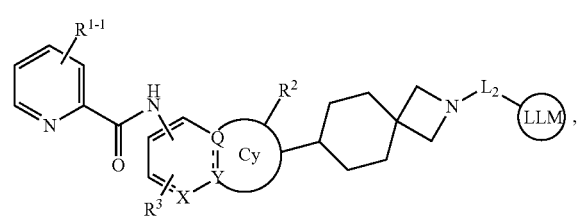
I-q
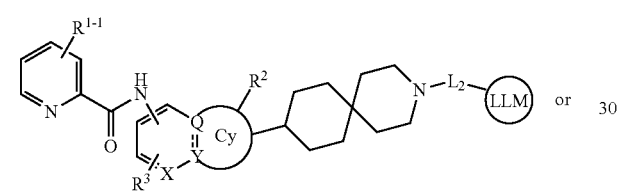
I-r
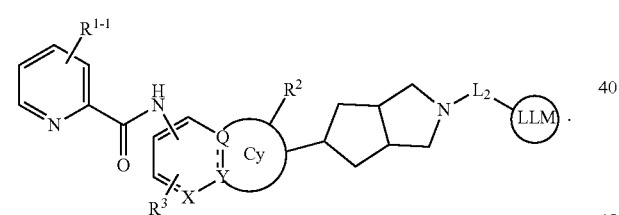
In a preferred embodiment, LLM is
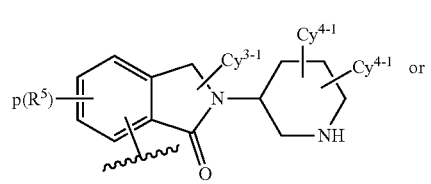
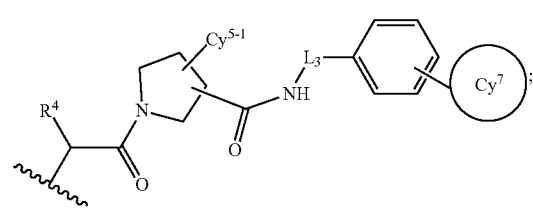
preferably is
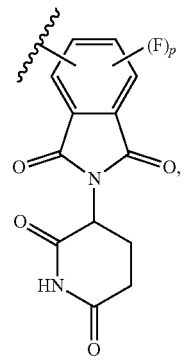
wherein p is 0 or 1;
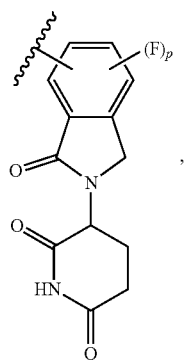
wherein p is 0 or 1; or
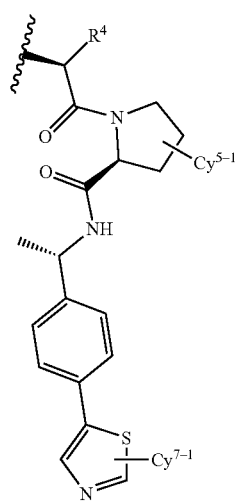

more preferably
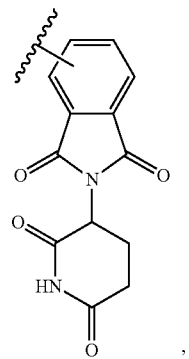,
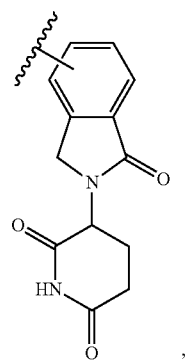,
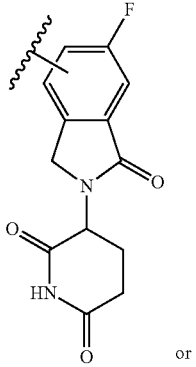 or
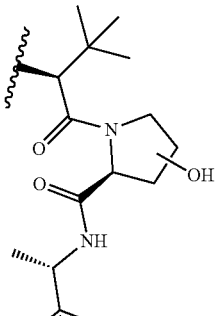,
such as
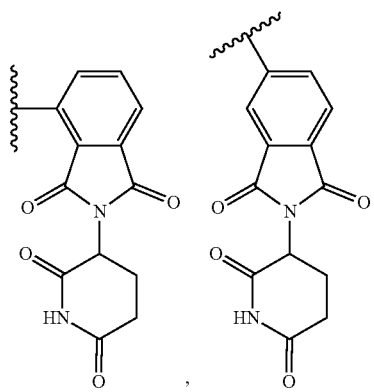,
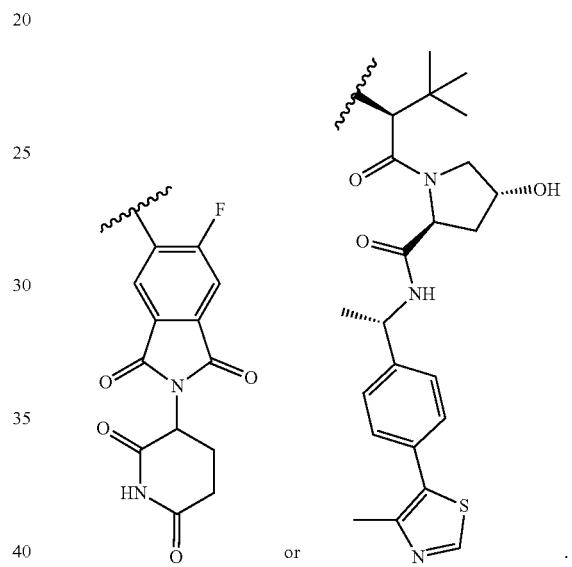 or
In a preferred embodiment, LLM is
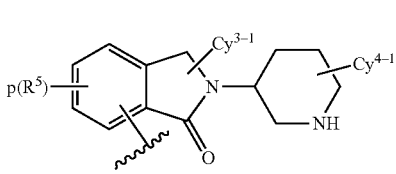,
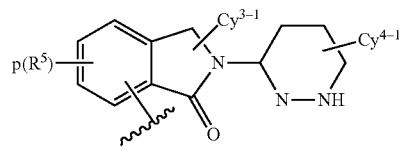 or
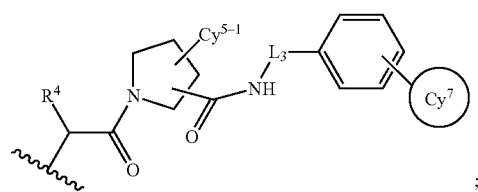;

preferably is
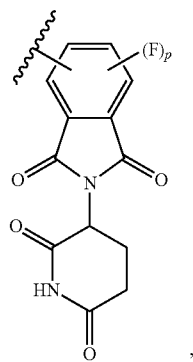
wherein p is 0 or 1;
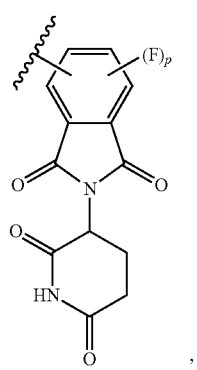
wherein p is 0 or 1;
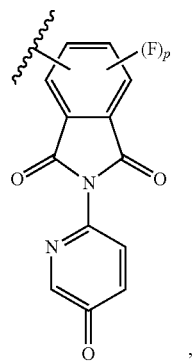
wherein p is 0 or 1; or
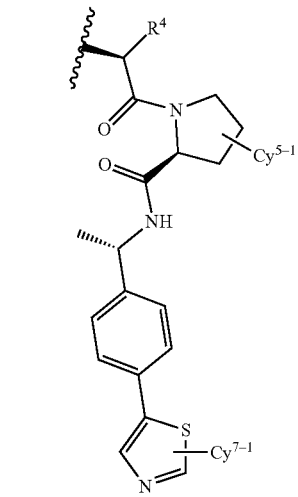
more preferably
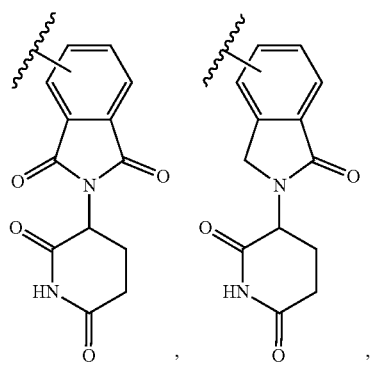
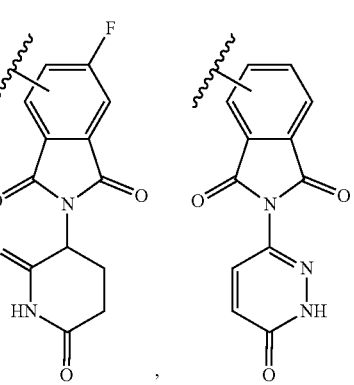
or

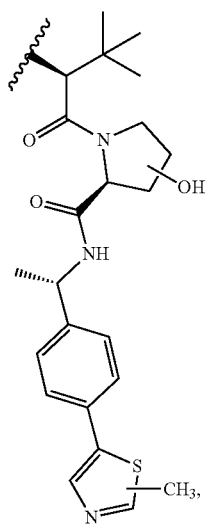
such as
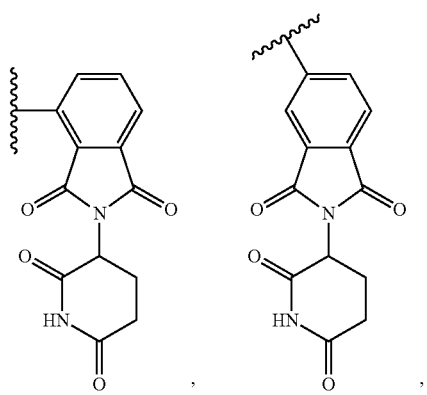
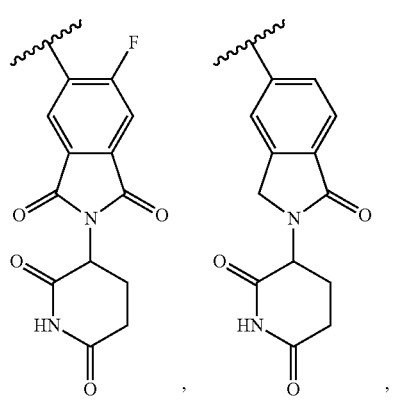
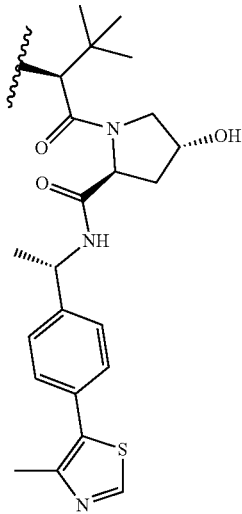
In a preferred embodiment, LLM is
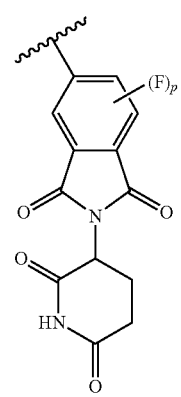
wherein p is 0 or 1; such as
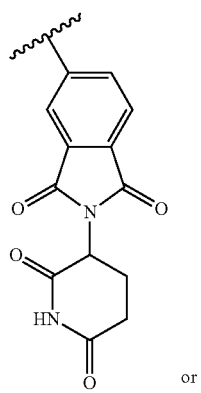
or -continued
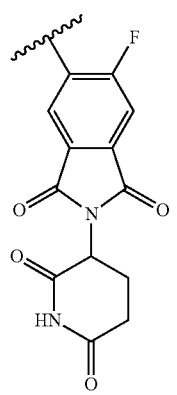
also such as
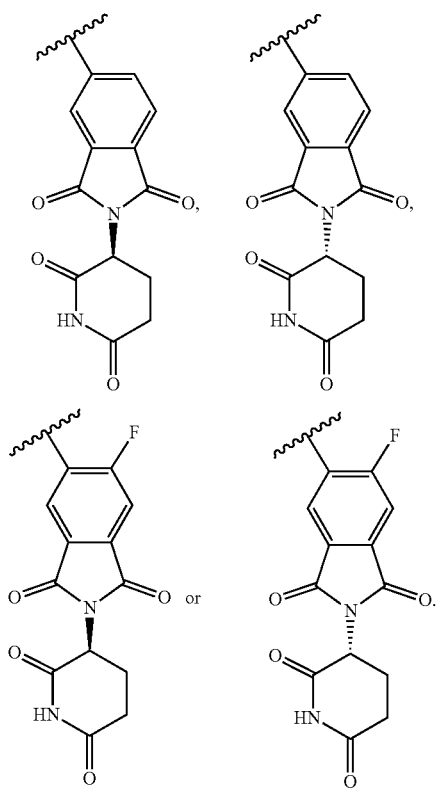
In a preferred embodiment, R¹ is
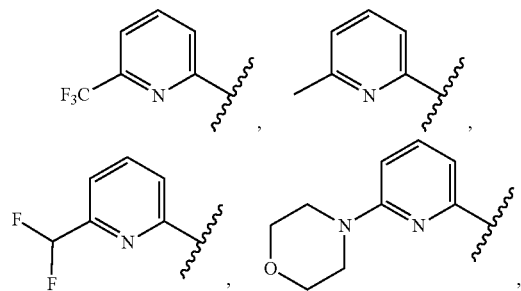
-continued
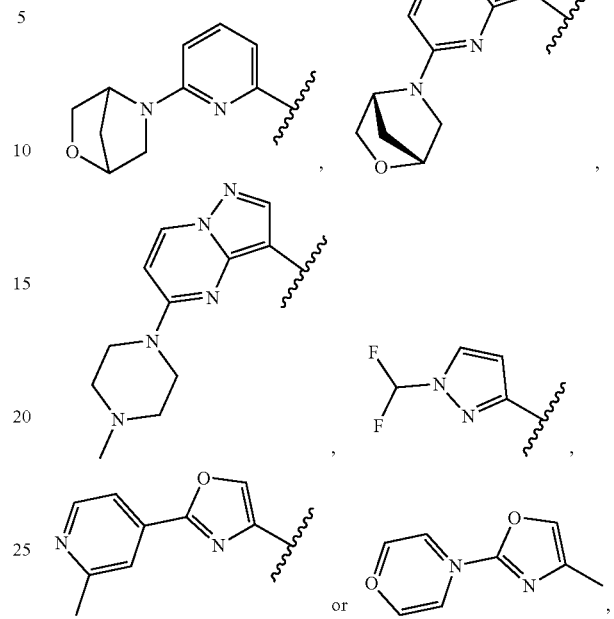
preferably
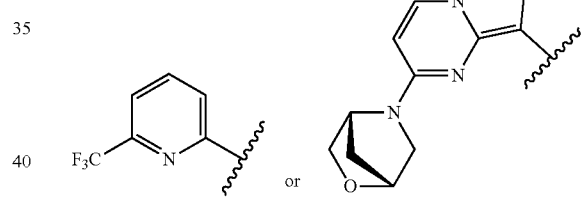
In a preferred embodiment, R³ is methoxy, isopropoxy, difluoromethoxy, trifluoromethoxy, carboxyl, fluorine,
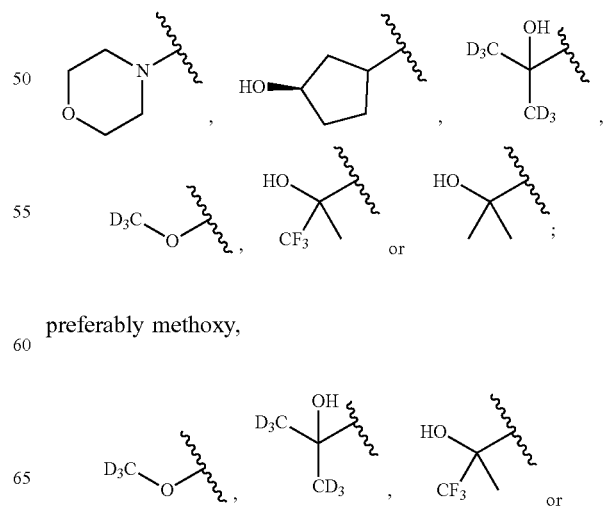
preferably methoxy, -continued
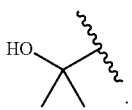
In a preferred embodiment,
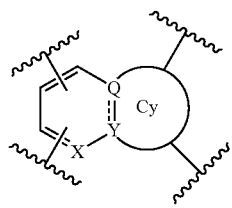
is
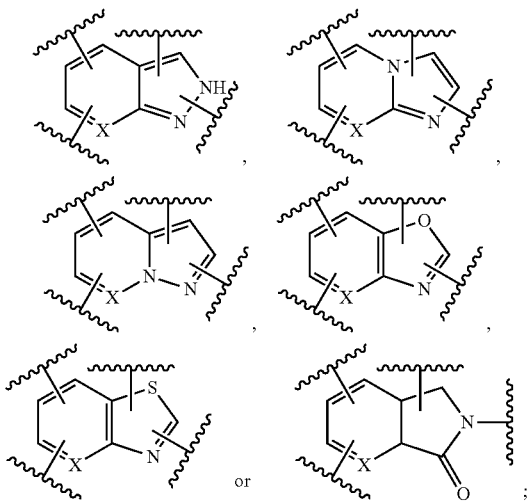
such as
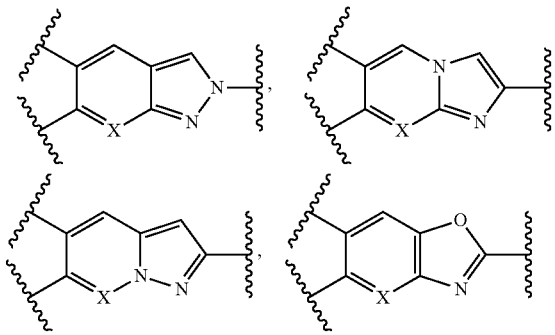
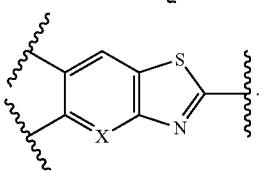
In a preferred embodiment, in the compounds of formula I,
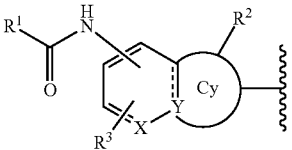
is
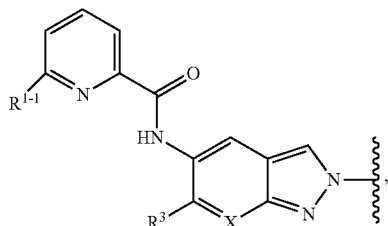
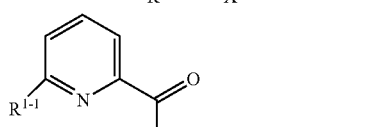
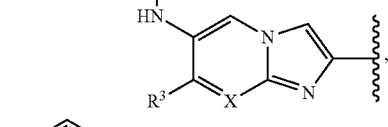
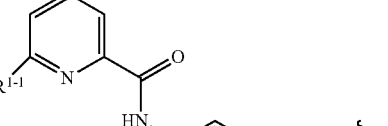
or
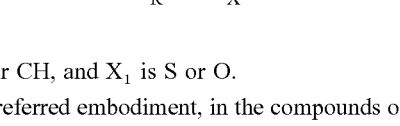
X is N or CH, and $X_1$ is S or O.
In a preferred embodiment, in the compounds of formula I,
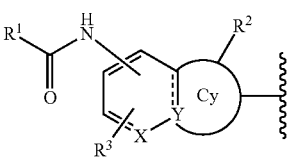

is
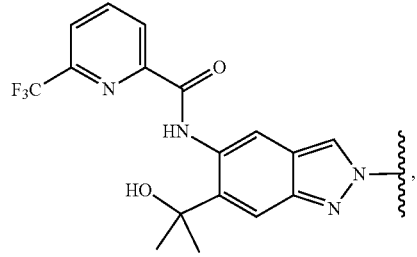
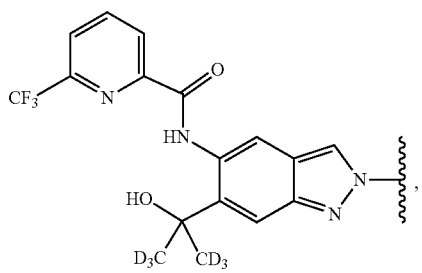
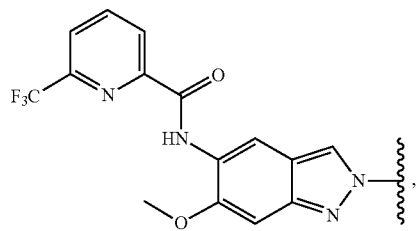
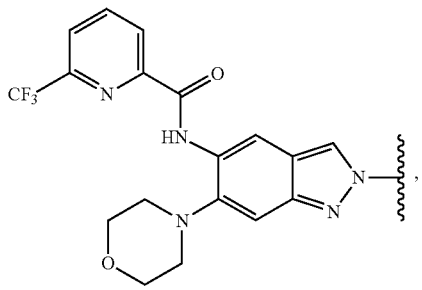
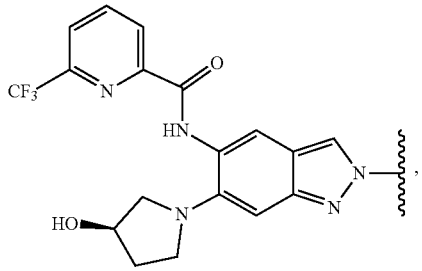
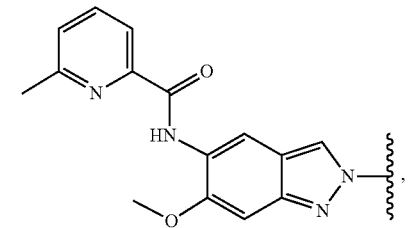
-continued
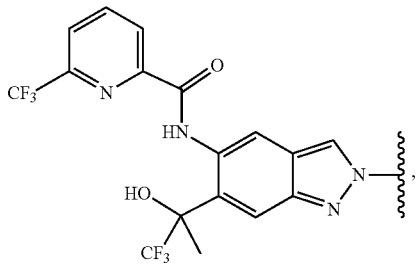
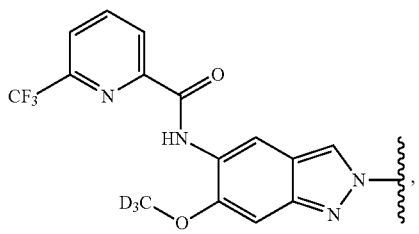
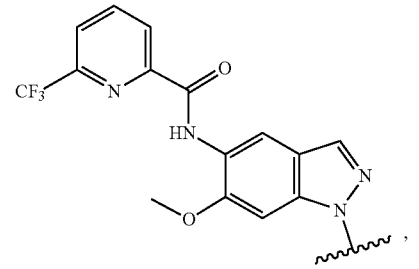
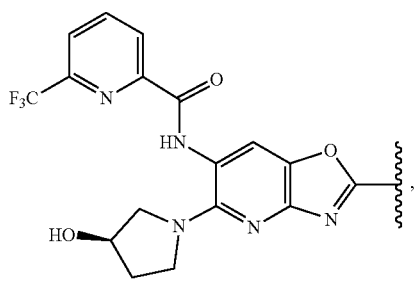
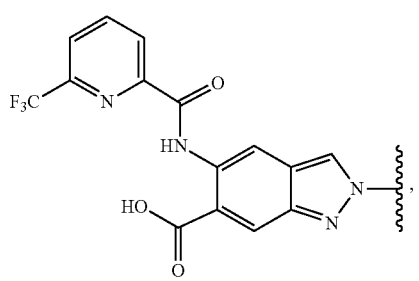
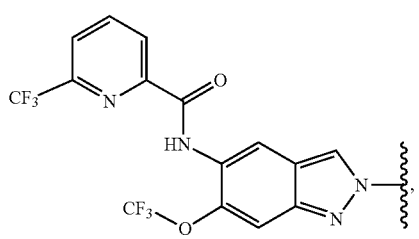

-continued
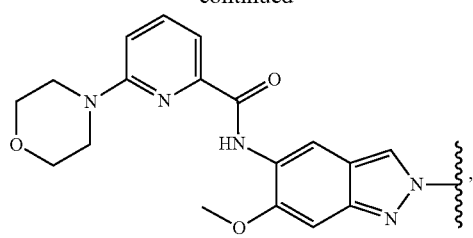
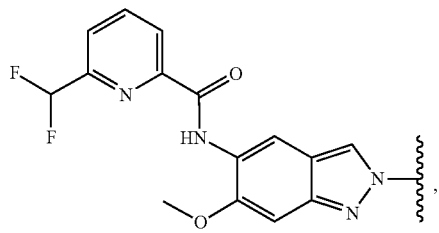
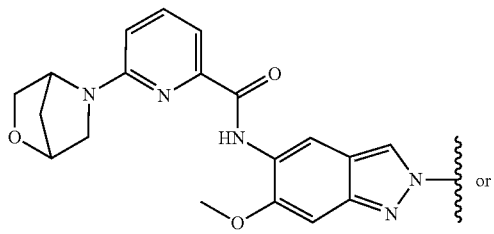
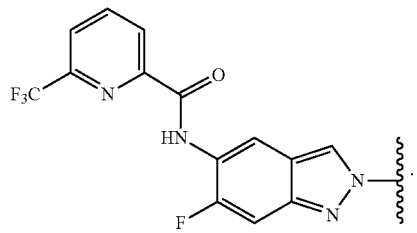
In a preferred embodiment, in the compounds of formula I,
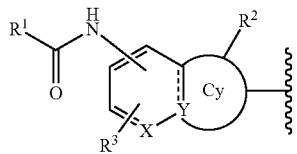
is
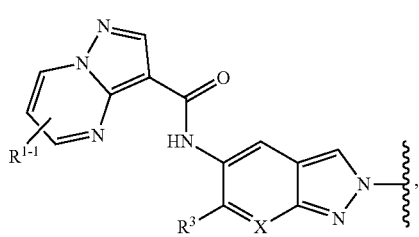
-continued
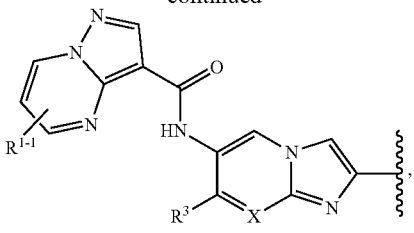
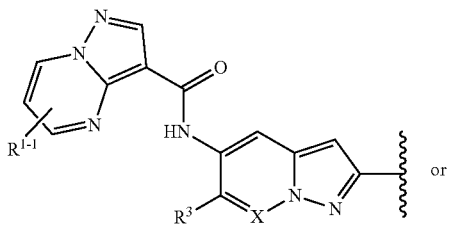
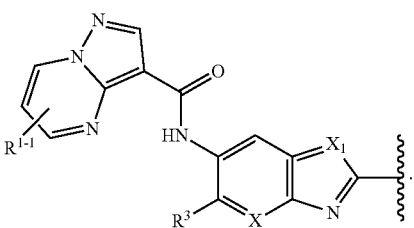
In a preferred embodiment, in the compounds of formula I,
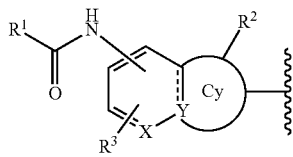
is
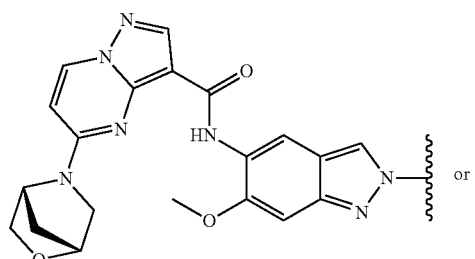
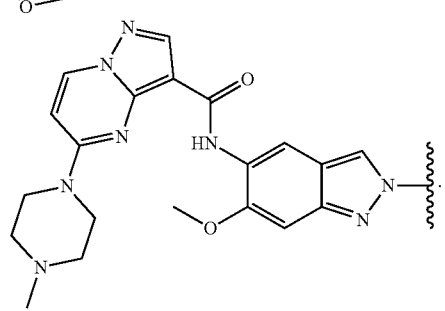

In a preferred embodiment, in the compounds of formula I,
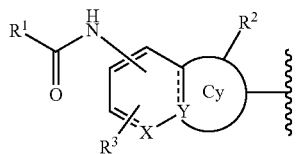
is
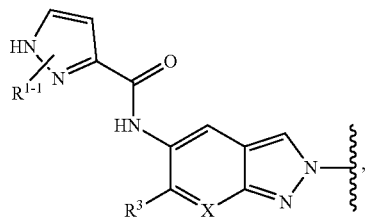
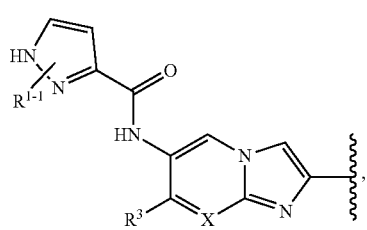
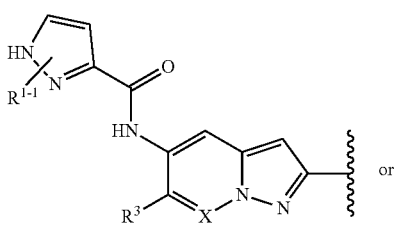
or
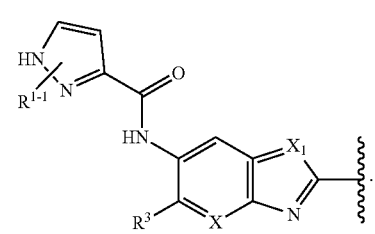
In a preferred embodiment, in the compounds of formula I,
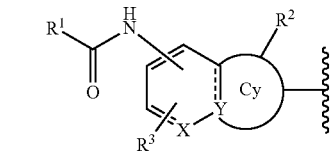
is
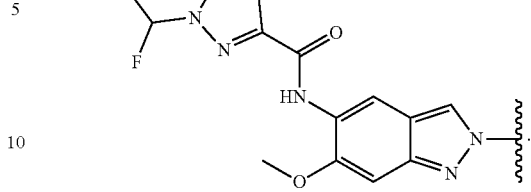
In a preferred embodiment, in the compounds of formula I,
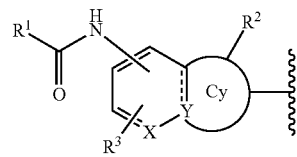
is
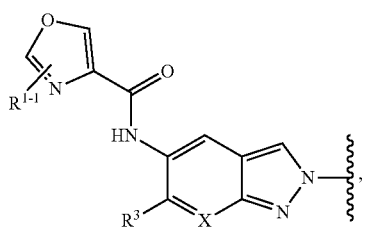
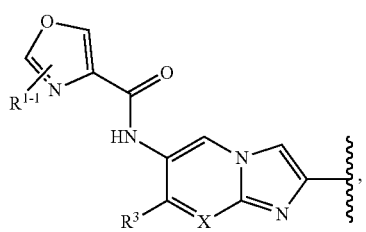
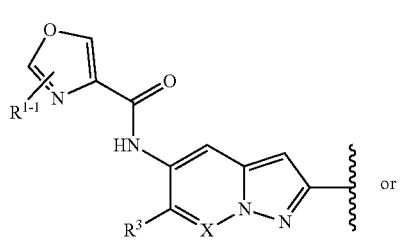
or
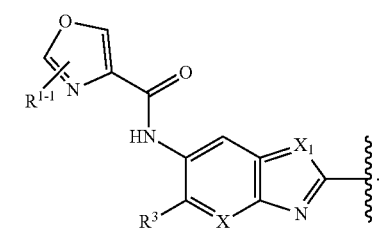

In a preferred embodiment, in the compounds of formula I,

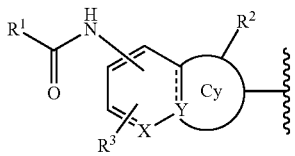

is

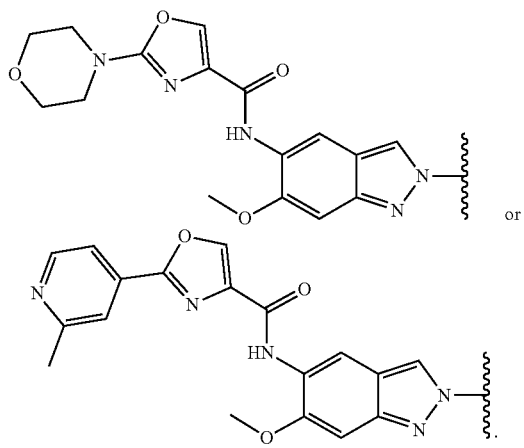

or

In a preferred embodiment, $L_0$ is

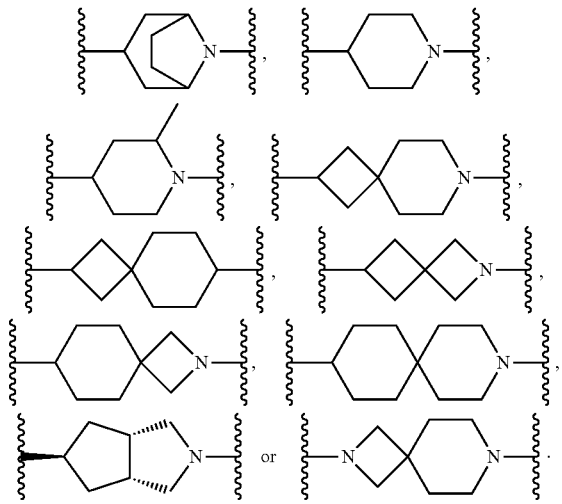

or

In a preferred embodiment, $L_0$ is

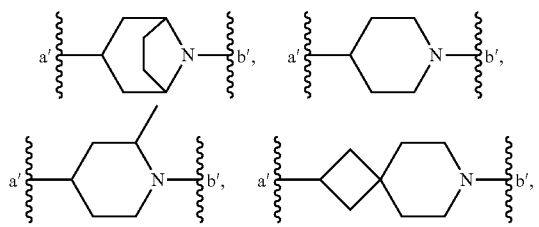

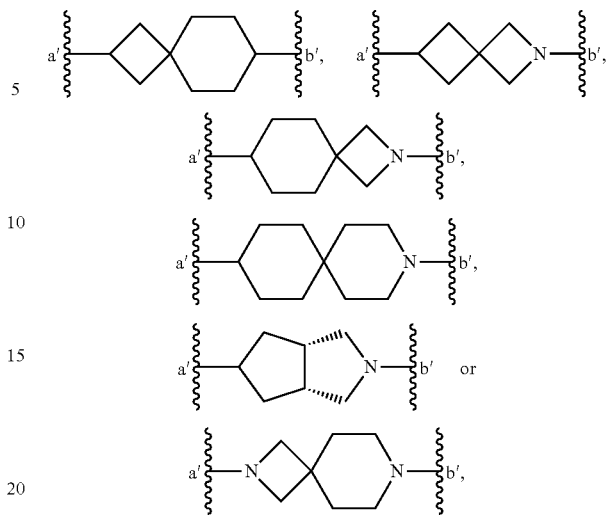

wherein the a' end is connected to ring Cy, and the b' end is connected to $L^2$.

In a preferred embodiment, $L_0$ is

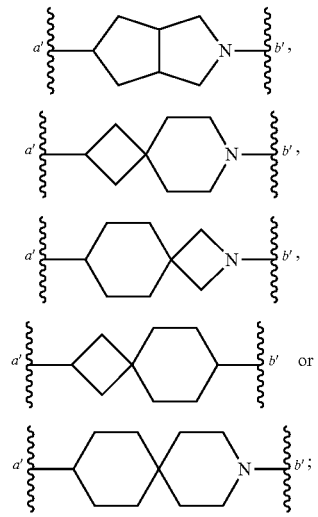

wherein the a' end is connected to ring Cy, and the b' end is connected to $L^2$.

In a preferred embodiment, in $L_0$,

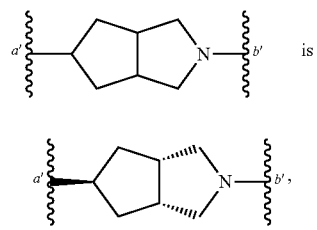

wherein the a' end is connected to ring Cy, and the b' end is connected to $L^2$.

In a preferred embodiment, $L_2$ is
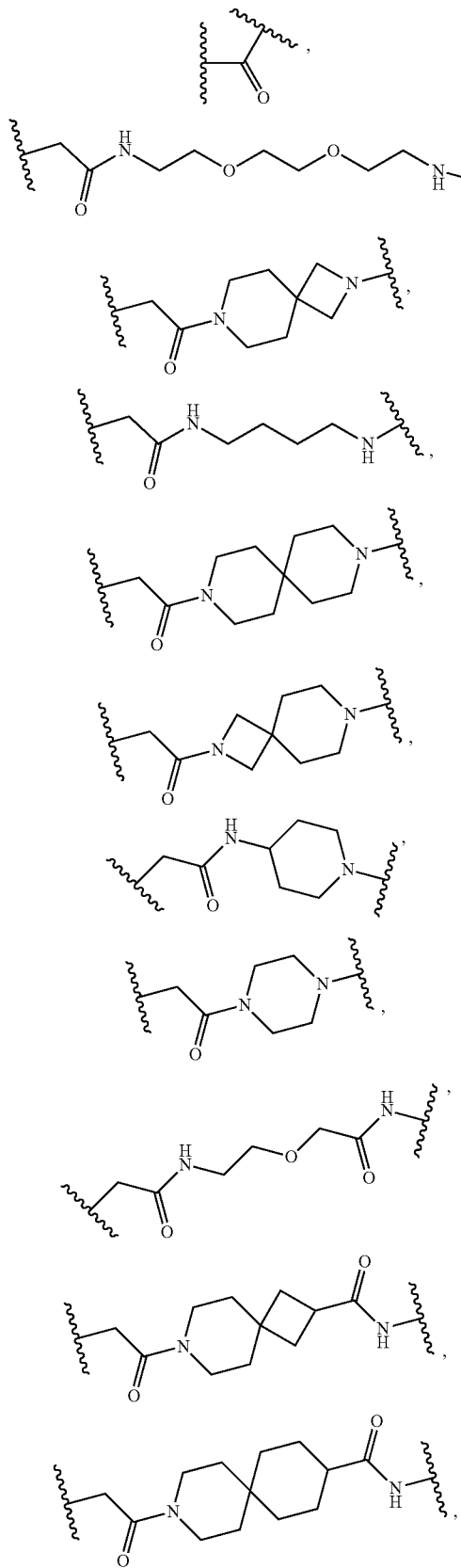
-continued
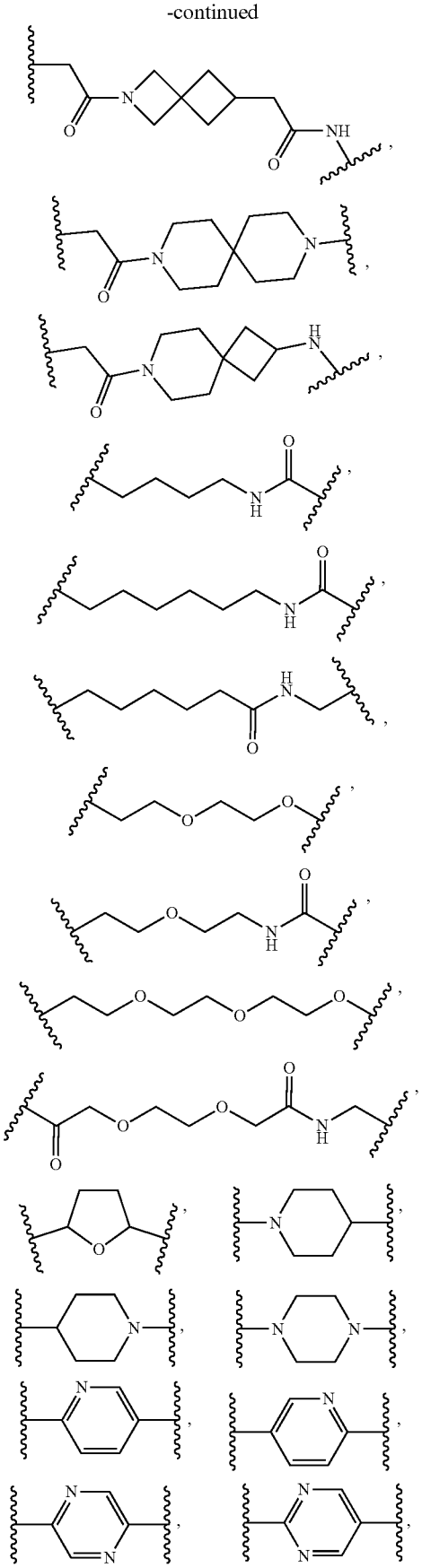

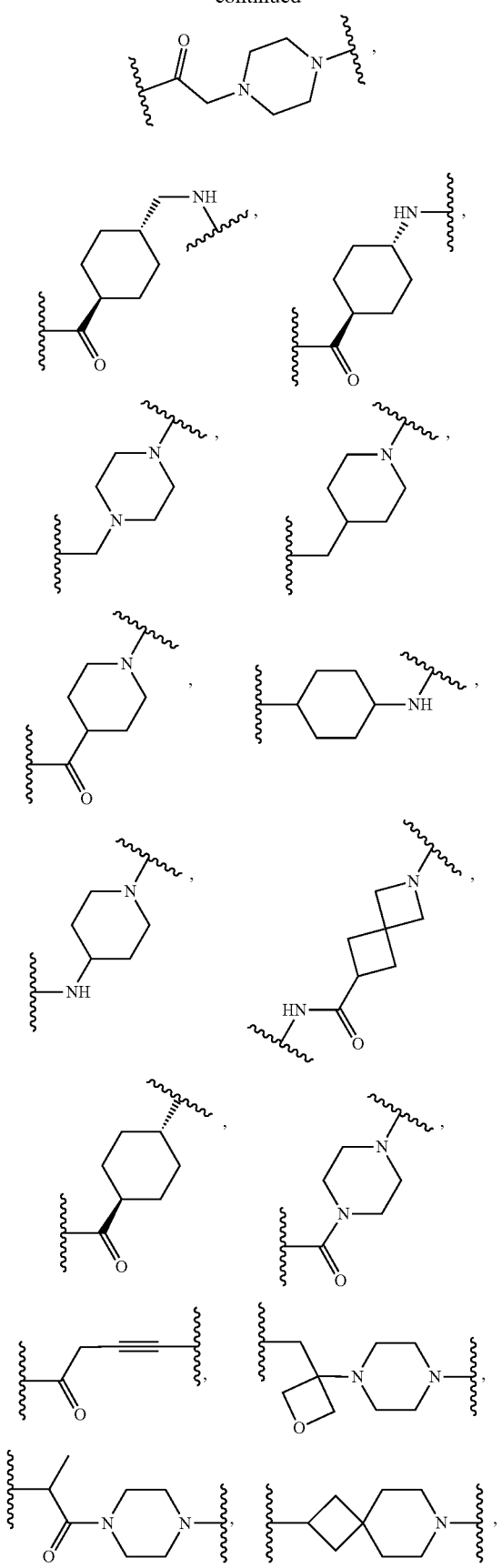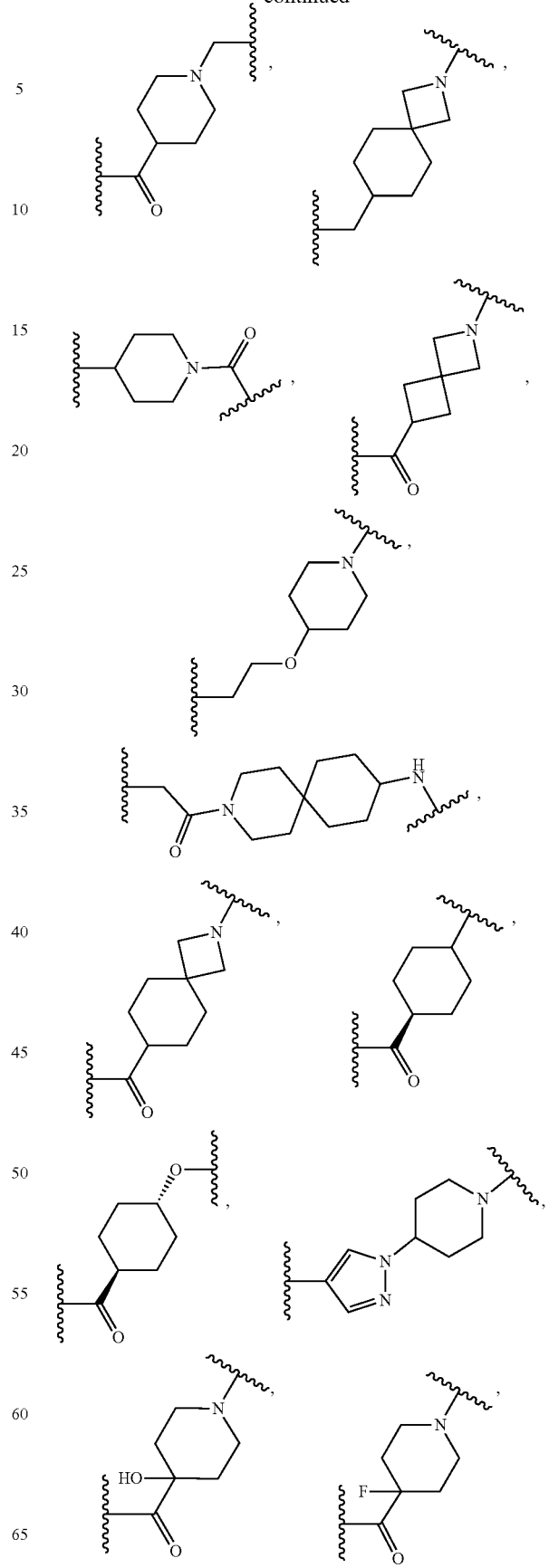

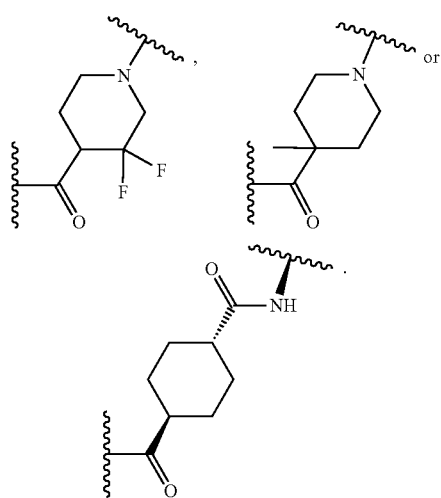
In a preferred embodiment, L$_2$ is
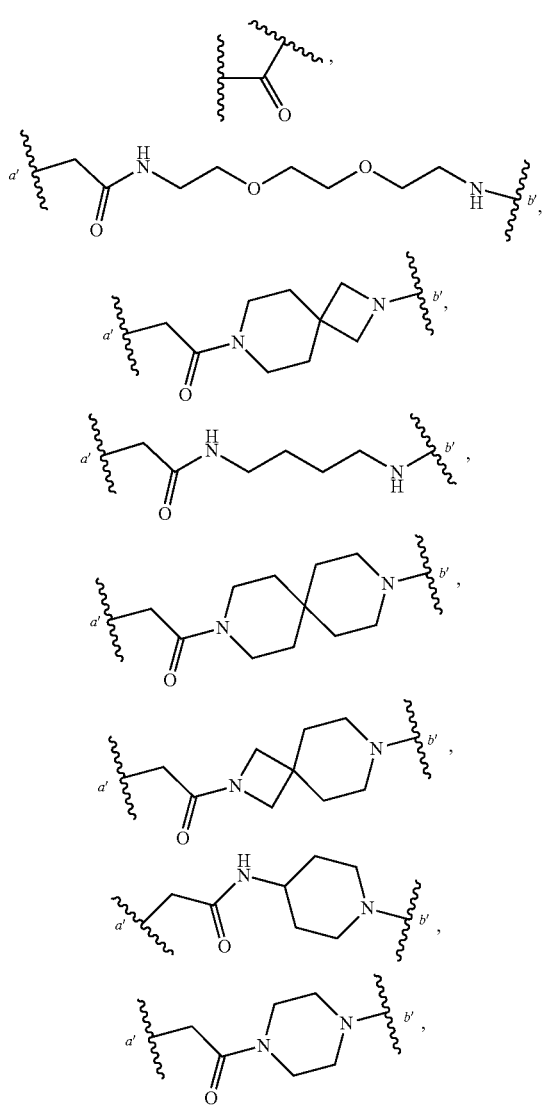
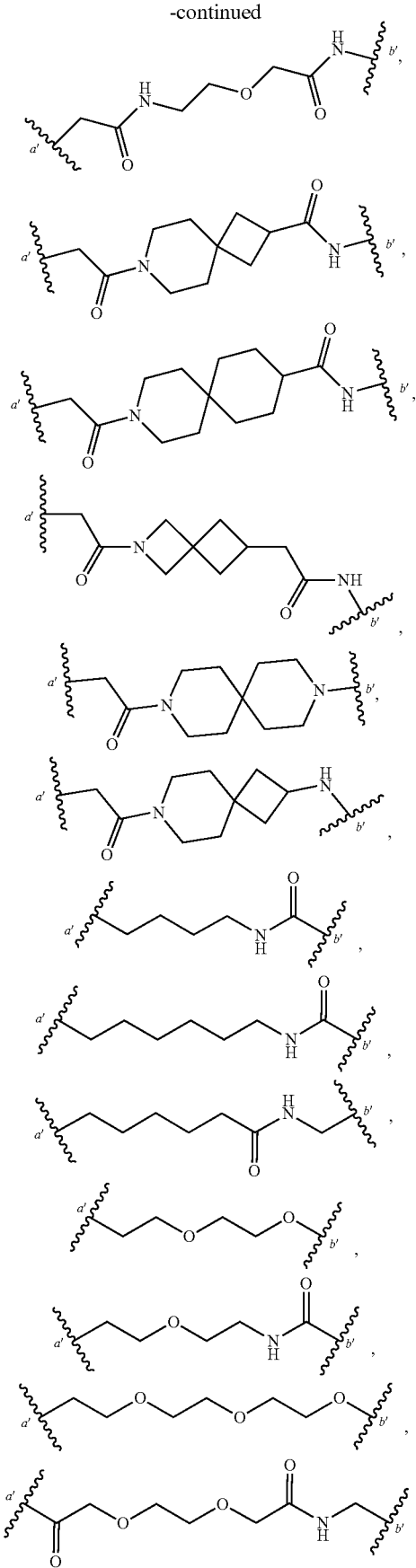

-continued

-continued
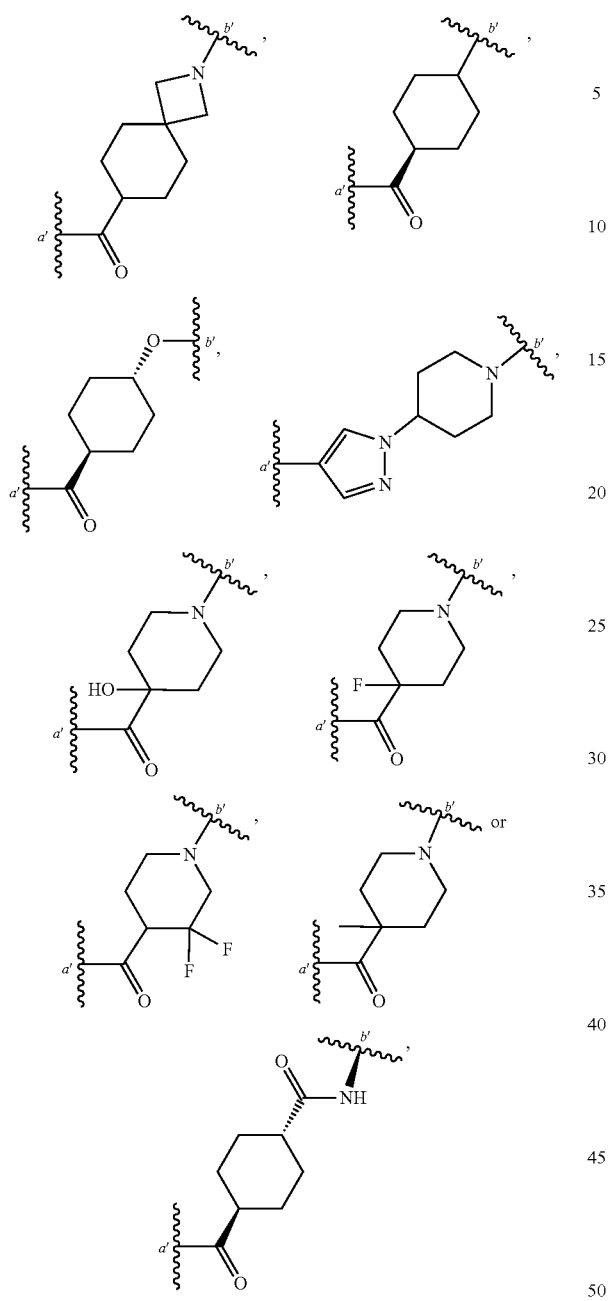
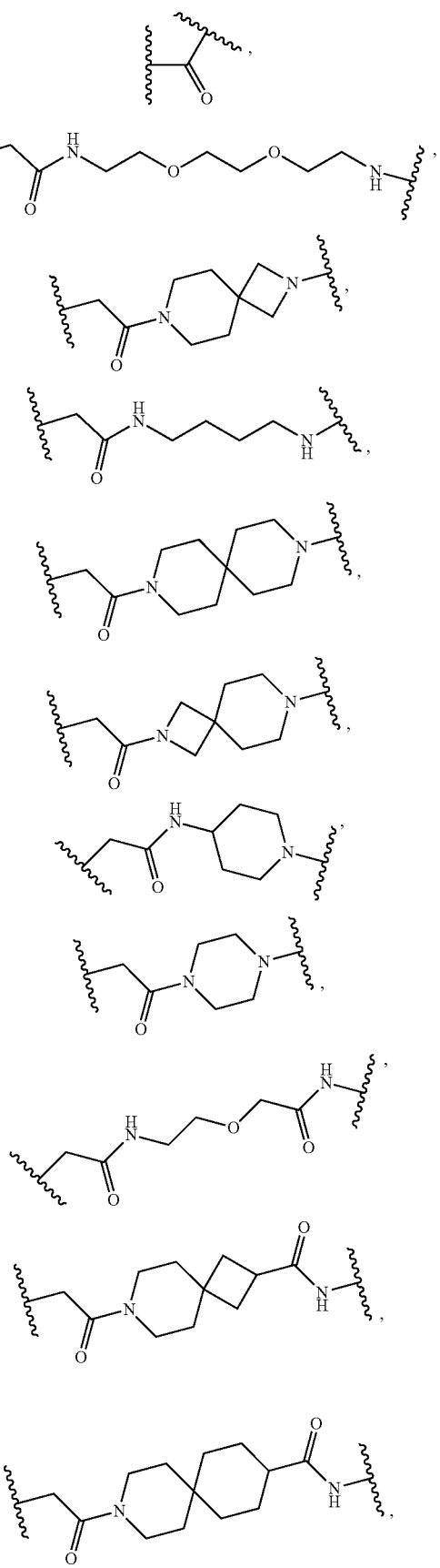
wherein the a' end is connected to $L_0$, and the b' end is connected to LLM.
In a preferred embodiment, when $L_0$ is
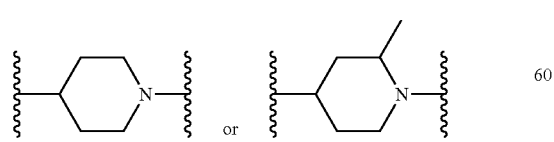
(Further, $L_0$ is a 5- to 12-membered heterocycloalkylene group that is unsubstituted or substituted by one or more $L_0^{-3}$), $L_2$

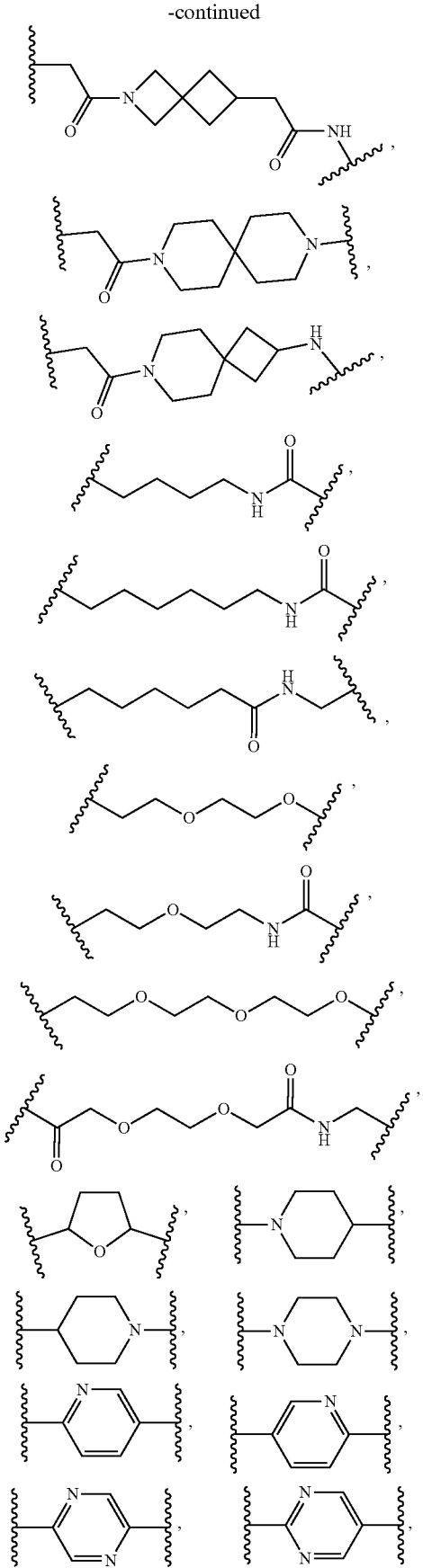
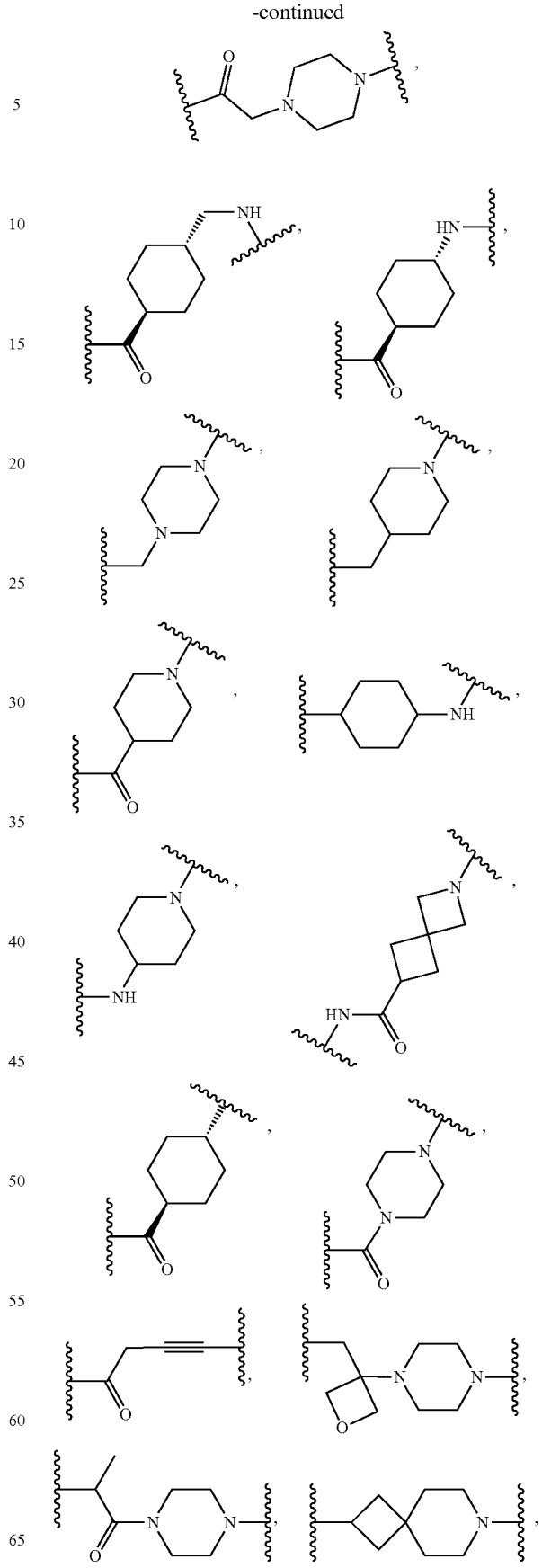

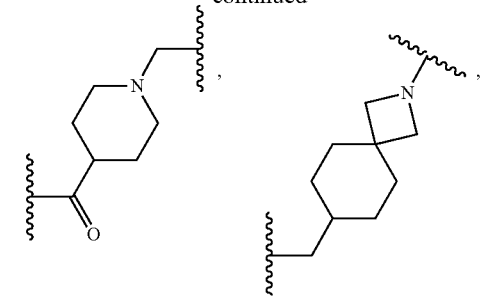
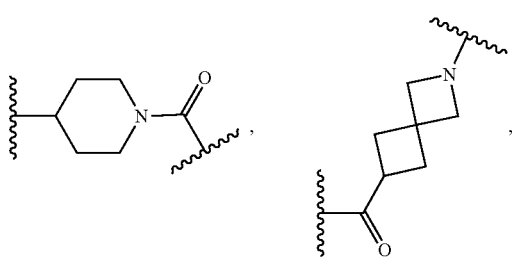
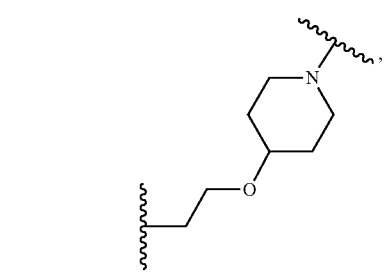
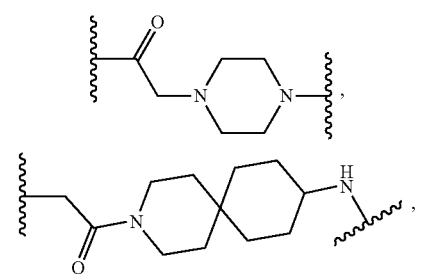
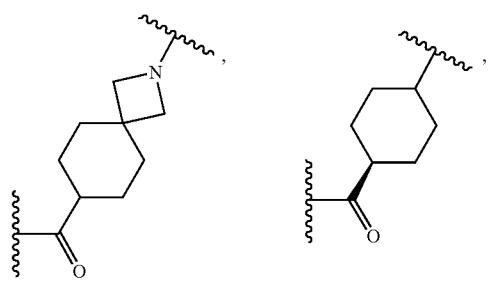
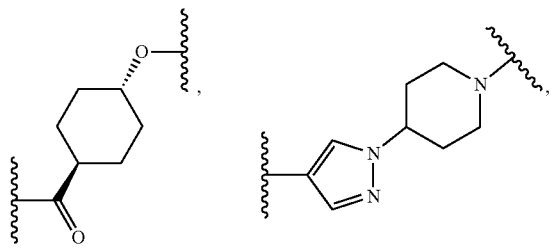
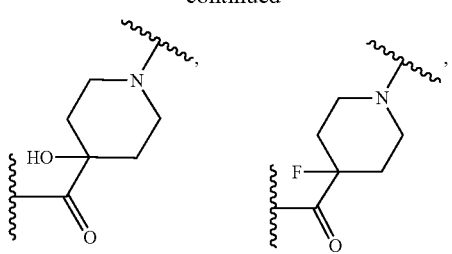
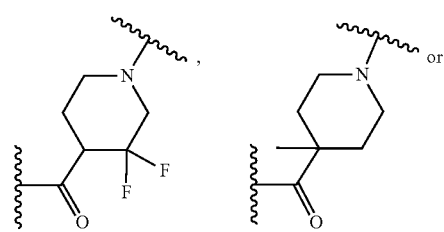
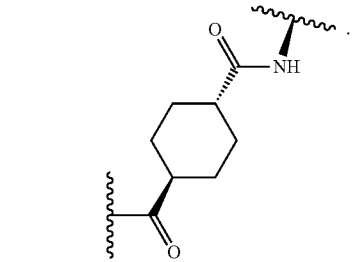
In a preferred embodiment, when $L_0$ is
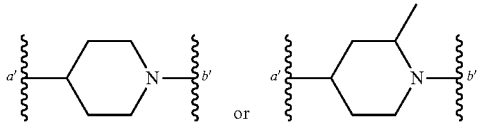
(Further, $L_0$ is a 5- to 12-membered heterocycloalkylene group that is unsubstituted or substituted by one or more $L_0^{-3}$), $L_2$ is
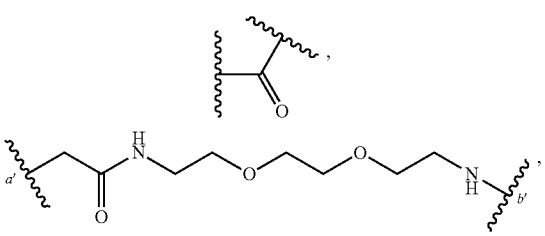
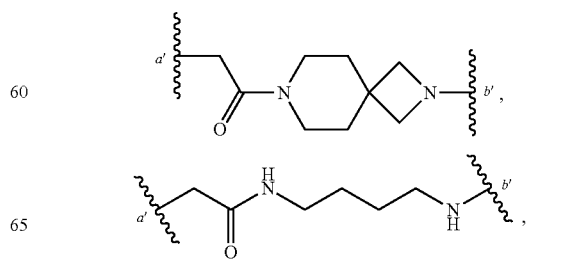

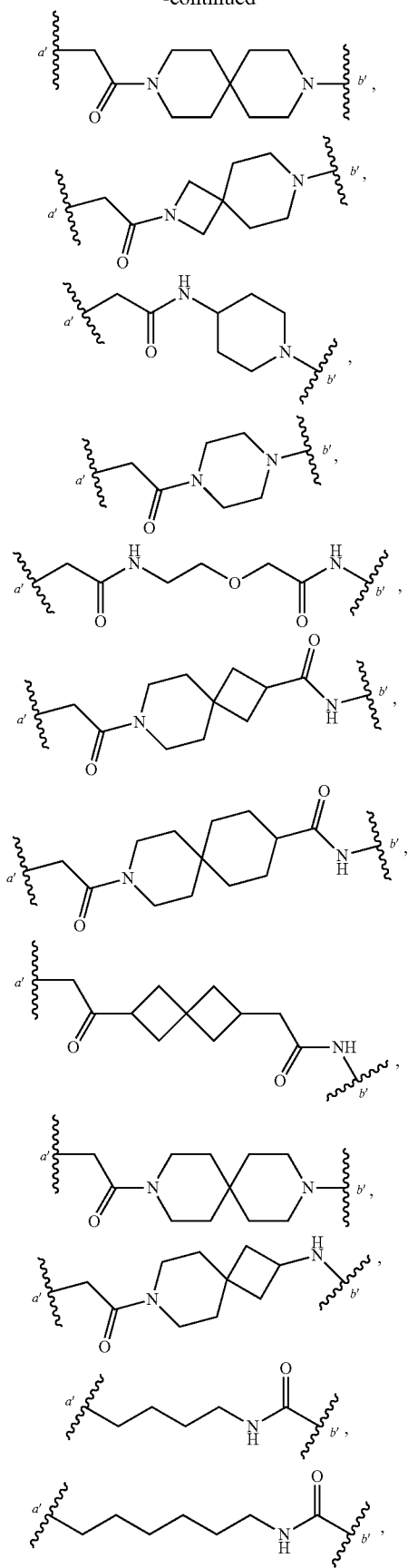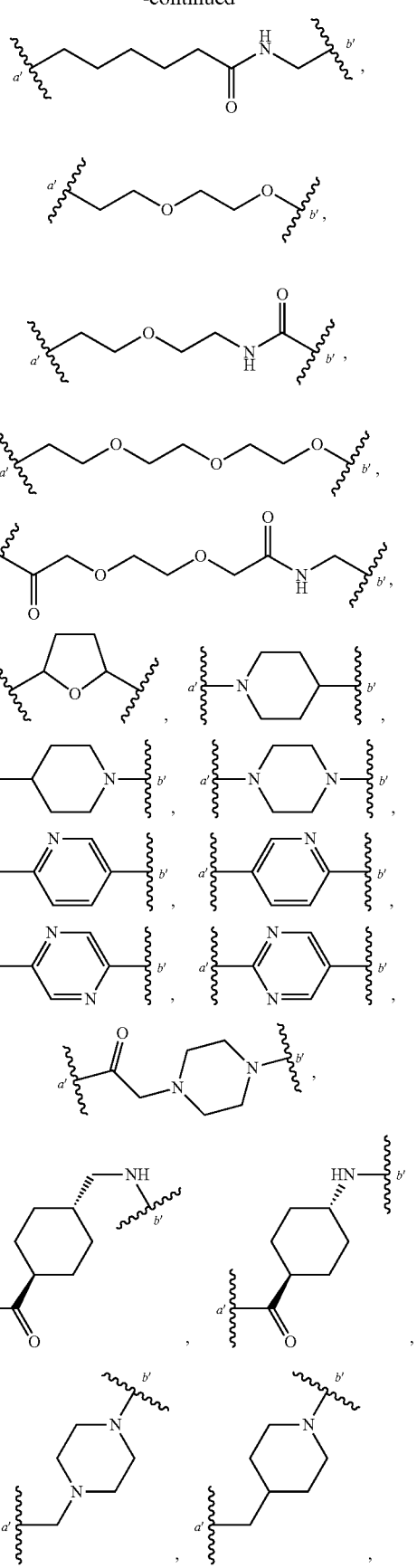

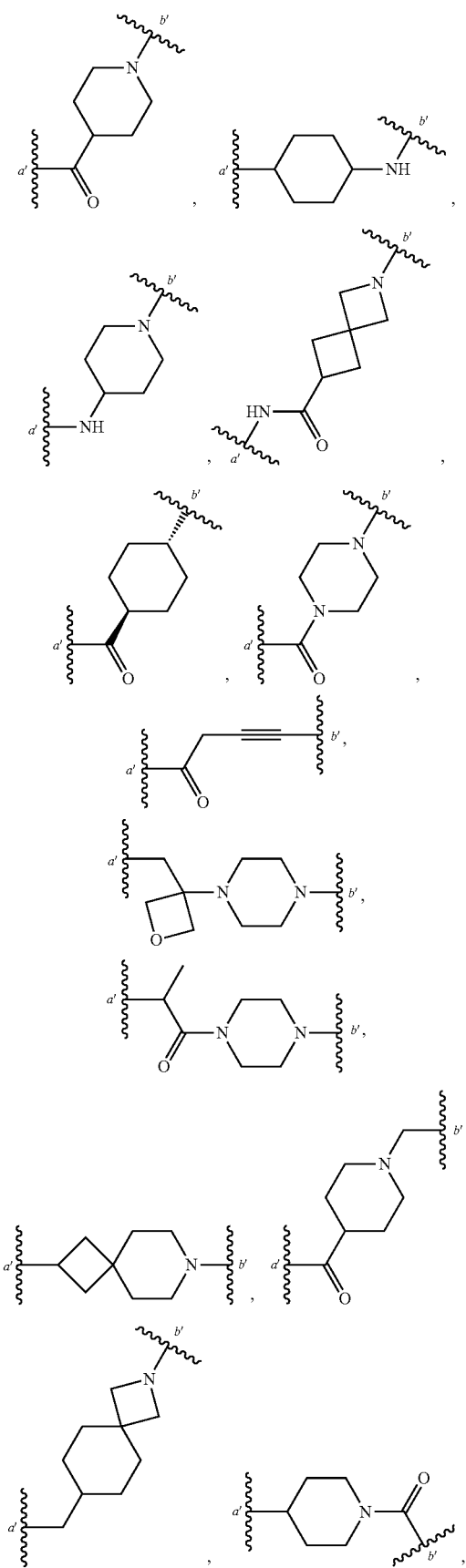
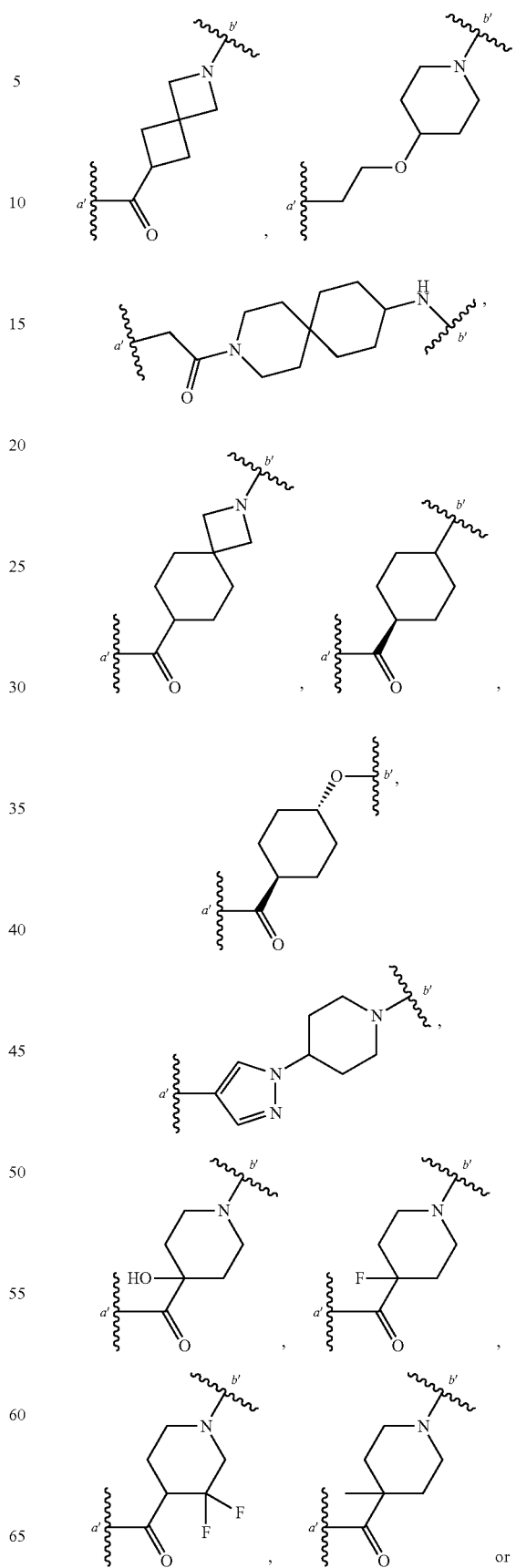

-continued

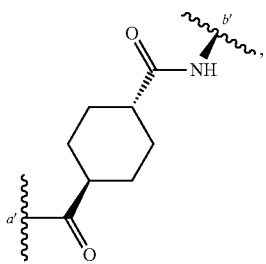

wherein the a' end of $L_2$ is connected to $L_0$, and the b' end of $L_2$ is connected to LLM.

In a preferred embodiment, when $R^1$ is

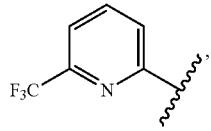

$L_0$ is

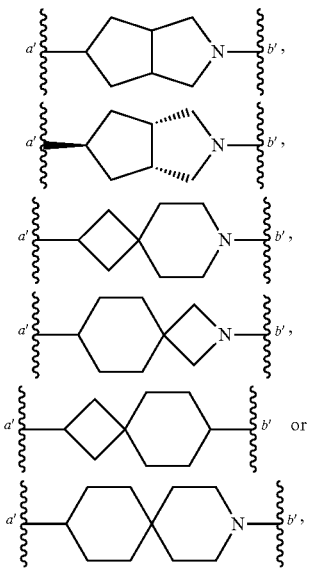

wherein the a' end is connected to ring Cy, and the b' end is connected to $L_2$.

In a preferred embodiment, when $R^1$ is

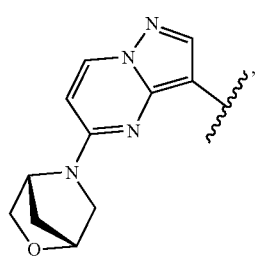 [SMILES: *c1cnn2ccc(N3C[C@H]4C[C@@H]3CO4)nc12]

$L_0$ is

wherein the a' end is connected to ring Cy, and the b' end is connected to $L_2$.

In a preferred embodiment, when $R^1$ is

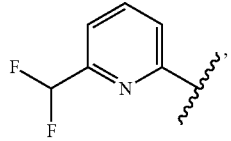 [SMILES: *c1cccc(C(F)F)n1]

$L_0$ is

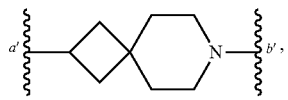

wherein the a' end is connected to ring Cy, and the b' end is connected to $L_2$.

In a preferred embodiment, when $R^1$ is

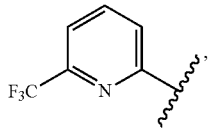

$L_2$- is

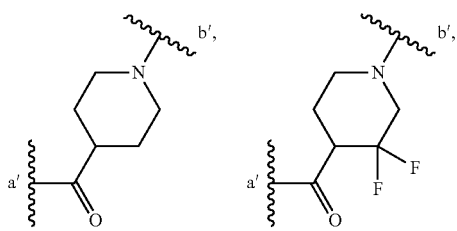

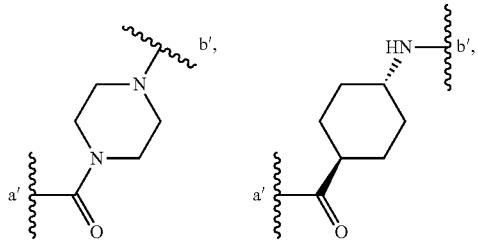

-continued

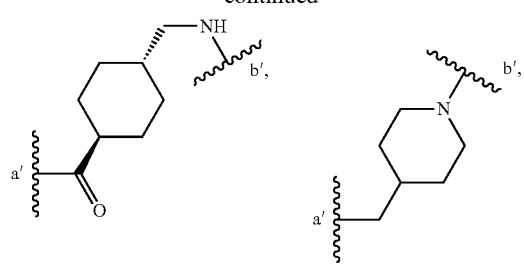

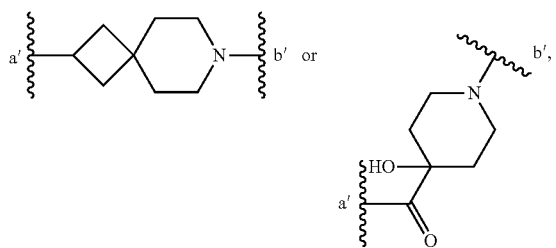

wherein the a' end of $L_2$ is connected to $L_0$, and the b' end of $L_2$ is connected to LLM.

In a preferred embodiment, when $R^1$ is

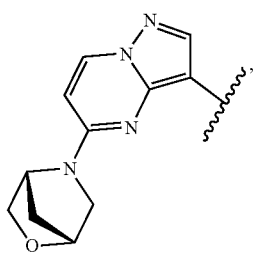 [SMILES: *c1cnn2ccc(N3C[C@H]4C[C@@H]3CO4)nc12]

$L_2$- is

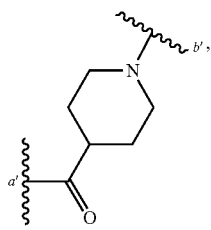 [SMILES: *C(=O)C1CCN(*)CC1]

wherein the a' end of $L_2$ is connected to $L_0$, and the b' end of $L_2$ is connected to LLM.

In a preferred embodiment, when $R^1$ is

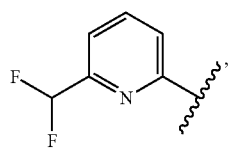 [SMILES: *c1cccc(C(F)F)n1]

$L_2$- is

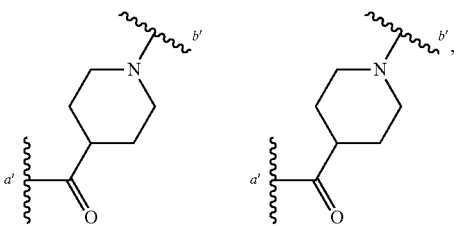 [SMILES: *C(=O)C1CCN(*)CC1 ; *C(=O)C1CCN(*)CC1]

wherein the a' end of $L_2$ is connected to $L_0$, and the b' end of $L_2$ is connected to LLM.

In a preferred embodiment, -$L_0$-$L_2$- is

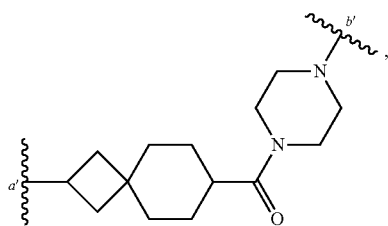

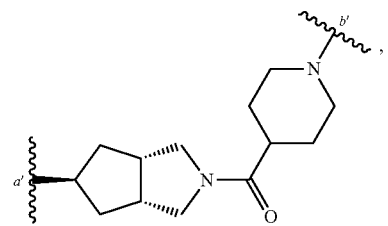

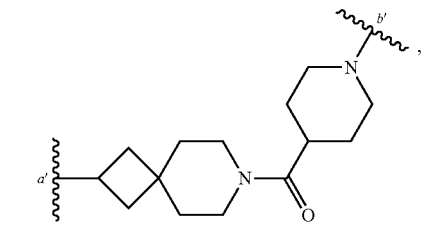

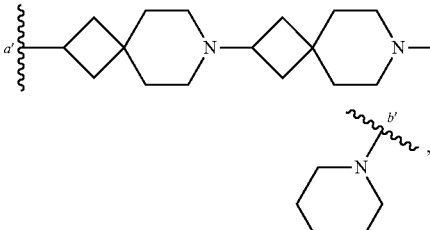

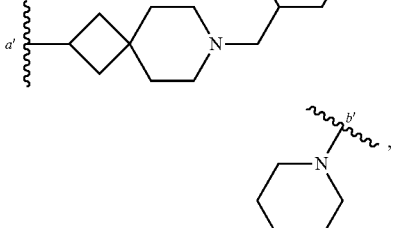

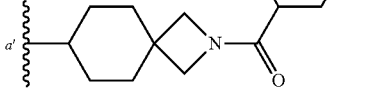

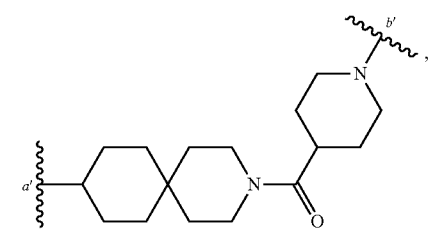
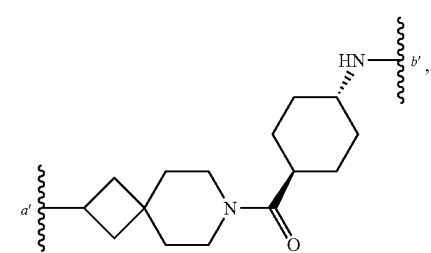
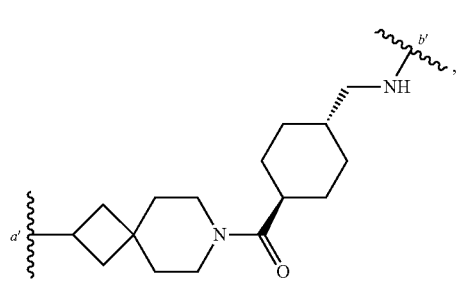
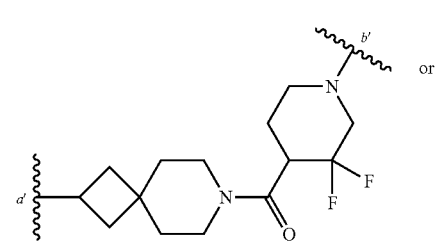
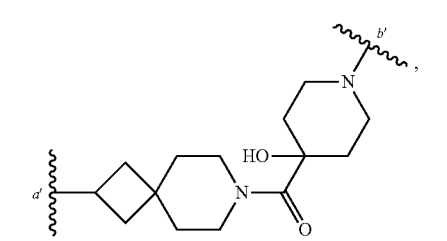
preferably
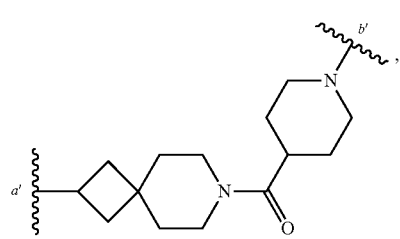
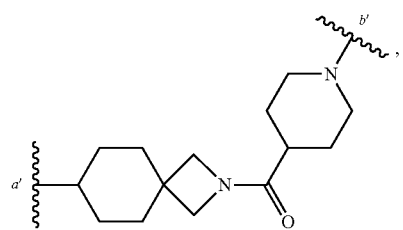
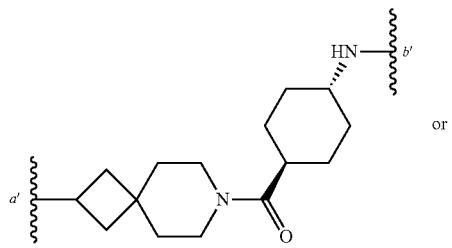
or
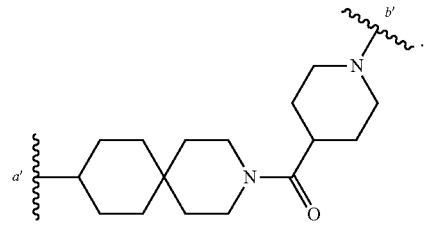
In a preferred embodiment, -$L_0$-$L_2$- is
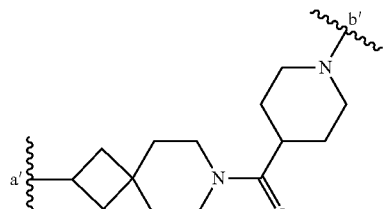
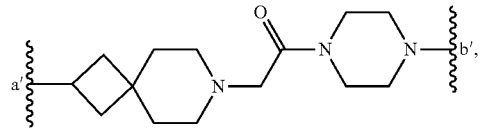
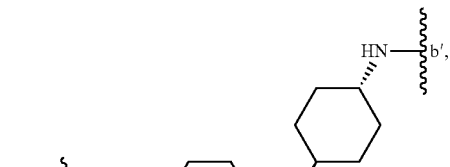
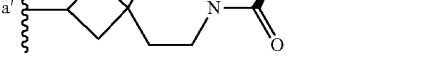
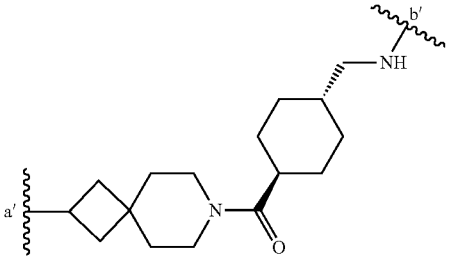

-continued
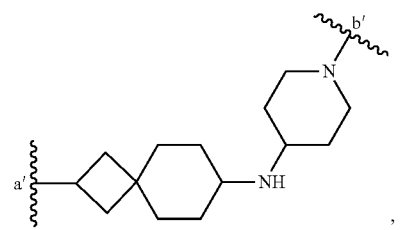
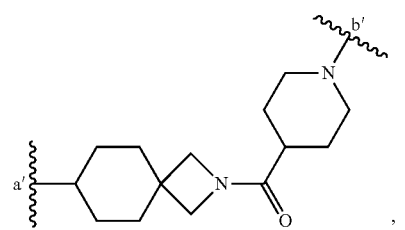
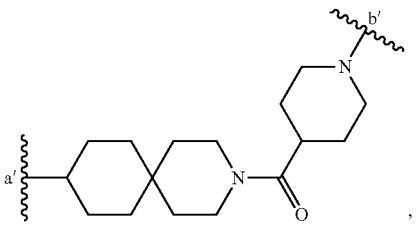
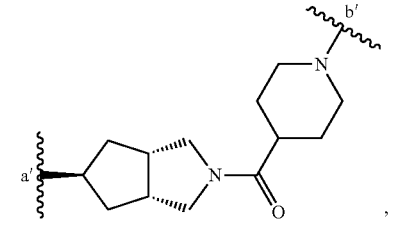
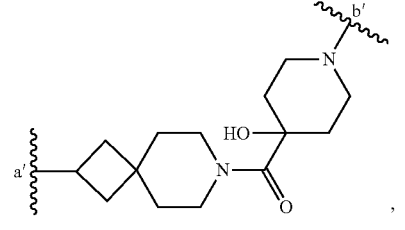
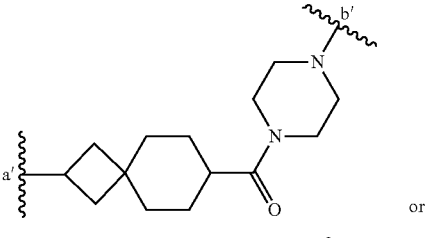
or
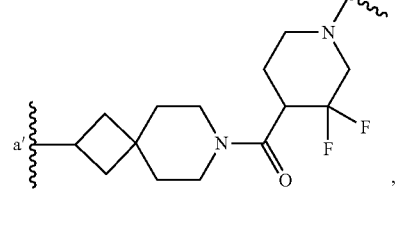
wherein the a' end is connected to ring Cy, and the b' end is connected to LLM.
In a preferred embodiment, when
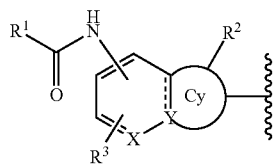
is
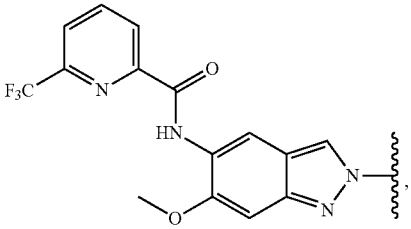 [SMILES: *n1cc2cc(NC(=O)c3cccc(C(F)(F)F)n3)c(OC)cc2n1]
-L₀-L₂- is
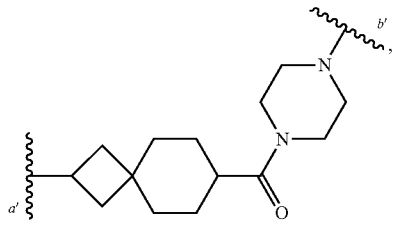
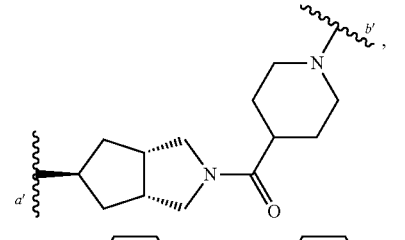
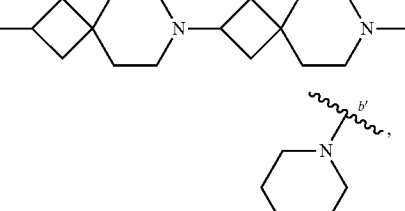
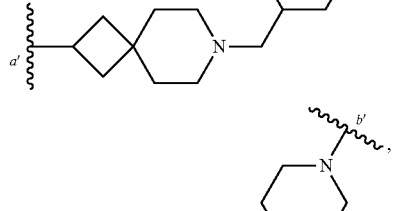
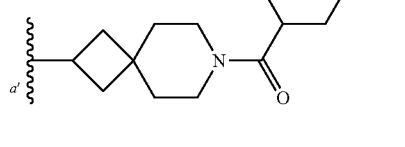

-continued
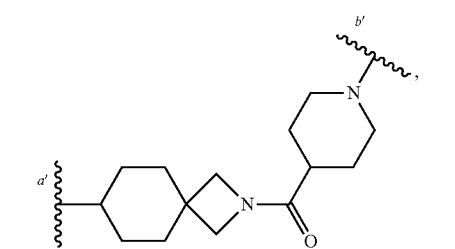
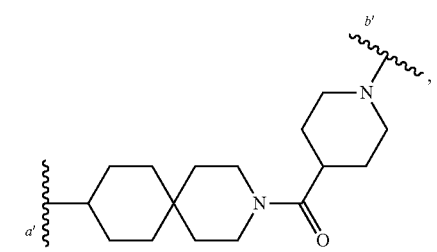
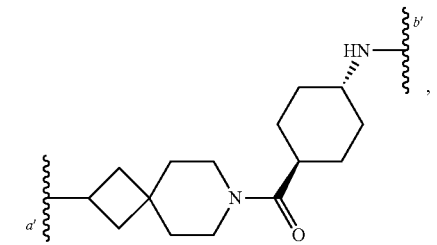
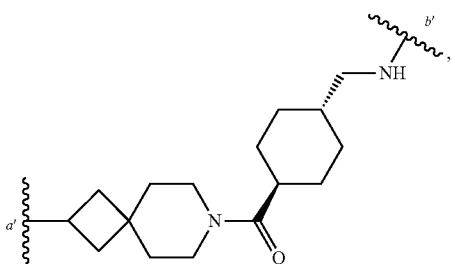
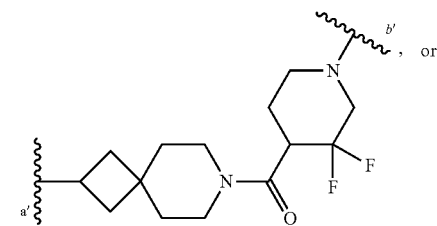
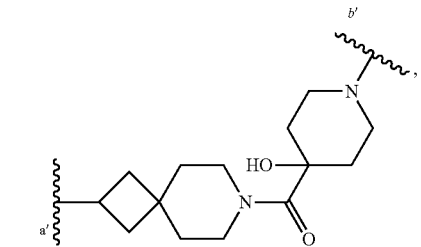
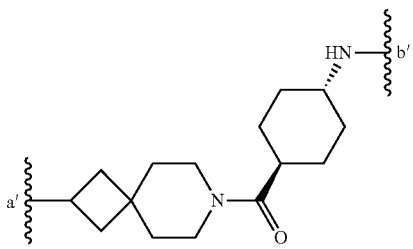
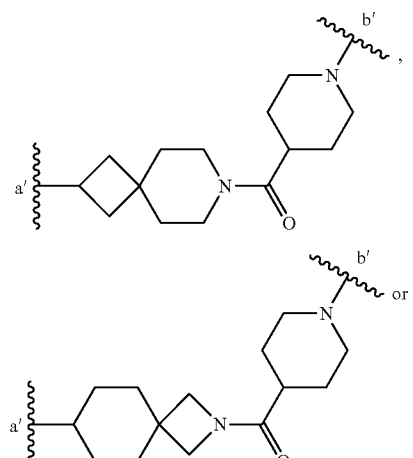
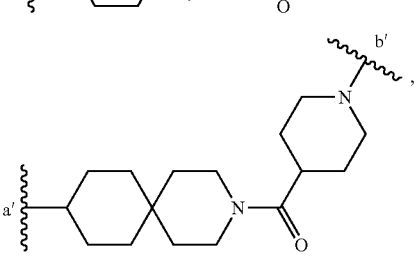
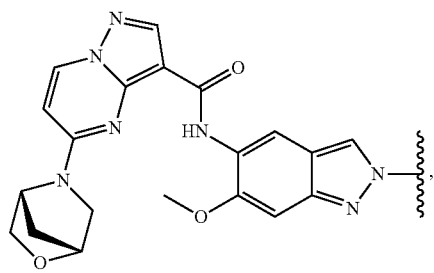 [SMILES: *n1cc2cc(NC(=O)c3cnn4ccc(N5C[C@H]6C[C@@H]5CO6)nc34)c(OC)cc2n1]
wherein the a' end is connected to ring Cy, and the b' end is connected to LLM.
In a preferred embodiment, when
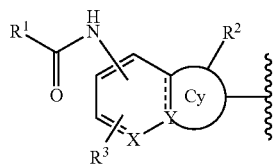
is
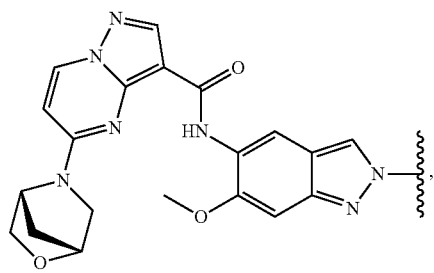 [SMILES: *n1cc2cc(NC(=O)c3cnn4ccc(N5C[C@H]6C[C@@H]5CO6)nc34)c(OC)cc2n1]
wherein the a' end is connected to ring Cy, and the b' end is connected to LLM; preferably -L$_0$-L$_2$- is

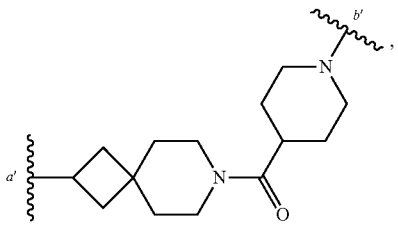 [SMILES: *C1CC2(CCN(C(=O)C3CCN(*)CC3)CC2)C1]

wherein the a' end is connected to ring Cy, and the b' end is connected to LLM.

In a preferred embodiment, when

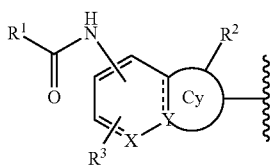

is

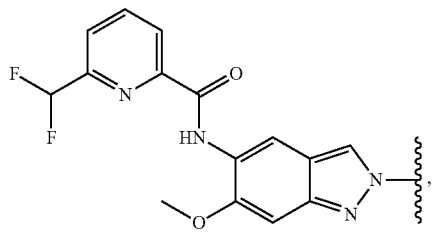 [SMILES: *n1cc2cc(NC(=O)c3cccc(C(F)F)n3)c(OC)cc2n1]

-L$_0$-L$_2$- is

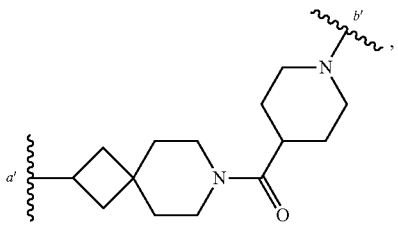 [SMILES: *C1CC2(CCN(C(=O)C3CCN(*)CC3)CC2)C1]

wherein the a' end is connected to ring Cy, and the b' end is connected to LLM.

In a preferred embodiment, the compound of formula I is a compound of formula I-d,

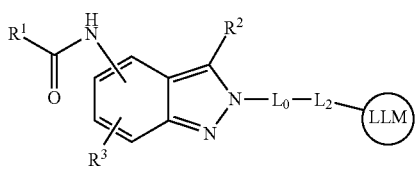

I-d

Wherein R$^1$ is pyridyl substituted by one or more R$^{1-1}$, or

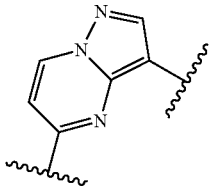 [SMILES: *c1ccn2ncc(*)c2n1]

substituted by one or more R$^{1-1}$;

When R$^1$ is pyridyl substituted by one or more R$^{1-1}$, each R$^{1-1}$ is independently a C$_1$-C$_6$ alkyl substituted by one or more R$^{1-1-4}$;

When R$^1$ is

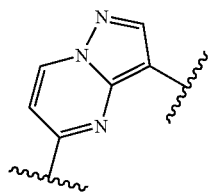 [SMILES: *c1ccn2ncc(*)c2n1]

substituted by one or more R$^{1-1}$, each R$^{1-1}$ is independently a 7- to 8-membered heterocycloalkyl that is unsubstituted or substituted by one or more R$^{1-1-1}$; the heteroatom of the 7- to 8-membered heterocycloalkyl is selected from N or O, and the number of the heteroatom is 2;

Each R$^{1-1-4}$ is independently halogen; each R$^{1-1-1}$ is independently a C$_1$-C$_6$ alkyl substituted by one or more halogens;

R$^2$ is hydrogen;

R$^3$ is a C$_1$-C$_6$ alkyl that is unsubstituted or substituted by one or more R$^{3-4}$ or a C$_1$-C$_6$ alkoxy that is unsubstituted or substituted by one or more R$^{3-7}$;

Each R$^{3-4}$ is independently deuterium, halogen or hydroxyl; and each R$^{3-7}$ is independently deuterium;

L$_0$ is a 9- to 11-membered heterospirylene group; the heteroatom of the 9- to 11-membered heterospirylene group is N, and the number of heteroatoms is 1;

L$_2$ is -L$_2^{-1}$-L$_2^{-2}$-L$_2^{-3}$-L$_2^{-4}$- or

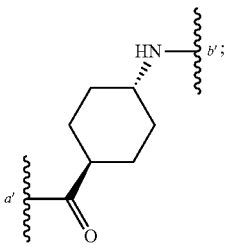 [SMILES: *N[C@H]1CC[C@H](C(*)=O)CC1]

L$_2^{-1}$ is

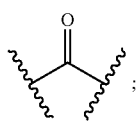

$L_2^{-2}$, $L_2^{-3}$ and $L_2^{-4}$ are independently absent,

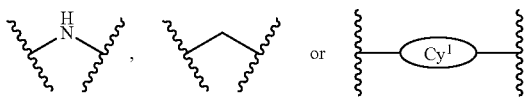

that is unsubstituted or substituted by one or more $L_2^{1-2}$, ring $Cy^1$ is a 4- to 6-membered heterocycle, the heteroatom of the 4- to 6-membered heterocycle is N, and the number of heteroatoms is 1; the 4- to 6-membered heterocycle is a monocyclic ring; and each $L_2^{1-2}$ is independently hydroxyl; LLM is

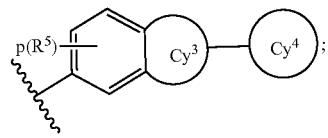

Ring $Cy^3$ is a 5- to 6-membered heterocycle that is unsubstituted or substituted by one or more $Cy^{3-1}$, the heteroatoms of the 5- to 6-membered heterocycle are selected from one or more of N, S and O, and the number of heteroatoms is 1; $Cy^{3-1}$ is independently oxo;

Ring $Cy^4$ is a 5- to 8-membered heterocycloalkyl that is unsubstituted or substituted by one or more $Cy^{4-1}$, the heteroatom of the 5- to 8-membered heterocycloalkyl is N, S or O, and the number of heteroatoms is 1; $Cy^{4-1}$ is independently oxo;

Each $R^5$ is independently halogen;

p is 0, 1, 2 or 3.

In a preferred embodiment, $R^1$ is pyridyl substituted by one or more $R^{1-1}$, or

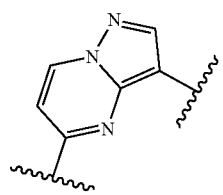 [SMILES: *c1ccn2ncc(*)c2n1]

substituted by one or more $R^{1-1}$.

In a preferred embodiment, when $R^1$ is pyridyl substituted by one or more $R^{1-1}$, each $R^{1-1}$ is independently a $C_1$-$C_6$ alkyl substituted by one or more $R^{1-1-4}$.

In a preferred embodiment, when $R^1$ is

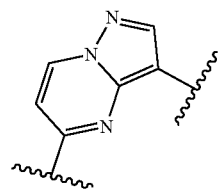 [SMILES: *c1ccn2ncc(*)c2n1]

substituted by one or more $R^{1-1}$, each $R^{1-1}$ is independently a 7- to 8-membered heterocycloalkyl that is unsubstituted or substituted by one or more $R^{1-1-1}$; the heteroatom of the 7- to 8-membered heterocycloalkyl is selected from N or O, and the number of the heteroatom is 2.

In a preferred embodiment, each $R^{1-1-4}$ is independently fluorine, chlorine or bromine, preferably fluorine.

In a preferred embodiment, when $R^{1-1}$ is independently a $C_1$-$C_6$ alkyl substituted by more $R^{1-1-4}$; the more is 2 or 3, preferably 3.

In a preferred embodiment, each $R^{1-1-1}$ is independently a $C_1$-$C_6$ alkyl substituted by one or more halogens.

In a preferred embodiment, $R^3$ is a $C_1$-$C_6$ alkyl that is unsubstituted or substituted by one or more $R^{3-4}$ or a $C_1$-$C_6$ alkoxy that is unsubstituted or substituted by one or more $R^{3-7}$.

In a preferred embodiment, each $R^{3-4}$ is independently deuterium, halogen or hydroxyl.

In a preferred embodiment, each $R^{3-7}$ is independently deuterium.

In a preferred embodiment, $L_0$ is a 9- to 11-membered heterospirylene group; the heteroatom of the 9- to 11-membered heterospirylene group is N, and the number of heteroatoms is 1.

In a preferred embodiment, $L_2$ is -$L_2^{-1}$-$L_2^{-2}$-$L_2^{-3}$-$L_2^{-4}$- or

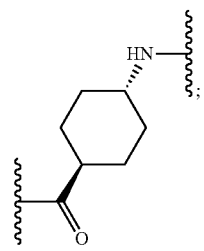 [SMILES: *N[C@H]1CC[C@H](C(*)=O)CC1]

$L_2^{-1}$ is

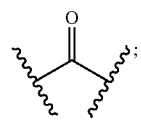 [SMILES: *C(*)=O]

$L_2^{-2}$, $L_2^{-3}$ and $L_2^{-4}$ are independently absent,

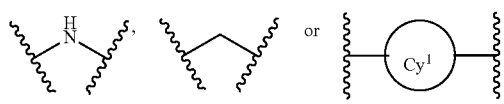

that is unsubstituted or substituted by one or more $L_2^{1-2}$, ring $Cy^1$ is a 4- to 6-membered heterocycle, the heteroatom of the 4- to 6-membered heterocycle is N, and the number of heteroatoms is 1; the 4- to 6-membered heterocycle is a monocyclic ring.

In a preferred embodiment, each $L_2^{1-2}$ is independently hydroxyl.

In a preferred embodiment, the compound of formula I is a compound of formula I-d,

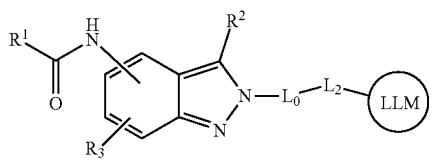

I-d

Wherein $R^1$ is a 5- to 9-membered heteroaryl that is unsubstituted or substituted by one or more $R^{1-1}$, the heteroatom of the 5- to 9-membered heteroaryl is one or two of N and O, and the number of heteroatoms is 1, 2 or 3;

Each $R^{1-1}$ is a $C_1$-$C_6$ alkyl that is unsubstituted or substituted by one or more $R^{1-1-4}$, a 3- to 11-membered heterocycloalkyl that is unsubstituted or substituted by one or more $R^{1-1-1}$ or a 5- to 10-membered heteroaryl group that is unsubstituted or substituted by one or more $R^{1-1-7}$; the heteroatoms of the 5- to 10-membered heteroaryl are selected from one or two of N, S and O, and the number of heteroatoms is 1 or 2; the heteroatoms of the 3 to 11-membered heterocycloalkyl are selected from one or two of N, S and O, and the number of heteroatoms is 1 or 2;

Each $R^{1-1-1}$, $R^{1-1-4}$ and $R^{1-1-7}$ are independently halogen or $C_1$-$C_6$ alkyl unsubstituted or substituted by one or more halogens;

$R^3$ is a $C_1$-$C_6$ alkyl that is unsubstituted or substituted by one or more $R^{3-4}$ or $C_1$-$C_6$ alkoxy that is unsubstituted or substituted by one or more $R^{3-7}$ or tetrahydropyrrolyl that is unsubstituted or substituted by one or more $R^{3-1}$;

Each $R^{3-1}$ is independently deuterium, halogen or hydroxyl, each $R^{3-4}$ is independently deuterium, halogen or hydroxyl, and each $R^{3-7}$ is independently deuterium or hydroxyl;

$L_0$ is an 8- to 11-membered cycloalkylene group or an 8- to 11-membered heterocycloalkylene group; the 8- to 11-membered cycloalkylene group is a spiro ring; the 8- to 11-membered heterocycloalkylene group is a spiro ring or a fused ring; the heteroatom of the 8- to 11-membered heterocycloalkylene group is N, and the number of heteroatoms is 1.

$L_2$ is one of the following situations:
Situation (1): $L_2$ is -$L_2^{-1}$-$L_2^{-2}$-$L_2^{-3}$-$L_2^{-4}$-; $L_2^{-1}$ and $L_2^{-2}$ are absent; $L_2^{-3}$ is

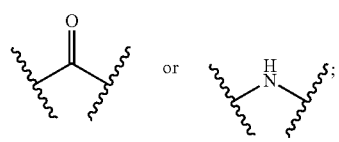

$L_2^{-4}$ is ring $Cy^1$ that is unsubstituted or substituted by one or more $L_2^{1-2}$, the ring $Cy^1$ is piperidinyl or piperazinyl; each $L_2^{1-2}$ is independently halogen or hydroxyl;

Situation (2): $L_2$ is -$L_2^{-1}$-$L_2^{-2}$-$L_2^{-3}$-$L_2^{-4}$-; $L_2^{-1}$ is absent; $L_2^{-2}$, $L_2^{-3}$ and $L_2^{-4}$ independently are

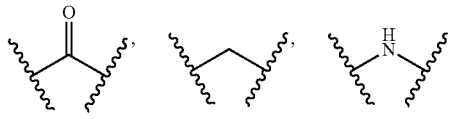

or ring $Cy^1$ that is unsubstituted or substituted by one or more $L_2^{1-2}$, the ring $Cy^1$ is cyclohexyl, piperidinyl or piperazinyl; each $L_2^{1-2}$ is independently halogen or hydroxyl;

Situation (3): $L_2$ is -$L_2^{-1}$-$L_2^{-2}$-$L_2^{-3}$-$L_2^{-4}$-; $L_2^{-1}$, $L_2^{-2}$, $L_2^{-3}$ and $L_2^{-4}$ independently are

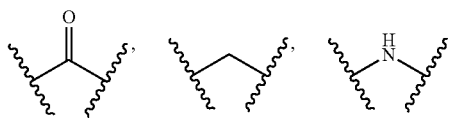

or ring $Cy^1$ that is unsubstituted or substituted by one or more $L_2^{1-2}$, the ring $Cy^1$ is cyclohexyl, piperidinyl or piperazinyl; each $L_2^{1-2}$ is independently halogen or hydroxyl;

LLM is

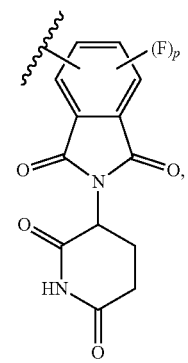

wherein p is 0 or 1.

In a preferred embodiment, the compound of Formula I is any of the following compounds:

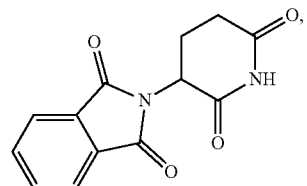
I-1
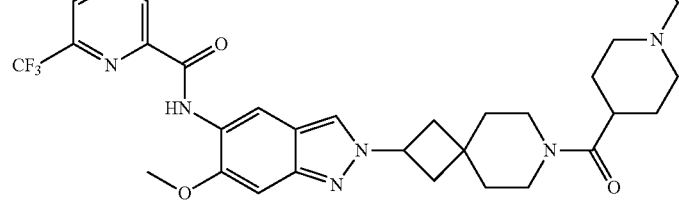
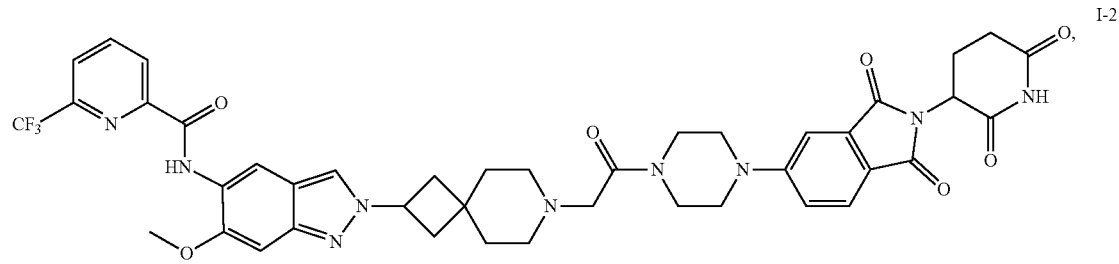
I-2
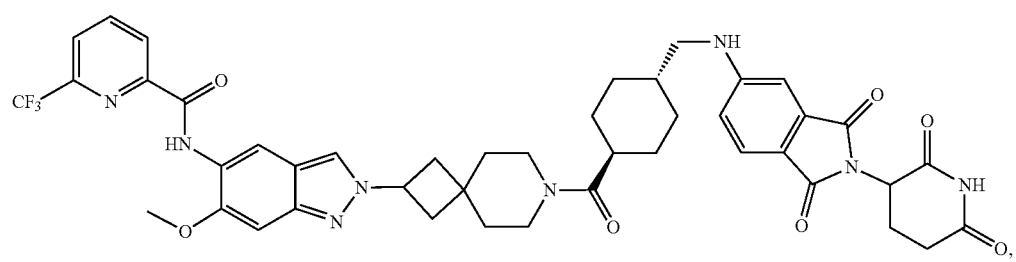
I-3
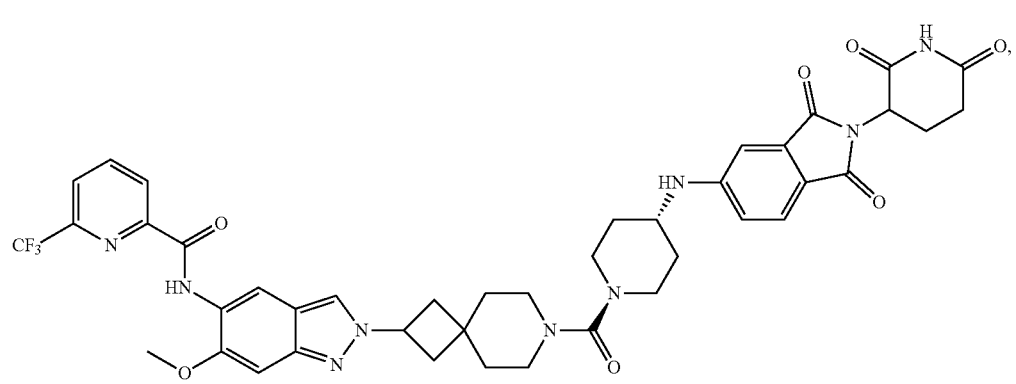
I-4

-continued
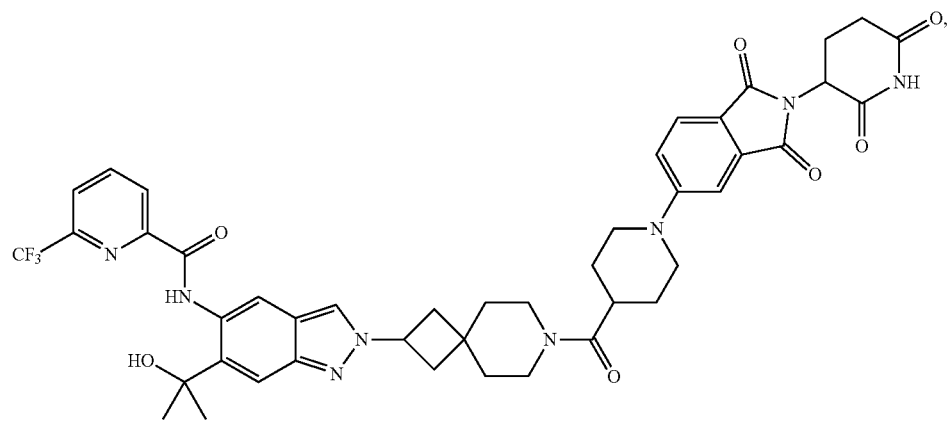
I-5
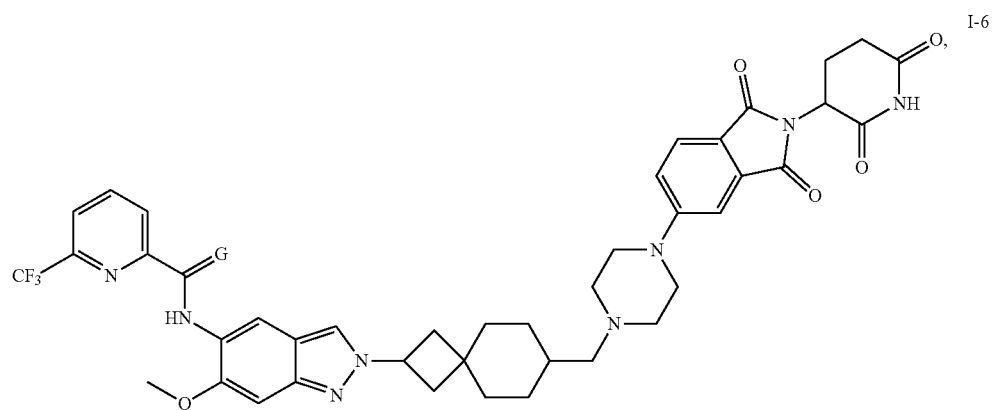
I-6
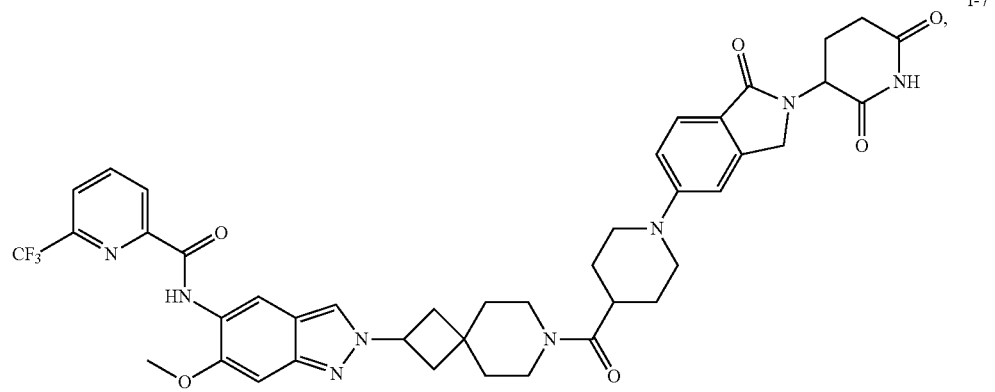
I-7
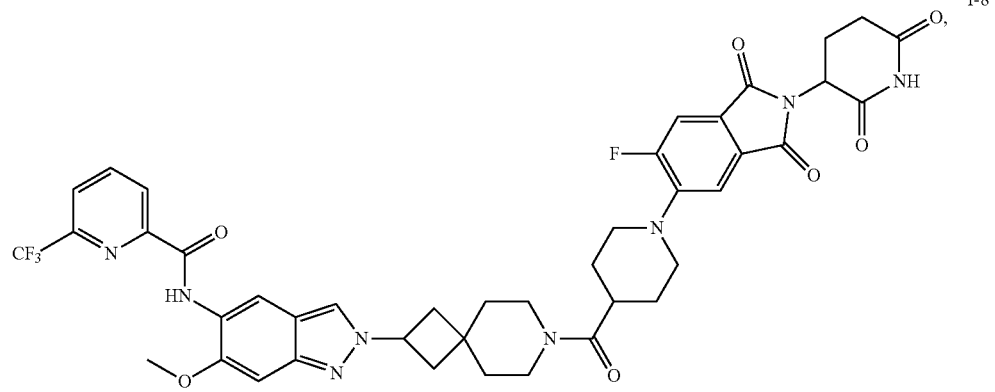
I-8

-continued
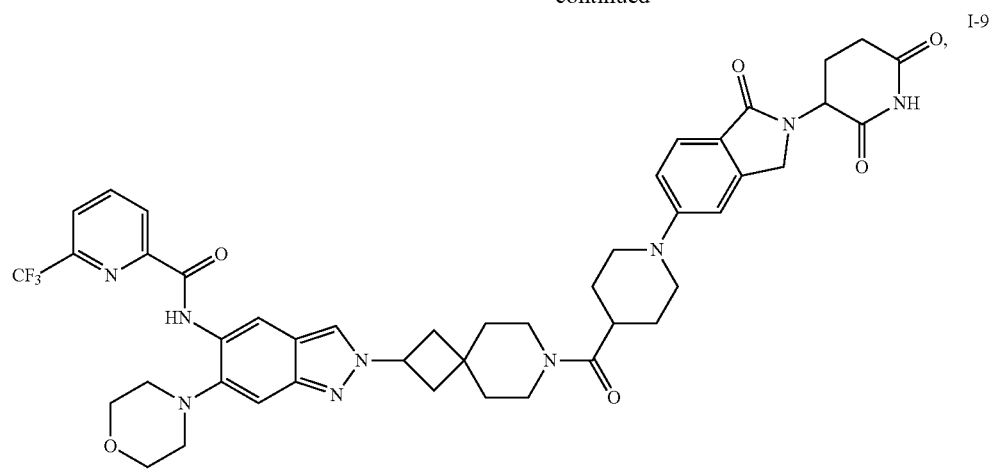
I-9
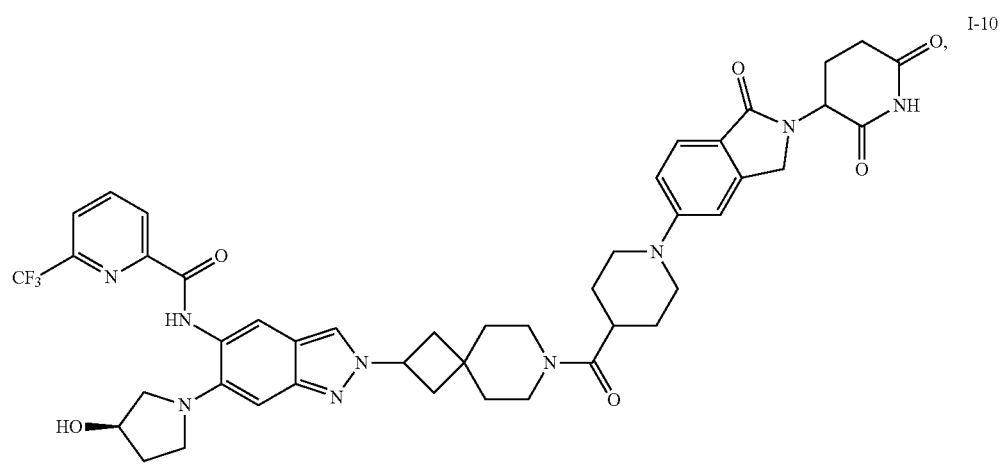
I-10
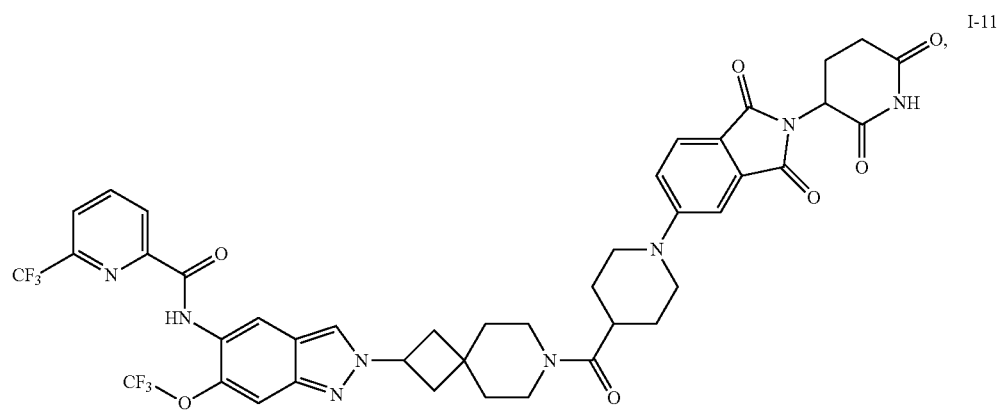
I-11

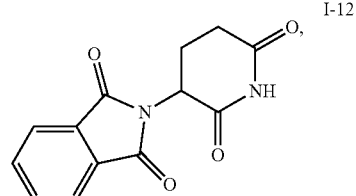
I-12
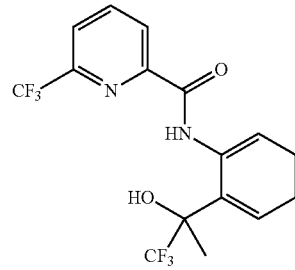
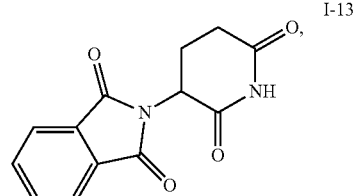
I-13
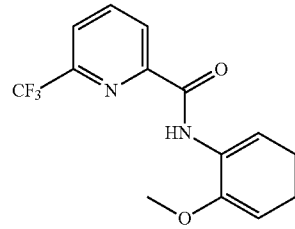
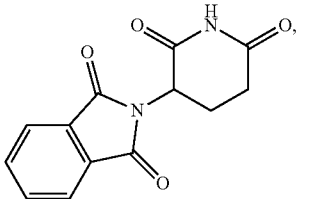
I-14
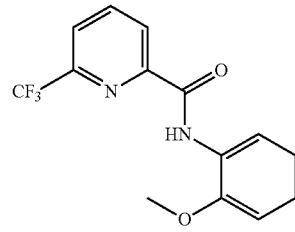
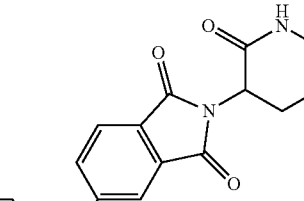
I-15
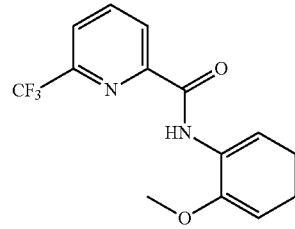

I-16
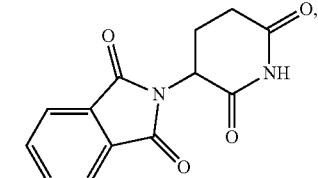
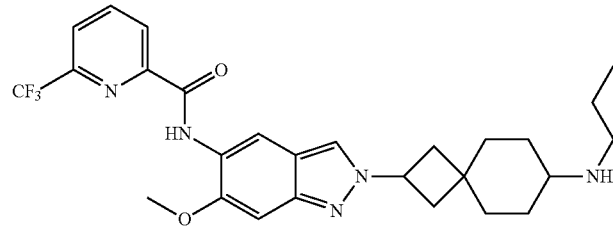
I-17
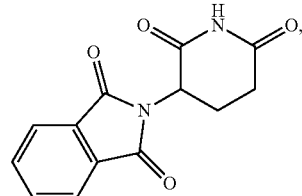
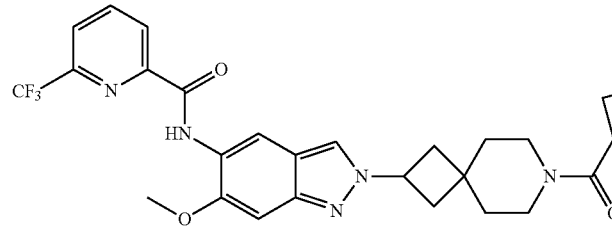
I-18
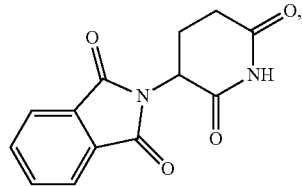
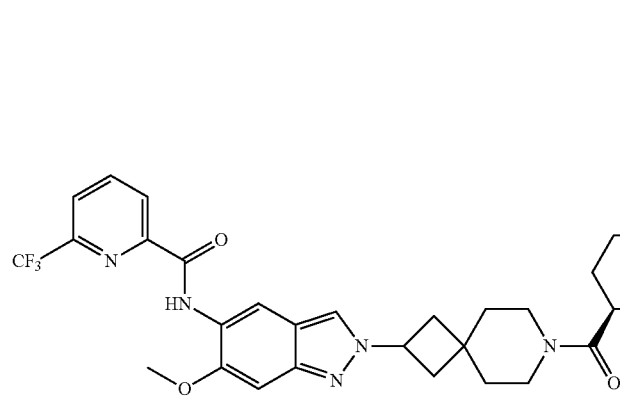
I-19
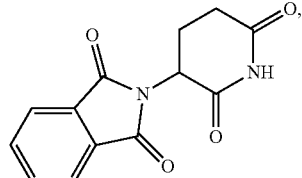
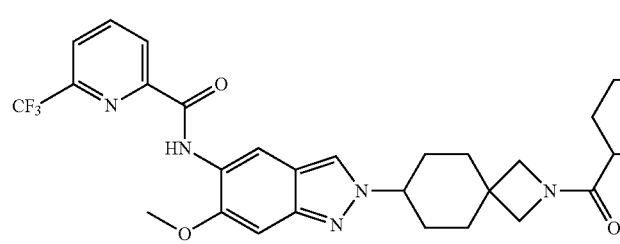

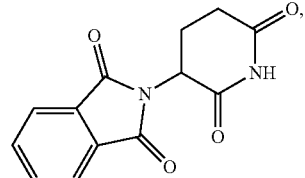
I-20
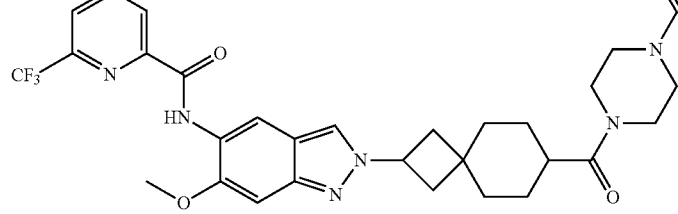
I-21
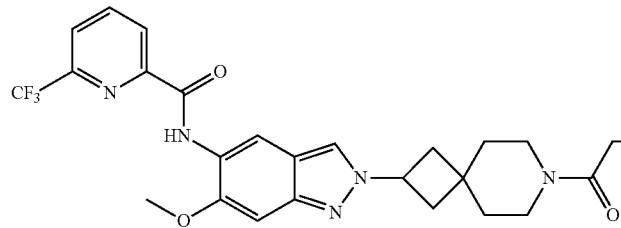
I-22
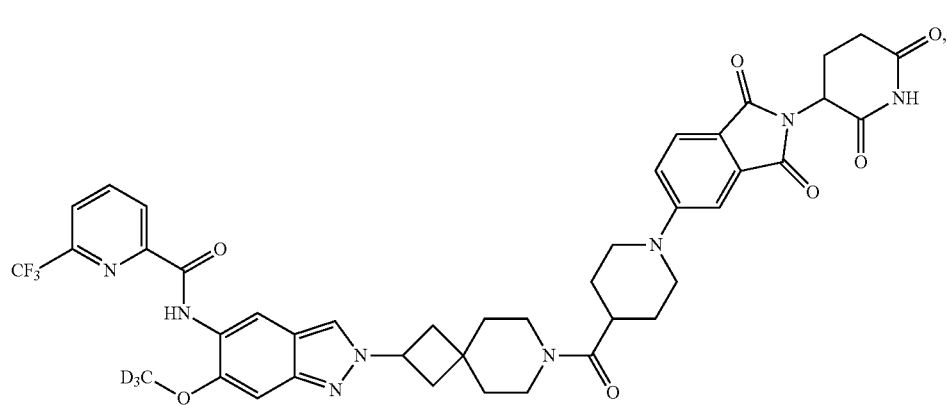
I-23
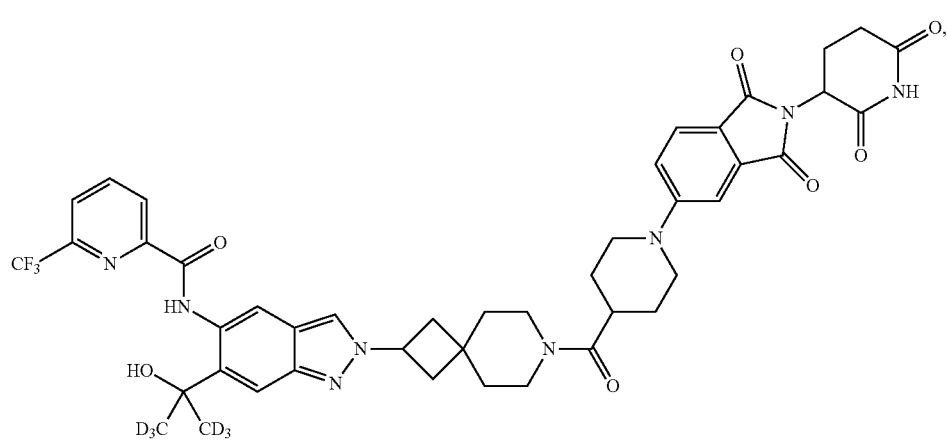

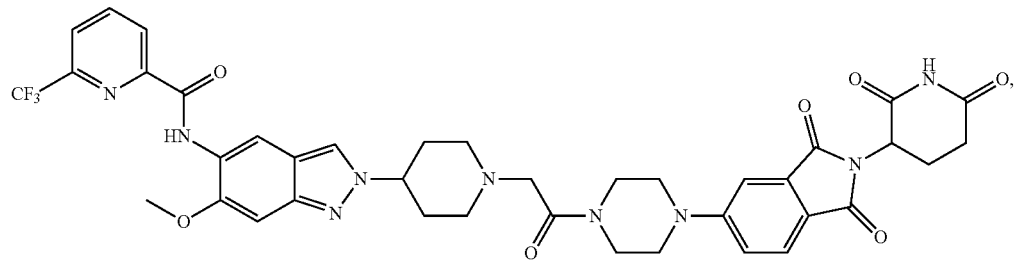
II-1
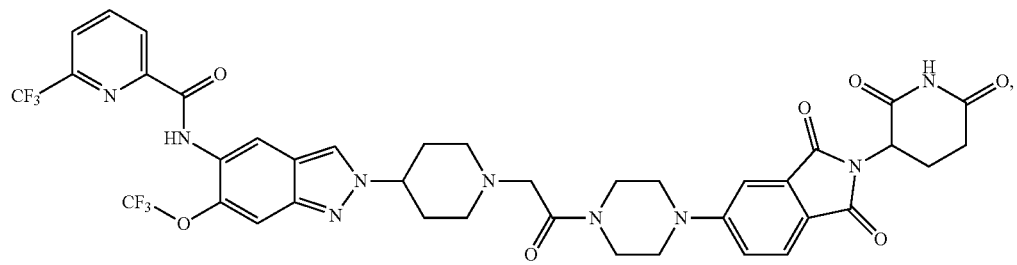
II-2
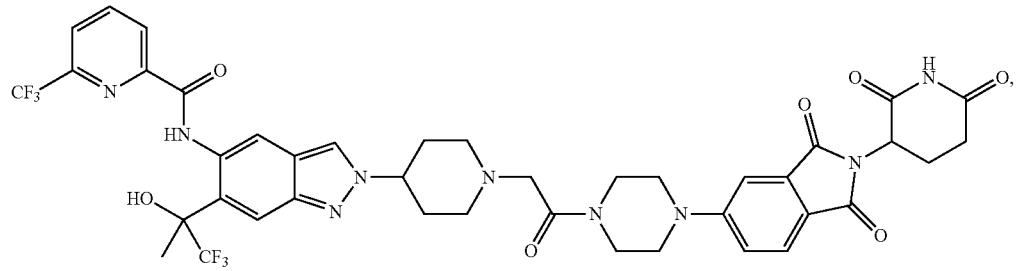
II-3
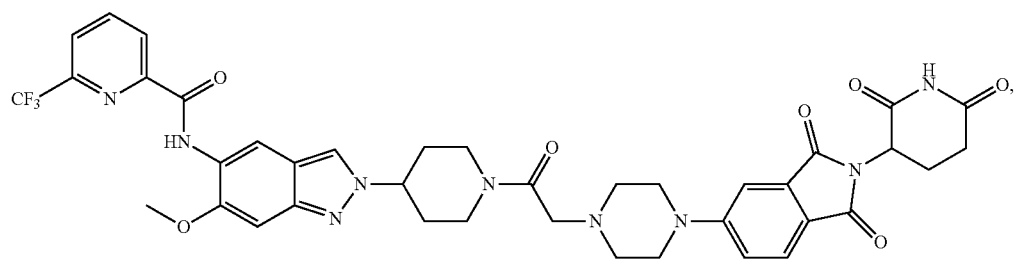
II-4
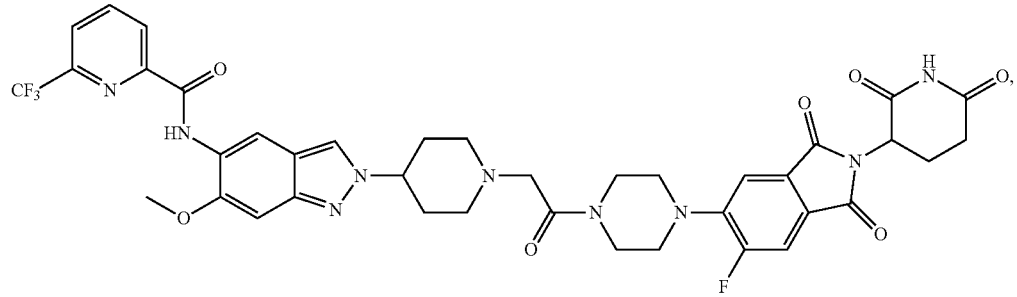
II-5

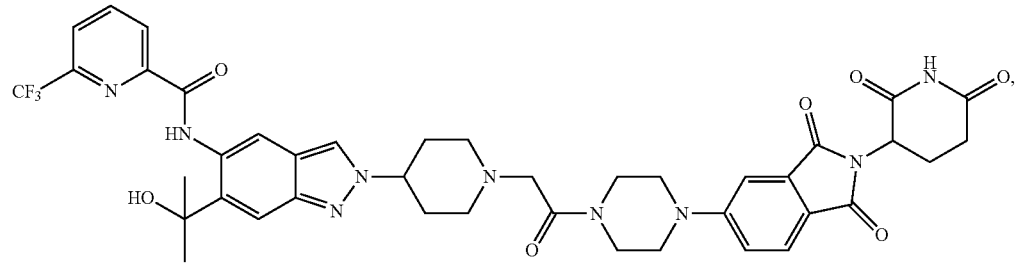
II-6
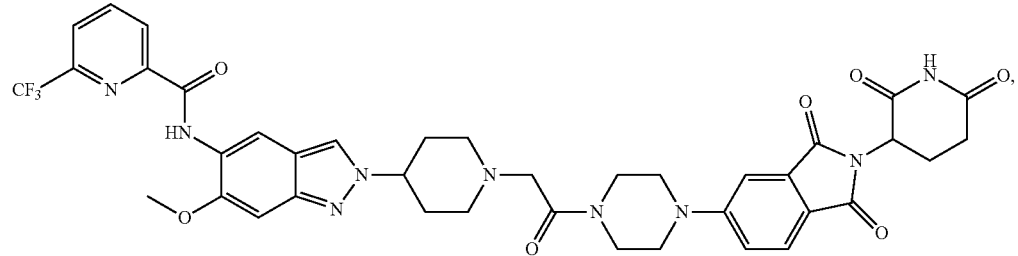
II-7
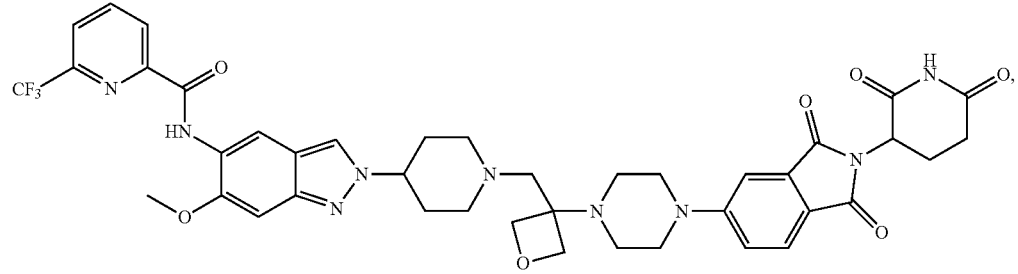
II-8
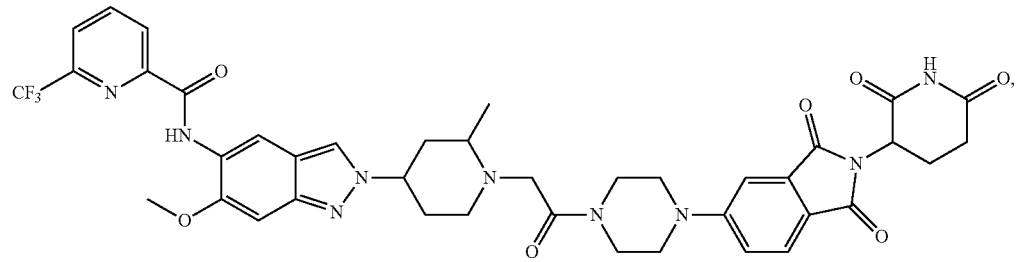
II-9
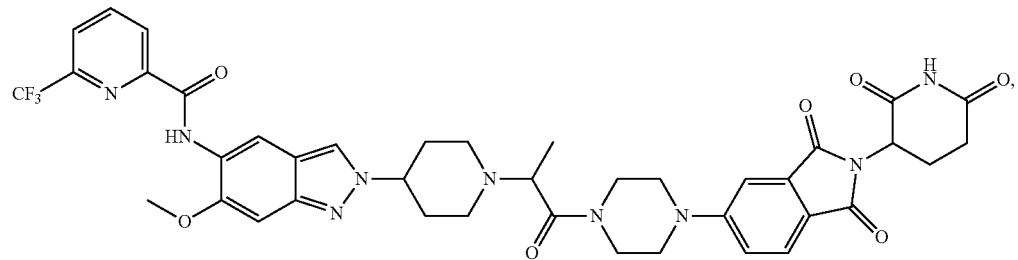
II-10

-continued
II-11
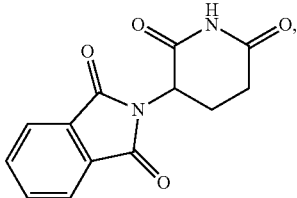
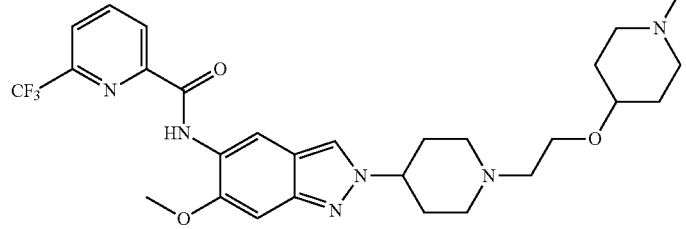
II-12
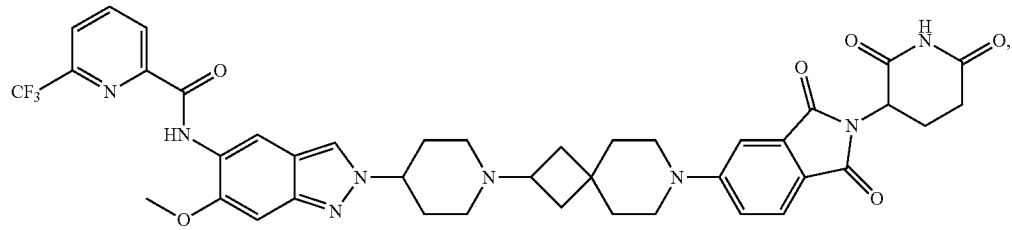
II-13
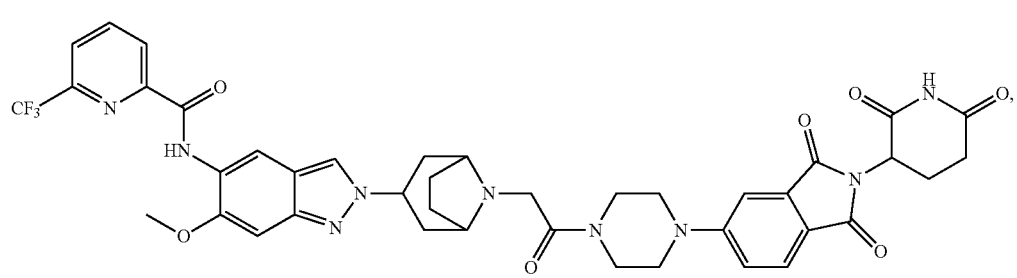
II-14
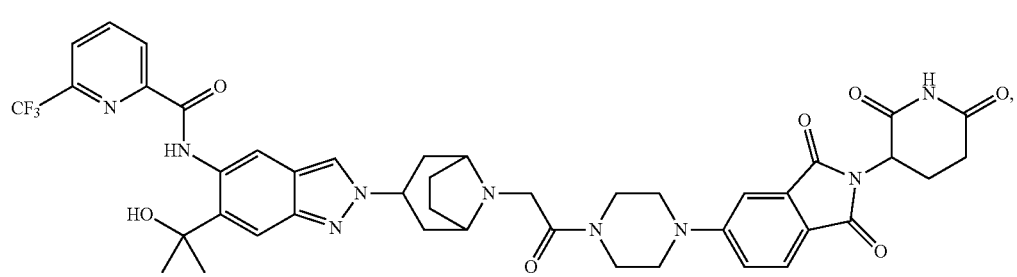

-continued
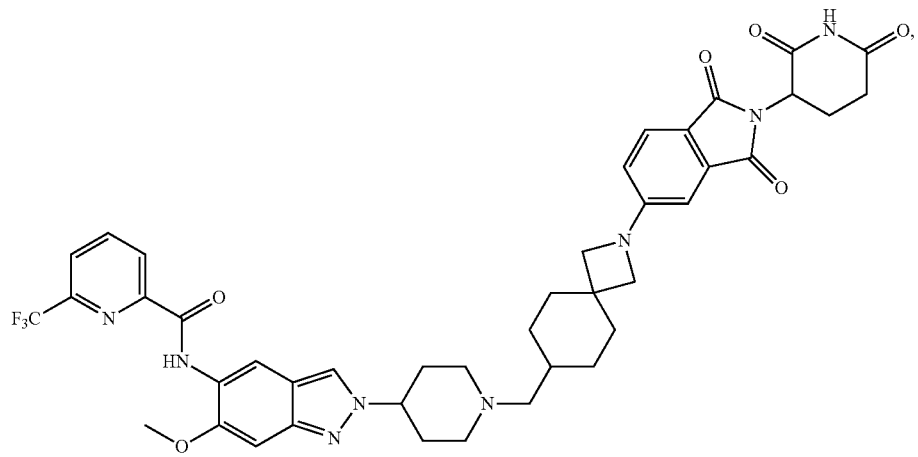
II-15
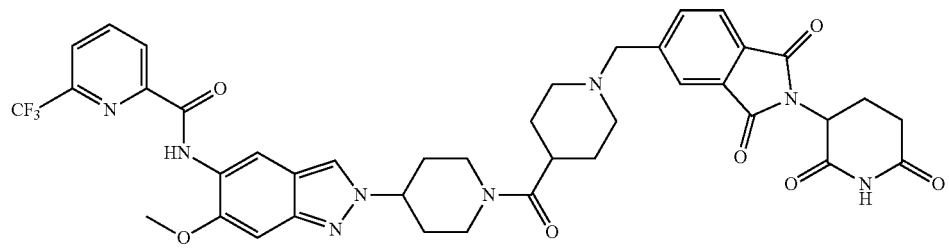
II-16
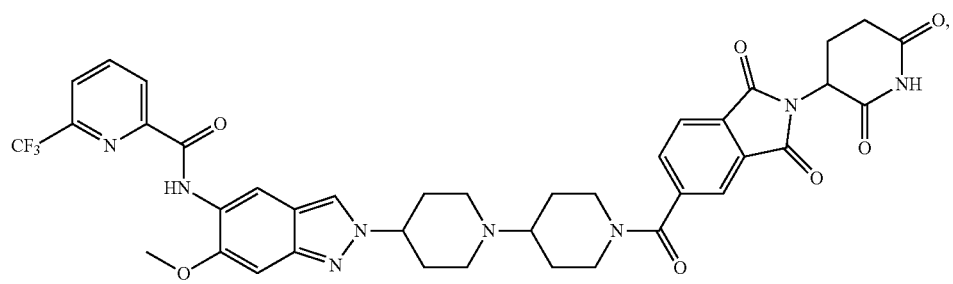
II-17
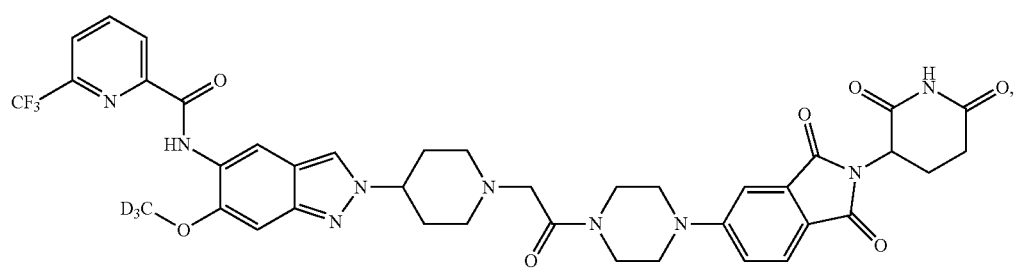
II-18
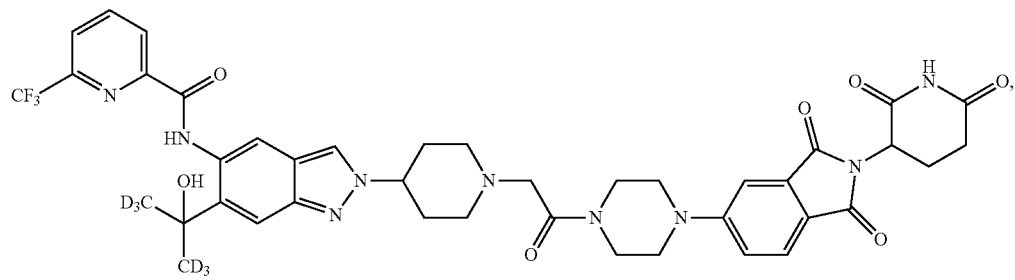
II-19

-continued
II-20
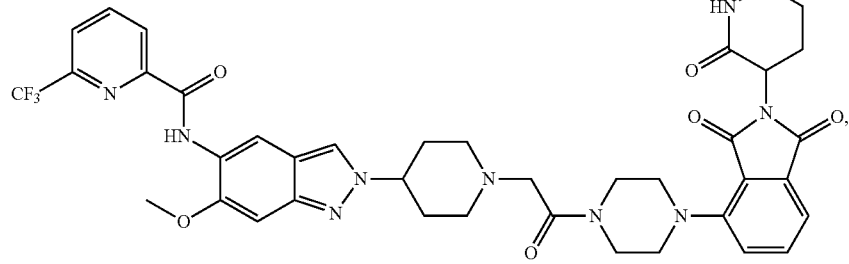
II-21
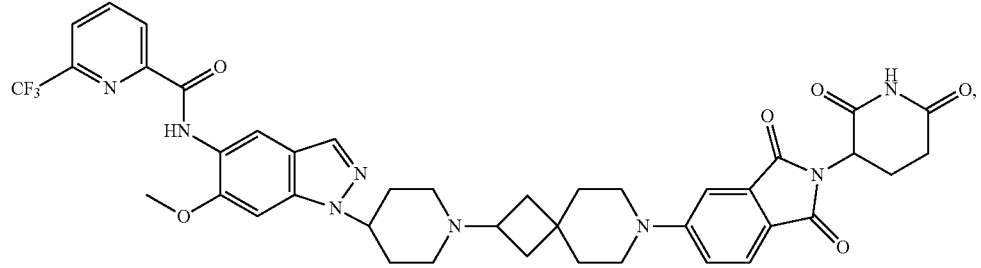
I-24
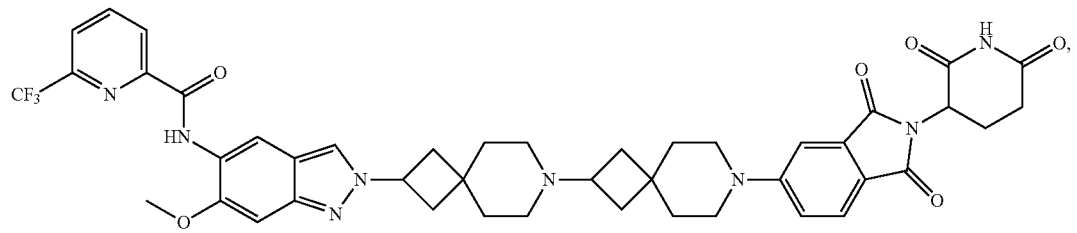
I-25
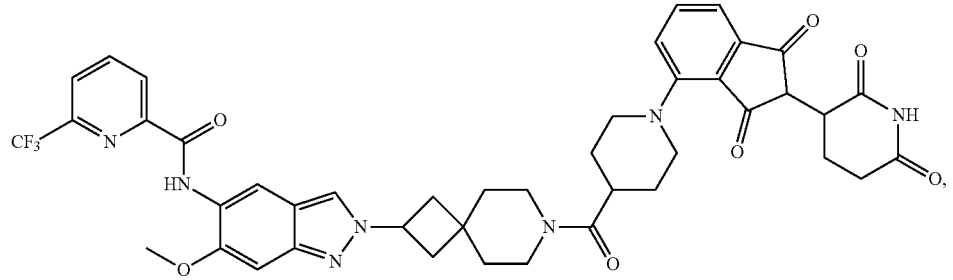
I-26
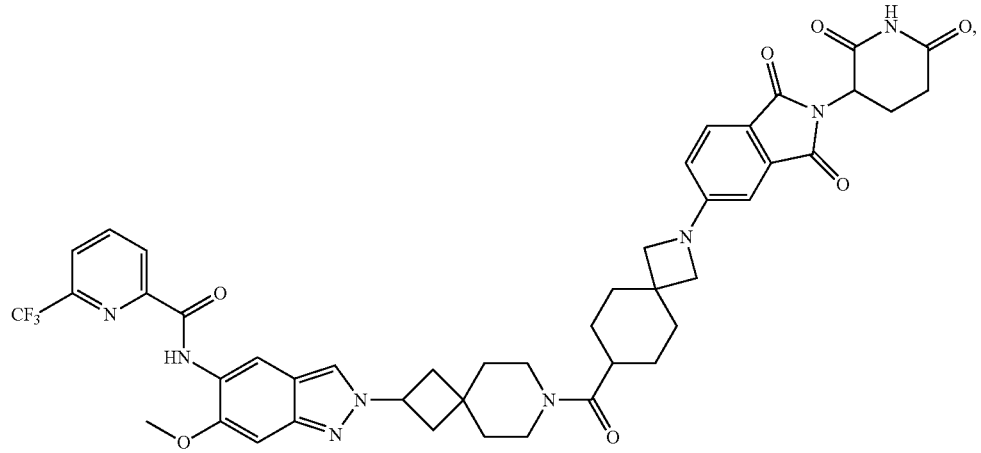

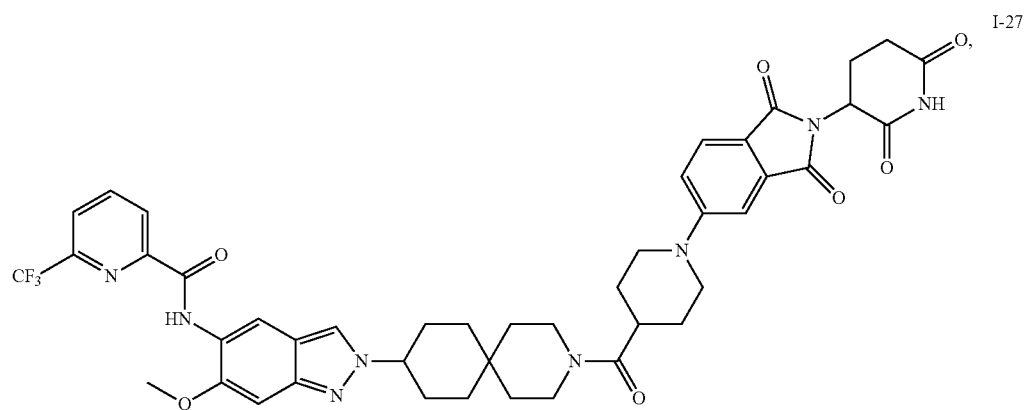
I-27
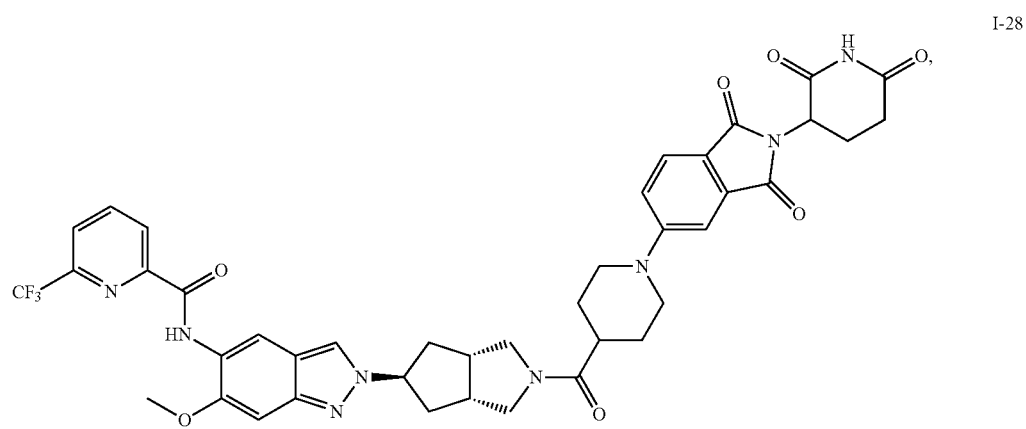
I-28
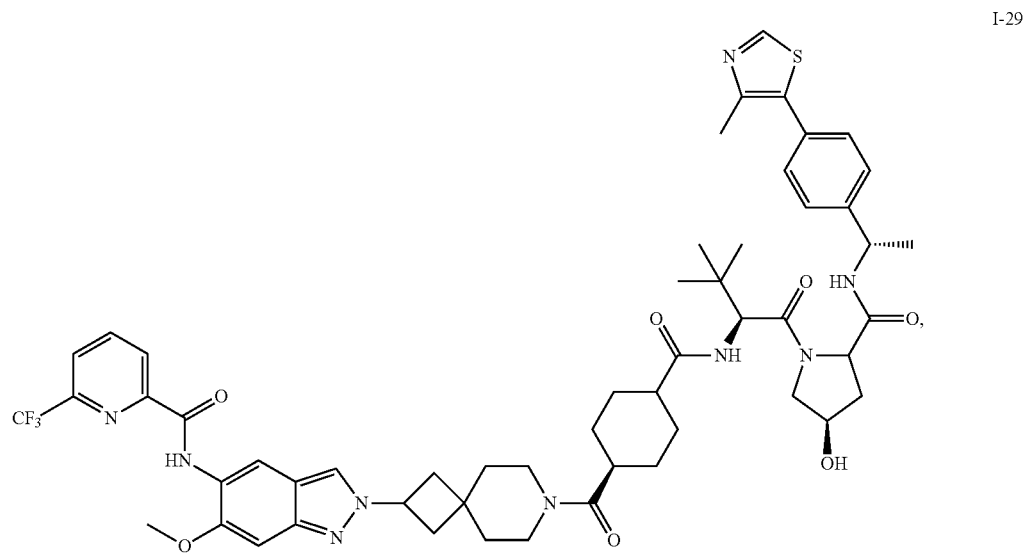
I-29

-continued
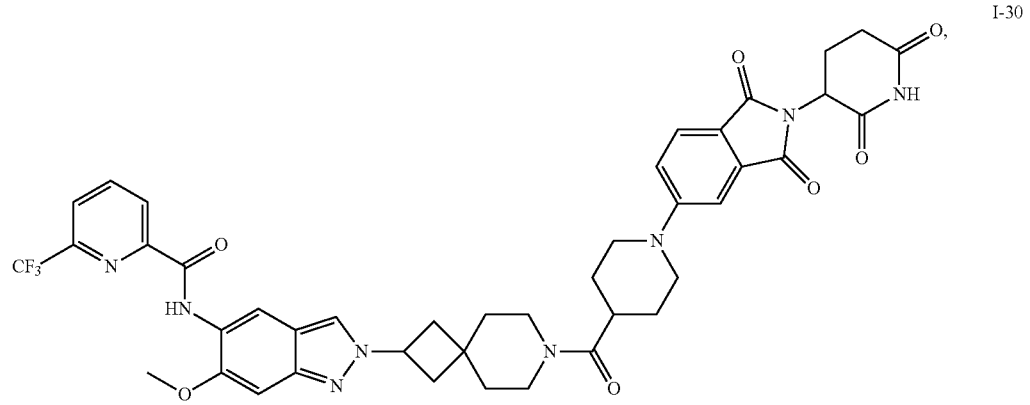
I-30
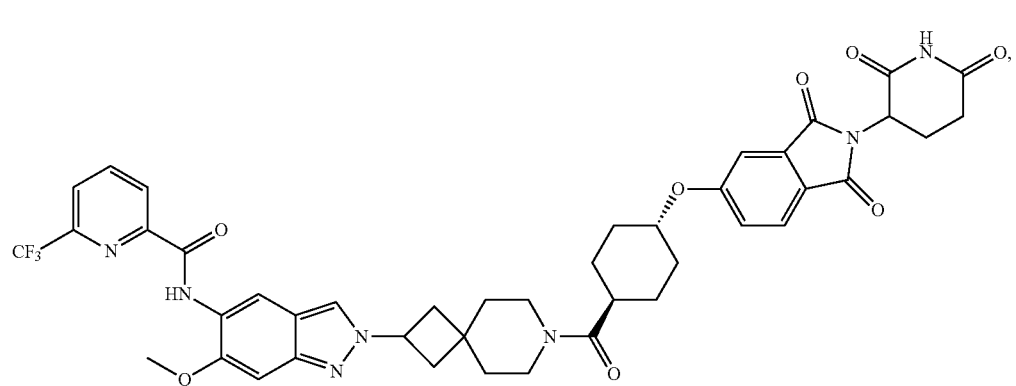
I-31
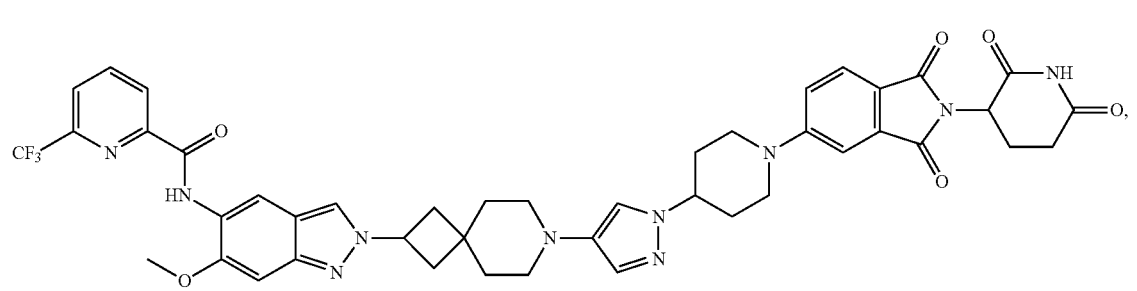
I-32
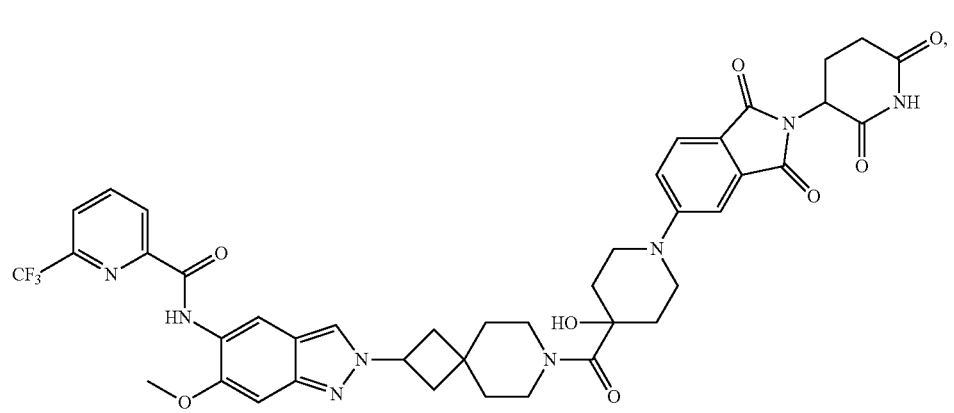
I-33

I-34
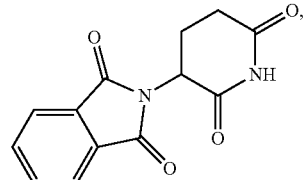
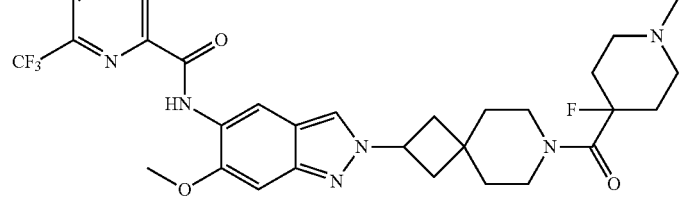
I-35
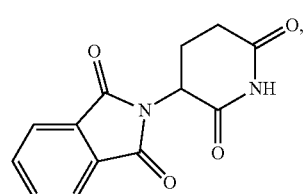
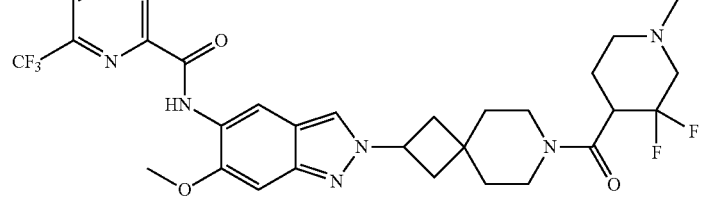
I-36
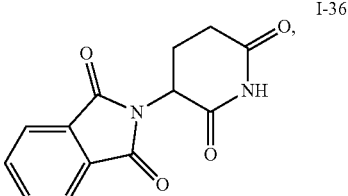
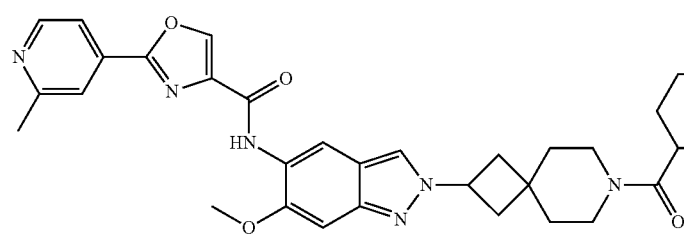
I-37
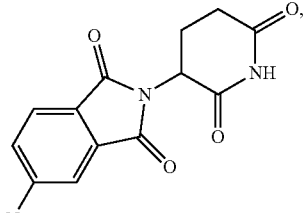
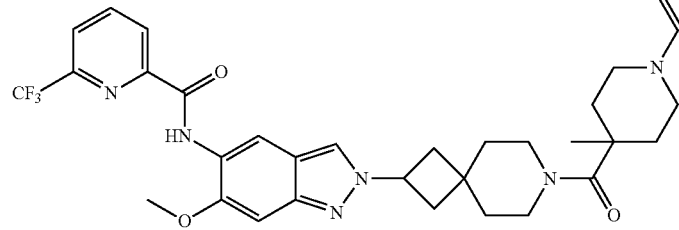

I-38
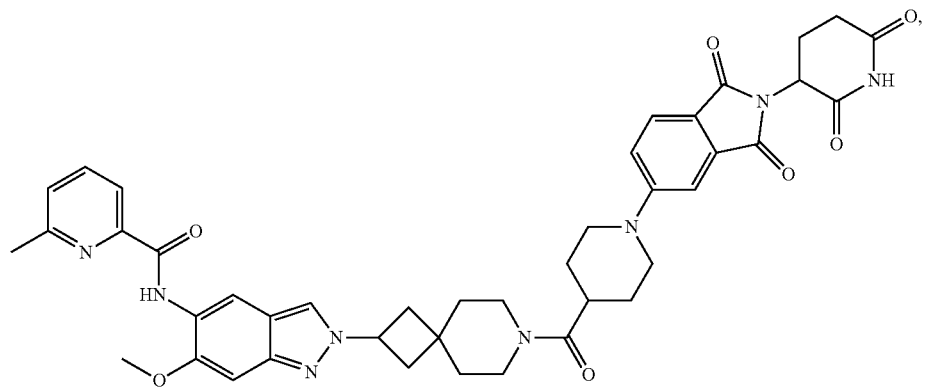
I-41
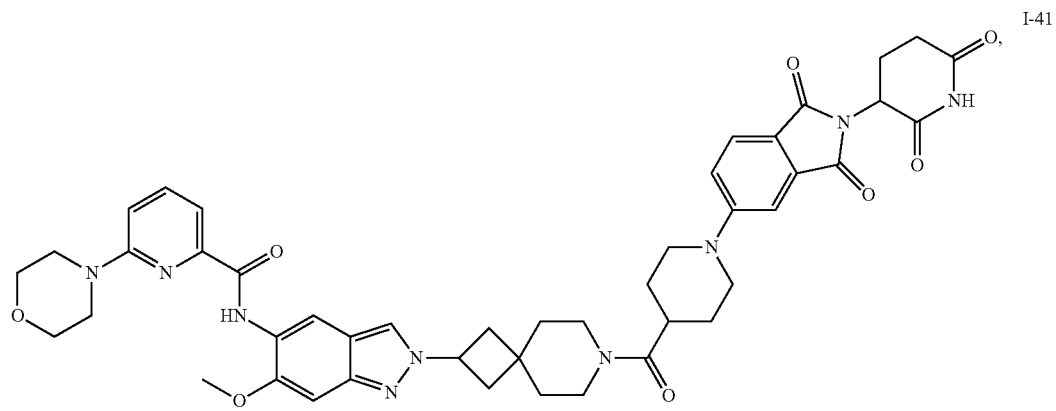
I-42
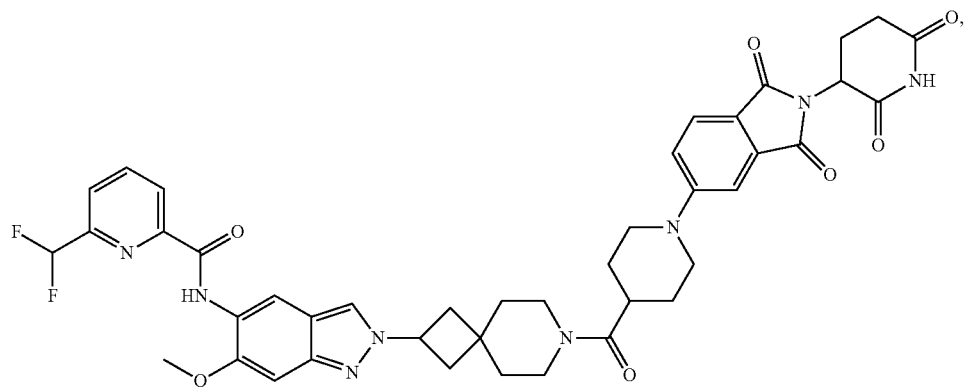
I-43
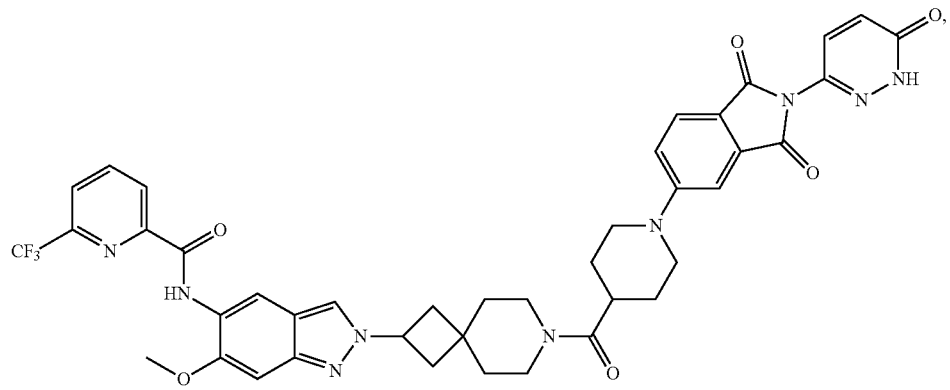

I-44
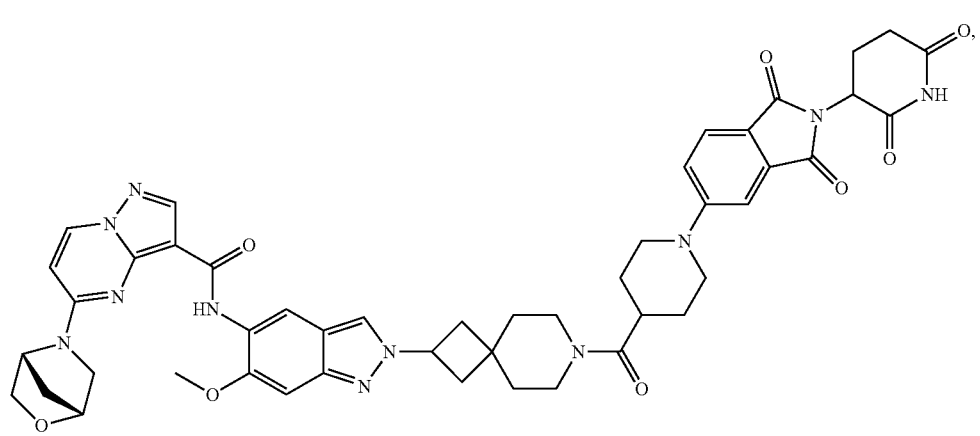
I-45
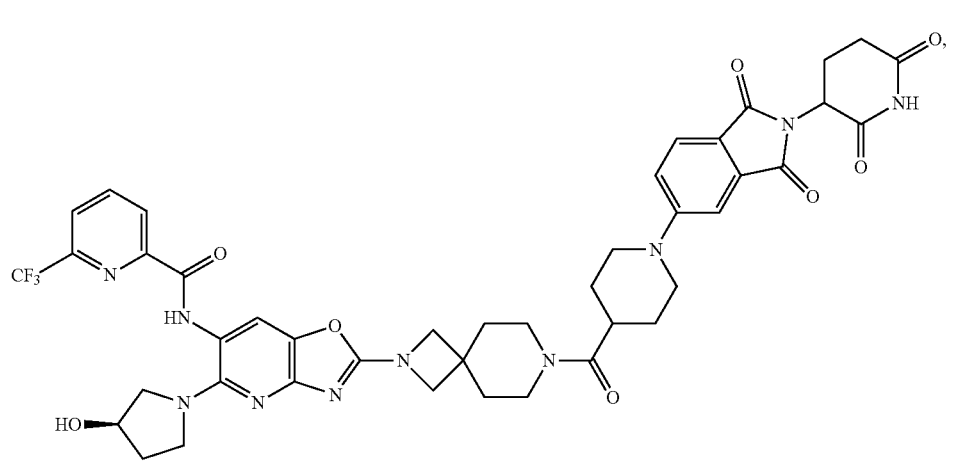
I-46
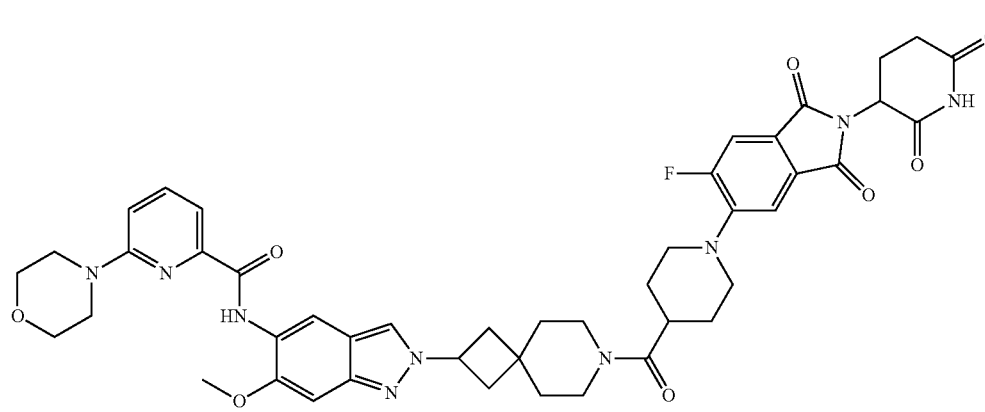
I-47
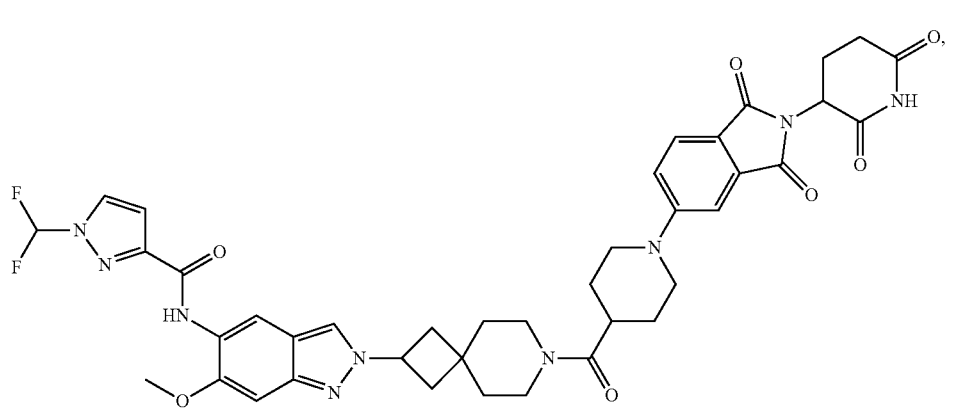

-continued
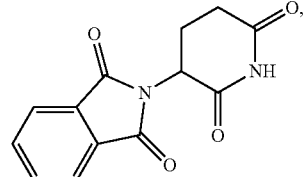
I-48
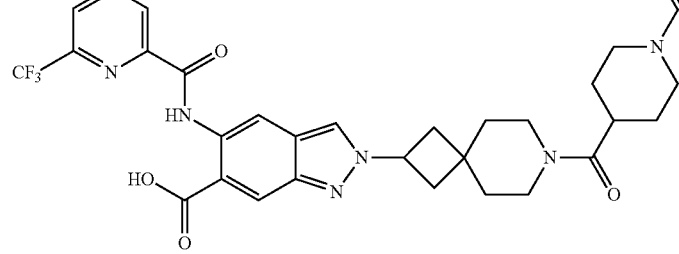
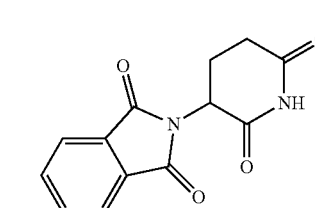
I-49
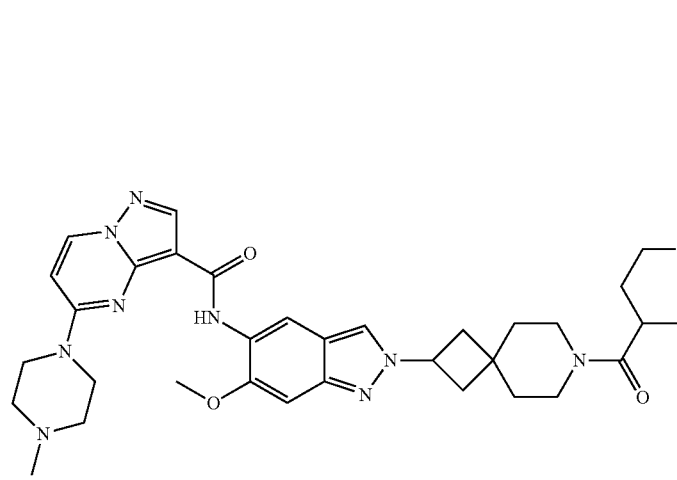
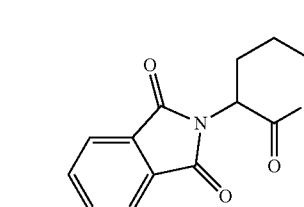
I-50
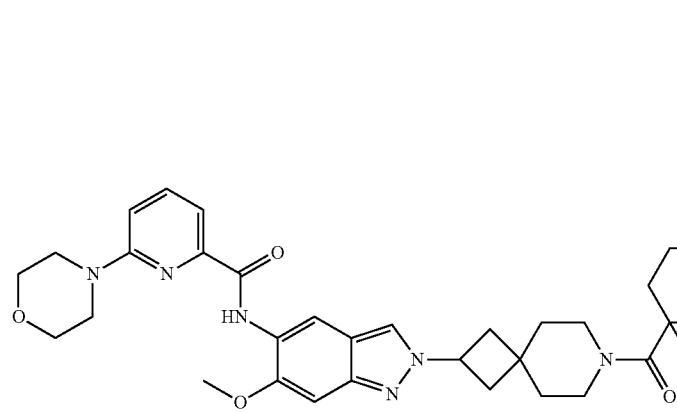

-continued
I-51
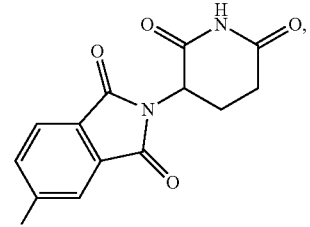
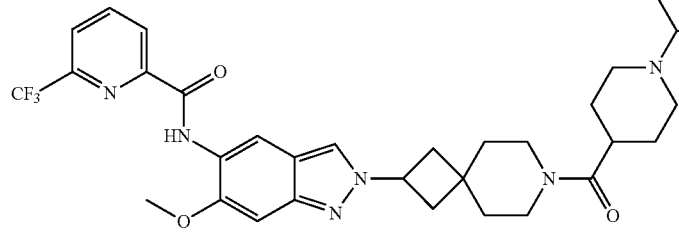
I-52
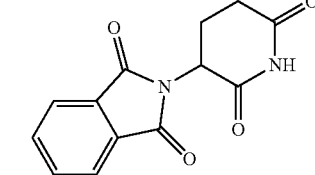
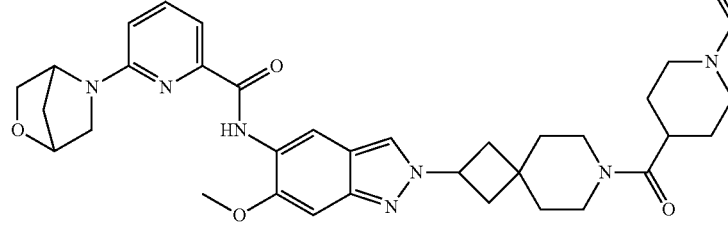
I-53
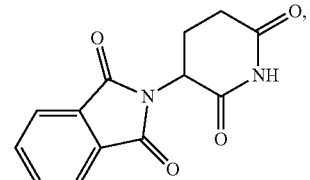
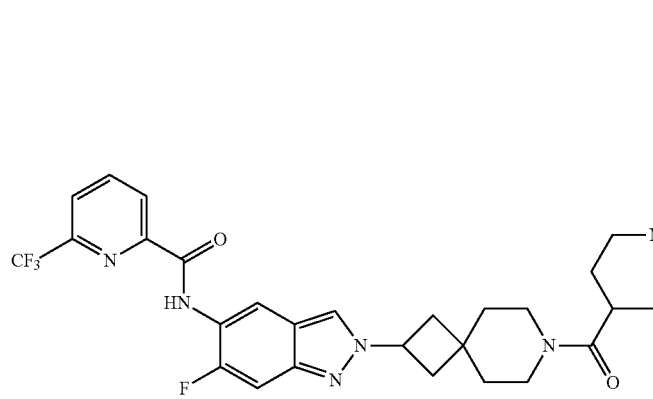
I-54
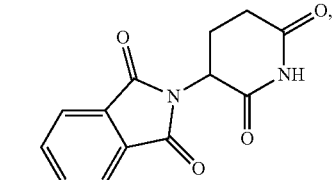
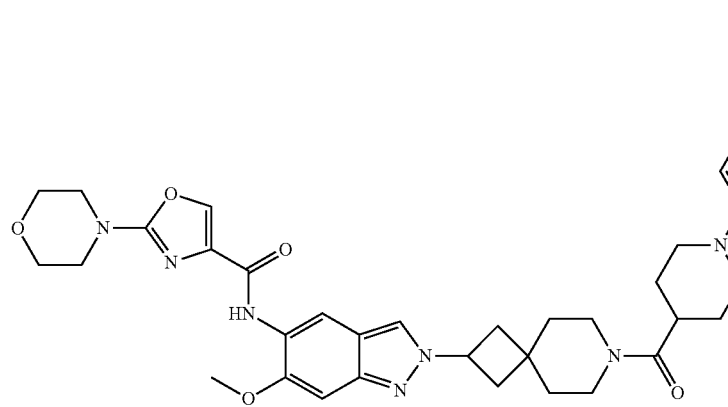
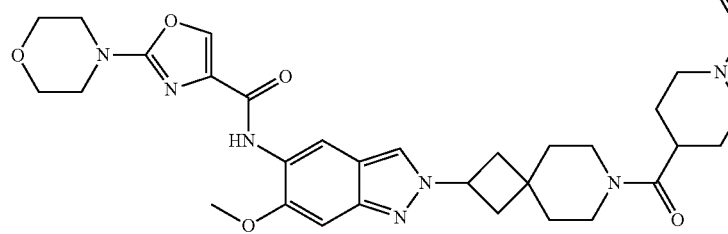

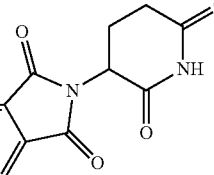
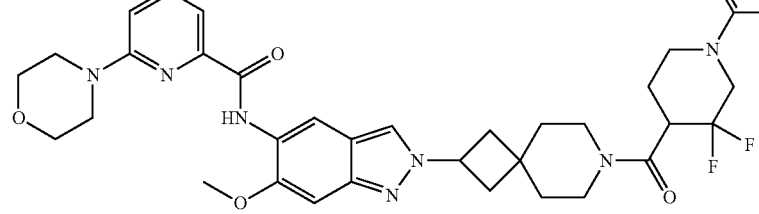
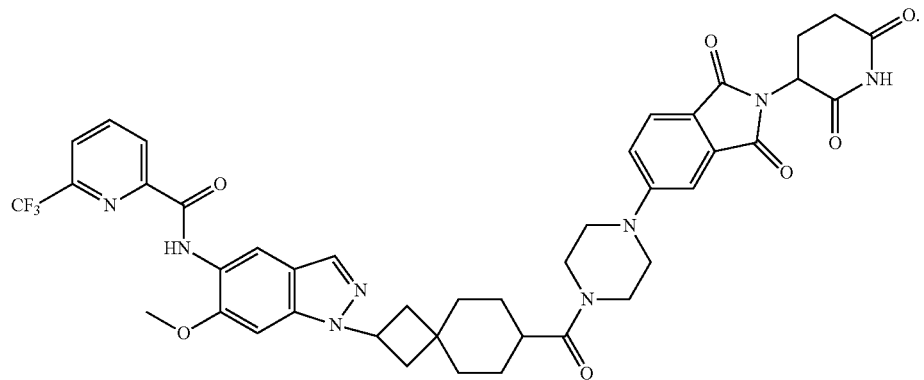
In a preferred embodiment,
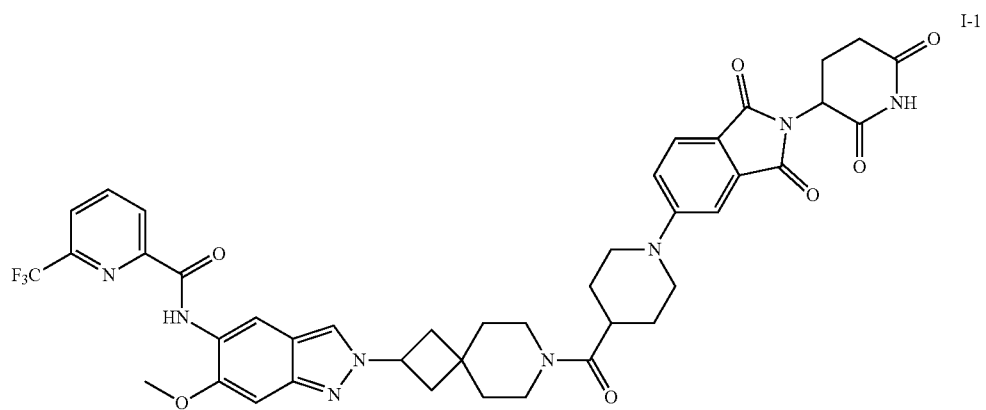 [SMILES: COc1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1]

is
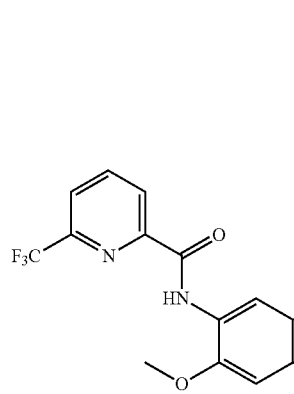 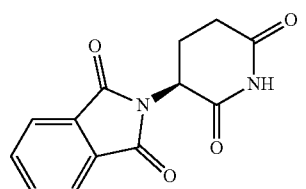 or
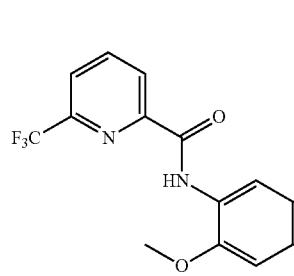 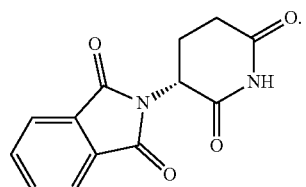
In a preferred embodiment,
I-4
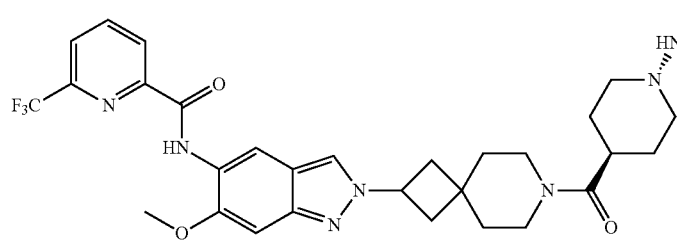 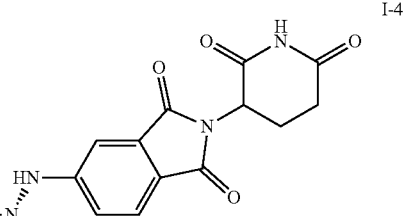

is
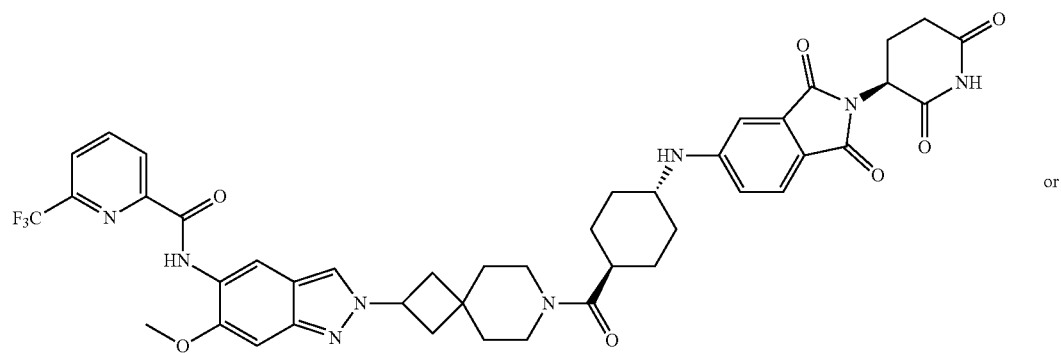
or
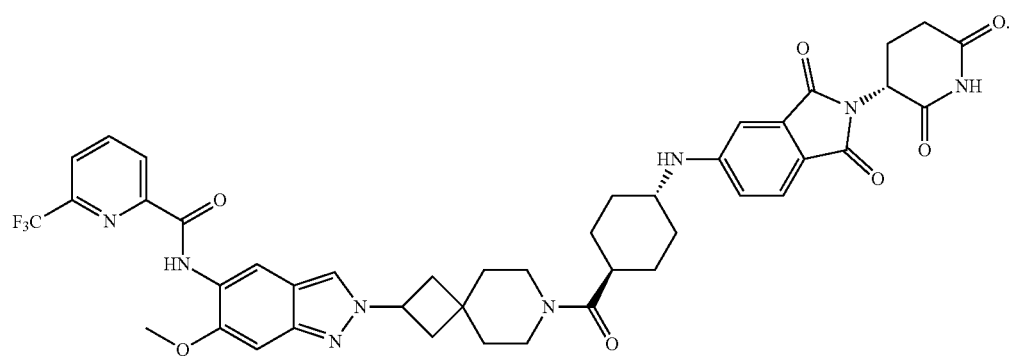
In a preferred embodiment,
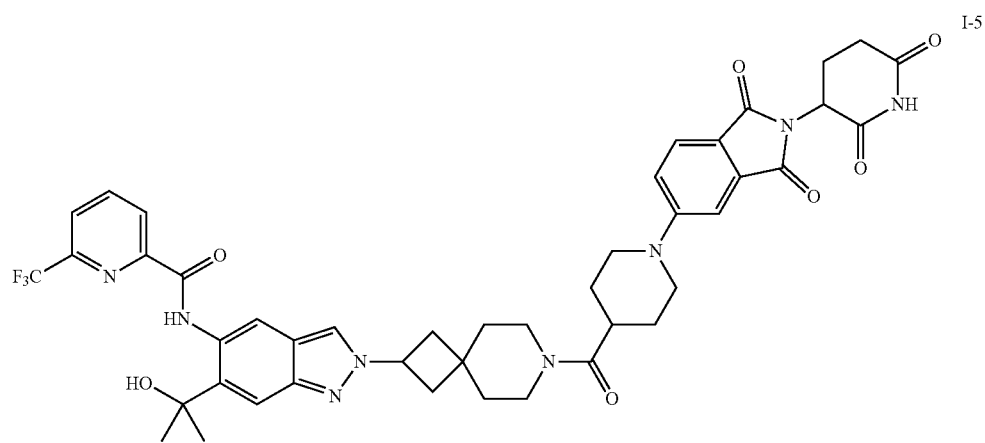 [SMILES: CC(C)(O)c1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1]

is
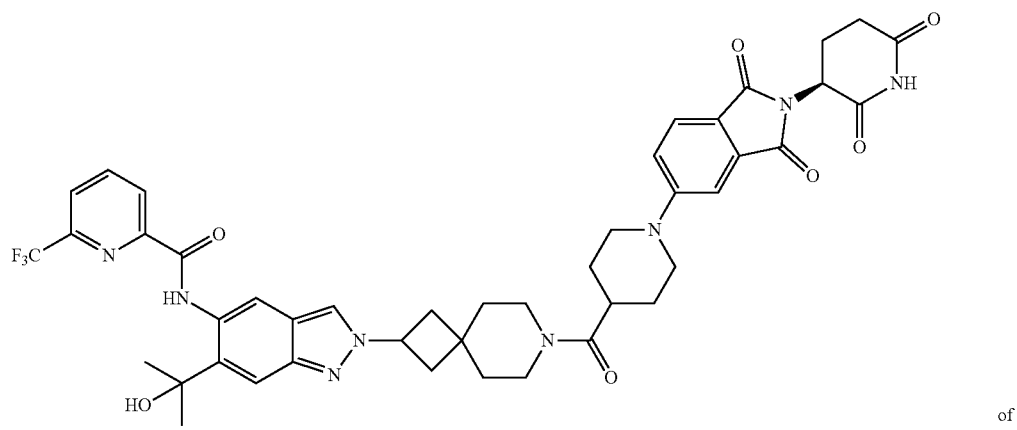
of
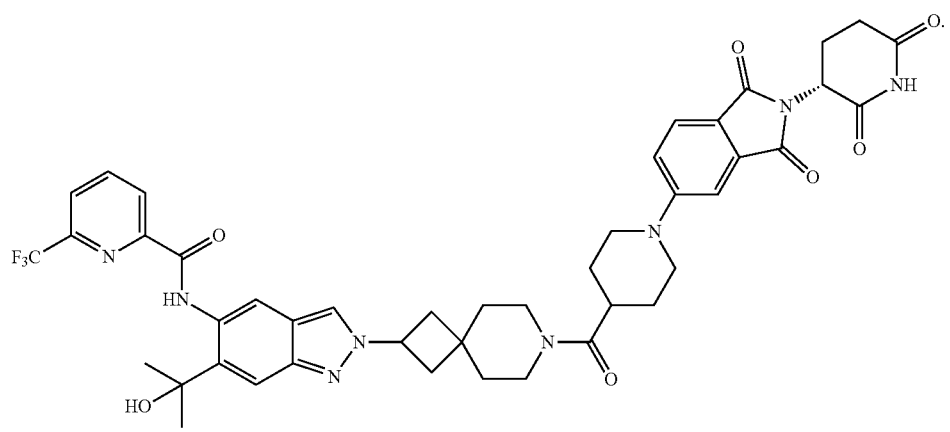
In a preferred embodiment,
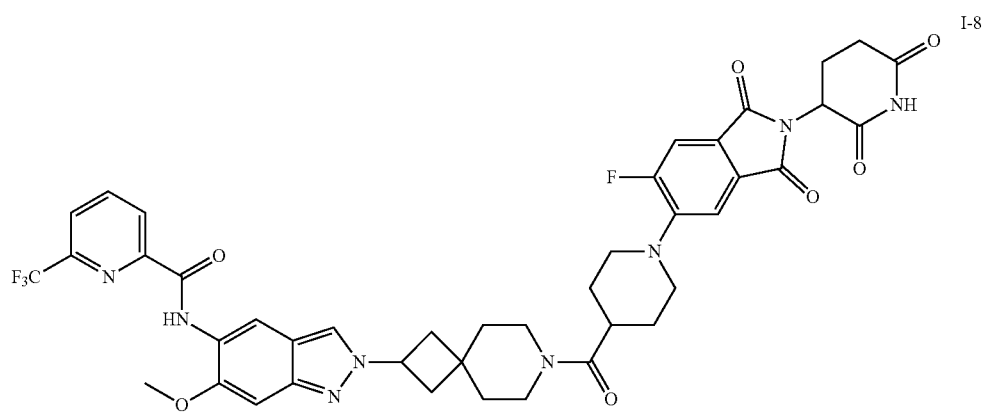 [SMILES: COc1cc2nn(C3CC4(CCN(C(=O)C5CCN(c6cc7c(cc6F)C(=O)N(C6CCC(=O)NC6=O)C7=O)CC5)CC4)C3)cc2cc1NC(=O)c1cccc(C(F)(F)F)n1]
I-8 is
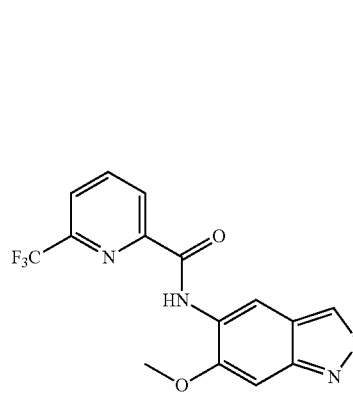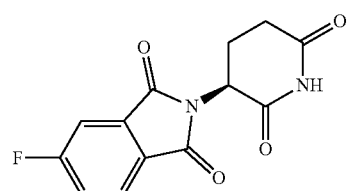
or
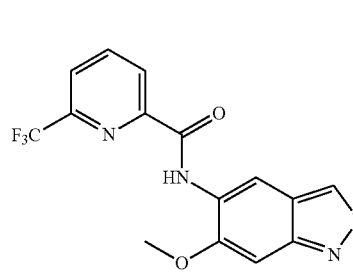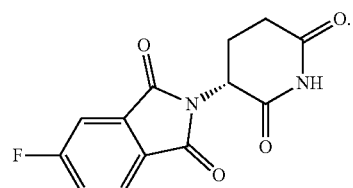
In a preferred embodiment,
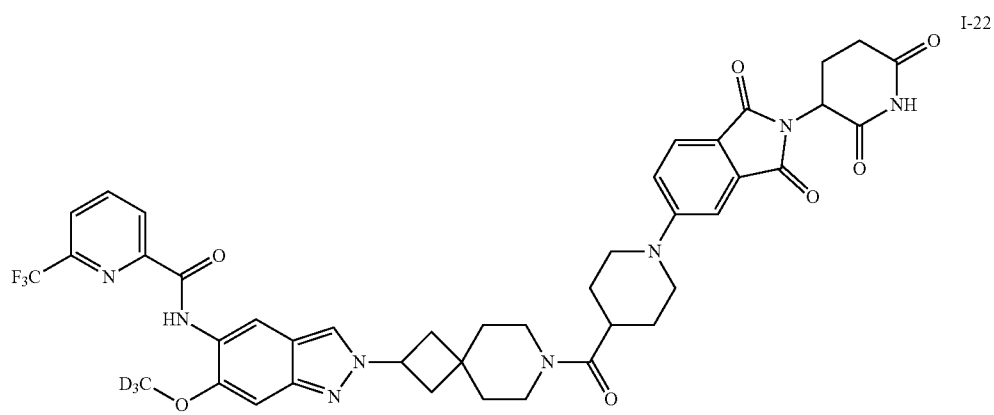 [SMILES: [2H]C([2H])([2H])Oc1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1]

is
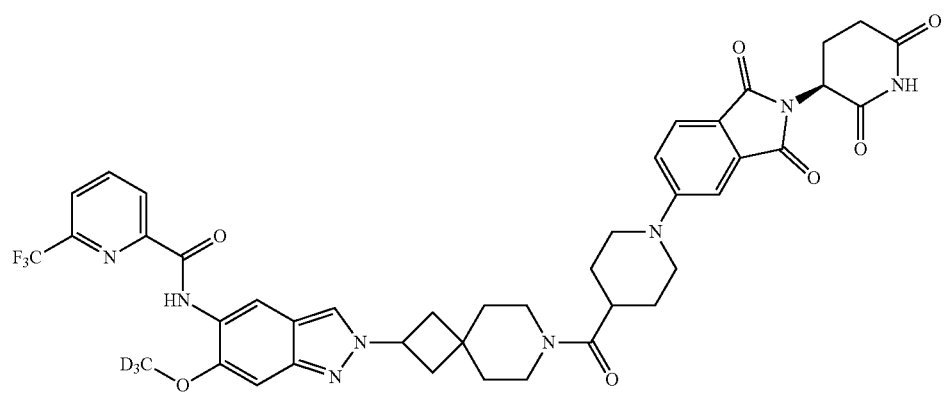
or
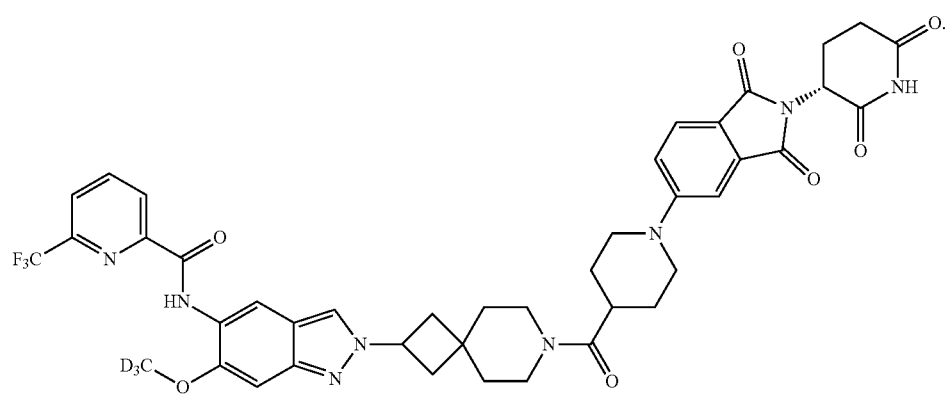
In a preferred embodiment,
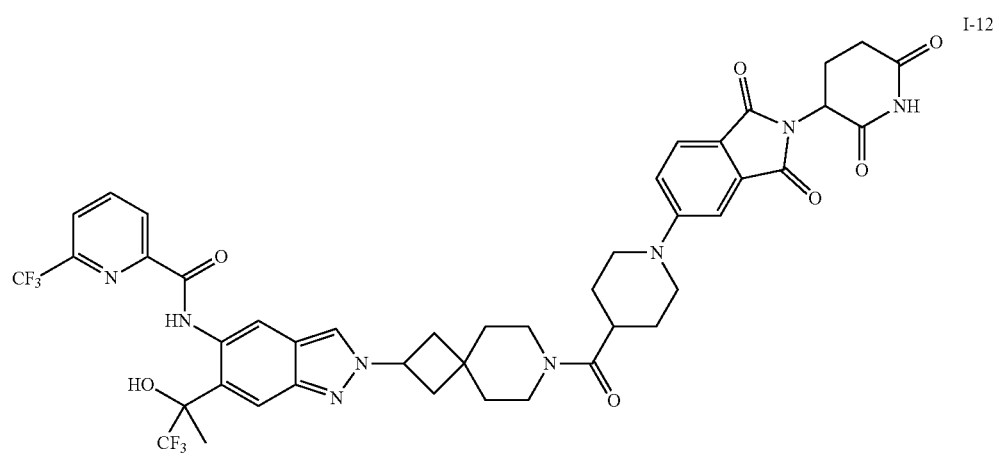 [SMILES: CC(O)(c1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1)C(F)(F)F]
I-12 is
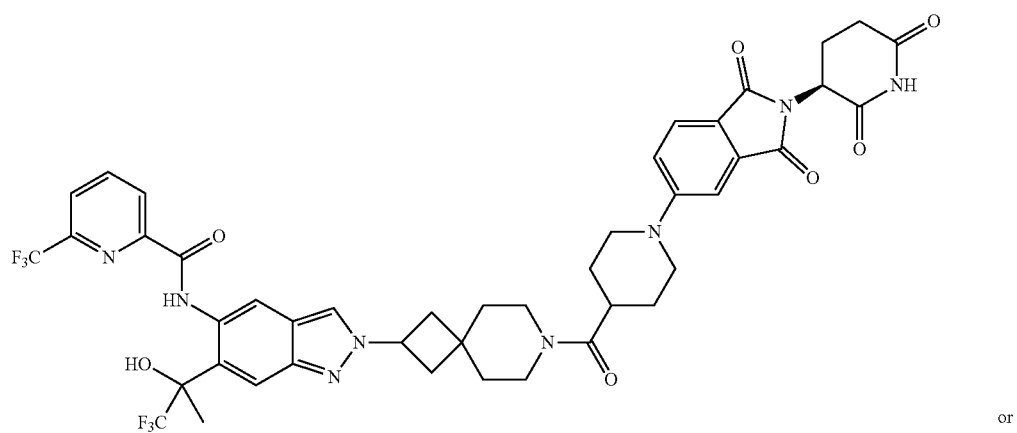
or
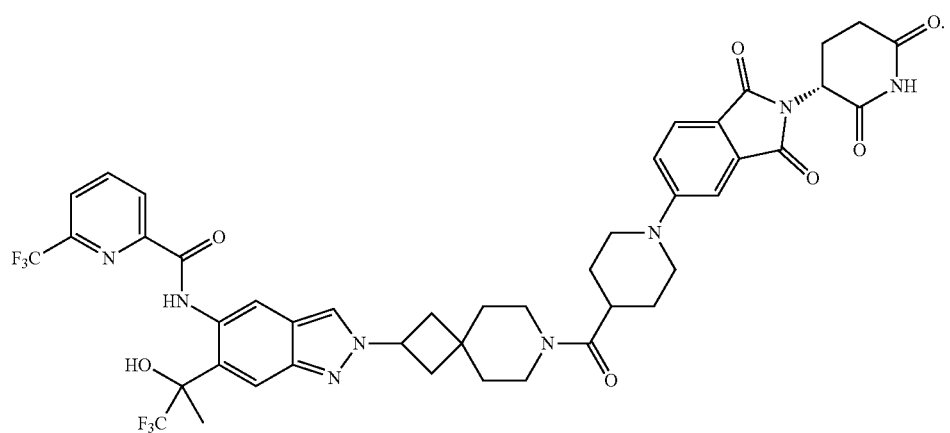
In a preferred embodiment,
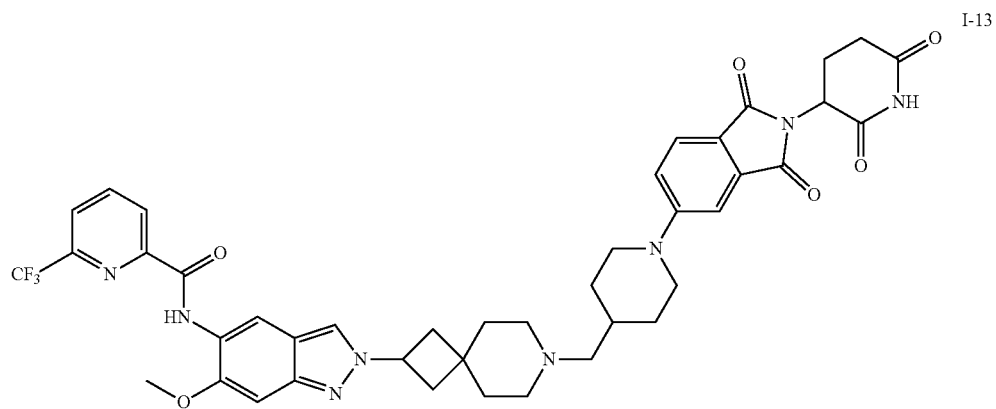 [SMILES: COc1cc2nn(C3CC4(CCN(CC5CCN(c6ccc7c(c6)C(=O)N(C6CCC(=O)NC6=O)C7=O)CC5)CC4)C3)cc2cc1NC(=O)c1cccc(C(F)(F)F)n1]
I-13 is
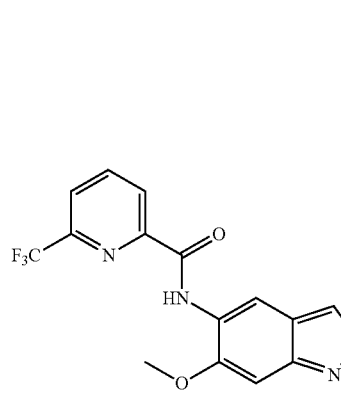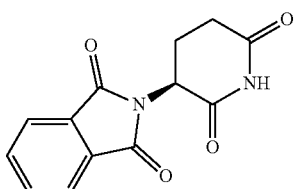
or
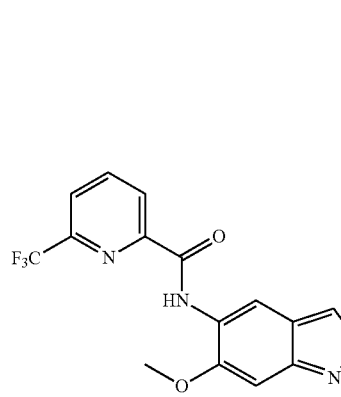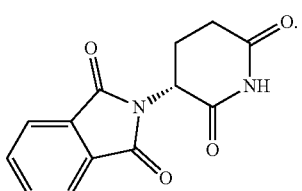
In a preferred embodiment,
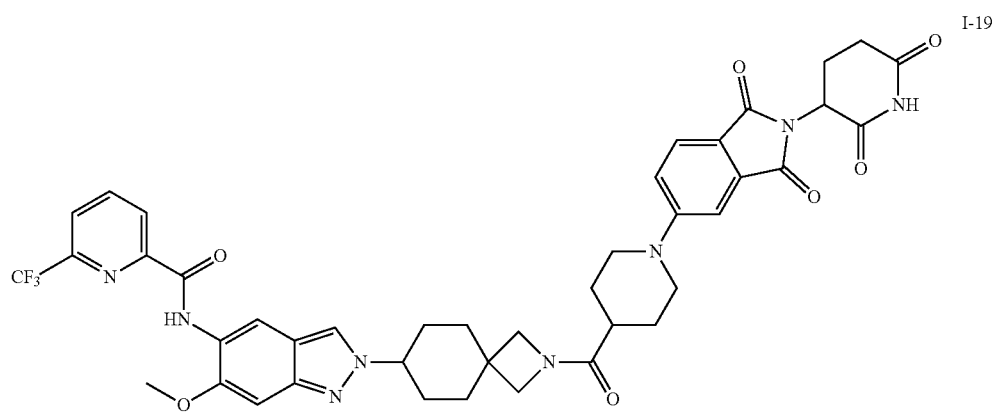 [SMILES: COc1cc2nn(C3CCC4(CC3)CN(C(=O)C3CCN(c5ccc6c(c5)C(=O)N(C5CCC(=O)NC5=O)C6=O)CC3)C4)cc2cc1NC(=O)c1cccc(C(F)(F)F)n1]

is
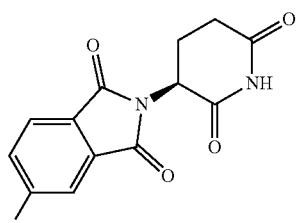
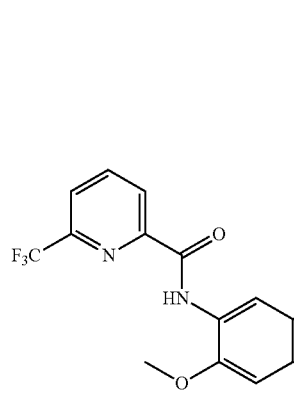
or
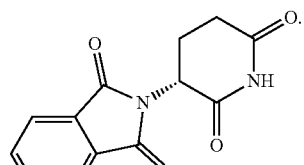
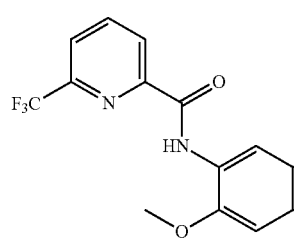
In a preferred embodiment,
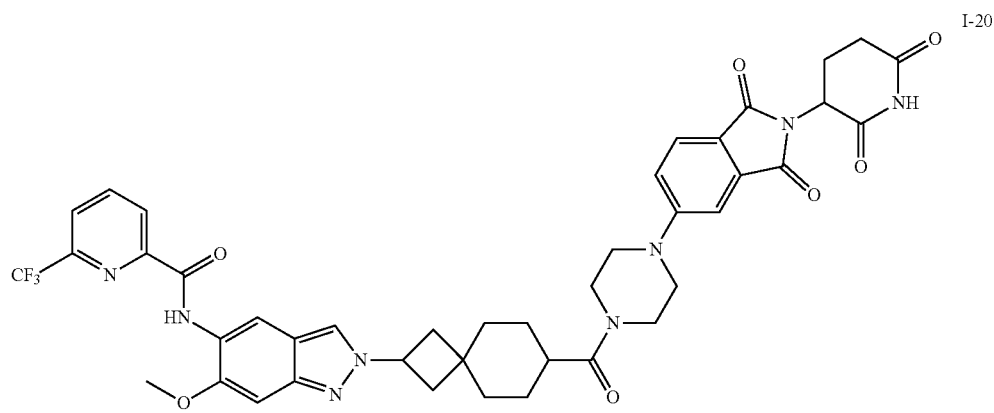 [SMILES: COc1cc2nn(C3CC4(CCC(C(=O)N5CCN(c6ccc7c(c6)C(=O)N(C6CCC(=O)NC6=O)C7=O)CC5)CC4)C3)cc2cc1NC(=O)c1cccc(C(F)(F)F)n1]

is
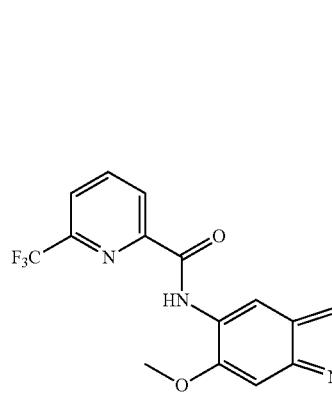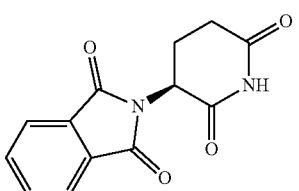
or
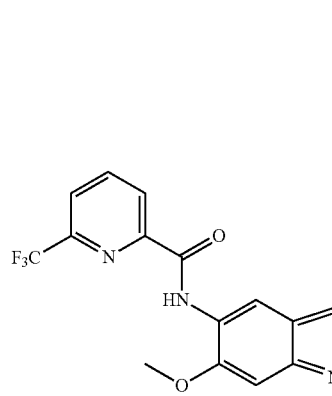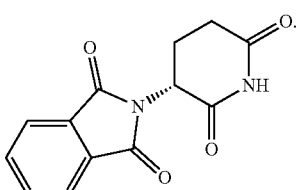
In a preferred embodiment,
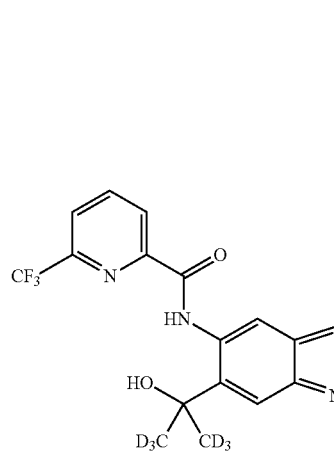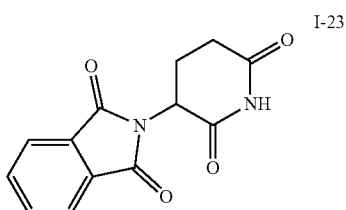
I-23 is
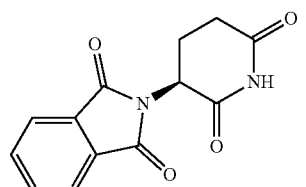
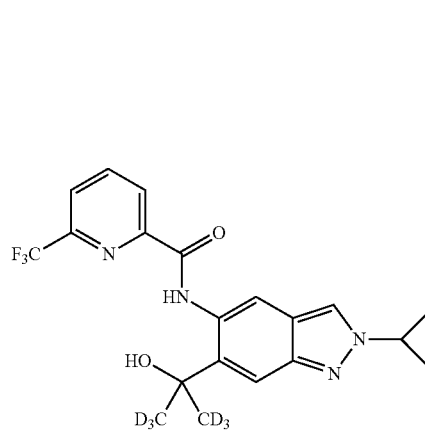
or
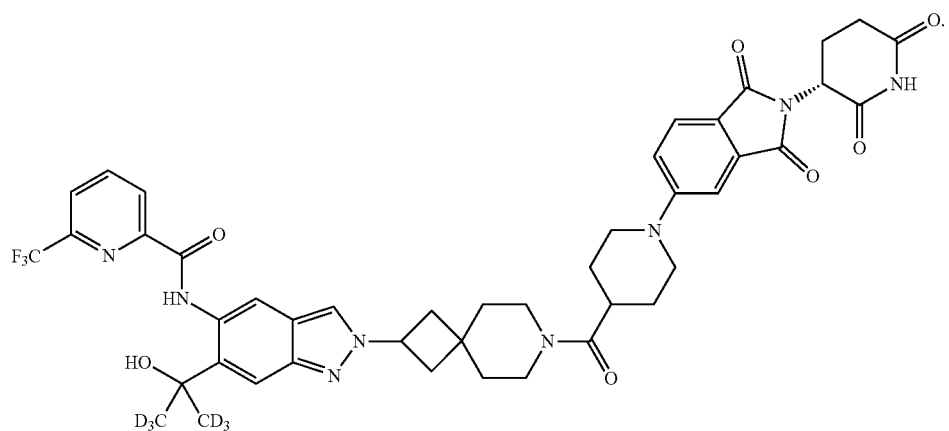
In a preferred embodiment,
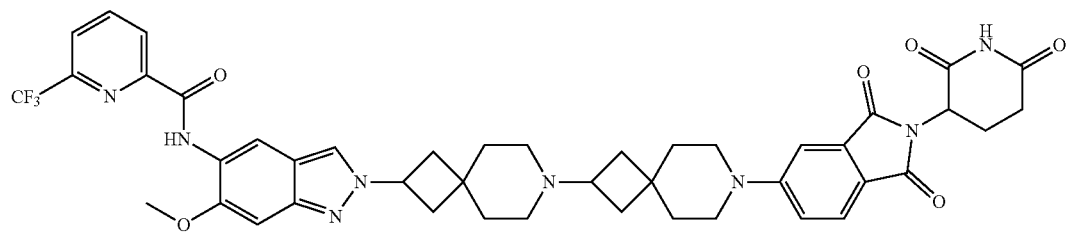
I-24
is
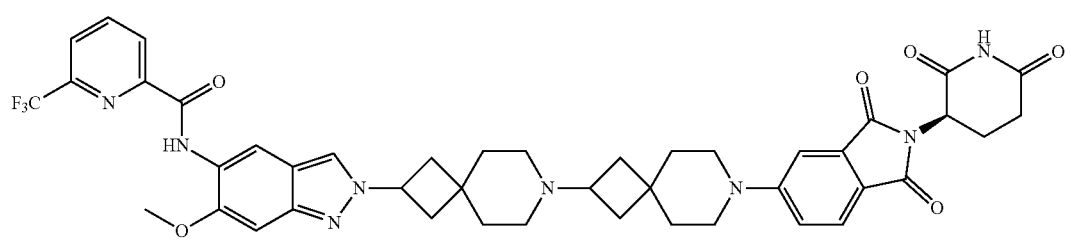
or

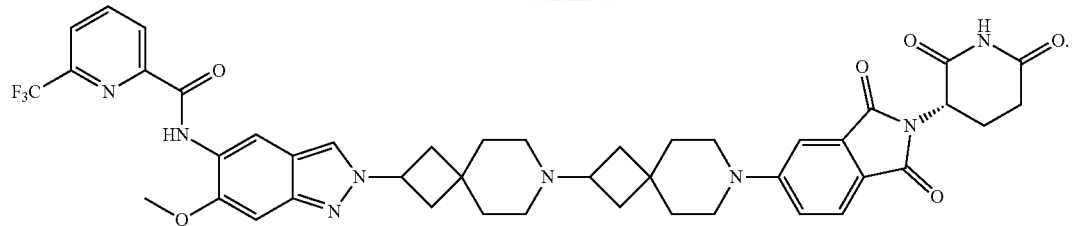
In a preferred embodiment,
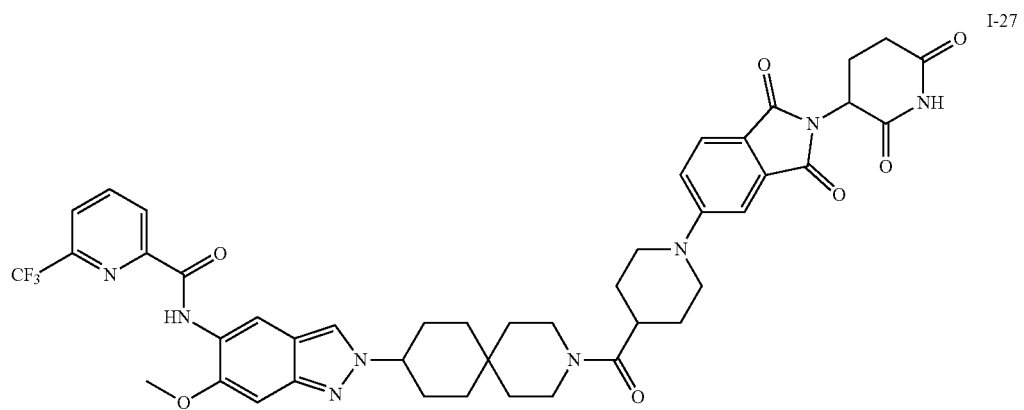 [SMILES: COc1cc2nn(C3CCC4(CC3)CCN(C(=O)C3CCN(c5ccc6c(c5)C(=O)N(C5CCC(=O)NC5=O)C6=O)CC3)CC4)cc2cc1NC(=O)c1cccc(C(F)(F)F)n1]
is
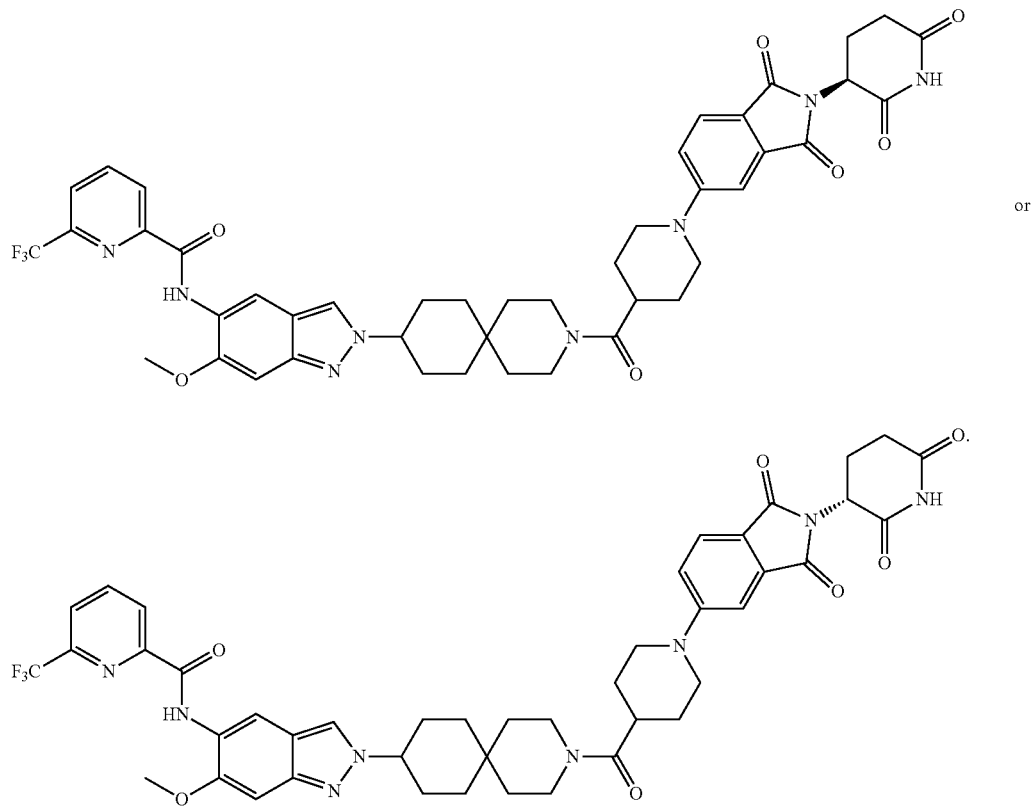
or

In a preferred embodiment,
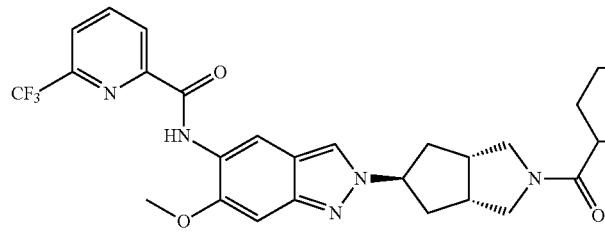
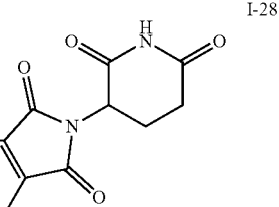
I-28
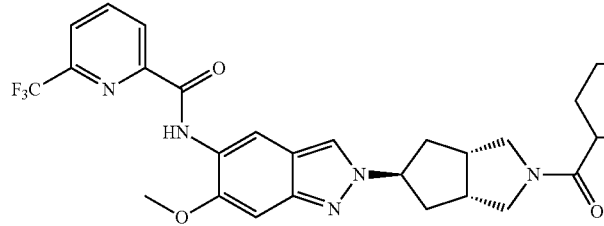
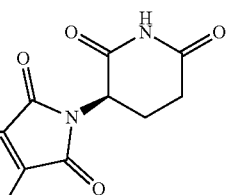
or
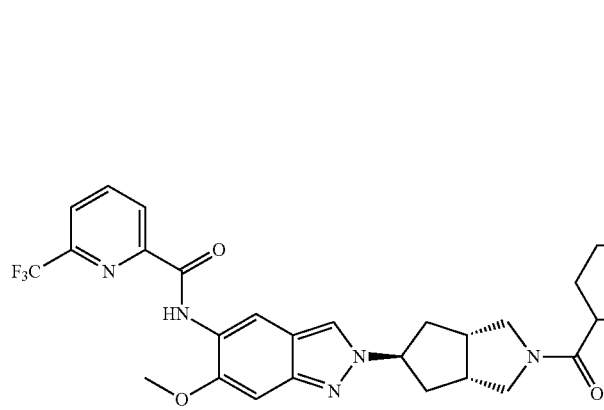
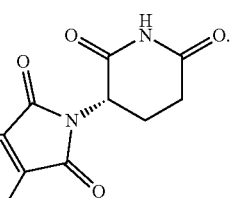

In a preferred embodiment,
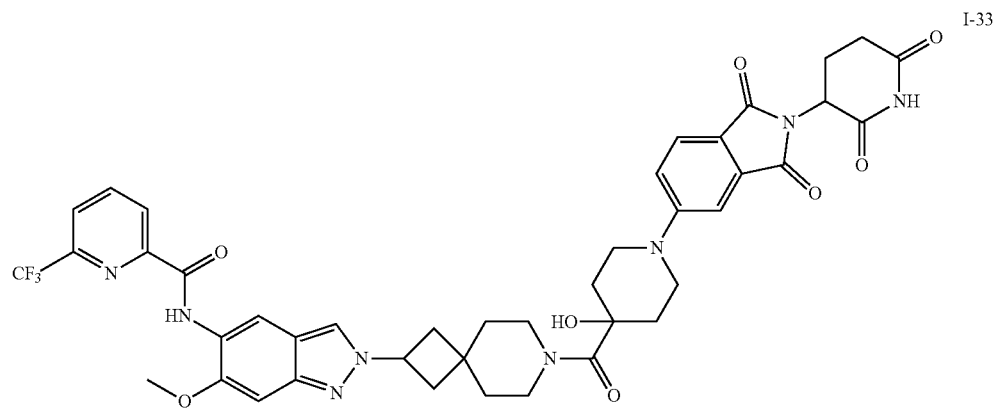 [SMILES: COc1cc2nn(C3CC4(CCN(C(=O)C5(O)CCN(c6ccc7c(c6)C(=O)N(C6CCC(=O)NC6=O)C7=O)CC5)CC4)C3)cc2cc1NC(=O)c1cccc(C(F)(F)F)n1]
I-33
is
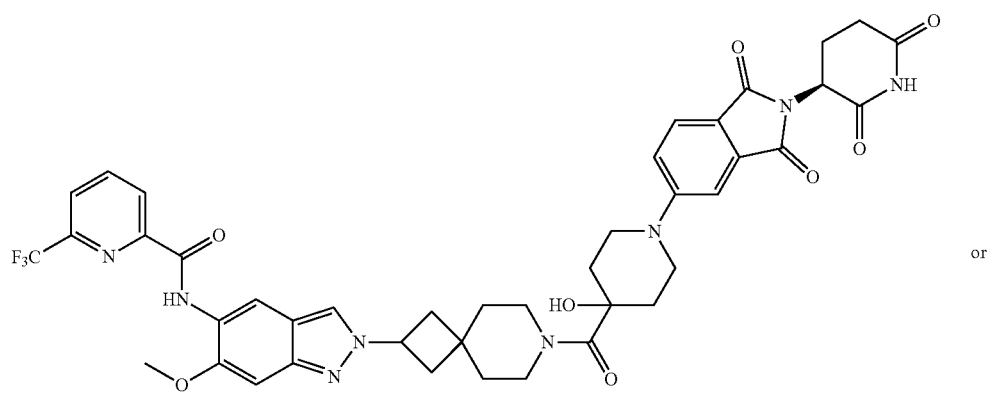
or
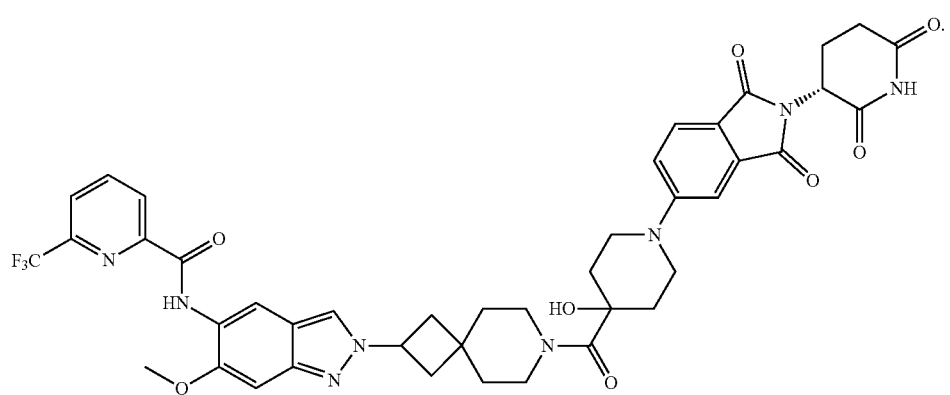

In a preferred embodiment,
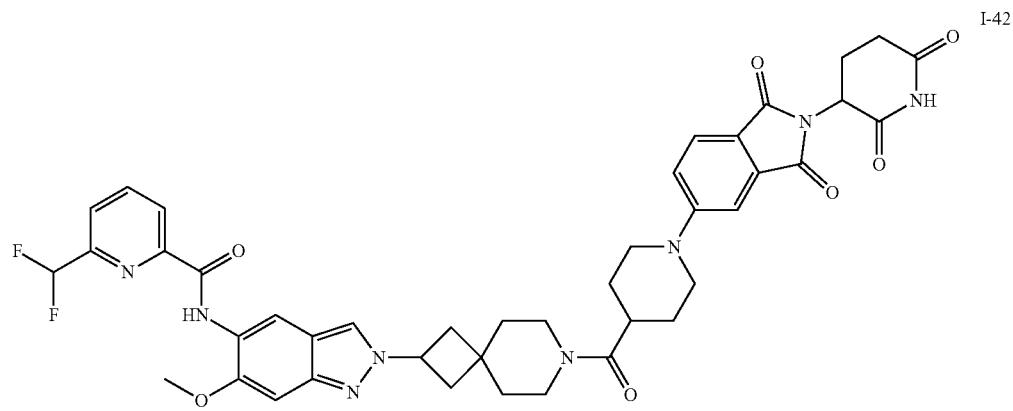 [SMILES: COc1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)F)n1]
I-42
is
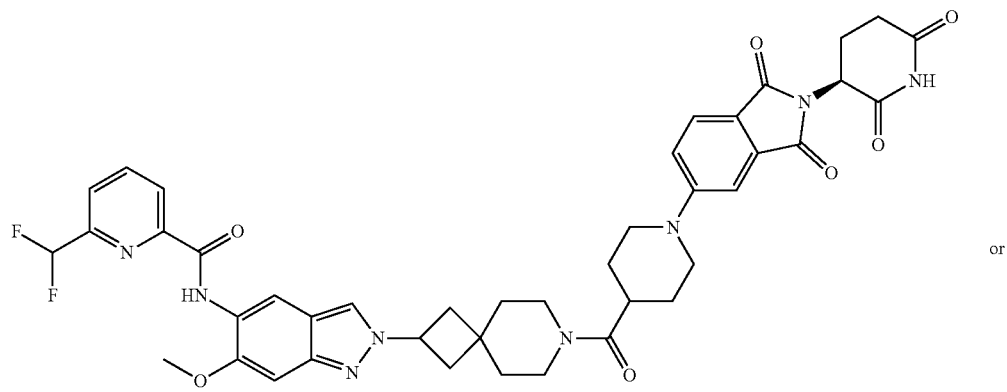
or
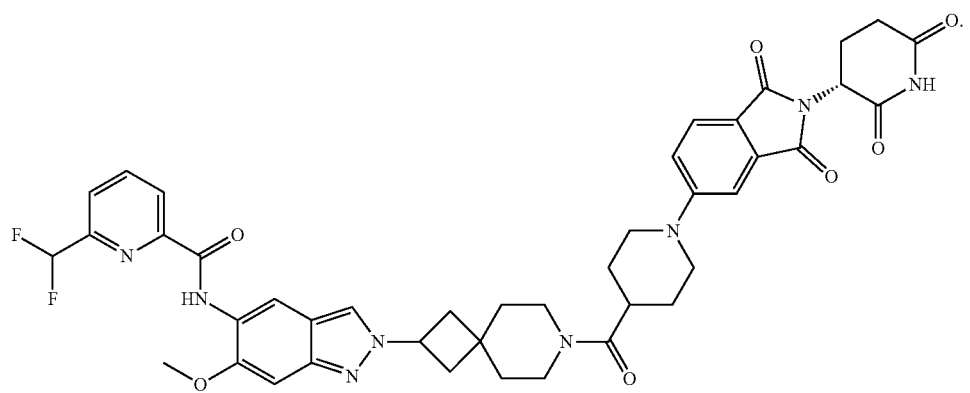

In a preferred embodiment,
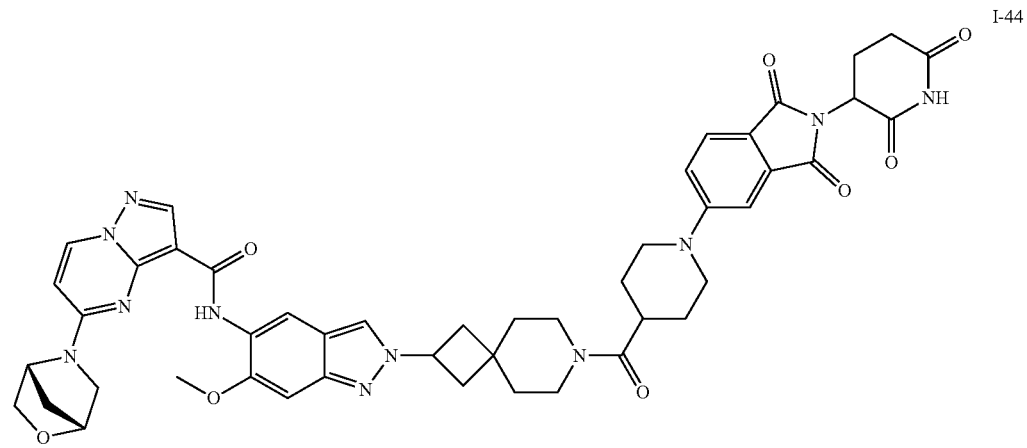 [SMILES: COc1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cnn2ccc(N3C[C@H]4C[C@@H]3CO4)nc12]
I-44
is
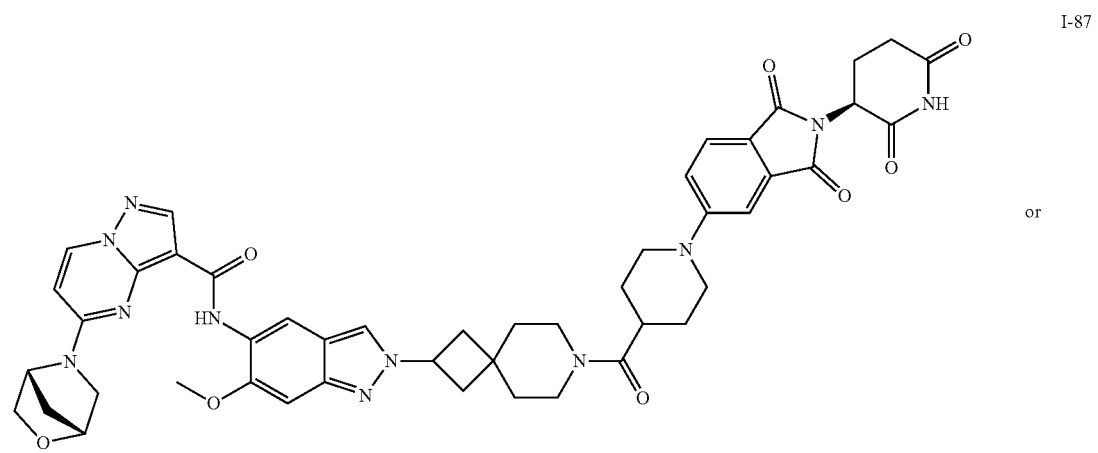
I-87
or
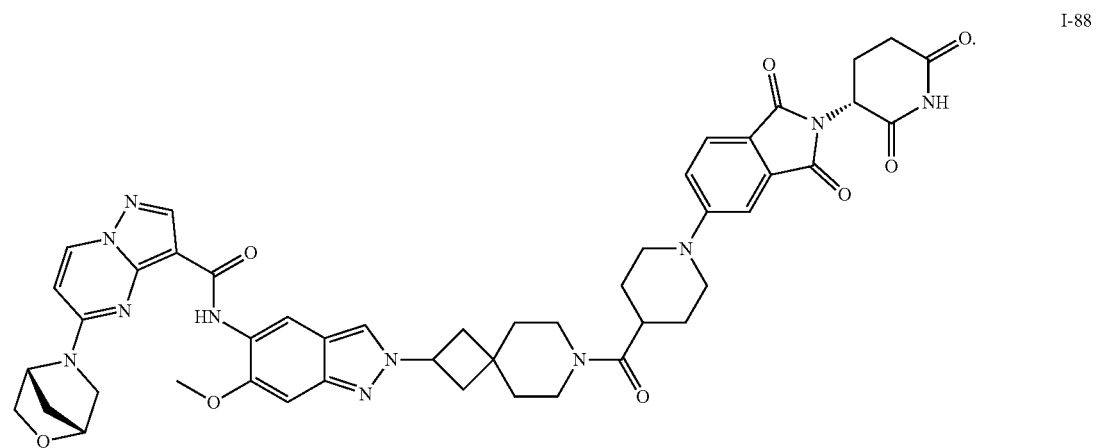
I-88.

In a preferred embodiment, the pharmaceutically acceptable salt of the compound of I-12 is
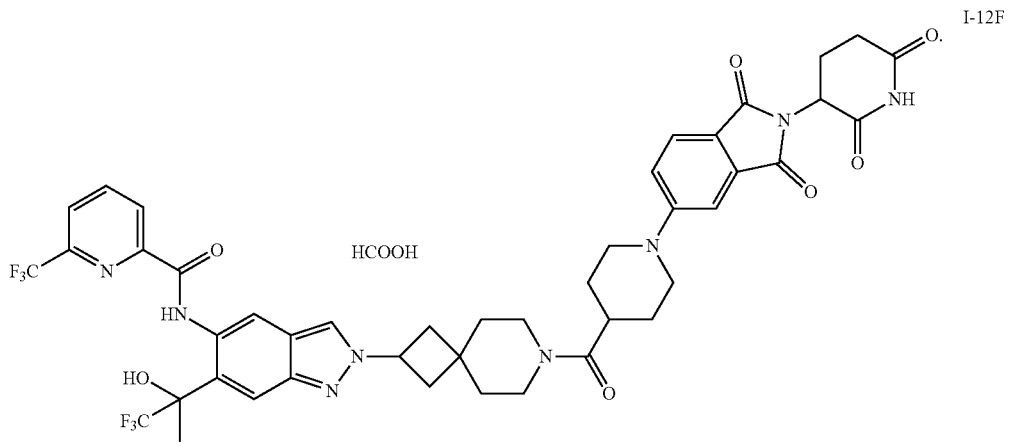 [SMILES: CC(O)(c1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1)C(F)(F)F ; "HCOOH"]
I-12F
In a preferred embodiment,
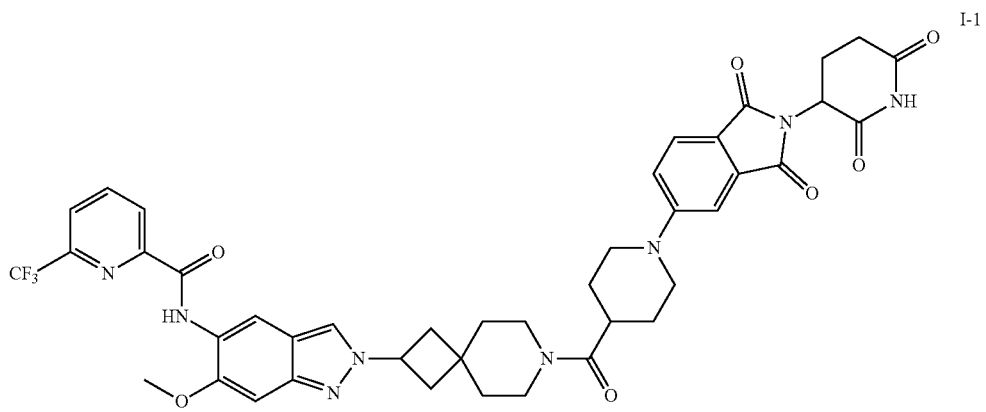
I-1
is a compound with a retention time of 2.262 min or 3.319 min under the following conditions: chromatographic column: IH 25×250 mm, 10 um (Daicel); mobile phase: CO$_2$/(MeOH:MeCN=1:1)=50/50; flow rate: 120 mL/min.
In a preferred embodiment,
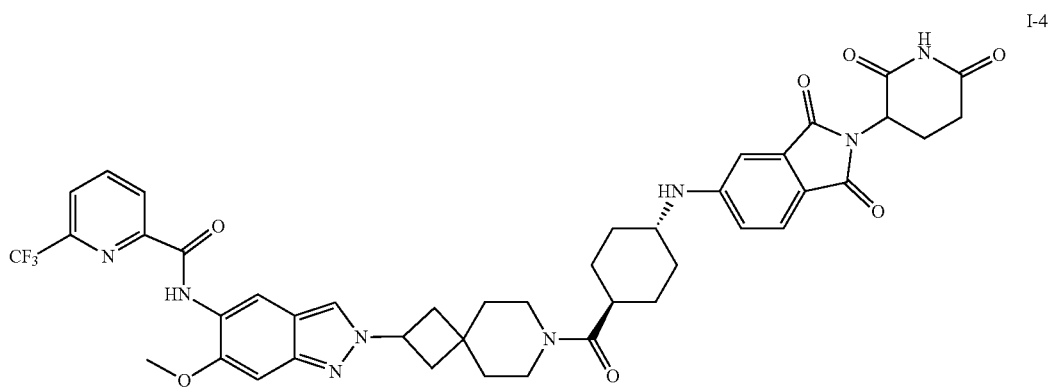 [SMILES: COc1cc2nn(C3CC4(CCN(C(=O)[C@H]5CC[C@H](Nc6ccc7c(c6)C(=O)N(C6CCC(=O)NC6=O)C7=O)CC5)CC4)C3)cc2cc1NC(=O)c1cccc(C(F)(F)F)n1]
I-4 is a compound with a retention time of 12.068 min or 14.283 min under the following conditions: chromatographic column: IC 25×250 mm, 10 um (Daicel); mobile phase: HEX (0.1% DEA):EtOH(0.1% DEA):=50:50; flow rate:50 mL/min.

In a preferred embodiment,

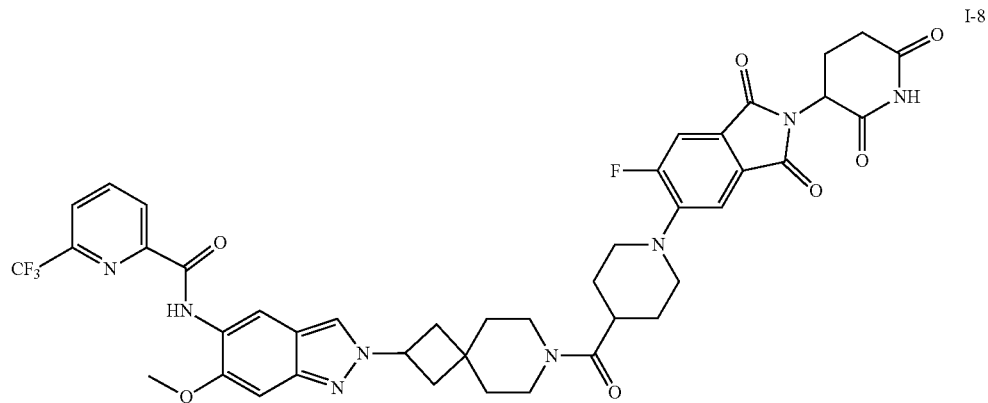 [SMILES: COc1cc2nn(C3CC4(CCN(C(=O)C5CCN(c6cc7c(cc6F)C(=O)N(C6CCC(=O)NC6=O)C7=O)CC5)CC4)C3)cc2cc1NC(=O)c1cccc(C(F)(F)F)n1]

I-8 is a compound with a retention time of 1.759 min or 2.520 min under the following conditions: chromatographic column: IH 25×250 mm, 10 um (Daicel); mobile phase: $CO_2$/[MeOH:MeCN=1:1]=50/50; flow rate:120 mL/min.

In a preferred embodiment,

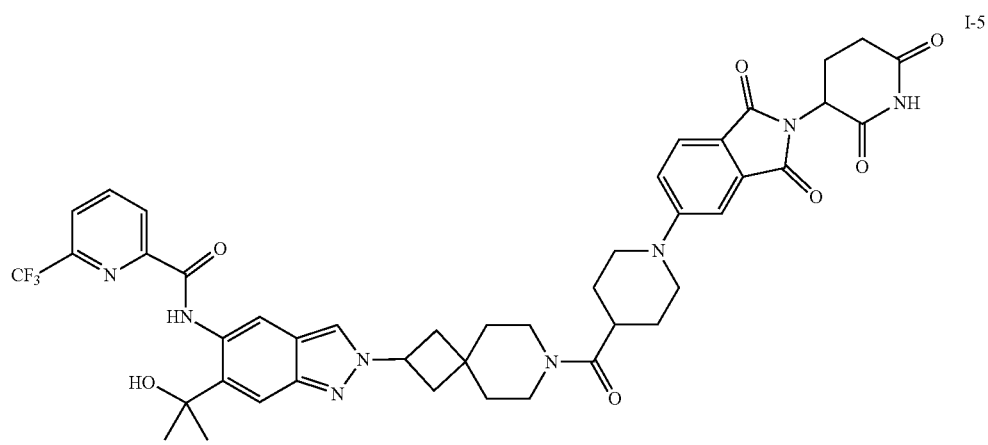 [SMILES: CC(C)(O)c1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1]

I-5 is a compound with a retention time of 1.299 min or 1.936 min under the following conditions: chromatographic column: AS 25×250 mm, 10 um (Daicel); mobile phase: $CO_2$/[MeOH(0.2% $NH_3$(7M in MeOH):MeCN=1:1]=40/60; flow rate:100 mL/min.

In a preferred embodiment,

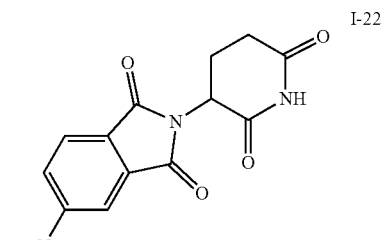
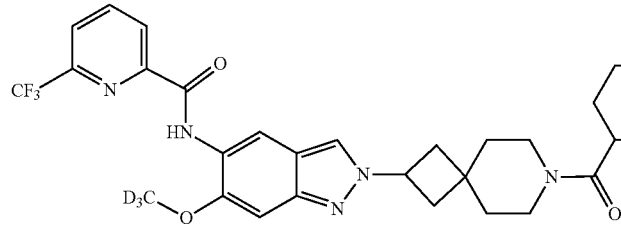

is a compound with a retention time of 2.309 min or 3.384 min under the following conditions: chromatographic column:IH 25×250 mm, 10 um (Daicel); mobile phase: $CO_2$/[MeOH:MeCN=1:1]=50/50; flow rate: 120 mL/min.

The present disclosure also provides a pharmaceutical composition comprising substance Z and pharmaceutical excipients, wherein the substance Z is a compound of formula I, a pharmaceutically acceptable salt or an isotope compound thereof.

In a preferred embodiment, in the pharmaceutical composition, the substance Z is an effective amount of substance Z.

In a preferred embodiment, the pharmaceutical composition is used to treat and/or prevent Myd88 and/or IRAK4-related diseases.

The present disclosure also provides a use of substance Z in the preparation of an IRAK4 degrading agent and a medicament for the treatment and/or prevention of Myd88 and/or IRAK4 related diseases, wherein the substance Z is a compound of formula I, and a pharmaceutically acceptable salt or an isotopic compound thereof.

The present disclosure also provides a method for treating and/or preventing Myd88 and/or IRAK4-related diseases, which includes administering an effective amount of substance Z to the patient, wherein the substance Z is a compound of formula I, and a pharmaceutically acceptable salt or an isotopic compound thereof.

In a preferred embodiment, the IRAK4-related diseases include one or more of autoimmune diseases, inflammatory diseases, tumors, cardiovascular and cerebrovascular diseases and central nervous system diseases.

In a preferred embodiment, the IRAK4-related diseases include one or more of chronic lung diseases, autoimmune diseases, inflammatory diseases, tumors, cardiovascular and cerebrovascular diseases and central nervous system diseases.

In a preferred embodiment, the autoimmune diseases include psoriasis and rheumatoid arthritis.

In a preferred embodiment, the autoimmune diseases include psoriasis, systemic lupus erythematosus and rheumatoid arthritis.

In a preferred embodiment, the inflammatory disease includes ulcerative colitis.

In a preferred embodiment, the inflammatory disease includes inflammatory bowel disease, such as ulcerative colitis.

In a preferred embodiment, the tumors can be hematological tumors and solid tumors.

In a preferred embodiment, the hematological tumors include large B-cell lymphoma and acute and chronic lymphocytic leukemia; In a preferred embodiment, the solid tumors include intestinal cancer and skin cancer caused by MYD88 mutations.

In a preferred embodiment, the cardiovascular and cerebrovascular diseases include stroke and atherosclerosis.

In a preferred embodiment, the central nervous system disease includes primary central nervous system lymphoma.

The present disclosure also provides a use of substance Z or the above-mentioned pharmaceutical composition in the preparation of a medicament, wherein the substance Z is a compound of formula I, a pharmaceutically acceptable salt or an isotope compound thereof; and the medicament is used for treatment one or more of autoimmune diseases, inflammatory diseases, tumors, cardiovascular and cerebrovascular diseases and central nervous system diseases.

In a preferred embodiment, the autoimmune diseases, inflammatory diseases, tumors, cardiovascular and cerebrovascular diseases and central nervous system diseases are as described in any embodiment of the present disclosure.

The present disclosure also provides a compound of formula II or III, a salt, a Boc-protected compound or an isotope compound thereof,

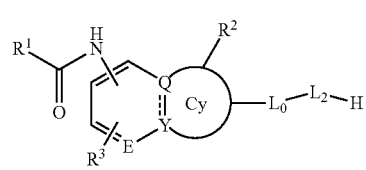

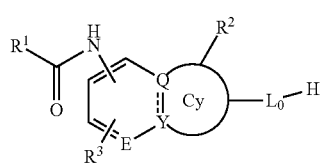

$R^1$, $R_2$, $R^3$, Q, Y, ring Cy, $L_0$ and $L_2$ are as described above;

Preferably, the compound of formula II or III is any of the following compounds:
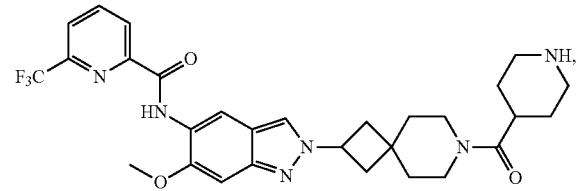
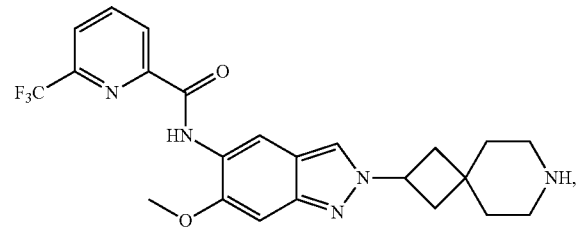
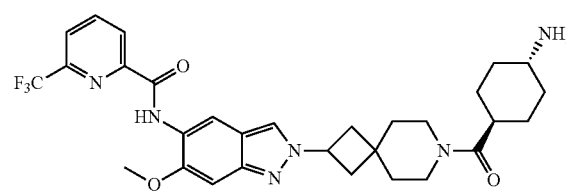
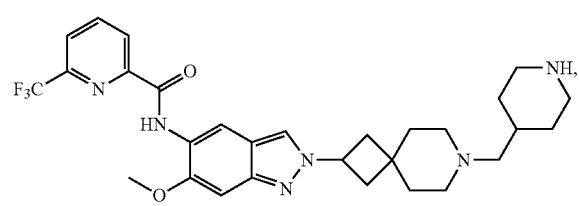
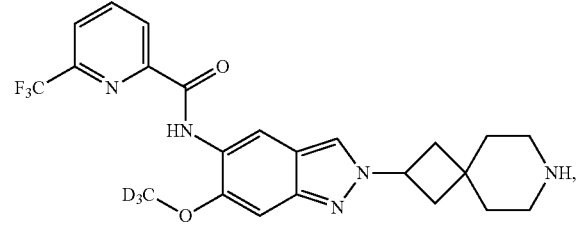
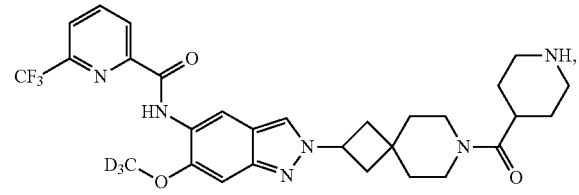
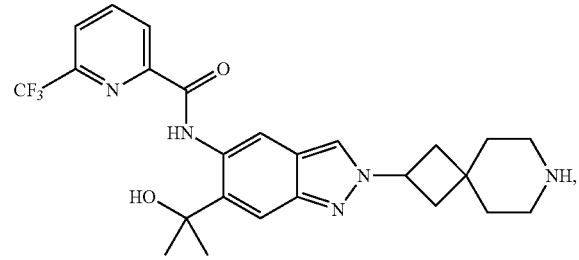
-continued
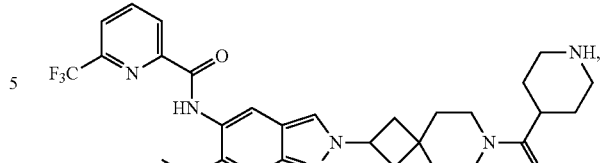
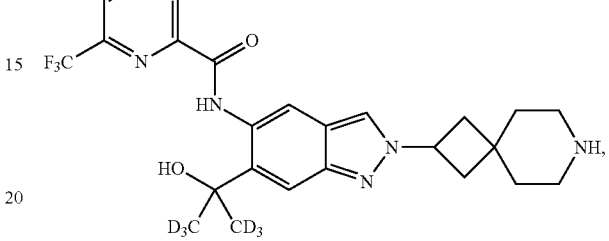
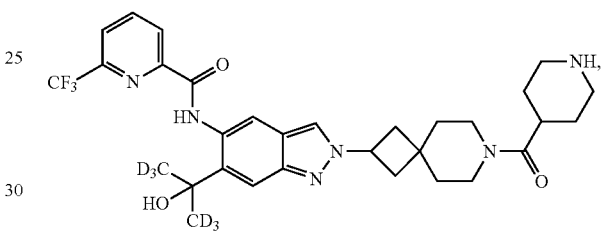
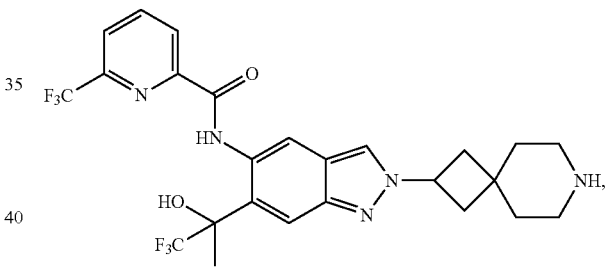
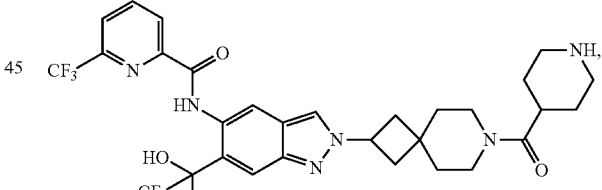
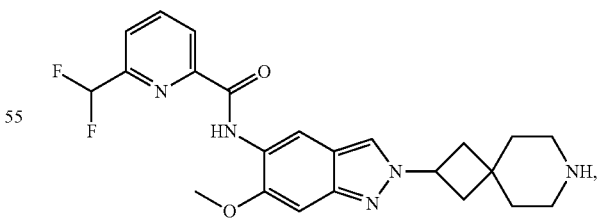
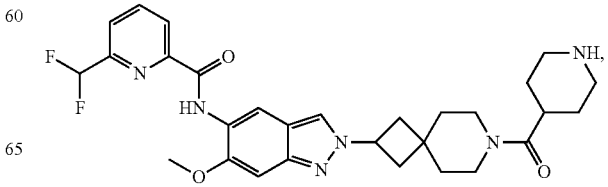

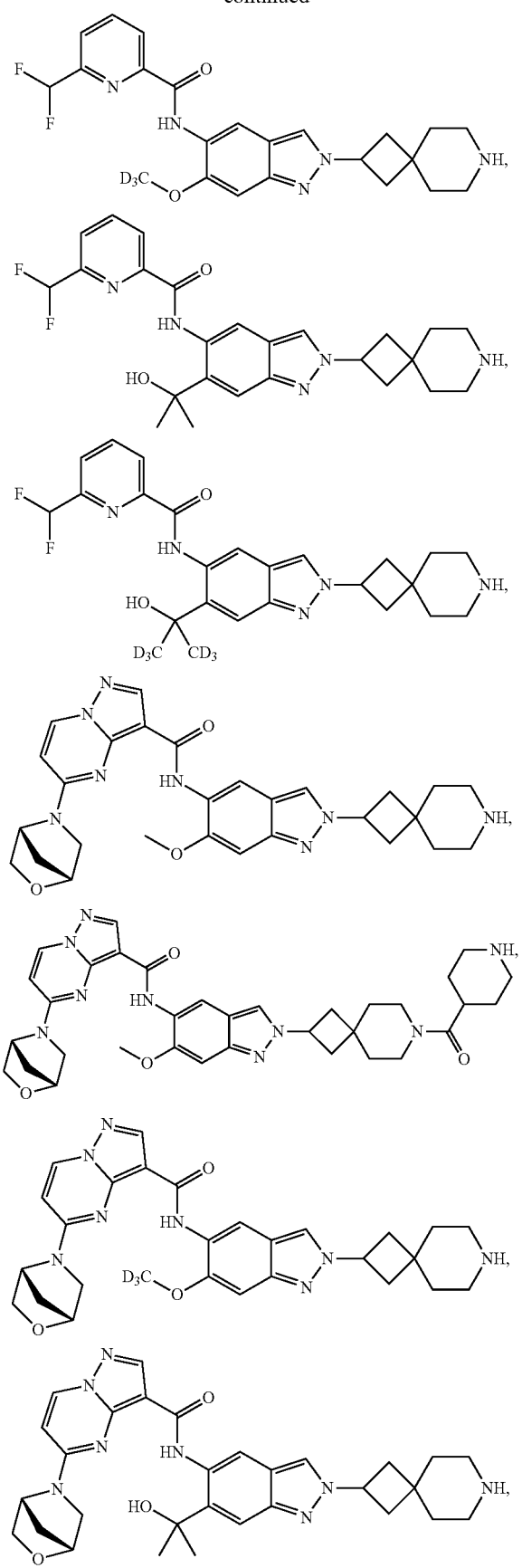
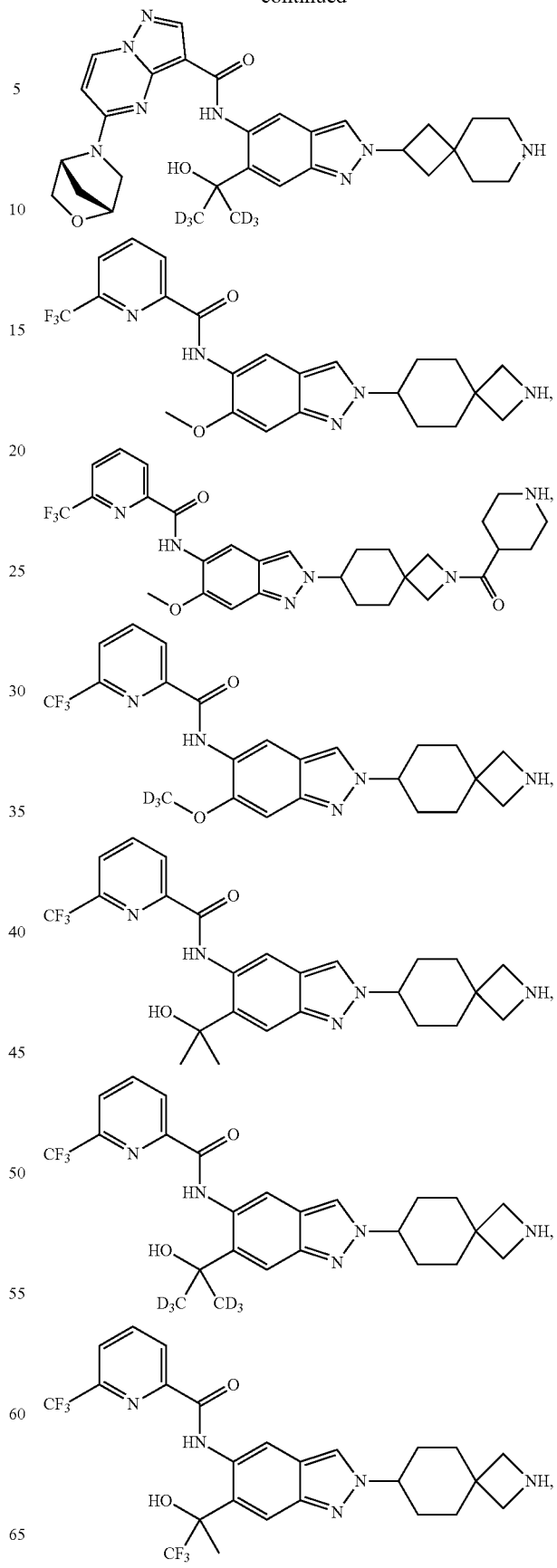

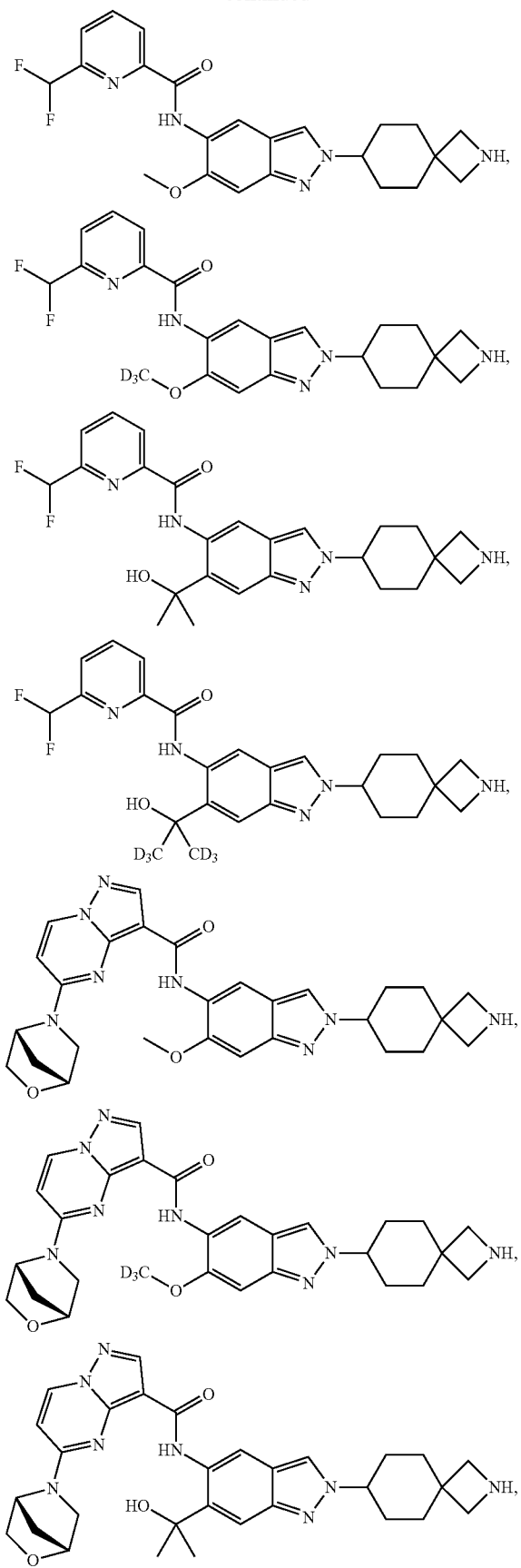
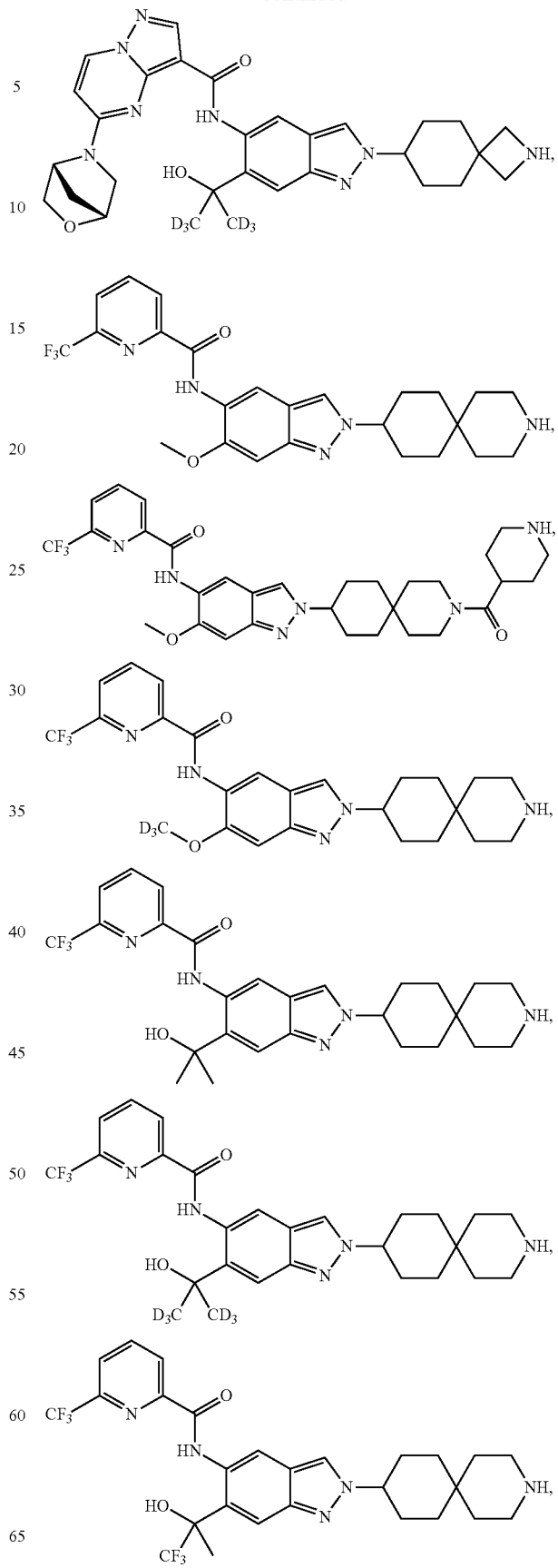

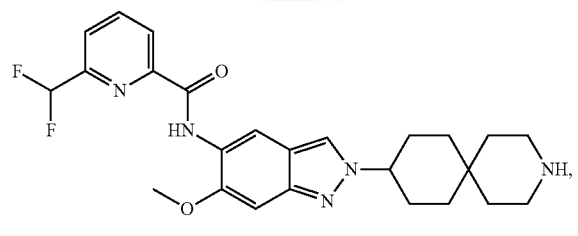
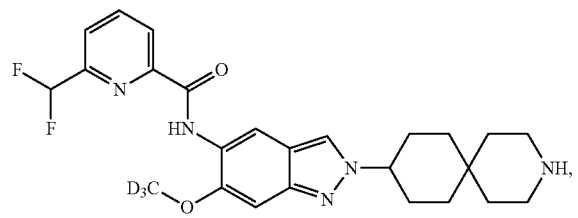
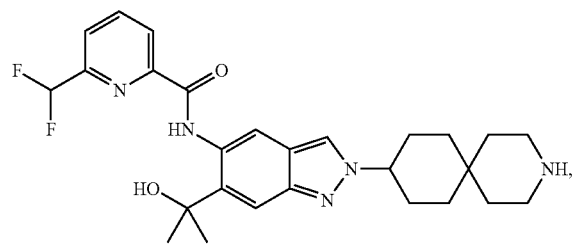
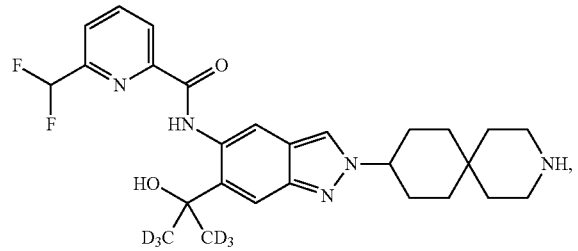
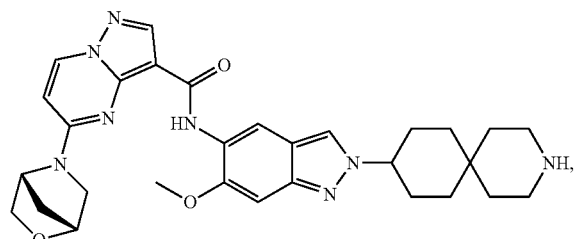
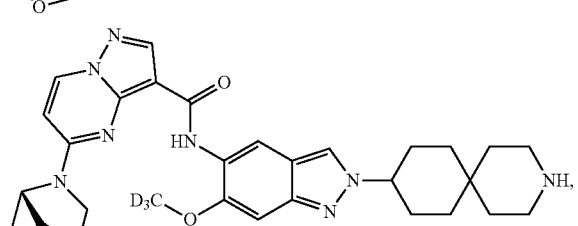
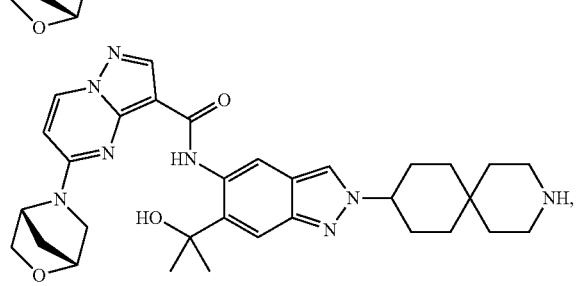
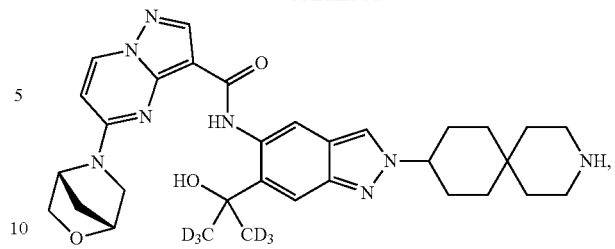
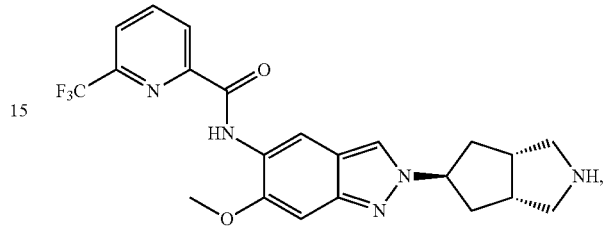
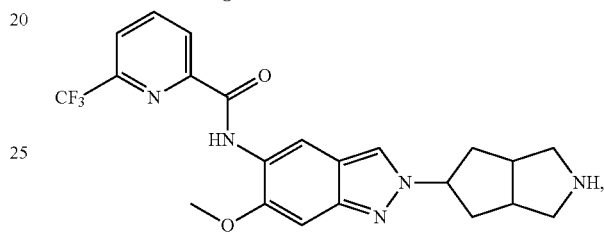
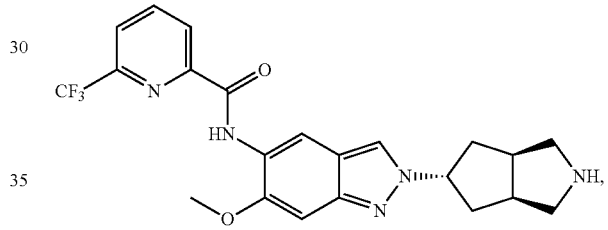
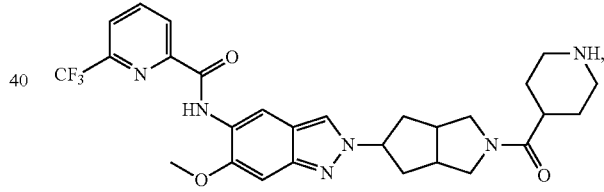
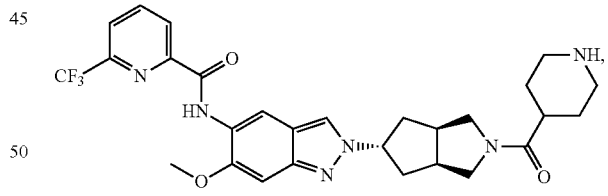
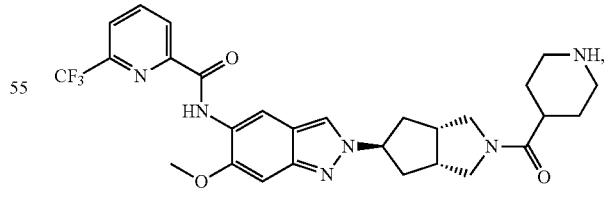
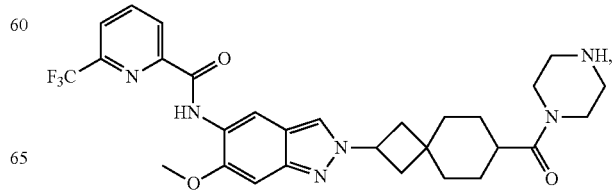

187
-continued
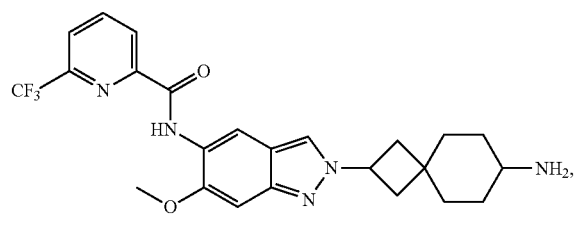
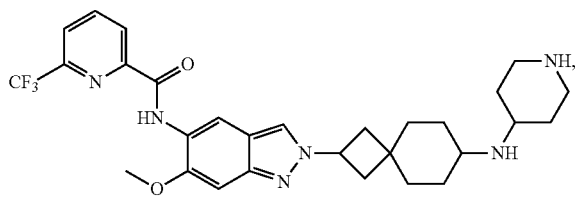
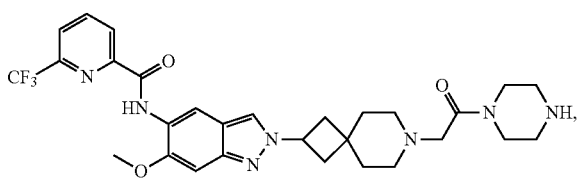
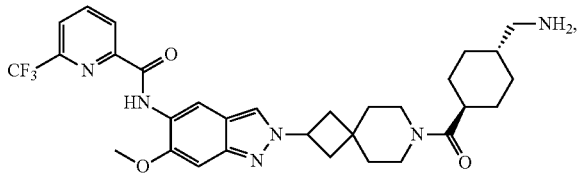
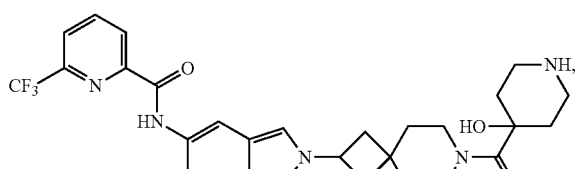
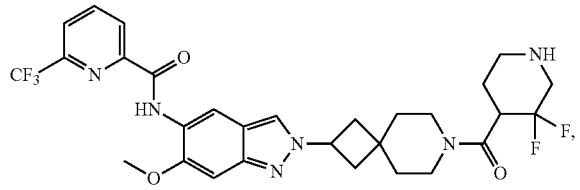
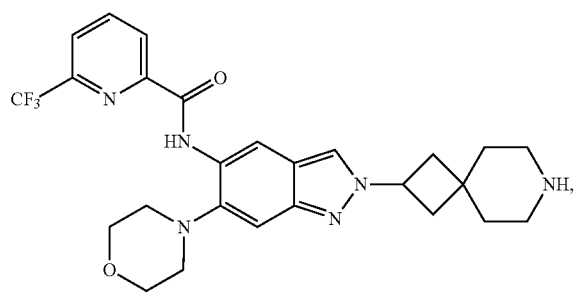
188
-continued
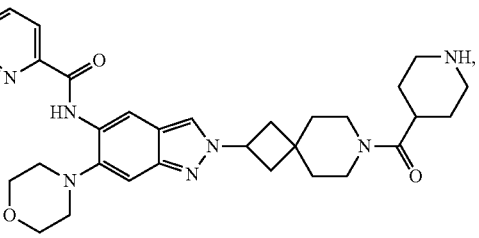
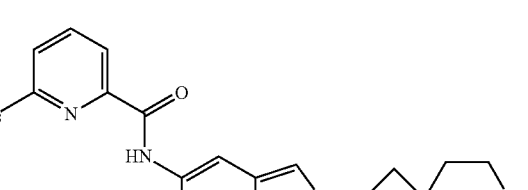
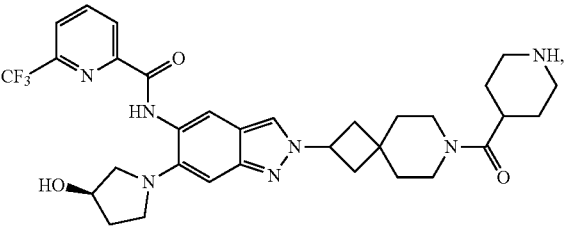
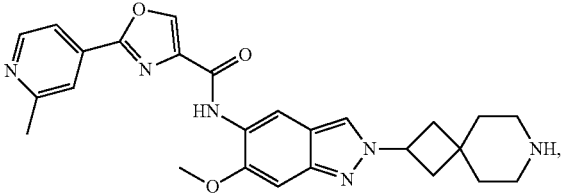
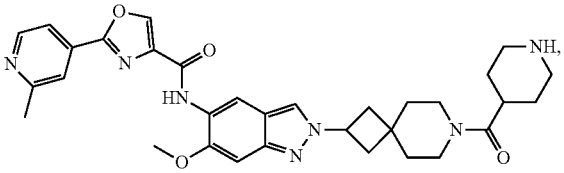
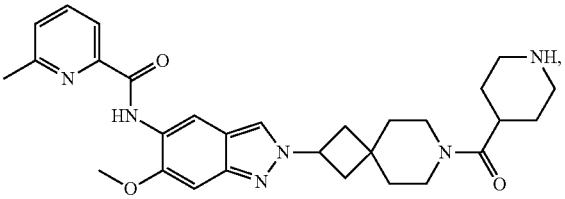

189
-continued

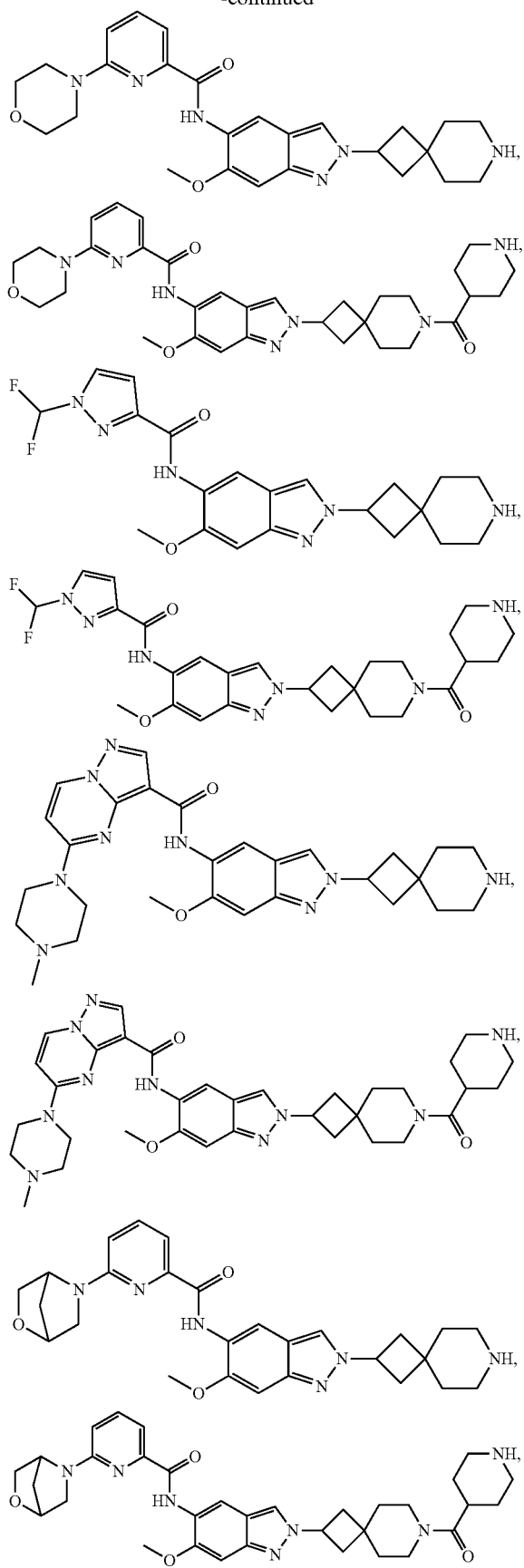

190
-continued

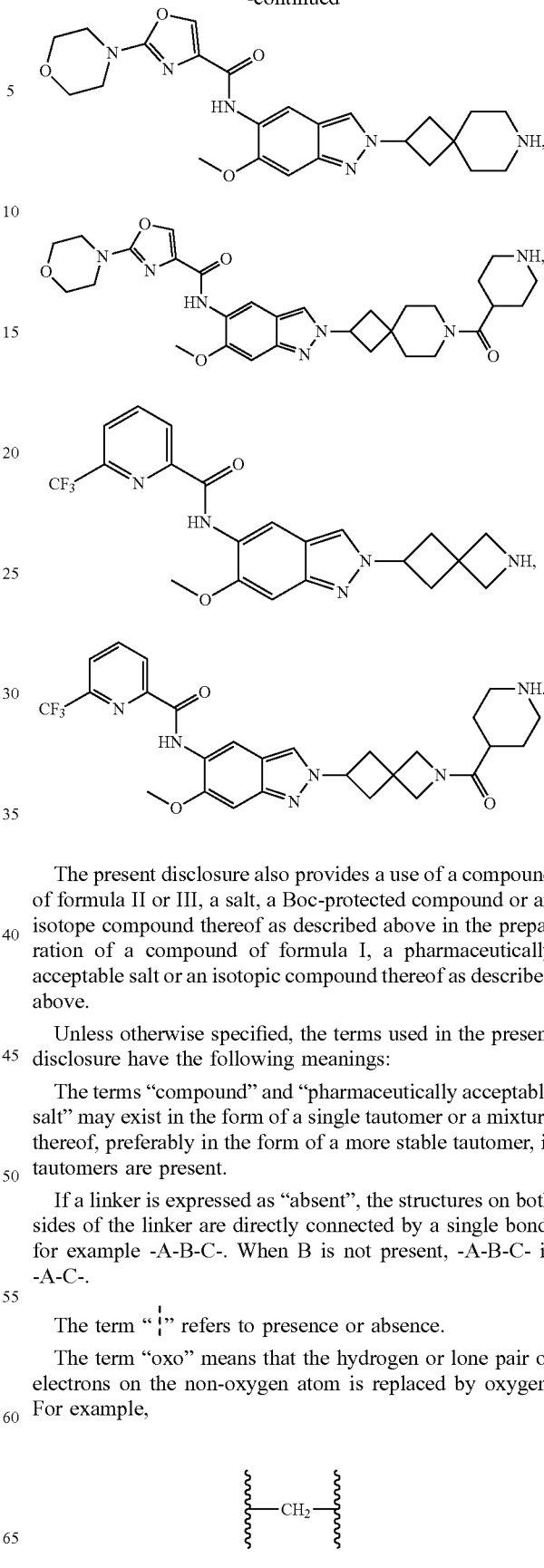

The present disclosure also provides a use of a compound of formula II or III, a salt, a Boc-protected compound or an isotope compound thereof as described above in the preparation of a compound of formula I, a pharmaceutically acceptable salt or an isotopic compound thereof as described above.

Unless otherwise specified, the terms used in the present disclosure have the following meanings:

The terms "compound" and "pharmaceutically acceptable salt" may exist in the form of a single tautomer or a mixture thereof, preferably in the form of a more stable tautomer, if tautomers are present.

If a linker is expressed as "absent", the structures on both sides of the linker are directly connected by a single bond, for example -A-B-C-. When B is not present, -A-B-C- is -A-C-.

The term " ¦ " refers to presence or absence.

The term "oxo" means that the hydrogen or lone pair of electrons on the non-oxygen atom is replaced by oxygen. For example, is

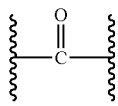

after being replaced by oxygen and

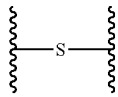

is

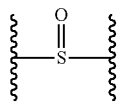 or 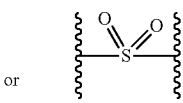

after being replaced by oxygen

The term "halogen" refers to fluorine, chlorine, bromine or iodine.

The term "cycloalkyl" refers to a saturated monocyclic cyclic group having a specified number of carbon atoms (e.g., $C_3$-$C_{10}$), which consists only of carbon atoms. The monocyclic alkyl groups include, but are not limited to, cyclopropyl, cyclobutyl, cyclopentyl, cyclohexyl, and the like.

The term "alkyl" refers to a straight or branched alkyl group having a specified number of carbon atoms (e.g., $C_1$-$C_6$). Alkyl groups include, but are not limited to, methyl, ethyl, n-propyl, isopropyl, n-butyl, tert-butyl, isobutyl, sec-butyl, n-pentyl, n-hexyl, and the like.

The term "heterocycloalkyl" refers to a cyclic group having a specified number of ring atoms (e.g., 3 to 11 members, also e.g., 3 to 8 members), a specified number of heteroatoms (such as 1, 2 or 3), and a specified heteroatom types (one or more of N, O and S), in which heteroatoms can be connected to other groups as connecting groups or not be connected to other groups (for example, the piperidinyl can be

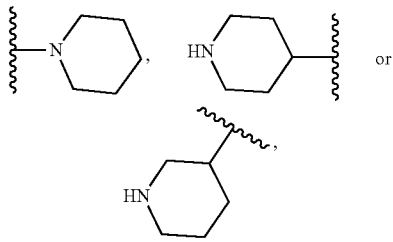

and the like). It is a monocyclic ring, a fused ring, a bridged ring or a spiro ring, and each ring is saturated. Heterocycloalkyl includes, but are not limited to, azetidinyl, tetrahydropyrrolyl, tetrahydrofuryl, morpholinyl, piperidinyl, and the like.

The term "heterocycle" refers to a cyclic group having a specified number of ring atoms (e.g., 3 to 12 members), a specified number of heteroatoms (e.g., 1, 2, or 3), and a specified type of heteroatoms (one or more of N, O, and S), in which heteroatoms can be connected to other groups as connecting groups, or not be connected to other groups (for example, the piperidine ring can be

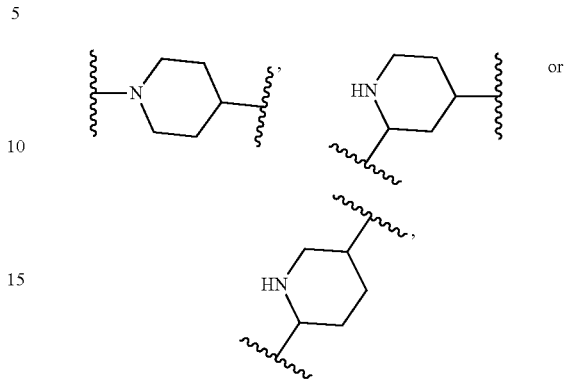

and the like). It is a monocyclic ring, a fused ring, a bridged ring or a spiro ring, and each ring is saturated. Heterocycloalkyl includes, but are not limited to, azetidine ring, tetrahydropyrrole ring, tetrahydrofuran ring, morpholine ring, and piperidyl ring.

The term "heteroaryl" refers to a cyclic group having a specified number of ring atoms (e.g., 5 to 9 members), a specified number of heteroatoms (e.g., 1, 2, or 3), and a specified type of heteroatom (one or more of N, O, and S), which is monocyclic or polycyclic, and at least one ring is aromatic (in compliance with Huckel's rule). The heteroaryl group is connected to other segments in the molecule through an aromatic ring or a non-aromatic ring. Heteroaryl groups include, but are not limited to, furyl, pyrrolyl, thienyl, pyrazolyl, imidazolyl, oxazolyl, thiazolyl, pyridyl, pyrimidinyl, indolyl, and the like.

The term "heteroaromatic ring" refers to a cyclic group having a specified number of ring atoms (e.g., 5 to 9 members), a specified number of heteroatoms (e.g., 1, 2, or 3), and a specified type of heteroatom (one or more of N, O, and S), which is monocyclic or polycyclic, and at least one ring is aromatic (in compliance with Huckel's rule). The heteroaromatic ring is connected to other segments in the molecule through an aromatic ring or a non-aromatic ring. Heteroaromatic rings include, but are not limited to, furan ring, pyrrole ring, thiophene ring, pyrazole ring, imidazole ring, oxazole ring, thiazole ring, pyridine ring, pyrimidine ring, indole ring, and the like.

The "—" at the end of a group means that the group is connected to other fragments in the molecule by this site. For example, $CH_3$—C($=$O)— refers to an acetyl group.

The

in a structural fragment means that the structural fragment is connected to other fragments in the molecule by this site. For example,

refers to an acetyl group.

The term "cycloalkylene group" is a divalent group connected to the rest of the molecule by two single bonds. Other definitions are the same as the term "cycloalkyl".

The term "heterocycloalkylene group" is a divalent group connected to the rest of the molecule by two single bonds. Other definitions are the same as the term "heterocycloalkyl".

The term "isotopic compound" refers to a compound in which one or more atoms have an isotopic abundance that differs from its natural abundance. For example, one or more atoms in a compound are replaced by atoms that have a lower mass number in nature—a hydrogen atom in the compound is replaced by deuterium, or a C is replaced by $^{13}C$.

The term "more" means 2, 3, 4 or 5.

The term "Boc-protected" generally means that N is protected by a Boc group.

Substituents such as heterocycle, aromatic ring, heteroaryl, aryl, heterocycloalkyl, alkoxy, alkyl, cycloalkyl, and the like described in the present disclosure serve as linker units to connect different components of the compound. Thus, they can also be called as heterocyclylene, arylene ring, heteroarylene group, arylene group, heterocycloalkylene group, alkyleneoxy group, alkylene group, and cycloalkylene group.

When any variable (such as the group $R^{1-1}$) appears multiple times in the definition of a compound, their definitions are independent of each other and do not affect each other. For example, a $C_6$-$C_{10}$ aryl substituted by 3 $R^{1-1}$ means that the $C_6$-$C_{10}$ aryl will be substituted by 3 $R^{1-1}$. The definitions of the 3 $R^{1-1}$ are independent of each other and do not affect each other.

The term "pharmaceutically acceptable salt" refers to a salt obtained by reacting a compound with a pharmaceutically acceptable (relatively nontoxic, safe, and suitable for use by a patient) acid or base. When the compound comprises relatively acidic functional groups, base addition salts can be obtained by contacting a free form of the compound with a sufficient amount of a pharmaceutically acceptable base in a suitable inert solvent. Pharmaceutically acceptable base addition salts include, but are not limited to, sodium salts, potassium salts, calcium salts, aluminum salts, magnesium salts, bismuth salts, ammonium salts, and the like. When the compound comprises relatively basic functional groups, acid addition salts can be obtained by contacting a free form of the compound with a sufficient amount of a pharmaceutically acceptable acid in a suitable inert solvent. Pharmaceutically acceptable acid addition salts include, but are not limited to, hydrochloride, acetate, trifluoroacetate, sulfate, methanesulfonate, and the like. For details, see Handbook of Pharmaceutical Salts: Properties, Selection, and Use (P. Heinrich Stahl, 2002).

The term "solvate of pharmaceutically acceptable salt" refers to a substance formed by combining a compound with a pharmaceutically acceptable (relatively non-toxic, safe, and suitable for use by a patient) acid or base, solvent (including but not limited to: water, methanol, ethanol, and the like), wherein the pharmaceutically acceptable salt here has the same meaning as the term "pharmaceutically acceptable salt" above, and the solvent is stoichiometric or non-stoichiometric. Pharmaceutically acceptable salt solvates include, but are not limited to, hydrochloride monohydrate.

The term "pharmaceutical excipients" refers to excipients and additives used in the preparation of a medicament and preparation of a prescription. Pharmaceutical excipients are all substances other than active ingredients included in pharmaceutical formulations. For details, see the Pharmacopoeia of the People's Republic of China (2020 Edition) or Handbook of Pharmaceutical EMcipients (Raymond C Rowe, 2009).

The term "treatment" refers to any of the following: (1) alleviating one or more biological manifestations of a disease; (2) interfering with one or more points in the biological cascade that causes the disease; and (3) slowing down the progression of one or more biological manifestations of a disease.

The term "prevention" refers to reducing the risk of developing a disease.

The term "patient" refers to any animal, preferably a mammal, most preferably a human, that has been or will be treated. Mammals include, but are not limited to, cattle, horses, sheep, pigs, cats, dogs, mice, rats, rabbits, guinea pigs, monkeys, humans, and the like.

As used in the specifications and claims, the singular form "a", "an" and "the" includes plural references unless the context clearly dictates otherwise.

On the basis of not violating common sense in the art, the above preferred embodiments can be combined arbitrarily to obtain preferred examples of the present disclosure.

The reagents and raw materials used in the present invention are all commercially available.

The positive and progressive effect of the present disclosure is that the compound of the present disclosure has an inhibitory or/and degradative effect on IRAK4, and can nearly completely degrade the IRAK4 protein at a lower drug concentration. The compounds of the present disclosure can also inhibit the scaffolding function of the Myddosome complex. The compounds of the present disclosure have potential clinical application value and are expected to be applied to various IRAK4-related immune diseases and various hematological diseases and solid tumors caused by Myd88 mutations.

DETAILED DESCRIPTION OF THE PREFERRED EMBODIMENT

The present disclosure is further described below by way of examples. However, the present disclosure is not limited to the scope of the described examples. Experimental methods that do not indicate specific conditions in the following examples should be selected according to conventional methods and conditions, or according to product specifications.

Example 1: Synthesis of Compound I-1

Synthesis of Compound 1-1

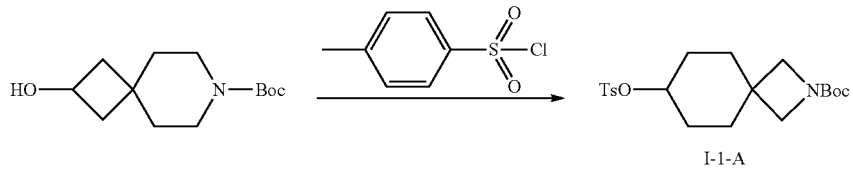

I-1-A

-continued
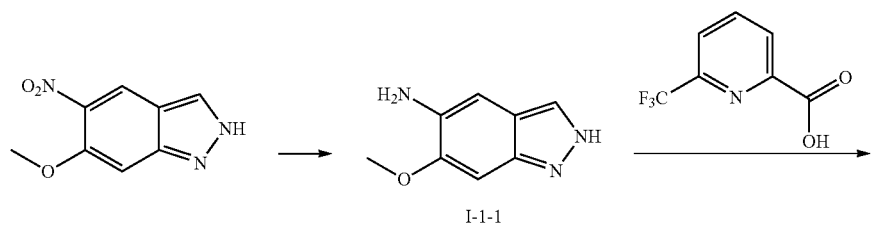
I-1-1
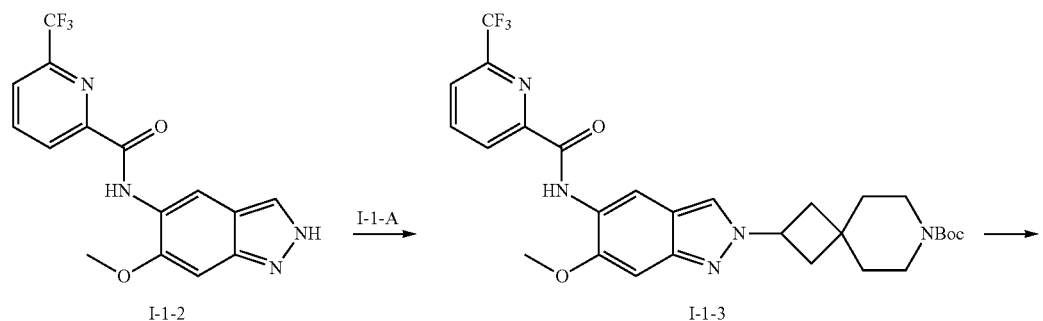
I-1-2 → I-1-3
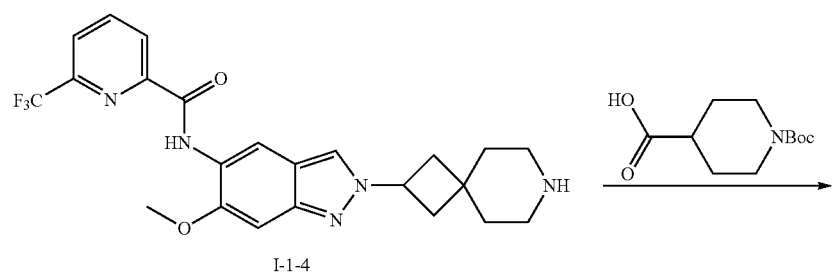
I-1-4
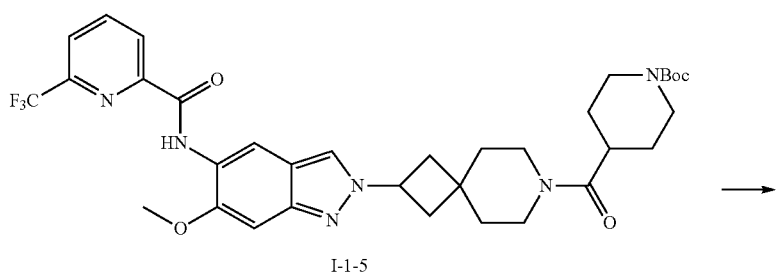
I-1-5
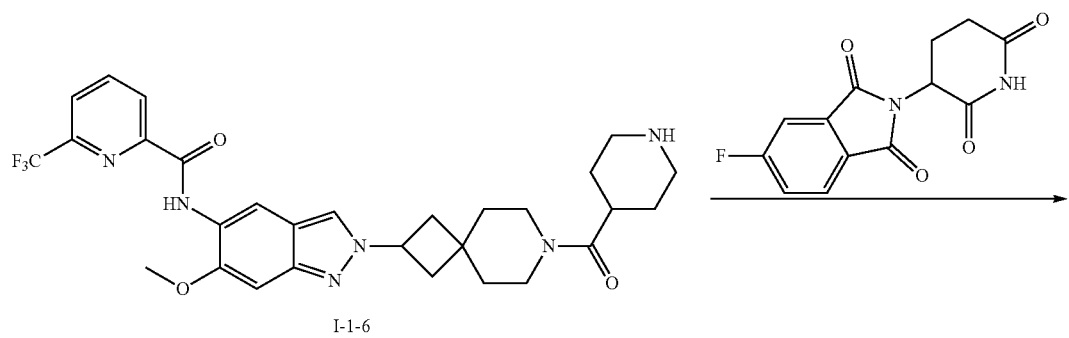
I-1-6

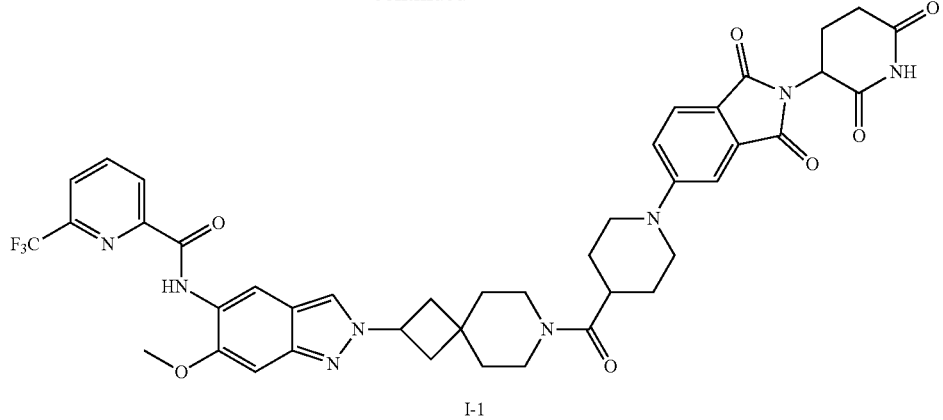

I-1

Step 1: Synthesis of I-1-A

A mixed solution of 7-tert-butoxycarbonyl-7-azaspiro [3.5]-2-nonanol (600 mg, 2.49 mmol), 4-dimethylaminopyridine (60.75 mg, 497.25 μmol, 83.68 μL), triethylamine (503.17 mg, 4.97 mmol, 693.07 μL) and methylene chloride (1.35 mL) was stirred to dissolve, and p-toluenesulfonyl chloride (521.40 mg, 2.73 mmol) was added. The reaction was raised to 40° C. and stirred for 18 hours until the reaction was complete. The reaction system was added with water (30 mL) to dilute, and stirred and extracted with dichloromethane (20 mL×3). The combined organic phase was washed with brine (20 mL), dried over anhydrous sodium sulfate, filtered and concentrated in vacuum to obtain I-1-A (1 g, crude product), MS (ESI) m/z: 396.2 [M+H]+.

Step 2: Synthesis of I-1-1

A mixed solution of 6-methoxy-5-nitro-2H-indazole (2 g, 10.35 mmol), Pd/C (0.3 g, 10% purity) and methanol (30 mL) was stirred and replaced with hydrogen three times. The reaction was continued under a hydrogen environment at 25° C. for 18 hours until the reaction was complete. The mixed solution was filtered through diatomaceous earth to remove the catalyst and the filter cake was washed with methanol (10 mL×2). The filtrate was concentrated under reduced pressure to obtain product I-1-1 as a brown solid (1.59 g, crude product), MS (ESI) m/z: 164.1 [M+H]+, which was used directly in the next step.

Step 3: Synthesis of I-1-2

To a mixed solution of I-1-1 (1.59 g, 9.74 mmol), 6-(trifluoromethyl)pyridine-2-carboxylic acid (2.05 g, 10.72 mmol), diisopropylethylamine (3.78 g, 29.23 mmol, 5.09 mL) and tetrahydrofuran (25 mL), 2,4, 6-tripropyl-1,3,5,2,4,6 trioxotriphosphonane 2,4,6-trioxide (7.44 g, 11.69 mmol, 50% purity) was added dropwise with stirring at 0° C. After the dropwise addition was completed, the reaction system was stirred under nitrogen protection at 15° C. for 2 hours until the reaction was complete. The reaction mixture was added with water (50 mL), and extracted with ethyl acetate (40 mL×5). The combined organic phase was washed with water (30 mL) and saturated brine, dried over anhydrous sodium sulfate, filtered and concentrated under vacuum and reduced pressure to obtain product I-1-2 as a brown solid (3.08 g, crude product), MS (ESI) m/z: 337.1 [M+H]+, which was directly used in the next step.

Step 4: Synthesis of I-1-3

A mixed solution of I-1-A (500 mg, 1.49 mmol), I-1-2 (705.71 mg, 1.78 mmol), cesium carbonate (968.93 mg, 2.97 mmol) and N,N-dimethylformamide (4 mL) was stirred at 90° C. for 5 hours until the reaction was complete. The reaction solution was cooled to room temperature, added with water (30 mL) to dilute, stirred and extracted with ethyl acetate (30 mL×3). The combined organic phase was washed with saturated brine (20 mL), dried over anhydrous sodium sulfate, filtered and concentrated in vacuum to obtain I-1-3 (250 mg, 446.76 μmol, yield 30.05%), MS (ESI) m/z: 560.2 [M+H]+.

Step 5: Synthesis of I-1-4

A mixed solution of I-1-3 (250 mg, 446.76 μmol), dichloromethane (3 mL) and trifluoroacetic acid (3 mL) was stirred at room temperature for 2 hours until the reaction was complete. The reaction solution was spin-dried, and the crude product was purified by C18 column chromatography to obtain I-1-4 as a yellow solid (200 mg, 435.29 μmol, yield 97.43%), MS (ESI) m/z: 460.2 [M+H]+.

Step 6: Synthesis of I-1-5

A mixed solution of I-1-4 (25.00 mg, 54.41 μmol), 1-Boc-4-piperidinecarboxylic acid (12.47 mg, 54.41 μmol), diisopropylethylamine (35.16 mg, 272.06 μmol, 47.39 μL), 2-(7-azobenzotriazole)-N,N,N',N'-tetramethylurea hexafluorophosphate (24.83 mg, 65.29 μmol) and N,N-dimethylformamide (2 mL) was added into a reaction bottle, stirred at room temperature for 12 hours until the reaction was complete. The reaction solution was diluted with water (30 mL), stirred and extracted with ethyl acetate (30 mL×3). The combined organic phase was washed with saturated brine (20 mL), dried over anhydrous sodium sulfate, filtered and concentrated in vacuum to obtain a crude product, which was purified by thin layer preparative chromatography to obtain I-1-5 (36 mg, 53.67 μmol, yield 98.64%), MS (ESI) m/z: 671.3 [M+H]+.

Step 7: Synthesis of I-1-6

Trifluoroacetic acid (2 mL) was added dropwise to a mixed solution of I-1-5 (36.00 mg, 53.67 μmol) and dichloromethane (2 mL) under stirring at 0° C. After completion of the addition, the reaction was carried out at room temperature for 1 hour until complete. The reaction solution was spin-dried to obtain I-1-6 (30 mg, crude trifluoroacetate salt), MS (ESI) m/z: 571.6 [M+H]+, which was directly used in the next step.

Step 8: Synthesis of I-1

A mixed solution of I-1-6 (30.00 mg, 52.58 μmol), 2-(2,6-dioxo-piperidin-3-yl)-5-fluoro-isoindole-1,3-dione (14.52 mg, 52.58 μmol), diisopropylethylamine (33.98 mg, 262.88 μmol, 45.79 μL) and N,N-dimethylformamide (2 mL) was reacted at 100° C. for 2 hours to complete the reaction. The reaction solution was diluted with water (20 mL), stirred and extracted with ethyl acetate (20 mL×3). The combined organic phase was washed with saturated brine (20 mL), dried over anhydrous sodium sulfate, filtered and concentrated in vacuum to obtain a crude product, which was purified by thin layer preparative chromatography to obtain I-1 (23 mg, 27.26 μmol, yield 51.85%), MS (ESI) m/z: 827.9 [M+H]$^+$, $^1$HNMR(500 MHz, DMSO-d$_6$) δ 11.08 (s, 1H),10.51 (s, 1H),8.69 (s, 1H), 8.46 (d, J=8.0 Hz, 1H), 8.41 (t, J=8.0 Hz, 1H), 8.37 (s, 1H), 8.22 (d, J=8.0 Hz, 1H), 7.67 (d, J=8.5 Hz, 1H), 7.33 (s, 1H), 7.25 (d, J=8.5 Hz, 1H), 7.21 (s, 1H), 5.24-5.12 (m, 1H), 5.07 (dd, J=13.0, 5.0 Hz, 1H), 4.07 (d, J=12.5 Hz, 2H), 3.99 (s, 3H), 3.60-3.38 (m, 4H), 3.15-3.05 (m, 2H), 3.04-2.95 (m, 1H), 2.94-2.83 (m, 1H), 2.66-2.52 (m, 2H), 2.50-2.46 (m, 2H), 2.467-2.38 (m, 2H), 2.06-1.98 (m, 1H), 1.81-1.67 (m, 4H), 1.67-1.54 (m, 4H).

Compounds I-2, I-3, 1-4, I-5 and I-8 can be prepared by referring to the method of Example 1 above. The structure and characterization data are shown in the following table:

| molecular ID | structure | MS (ESI) m/z: [M + H]$^+$ | $^1$H NMR |
|---|---|---|---|
| I-2 | 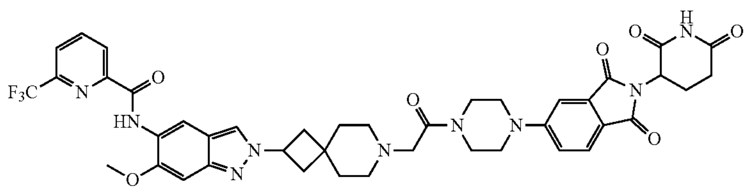 [SMILES: COc1cc2nn(C3CC4(CCN(CC(=O)N5CCN(c6ccc7c(c6)C(=O)N(C6CCC(=O)NC6=O)C7=O)CC5)CC4)C3)cc2cc1NC(=O)c1cccc(C(F)(F)F)n1] | 842.3 | (500 MHz, DMSO-d$_6$) δ 11.08 (s, 1H), 10.50 (s, 1H), 8.68 (s, 1H), 8.46 (d, J = 8.0 Hz, 1H), 8.41 (t, J = 8.0 Hz, 1H), 8.35 (s, 1H), 8.22 (dd, J = 8.0, 1.0 Hz, 1H), 7.71 (d, J = 8.5 Hz, 1H), 7.38 (d, J = 2.0 Hz, 1H), 7.28 (dd, J = 8.5, 2.0 Hz, 1H), 7.20 (s, 1H), 5.16-5.03 (m, 2H), 3.99 (s, 3H), 3.79-3.68 (m, 2H), 3.66-3.59 (m, 2H), 3.58-3.44 (m, 4H), 3.25-3.08 (m, 2H), 3.01-2.80 (m, 2H), 2.65-2.52 (m, 3H), 2.46-2.33 (m, 6H), 2.05-1.98 (m, 1H), 1.82-1.62 (m, 4H). |
| I-3 | 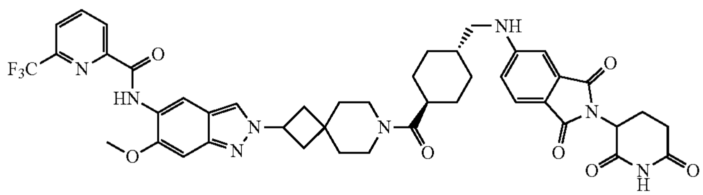 [SMILES: COc1cc2nn(C3CC4(CCN(C(=O)[C@H]5CC[C@H](CNc6ccc7c(c6)C(=O)N(C6CCC(=O)NC6=O)C7=O)CC5)CC4)C3)cc2cc1NC(=O)c1cccc(C(F)(F)F)n1] | 855.3 | (500 MHz, CDCl$_3$) δ 10.72 (s, 1H), 8.82 (s, 1H), 8.49 (d, J = 8.0 Hz, 1H), 8.12 (t, J = 8.0 Hz, 1H), 7.99 (s, 1H), 7.90-7.84 (m, 2H), 7.62 (d, J = 8.5 Hz, 1H), 7.11 (d, J = 8.5 Hz, 1H), 6.97 (s, 1H), 6.75 (d, J = 8.0 Hz, 1H), 5.08-5.00 (m, 1H), 4.93 (dd, J = 12.5, 5.0 Hz, 1H), 4.04 (s, 3H), 3.65-3.61 (m, 1H), 3.58-3.47 (m, 2H), 3.45-3.38 (m, 1H), 3.11 (d, J = 6.0 Hz, 2H), 2.92-2.86 (m, 1H), 2.85-2.78 (m, 1H), 2.77-2.69 (m, 1H), 2.63-2.53 (m, 4H), 2.16-2.10 (m, 1H), 1.99-1.92 (m, 2H), 1.87-1.71 (m, 8H), 1.68-1.59 (m, 5H). |
| I-4 | 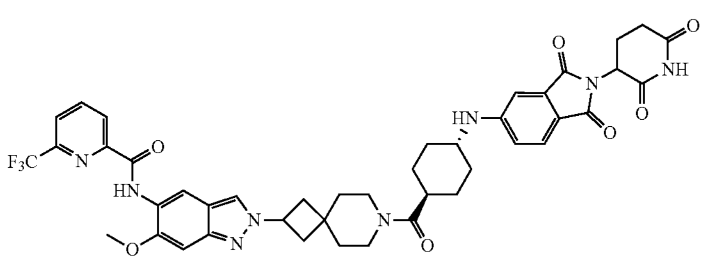 [SMILES: COc1cc2nn(C3CC4(CCN(C(=O)[C@H]5CC[C@H](Nc6ccc7c(c6)C(=O)N(C6CCC(=O)NC6=O)C7=O)CC5)CC4)C3)cc2cc1NC(=O)c1cccc(C(F)(F)F)n1] | 841.3 | (500 MHz, DMSO-d$_6$) δ 11.05 (s, 1H), 10.51 (s, 1H), 8.69 (s, 1H), 8.46 (d, J = 8.0 Hz, 1H), 8.41 (t, J = 8.0 Hz, 1H), 8.37 (s, 1H), 8.22 (d, J = 8.0 Hz, 1H), 7.55 (d, J = 8.0 Hz, 1H), 7.21 (s, 1H), 7.00 (d, J = 7.0 Hz, 2H), 6.88 (d, J = 8.5 Hz, 1H), 5.21-5.13 (m, 1H), 5.03 (dd, J = 13.0, 5.5 Hz, 1H), 3.99 (s, 3H), 3.57-3.47 (m, 2H), 3.47-3.37 (m, 3H), 2.93-2.79 (m, 1H), 2.71-2.54 (m, 2H), 2.54-2.51 (m, 1H), 2.47-2.35 (m, 3H), 2.05-1.95 (m, 3H), 1.79-1.52 (m, 8H), 1.38-1.22 (m, 3H). |

-continued
| molecular ID | structure | MS (ESI) m/z: [M + H]+ | ¹H NMR |
|---|---|---|---|
| I-5 | 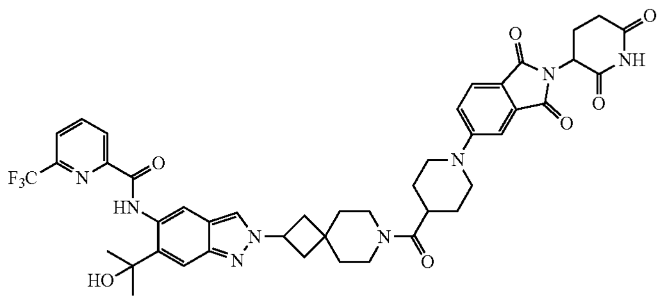 [SMILES: CC(C)(O)c1cc2nn(C3CC4(CCN(C(=O)C5CCN(c6ccc7c(c6)C(=O)N(C6CCC(=O)NC6=O)C7=O)CC5)CC4)C3)cc2cc1NC(=O)c1cccc(C(F)(F)F)n1] | 855.2 | (500 MHz, DMSO-d₆) δ 12.42-12.36 (m, 1H), 11.08 (s, 1H), 8.73 (s, 1H), 8.45 (d, J = 8.0 Hz, 1H), 8.41 (s, 1H), 8.37 (t, J = 8.0 Hz, 1H), 8.16 (d, J = 8.0 Hz, 1H), 7.67 (d, J = 8.5 Hz, 1H), 7.62 (s, 1H), 7.33 (s, 1H), 7.25 (d, J = 8.5 Hz, 1H), 5.97 (s, 1H), 5.28-5.18 (m, 1H), 5.07 (dd, J = 13.0, 5.0 Hz, 1H), 4.07 (d, J = 13.0 Hz, 2H), 3.66-3.38 (m, 5H), 3.15-3.05 (m, 2H), 3.05-2.94 (m, 1H), 2.94-2.84 (m,1H), 2.63-2.53 (m, 2H), 2.47-2.39 (m, 2H), 2.05-1.98 (m, 1H), 1.77-1.67 (m, 4H), 1.65 (s, 1H), 1.63 (s, 6H), 1.62-1.56 (m, 2H), 1.27-1.22 (m, 2H). |
| I-8 | 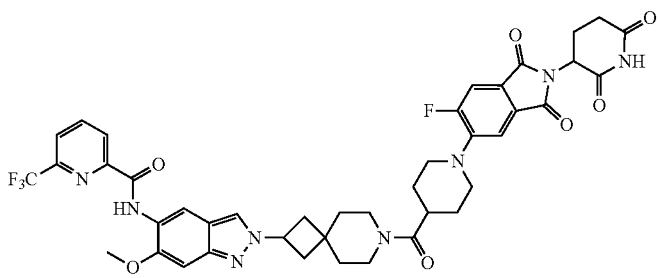 [SMILES: COc1cc2nn(C3CC4(CCN(C(=O)C5CCN(c6cc7c(cc6F)C(=O)N(C6CCC(=O)NC6=O)C7=O)CC5)CC4)C3)cc2cc1NC(=O)c1cccc(C(F)(F)F)n1] | 845.3 | (500 MHz, DMSO-d₆) δ 11.10 (s, 1H), 10.51 (s, 1H), 8.69 (s, 1H), 8.46 (d, J = 8.0 Hz, 1H), 8.41 (t, J = 8.0 Hz, 1H), 8.38 (s, 1H), 8.22 (d, J = 8.0 Hz, 1H), 7.71 (d, J = 11.0 Hz, 1H), 7.45 (d, J = 7.0 Hz, 1H), 7.21 (s, 1H), 5.23-5.14 (m, 1H), 5.11 (dd, J = 13.0, 5.5 Hz, 1H), 3.99 (s, 3H), 3.64 (d, J = 11.5 Hz, 2H), 3.58-3.39 (m, 4H), 3.09-2.97 (m, 2H), 2.96-2.83 (m, 2H), 2.66-2.53 (m, 2H), 2.49-2.34 (m, 4H), 2.10-2.01 (m, 1H), 1.79-1.57 (m, 8H). |
Example 2: Synthesis of Compound II-1
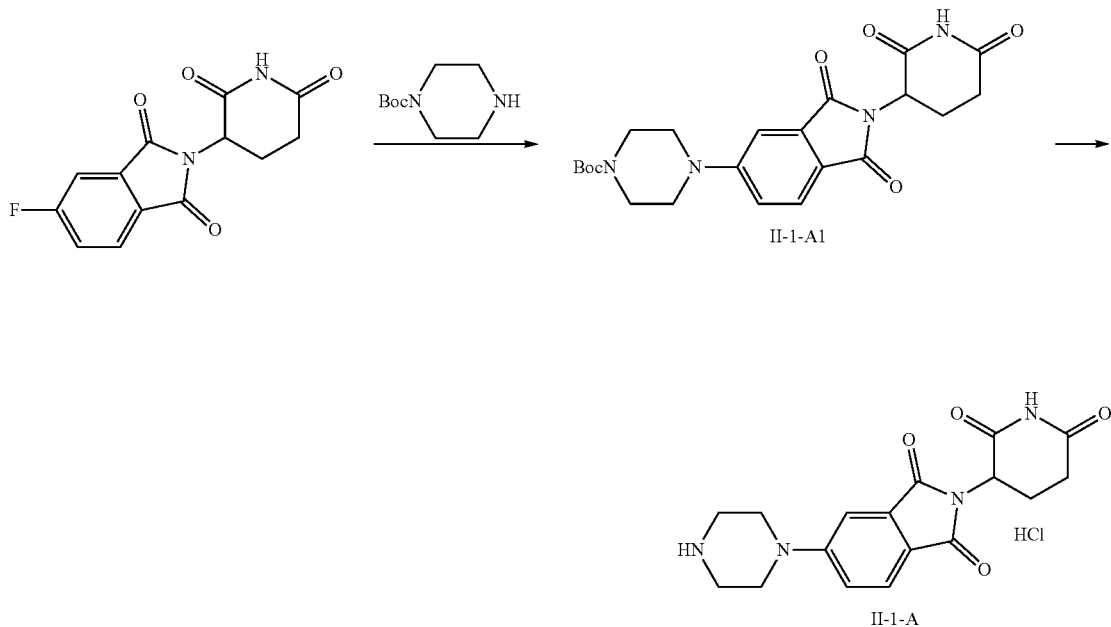

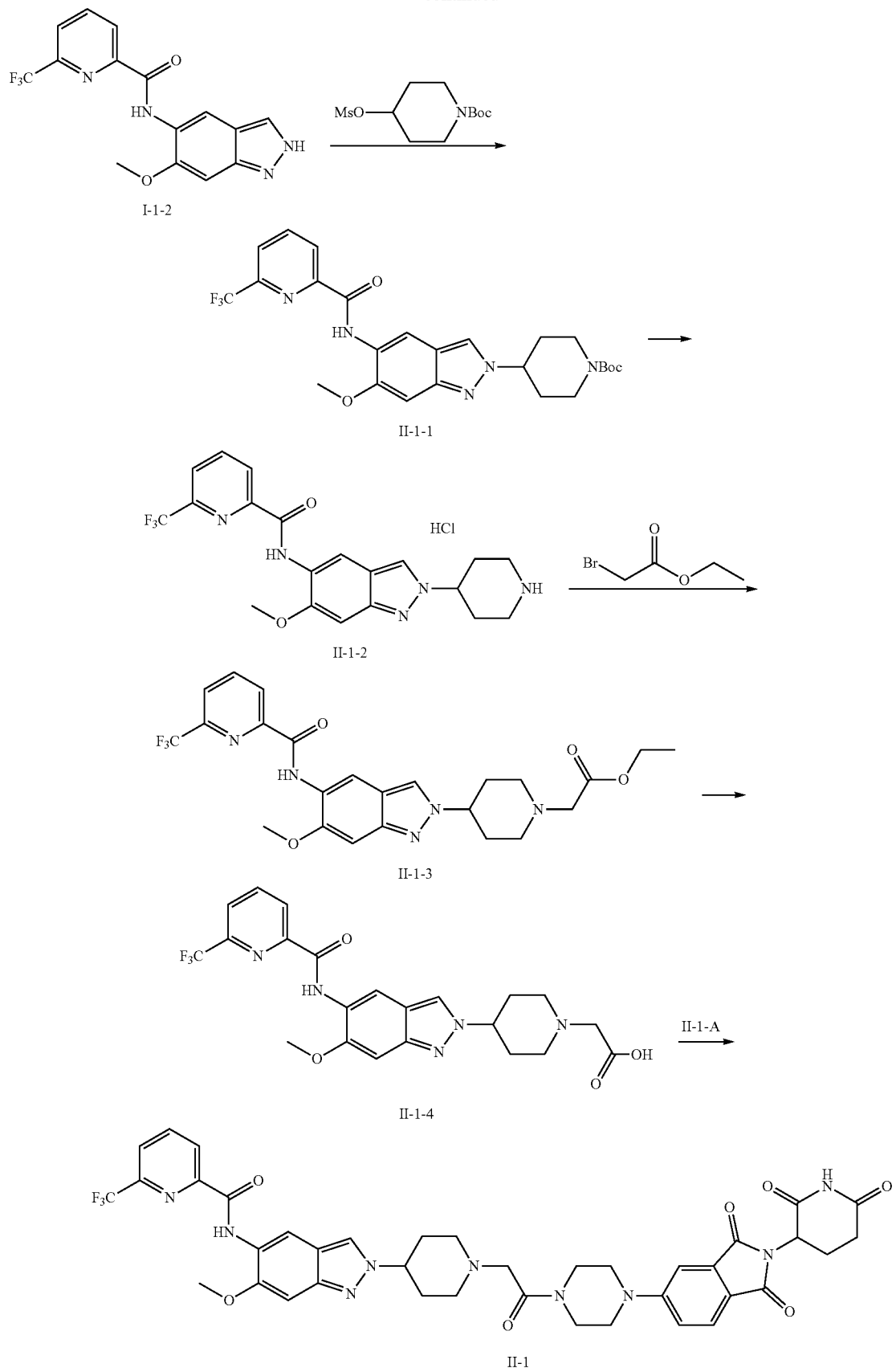

Step 1: Synthesis of II-1-A1

2-(2,6-dioxy-3-piperidyl)-5-fluoro-isoindole-1,3-dione (247.18 mg, 894.85 μmol) and piperazine-1-carboxylic acid tert-butyl ester (200 mg, 1.07 mmol) were dissolved in dimethyl sulfoxide (3 mL), then diisopropylethylamine (346.95 mg, 2.68 mmol, 467.59 μL) was weighed and added to the reaction system. The mixed solution was stirred at 100° C. for 2 hours until the reaction was complete. The reaction system was added with water (50 mL) to to dilute, stirred and extracted with ethyl acetate (50 mL×3). The combined organic phase was washed with brine (30 mL), dried over anhydrous sodium sulfate, filtered and concentrated in vacuum to obtain a crude product, which was purified by silica gel column chromatography (dichloromethane: methanol=20:1) to obtain product II-1-A1 as a yellow solid (260 mg, 587.62 μmol, yield 65.67%), MS (ESI) m/z: 443.2 [M+H]$^+$.

Step 2: Synthesis of II-1-A

II-1-A1 (260 mg, 587.62 μmol) was dissolved in dichloromethane (3 mL), and added with hydrochloric acid-dioxane (4 M, 2 mL) dropwise under stirring at 0° C. After the dropwise addition was completed, the mixed solution was stirred at 25° C. for 2 hours until the reaction was complete. The reaction system was filtered, washed with dichloromethane (10 mL), and the filter cake was dried to obtain product II-1-A as a white solid (204 mg, 538.52 μmol, yield 91.65%), MS (ESI) m/z: 343.2 [M+H]$^+$.

Step 3: Synthesis of II-1-1

A mixed solution of I-1-2 (1.02 g, 3.03 mmol), tert-butyl 4-methylsulfonyloxypiperidine-1-carboxylate (1.10 g, 3.94 mmol), cesium carbonate (1.98 g, 6.07 mmol) and N,N-dimethylformamide (10 mL) was stirred and reacted under nitrogen protection at 70° C. for 2 hours until the reaction was complete. The reaction mixture was added with water (30 mL), and extracted with ethyl acetate (20 mL×3). The combined organic phases were washed with water (20 mL×3) and brine, dried over anhydrous sodium sulfate, filtered and concentrated under vacuum and reduced pressure to obtain a crude product, which was purified by flash chromatography column (elution with petroleum ether/ethyl acetate=5/1-1/1) to obtain product II-1-1 as an off-white solid (0.35 g, 673.70 μmol, yield 22.21%), MS (ESI) m/z: 520.2 [M+H]$^+$.

Step 4: Synthesis of II-1-2

II-1-1 (0.35 g, 673.70 μmol) was dissolved in dichloromethane (5 mL), and added with hydrochloric acid-dioxane (4 M, 7.9 mL) dropwise under stirring at 0° C. After the dropwise addition was completed, the mixed solution was stirred at 25° C. for 2 hours until the reaction was complete. The reaction system was filtered, washed with dichloromethane (10 mL), and the filter cake was dried to obtain product II-1-2 as a white solid (280 mg, 667.62 μmol, yield 99.10%), MS (ESI) m/z: 420.2 [M+H]$^+$.

Step 5: Synthesis of II-1-3

II-1-2 (120 mg, 286.12 μmol) was dissolved in N,N-dimethylformamide (2 mL), and added with potassium carbonate (79.09 mg, 572.25 μmol) and ethyl 2-bromoacetate (71.67 mg, 429.19 μmol, 47.59 μL). The reaction system was stirred at 25° C. for 6 hours until the reaction was complete. The reaction system was added with water (50 mL) to dilute, stirred and extracted with ethyl acetate (50 mL×3). The combined organic phase was washed with brine (30 mL), dried over anhydrous sodium sulfate, filtered and concentrated in vacuum to obtain a crude product, which was purified by silica gel column chromatography (petroleum ether: ethyl acetate=1:1) to obtain II-1-3 as a yellow solid (80 mg, 158.26 μmol, yield 55.31%), MS (ESI) m/z: 506.2 [M+H]$^+$.

Step 6: Synthesis of II-1-4

A mixed solution of II-1-3 (100 mg, 197.83 μmol), water (1 mL), lithium hydroxide (4.74 mg, 197.83 μmol) and methanol (2 mL) was stirred at room temperature for 1 hour until the reaction was complete. Methanol was distilled off under reduced pressure, and dilute hydrochloric acid (2 M) was added to the system to adjust the pH to about 6-7. The reaction system was purified through a C18 reversed-phase chromatography column and freeze-dried to obtain II-1-4 as a yellow solid (30 mg, 62.84 μmol, collected rate 31.76%), MS (ESI) m/z: 478.2 [M+H]$^+$.

Step 7: Synthesis of II-1

A mixed solution of II-1-4 (15 mg, 31.42 μmol), II-1-A (12.91 mg, 34.07 μmol), 2-(7-azobenzotriazole)-N,N,N',N'-tetramethylurea hexafluorophosphate (17.92 mg, 47.13 μmol), diisopropylethylamine (12.18 mg, 94.25 μmol, 16.42 μL) and N,N-dimethylformamide (1 mL) was reacted under nitrogen protection at 25° C. for 2 hours until the reaction was complete. The reaction mixture was added with water (25 mL), and extracted with ethyl acetate (25 mL×3). The combined organic phases were washed with brine (30 mL), dried over anhydrous sodium sulfate, filtered and concentrated in vacuo to obtain a crude product, which was purified by C18 column chromatography to obtain product II-1 as a yellow solid (6 mg, 7.41 μmol, yield 23.58%), MS (ESI) m/z: 802.8 [M+H]$^+_o$ $^1$H NMR (500 MHz, DMSO-d$_6$) δ 11.08 (s, 1H), 10.50 (s, 1H), 8.69 (s, 1H), 8.46 (d, J=8.0 Hz, 1H), 8.40 (t, J=8.0 Hz, 1H), 8.37 (s, 1H), 8.22 (dd, J=8.0, 1.0 Hz, 1H), 7.71 (d, J=8.5 Hz, 1H), 7.39 (d, J=2.0 Hz, 1H), 7.29 (dd, J=8.5, 2.0 Hz, 1H), 7.17 (s, 1H), 5.08 (dd, J=13.0, 5.5 Hz, 1H), 4.46-4.36 (m, 1H), 3.98 (s, 3H), 3.83-3.72 (m, 2H), 3.70-3.61 (m, 2H), 3.61-3.53 (m, 2H), 3.52-3.43 (m, 2H), 3.29 (s, 2H), 3.04-2.94 (m, 2H), 2.93-2.85 (m, 1H), 2.62-2.52 (m, 2H), 2.33-2.24 (m, 2H), 2.19-2.07 (m, 4H), 2.05-2.00 (m, 1H).

Compounds II-5 and II-6 can be prepared by referring to the method of Example 2 above. The structure and characterization data are shown in the following table:

| molecular ID | structure | MS (ESI) m/z: [M + H]+ | 1H NMR |
|---|---|---|---|
| II-5 | 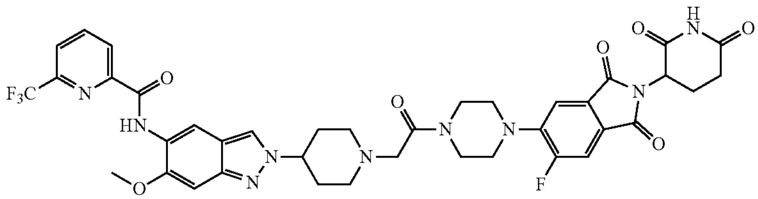 [SMILES: COc1cc2nn(C3CCN(CC(=O)N4CCN(c5cc6c(cc5F)C(=O)N(C5CCC(=O)NC5=O)C6=O)CC4)CC3)cc2cc1NC(=O)c1cccc(C(F)(F)F)n1] | 820.3 | (500 MHz, DMSO-d6) δ 11.12 (s, 1H), 10.50 (s, 1H), 8.69 (s, 1H), 8.46 (d, J = 8.0 Hz, 1H), 8.40 (t, J = 8.0 Hz, 1H), 8.37 (s, 1H), 8.21 (d, J = 8.0 Hz, 1H), 7.77 (d, J = 11.0 Hz, 1H), 7.52 (d, J = 7.5 Hz, 1H), 7.17 (s, 1H), 5.12 (dd, J = 13.0, 5.0 Hz, 1H), 4.49-4.36 (m, 1H), 3.85-3.75 (m, 2H), 3.70-3.61 (m, 2H), 3.36-3.31 (m, 5H), 3.28 (s, 2H), 3.26-3.22 (m, 2H), 2.99 (d, J = 11.0 Hz, 2H), 2.94-2.84 (m, 1H), 2.66-2.52 (m, 2H), 2.34-2.24 (m, 2H), 2.19-2.01 (m, 5H). |
| II-6 | 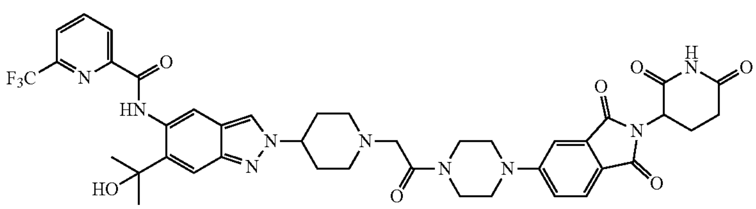 [SMILES: CC(C)(O)c1cc2nn(C3CCN(CC(=O)N4CCN(c5ccc6c(c5)C(=O)N(C5CCC(=O)NC5=O)C6=O)CC4)CC3)cc2cc1NC(=O)c1cccc(C(F)(F)F)n1] | 830.2 | (500 MHz, DMSO-d6) δ 12.37 (s, 1H), 11.09 (s, 1H), 8.71 (s, 1H), 8.45 (d, J = 8.0 Hz, 1H), 8.40 (s, 1H), 8.37 (t, J = 8.0 Hz, 1H), 8.16 (d, J = 8.0 Hz, 1H), 7.72 (d, J = 8.5 Hz, 1H), 7.58 (s, 1H), 7.39 (d, J = 2.0 Hz, 1H), 7.29 (dd, J = 8.5, 2.0 Hz, 1H), 5.95 (s, 1H), 5.08 (dd, J = 13.0, 5.0 Hz, 1H), 4.51-4.38 (m, 1H), 3.82-3.75 (m, 2H), 3.66-3.54 (m, 4H), 3.52-3.46 (m, 2H), 3.29 (s, 2H), 3.00 (d, J = 11.0 Hz, 2H), 2.93-2.83 (m, 1H), 2.66-2.54 (m, 2H), 2.34-2.26 (m, 2H), 2.18-2.08 (m, 4H), 2.06-1.99 (m, 1H), 1.62 (s, 6H). |
Example 3: Synthesis of Compound I-9
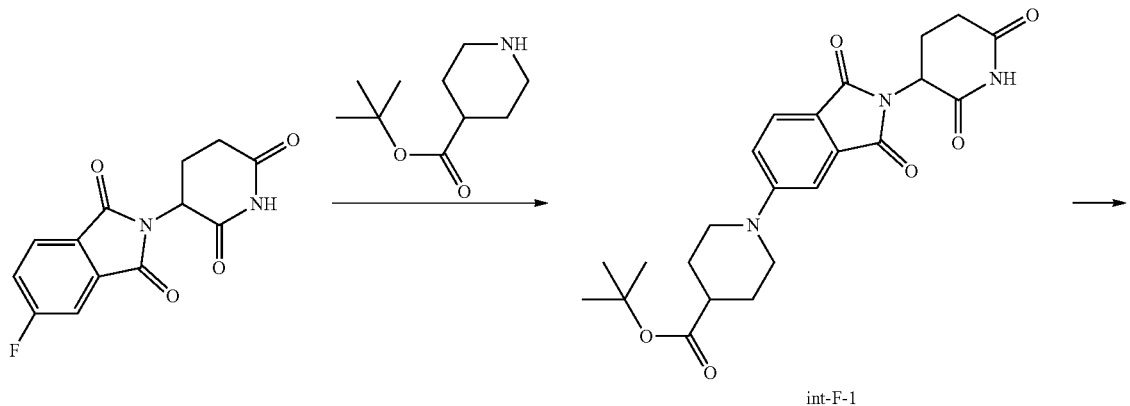

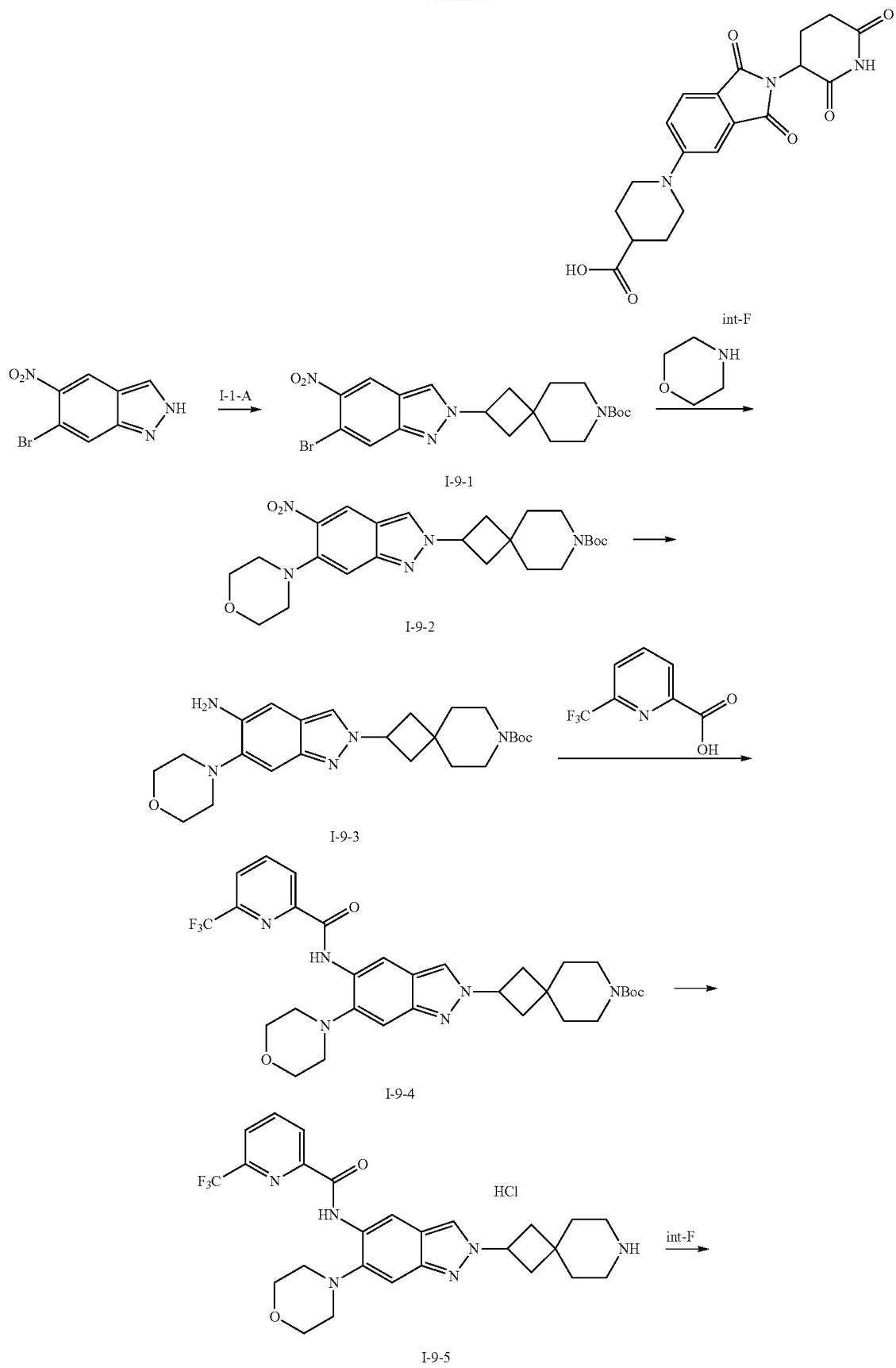

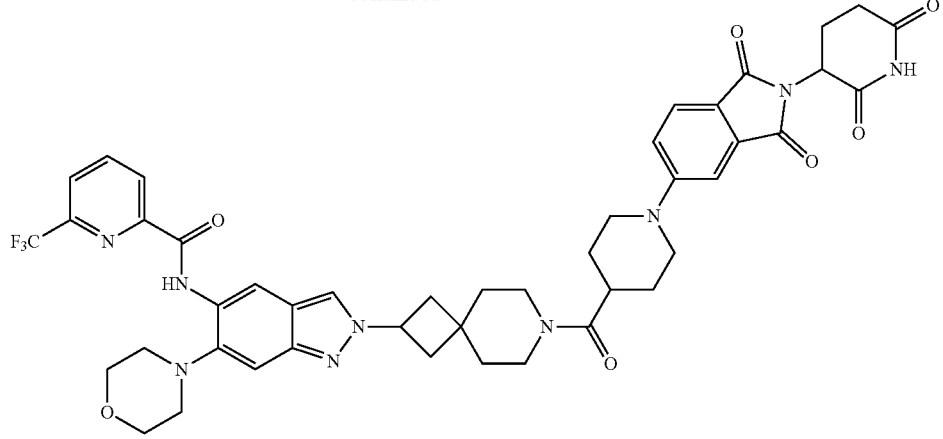

I-9

Step 1: Synthesis of (int-F-1)

To a solution of 2-(2,6-dioxopiperidin-3-yl)-5-fluoroisoindole-1,3-dione (5.0 g, 18.0 mmol) in anhydrous DMSO (20.0 mL) was added DIPEA (4.7 g, 36.2 mmol) and piperidine-4-carboxylic acid tert-butyl ester (4.0 g, 21.6 mmol), and the reaction mixture was stirred at 90° C. for 2 hours. After cooling to room temperature, the reaction mixture was diluted with water (50 mL) and extracted with ethyl acetate (50 mL×3). The combined organic phases were washed with saturated brine (50 mL), dried over magnesium sulfate, filtered, and concentrated under reduced pressure. The crude product was purified by silica gel column chromatography (PE/EA=5/1) to obtain product int-F-1 as a yellow solid (7.5 g, yield 94.2%), MS (ESI) m/z: 442.2 [M+H]$^+$.

Step 2: Synthesis of (int-F)

TFA (20 mL) was added dropwise to a solution of int-F-1 (5 g, 11.3 mmol) in DCM (50 mL) at 0° C. After the dropwise addition was completed, the mixture was stirred at 25° C. for 16 hours. Diethyl ether was added to the reaction solution under stirring, the solid was filtered after precipitating, and the filter cake was washed with diethyl ether to obtain product int-F as a yellow solid (3.7 g, yield 84.9%), MS (ESI) m/z: 386.1 [M+H]$^+$.

Step 3: Synthesis of (I-9-1)

6-bromo-5-nitro-2H-indazole (1 g, 4.13 mmol) and I-1-A (2.45 g, 6.20 mmol) were dissolved in DMF (20 mL), and added with Cs$_2$CO$_3$ (1.35 g) and KI (685.87 mg, 4.13 mmol) with stirring. The reaction solution was stirred at 100° C. for 2 hours, added with water (50 mL), and extracted with ethyl acetate (50 mL×3. The combined organic phases were washed with saturated brine, dried over anhydrous sodium sulfate, filtered, and concentrated under reduced pressure. The crude product was purified by silica gel column chromatography (PE:EA=1:1) to obtain solid I-9-1 as a light yellow (500 mg, yield 26.01%), MS (ESI) m/z: 465.1 [M+H]$^+$.

Step 4: Synthesis of (I-9-2)

I-9-1 (250 mg, 537.24 µmol) and morpholine (936.09 mg, 10.74 mmol) were dissolved in 1,4-dioxane (2 mL), and added with CuI (51.16 mg, 268.62 µmol) and K$_3$PO$_4$ (456.15 mg, 2.15 mmol) with stirring. The mixture was reacted at 90° C. for 6 hours under nitrogen protection, added with saturated ammonium chloride solution, and extracted with ethyl acetate (50 mL×3). The combined organic phases were washed with saturated brine, dried over anhydrous sodium sulfate, filtered, and concentrated under reduced pressure. The crude product was purified by silica gel column chromatography to obtain I-9-2 as a light yellow solid (70 mg, yield 27.63%), MS (ESI) m/z: 472.2 [M+H]$^+$.

Step 5: Synthesis of (I-9-3)

I-9-2 (70 mg, 148.45 µmol) was dissolved in MeOH (2 mL), added with wet Pd/C (70 mg, 10% w/w) and replaced with hydrogen three times. The mixture was reacted at 25° C. under a hydrogen atmosphere for 6 hours, and filtered through diatomaceous earth. The filter cake was rinsed three times with ethyl acetate (30 mL), and the filtrate was collected. The solvent was distilled off under reduced pressure to obtain product I-9-3 as a white solid (60 mg, yield 91.53%), MS (ESI) m/z: 442.3 [M+H]$^+$.

Step 6: Synthesis of (I-9-4)

6-(trifluoromethyl)pyridine-2-carboxylic acid (25 mg, 130.82 µmol) and I-9-3 (57.76 mg, 130.82 µmol) were dissolved in DMF (1 mL), added with DIPEA (50.72 mg, 392.45 µmol) and HATU (74.61 mg, 196.22 µmol) under stirring. mg, 392.45 µmol), and reacted at 25° C. for 2 hours. The reaction system was added with water (30 mL), and extracted with ethyl acetate (30 mL×3). The combined organic phases were washed with saturated brine, dried over anhydrous sodium sulfate, filtered, and concentrated under reduced pressure. The crude product was purified by silica gel column chromatography to obtain the product I-9-4 as a light yellow solid (50 mg, yield 62.18%), MS (ESI) m/z: 615.3 [M+H]$^+$.

Step 7: Synthesis of (I-9-5)

I-9-4 (70 mg, 113.88 µmol) was dissolved in DCM (3 mL), added with HCl-dioxane solution (4 M, 284.71 µL) dropwise under stirring. After the dropwise addition was completed, the reaction system was reacted at 25° C. for 2 hours. The reaction solution was filtered, and the filter cake was washed three times with DCM (30 mL) and dried to obtain the product I-9-5 as a white solid (50 mg, yield 79.68%, hydrochloride), MS (ESI) m/z: 515.2 [M+H]+.

Step 8: Synthesis of (I-9)

To a solution of I-9-5 (40 mg, 72.59 µmol, hydrochloride), int-F (33.57 mg, 87.11 µmol) and DMF (1.5 mL) was added DIPEA (28.15 mg, 217.78 µmol) and HATU (41.40 mg, 108.89 µmol), and the resulting mixture was stirred at 25° C. for 1 hour. The reaction system was added with water (20 mL), and extracted with ethyl acetate (20 mL×3). The combined organic phases were washed with saturated brine, dried over anhydrous sodium sulfate, filtered, and concentrated under reduced pressure. The crude product was purified by preparative thin layer chromatography (DCM: MeOH=20:1) to obtain product I-9 as a yellow solid (23 mg, yield 35.93%), MS (ESI) m/z: 882.7 [M+H]+, 1H NMR (500 MHz, DMSO-d6) δ 11.15 (s, 1H), 11.14 (s, 1H), 8.85 (s, 1H), 8.56 (d, J=7.5 Hz, 1H), 8.49-8.46 (m, 2H), 8.29 (d, J=8.5 Hz, 1H), 7.73 (d, J=8.5 Hz, 1H), 7.62 (s, 1H), 7.39 (s, 1H), 7.31 (d, J=8.5 Hz, 1H), 5.29-5.25 (m, 1H), 5.13 (dd, J=12.5, 5.5 Hz, 1H), 4.15-4.10 (m, 2H), 3.96-3.92 (m, 4H), 3.63-3.47 (m, 4H), 3.19-3.13 (m, 2H), 3.09-3.04 (m, 1H), 3.01-2.98 (m, 4H), 2.96-2.91 (m, 1H), 2.71-2.65 (m, 11H), 2.65-2.60 (m, 11H), 2.53-2.45 (m, 3H), 2.11-2.03 (m, 2H), 1.82-1.74 (m, 4H), 1.72-1.64 (m, 4H).

Compound I-10 can be prepared by referring to the method of Example 3 above. The structure and characterization data are shown in the following table:

| Molecular ID | structure | MS (ESI) m/z: [M + H]+ | 1H NMR |
|---|---|---|---|
| I-10 | 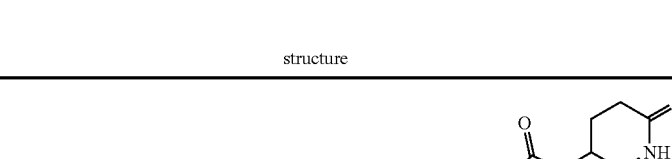<br>I-10 | 882.6 | (500 MHz, DMSO-d6) δ 11.08 (s, 1H), 10.74 (s, 1H), 8.65 (s, 1H), 8.48 (d, J = 8.0 Hz, 1H), 8.40 (t, J = 8.0 Hz, 1H), 8.38 (s, 1H), 8.21 (d, J = 8.0 Hz, 1H), 7.67 (d, J = 8.5 Hz, 1H), 7.42 (s, 1H), 7.33 (s, 1H), 7.25 (d, J = 8.5 Hz, 1H), 5.21-5.15 (m, 1H), 5.07 (dd, J = 13.0, 5.5 Hz, 1H), 5.01 (d, J = 3.9 Hz, 1H), 4.48-4.44 (m, 1H), 4.07 (d, J = 13.5 Hz, 2H), 3.58-3.52 (m, 2H), 3.51-3.46 (m, 2H), 3.32-3.28 (m, 2H), 3.27-3.18 (m, 2H), 3.15-3.08 (m, 3H), 3.04-2.99 (m, 1H), 2.90-2.84 (m, 1H), 2.81 (dd, J = 9.5, 4.5 Hz, 1H), 2.65-2.53 (m, 2H), 2.45-2.38 (m, 2H), 2.22-2.16 (m, 1H), 2.03-1.99 (m, 1H), 1.88-1.83 (m, 1H), 1.76-1.68 (m, 4H), 1.66-1.58 (m, 4H). |

Example 4: Synthesis of I-12F

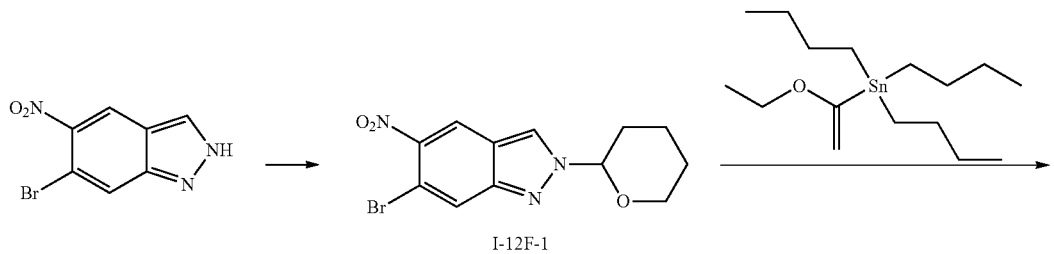

I-12F-1

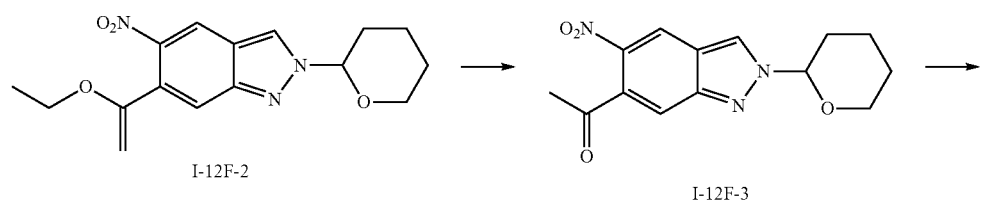

I-12F-2      I-12F-3

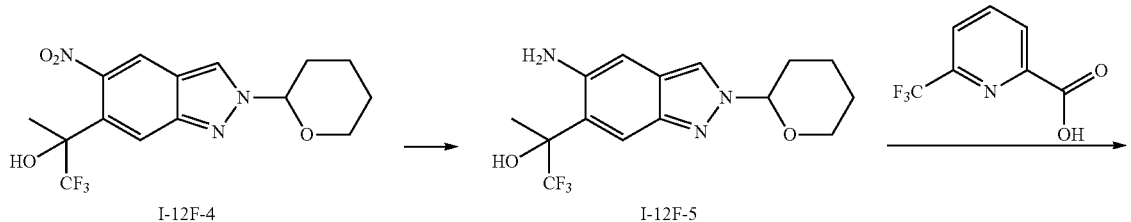

I-12F-4      I-12F-5

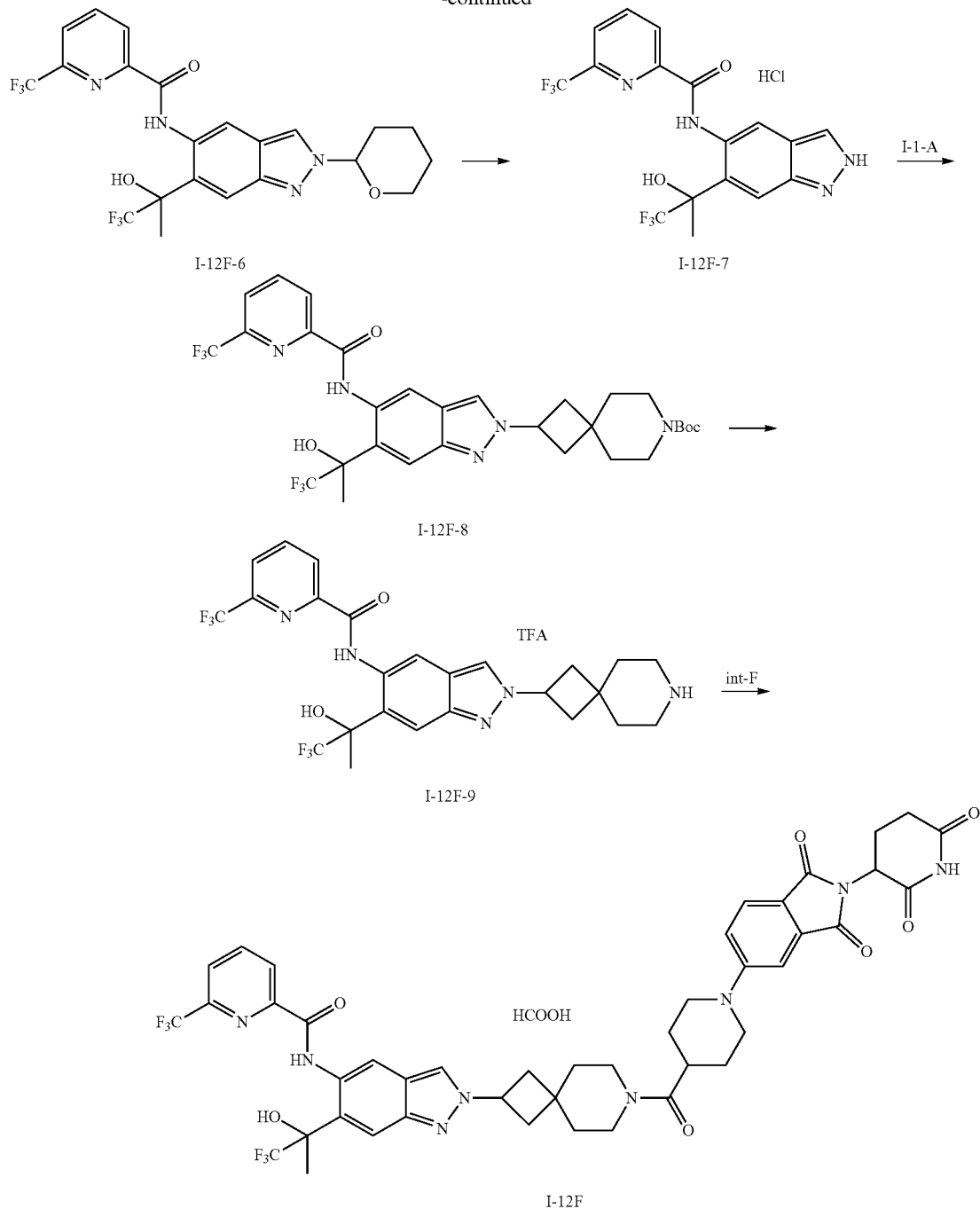

Step 1: Synthesis of (I-12F-1)

To a solution of 6-bromo-5-nitro-1H-indazole (4 g, 16.7 mmol) and 3,4-dihydro-2H-pyran (DHP, 2.8 g, 33.3 mmol) in DCM (50 mL) was added TsOH (627 mg, 3.3 mmol), and the mixture was stirred at 0° C. for 0.5 h. The reaction mixture was diluted with H₂O (120 mL) and extracted with EA (30 mL×3). The combined organic layers were dried over anhydrous Na₂SO₄, filtered and concentrated to obtain a crude product, which was purified by silica gel column chromatography to obtain product I-12F-1 as a yellow solid (4.8 g, yield 88%), MS (ESI) m/z: 326.0 [M+H]⁺.

Step 2: Synthesis of (I-12F-2)

To a solution of I-12F-1 (4.1 g, 15.6 mmol) in 1,4-dioxane (15 mL) were added tributyl(1-ethoxyvinyl)stannane (5.45 g, 15.1 mmol) and TEA (3.2 g, 31.5 mmol), and the mixture was stirred at 25° C. for 15 minutes under a nitrogen atmosphere. Then Pd(PPh₃)₂Cl₂ (0.9 g, 1.3 mmol) was added, and the resulting mixture was stirred at 100° C. for 16 hours. The reaction solution was cooled to room temperature and diluted with saturated aqueous potassium fluoride solution (50 mL). The resulting mixture was filtered and the filtrate was extracted with EtOAc (60 mL×3). The combined organic layers were dried over anhydrous Na₂SO₄ and concentrated. The crude product was purified by silica gel column chromatography (PE:EtOAc=3:1) to obtain the product I-12F-2 as a yellow oil (2.9 g, yield 72.7%), MS (ESI) m/z: 318.3 [M+H]$^+$.

Step 3: Synthesis of (I-12F-3)

To a solution of I-12F-2 (2.5 g, 7.9 mmol), acetone (15 mL) and water (15 mL) was added TsOH (0.15 g, 0.8 mmol), and the mixture was stirred at 50° C. for 2 h, diluted with water (30 mL) and extracted with ethyl acetate (50 mL×3). The combined organic layers were washed with saturated brine, dried over anhydrous sodium sulfate, filtered and concentrated to obtain the product I-12F-3 as a white solid (1.8 g, yield 78.8%), MS (ESI) m/z: 290.1 [M+H]$^+$.

Step 4: Synthesis of (I-12F-4)

To a solution of I-12F-3 (2.0 g, 6.92 mmol) in THF (20 mL) was added a solution of trifluoromethyltrimethylsilane (2.04 mL, 13.84 mmol) in THF (27.6 mL) at 25° C. After stirring for 15 minutes, TBAF (6.92 mL, 6.92 mmol) was added, and then the mixture was microwaved at room temperature for 16 hours. The reaction system was poured into a saturated NH$_4$Cl solution, and then extracted with ethyl acetate (50 mL×2). The combined organic layers were washed with saturated brine, dried over anhydrous sodium sulfate, filtered and concentrated under reduced pressure. The crude product was purified by flash silica gel column chromatography (petroleum ether: ethyl acetate=2:1) to obtain the product I-12F-4 as a yellow solid (1.4 g, yield 22.5%), MS (ESI) m/z: 360.1 [M+H]$^+$.

Step 5: Synthesis of (I-12F-5)

To a solution of I-12F-4 (0.6 g, 1.7 mmol) and MeOH (10 mL) was added wet Pd/C (0.3 g, 10% purity) at 25° C., and the mixture was replaced with H2 three times under stirring and continued to stir under H$_2$ environment for 16 hours. The resulting mixture was filtered and concentrated to obtain the product I-12F-5 as a brown solid (0.5 g, yield 91%), MS (ESI) m/z: 330.2 [M+H]$^+$.

Step 6: Synthesis of (I-12F-6)

A mixture of I-12F-5 (1 g, 3.04 mmol), 6-(trifluoromethyl)pyridine-2-carboxylic acid (696.38 mg, 3.64 mmol), HATU (1.39 g, 3.64 mol), DIPEA (784.90 mg, 6.07 mmol, 1.06 mL) and DMF (10 mL) was stirred at 25° C. for 3 hours until the reaction was complete. The reaction was quenched with water and the aqueous layer was extracted with EA (50 mL×3). The combined organic layers were washed with saturated brine, dried over anhydrous sodium sulfate, filtered and concentrated under reduced pressure. The crude product was purified by silica gel column chromatography and eluted with PE/EA (0-45%) to obtain the product I-12F-6 as a white solid (1.4 g, yield 91.77%), MS (ESI) m/z: 503.3 [M+H]$^+$.

Step 7: Synthesis of (I-12F-7)

A mixture of I-12F-6 (0.7 g, 1.39 mmol) and HCl-dioxane solution (4.0 M, 1.39 mmol, 2 mL) was stirred at 25° C. for 16 h. The resulting mixture was concentrated to dryness under reduced pressure to obtain product I-12F-7 as a white solid (0.4 g, yield 63.13%, hydrochloride), MS (ESI) m/z: 419.3 [M+H]$^+$.

Step 8: Synthesis of (I-12F-8)

A mixture of I-12F-7 (1 g, 2.20 mmol), I-1-A (1.30 g, 3.30 mmol), Cs$_2$CO$_3$ (3.58 g, 10.99 mmol) and KI (365.03 mg, 2.20 mmol) in DMF (10 mL) was stirred at 90° C. under nitrogen protection for 4 hours. The reaction was quenched with water (50 mL) and extracted with EA (30 mL×3). The combined organic layers were washed with saturated brine, dried over anhydrous sodium sulfate, filtered and concentrated in vacuo. The crude product was purified by reverse-phase C18 column chromatography (mobile phase: MeCN and water containing 0.1% HCOOH, gradient from 1% to 70% over 60 minutes; detector: UV 254 nm) to obtain the product I-12F-8 as a white solid (0.21 g, yield 14.88%), MS (ESI) m/z: 642.5 [M+H]$^+$.

Step 9: Synthesis of (I-12F-9)

I-12F-8 (0.1 g, 155.86 µmol) was dissolved in DCM (2 mL), then TFA (1.49 g, 13.07 mmol, 1 mL) was added, and the mixture was stirred at 25° C. for 2 h. The resulting mixture was concentrated under reduced pressure to obtain the product I-12F-9 as a white solid (0.1 g, crude product, TFA salt), MS (ESI) m/z: 542.3 [M+H]$^+$.

Step 10: Synthesis of (I-12F)

I-12F-9 (0.084 g, 128.14 µmol, A), int-F (74.07 mg, 192.22 µmol), HATU (63.34 mg, 166.59 µmol) and DIPEA (33.12 mg, 256.29 µmol, 44.64 µL) were dissolved in DMF (1.21 mL), and the mixture was stirred at 25° C. for 2 h. The reaction solution was purified by reverse-phase C18 column chromatography (mobile phase: MeCN and water containing 0.1% HCOOH, gradient from 1% to 60% over 10 minutes; detector: UV 254 nm) to obtain the product I-12F as a yellow solid (0.032 g, yield 25.37%, formate), MS (ESI) m/z: 909.6 [M+H]$^+_o$ $^1$H NMR (500 MHz, DMSO-d$_6$) δ 12.28 (s, 1H), 11.08 (s, 1H), 8.83 (s, 1H), 8.48 (s, 1H), 8.44 (d, J=7.5 Hz, 1H), 8.37 (t, J=7.5 Hz, 1H), 8.17 (d, J=7.5 Hz, 1H), 7.87 (s, 1H), 7.76 (s, 1H), 7.67 (d, J=8.5 Hz, 1H), 7.33 (s, 1H), 7.25 (d, J=9.0 Hz, 1H), 5.35-5.20 (m, 2H), 5.07 (dd, J=12.5, 5.5 Hz, 1H), 4.07 (d, J=12.5 Hz, 2H), 3.58-3.52 (m, 4H), 3.12-3.01 (m, 3H), 2.94-2.83 (m, 2H), 2.65-2.54 (m, 3H), 2.36 (s, 2H), 2.04-1.99 (m, 1H), 1.97 (s, 3H), 1.69-1.57 (m, 10H).

Compounds I-7, I-13, I-14, I-16, I-17, I-19, and I-20 can be prepared by referring to the method of Example 1 and Example 4 above. The structure and characterization data are shown in the following table:

| Molecular ID | structure | MS (ESI) m/z: [M + H]⁺ | ¹H NMR |
|---|---|---|---|
| I-7 | (structure) | 813.5 | (500 MHz, DMSO-d₆) δ 10.95 (s, 1H), 10.51 (s, 1H), 8.69 (s, 1H), 8.47 (d, J = 8.0 Hz, 1H), 8.41 (t, J = 8.0 Hz, 1H), 8.38 (s, 1H), 8.25-8.20 (m, 1H), 7.51 (d, J = 8.5 Hz, 1H), 7.21 (s, 1H), 7.07 (s, 1H), 7.06-7.01 (m, 1H), 5.22-5.12 (m, 1H), 5.05 (dd, J = 13.5, 5.0 Hz, 1H), 4.33 (d, J = 16.9 Hz, 1H), 4.21 (d, J = 16.9 Hz, 1H), 3.99 (s, 3H), 3.94-3.86 (m, 2H), 3.60-3.40 (m, 4H), 3.00-2.86 (m, 4H), 2.67-2.56 (m, 1H), 2.53 (m, 1H), 2.49-2.46 (m, 1H), 2.45-2.34 (m, 4H), 2.00-1.93 (m, 1H), 1.77-1.72 (m, 1H), 1.72-1.62 (m, 6H), 1.62-1.56 (m, 2H). |
| I-13 | (structure) | 813.7 | (500 MHz, DMSO-d₆) δ 11.07 (s, 1H), 10.51 (s, 1H), 8.68 (s, 1H), 8.46 (d, J = 7.5 Hz, 1H), 8.41 (t, J = 7.5 Hz, 1H), 8.35 (s, 1H), 8.22 (d, J = 7.5 Hz, 1H), 7.65 (d, J = 8.5 Hz, 1H), 7.31 (d, J = 2.0 Hz, 1H), 7.23 (dd, J = 8.8, 2.1 Hz, 1H), 7.21 (s, 1H), 5.14-5.04 (m, 2H), 4.07-4.01 (m, 2H), 3.99 (s, 3H), 3.00-2.93 (m, 2H), 2.92-2.84 (m, 1H), 2.65-2.54 (m, 2H), 2.44-2.23 (m, 8H), 2.12 (d, J = 6.5 Hz, 2H), 2.05-1.98 (m, 1H), 1.88-1.76 (m, 3H), 1.73-1.62 (m, 4H), 1.19-1.09 (m, 2H). |

| Molecular ID | structure | MS (ESI) m/z: [M + H]+ | 1H NMR |
|---|---|---|---|
| I-14 | (structure I-14) | 799.5 | (500 MHz, CDCl₃) δ 10.72 (s, 1H), 8.82 (s, 1H), 8.49 (d, J = 8.0 Hz, 1H), 8.13 (t, J = 8.0 Hz, 1H), 7.97 (s, 1H), 7.87-7.85 (m, 2H), 7.69 (dd, J = 8.5, 1.5 Hz, 1H), 7.28 (d, J = 2.5 Hz, 1H), 7.10 (s, 1H), 7.06 (dd, J = 8.5, 2.5 Hz, 1H), 4.96-4.92 (m, 2H), 4.36 (s, 1H), 4.32 (s, 1H), 4.16 (s, 1H), 4.12 (s, 1H), 4.04 (s, 3H), 3.99-3.96 (m, 2H), 3.09-3.04 (m, 4H), 2.91-2.84 (m, 4H), 2.74-2.69 (m, 1H), 2.49-2.44 (m, 1H), 2.16-2.11 (m, 1H), 1.91-1.82 (m, 4H). |
| I-16 | (structure I-16) | 813.5 | (500 MHz, DMSO-d₆) δ 11.08 (s, 1H), 10.51 (s, 1H), 8.68 (s, 1H), 8.46 (d, J = 7.5 Hz, 1H), 8.41 (t, J = 7.5 Hz, 1H), 8.36 (s, 1H), 8.22 (d, J = 8.0 Hz, 2H), 7.68 (d, J = 8.5 Hz, 1H), 7.35 (s, 1H), 7.27 (d, J = 8.5 Hz, 1H), 7.20 (s, 1H), 5.12-5.05 (m, 2H), 4.06 (d, J = 12.5 Hz, 2H), 3.99 (s, 3H), 3.09-3.01 (m, 3H), 2.87-2.82 (m, 3H), 2.65-2.57 (m, 2H), 2.42-2.35 (m, 2H), 2.34-2.28 (m, 2H), 2.05-1.99 (m, 1H), 1.96-1.91 (m, 3H), 1.86-1.80 (m, 4H), 1.50-1.42 (m, 2H), 1.39-1.34 (m, 2H). |

-continued

| Molecular ID | structure | MS (ESI) m/z: [M + H]+ | 1H NMR |
|---|---|---|---|
| I-17 | I-17 | 839.6 | (500 MHz, DMSO-d6) δ 1H NMR (500 MHz, DMSO) δ 11.07 (s, 1H), 10.51 (s, 1H), 8.69 (s, 1H), 8.46 (d, J = 7.5 Hz, 1H), 8.41 (t, J = 8.0 Hz, 1H), 8.37 (s, 1H), 8.22 (dd, J = 8.0, 1.0 Hz, 1H), 7.63 (d, J = 8.0 Hz, 1H), 7.21 (s, 1H), 6.79 (d, J = 2.0 Hz, 1H), 6.65 (dd, J = 8.5, 2.0 Hz, 1H), 5.19-5.13 (m, 1H), 5.05 (dd, J = 12.8, 5.4 Hz, 1H), 3.99 (s, 3H), 3.78 (s, 2H), 3.70 (s, 2H), 3.50 (br, 2H), 3.41 (br, 2H), 2.64-2.56 (m, 2H), 2.53 (s, 2H), 2.44-2.39 (m, 2H), 2.04-1.98 (m, 1H), 1.94 (d, J = 10.5 Hz, 2H), 1.74-1.66 (m, 2H), 1.65-1.55 (m, 6H). |
| I-19 | I-19 | 827.5 | (500 MHz, DMSO-d6) δ 11.08 (s, 1H), 10.50 (d, J = 2.0 Hz, 1H), 8.69 (d, J = 3.5 Hz, 1H), 8.46 (d, J = 7.5 Hz, 1H), 8.41 (t, J = 7.5 Hz, 1H), 8.34 (d, J = 2.5 Hz, 1H), 8.22 (d, J = 7.5 Hz, 1H), 7.67 (d, J = 8.5 Hz, 1H), 7.35 (d, J = 1.3 Hz, 1H), 7.27 (dd, J = 8.7, 1.7 Hz, 1H), 7.16 (d, J = 14.0 Hz, 1H), 5.07 (dd, J = 12.5, 5.5 Hz, 1H), 4.47-4.37 (m, 1H), 4.12-4.05 (m, 2H), 4.04 (s, 1H), 3.98 (d, J = 3.0 Hz, 3H), 3.91 (s, 1H), 3.66 (s, 1H), 3.56 (s, 1H), 3.10-3.00 (m, 2H), 2.94-2.83 (m, 2H), 2.66-2.53 (m, 3H), 2.10-1.99 (m, 4H), 1.98-1.88 (m, 2H), 1.78-1.66 (m, 4H), 1.63-1.53 (m, 2H). |

-continued
| Molecular ID | structure | MS (ESI) m/z: [M + H]+ | 1H NMR |
|---|---|---|---|
| I-20 | 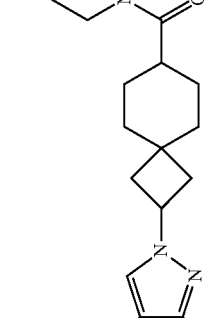 | 827.5 | (400 MHz, DMSO-d6) δ 11.09 (s, 1H), 10.51 (s, 1H), 8.68 (s, 1H), 8.46 (d, J = 8.0 Hz, 1H), 8.40 (t, J =7.5 Hz, 1H), 8.36 (s, 1H), 8.21 (d, J = 7.5 Hz, 1H), 7.71 (d, J = 8.5 Hz, 1H), 7.36 (s, 1H), 7.26 (d, J = 8.5 Hz, 1H), 7.21 (s, 1H), 5.19-5.00 (m, 2H), 3.99 (s, 3H), 3.69 (br, 2H), 3.61 (br, 2H), 3.55-3.46 (m, 6H), 2.95-2.82 (m, 1H), 2.68-2.58 (m, 2H), 2.42-2.35 (m, 1H), 2.35-2.25 (m, 2H), 2.07-1.92 (m, 2H), 1.87-1.78 (m, 1H), 1.67-1.39 (m, 6H). |

Example 5: Synthesis of I-22

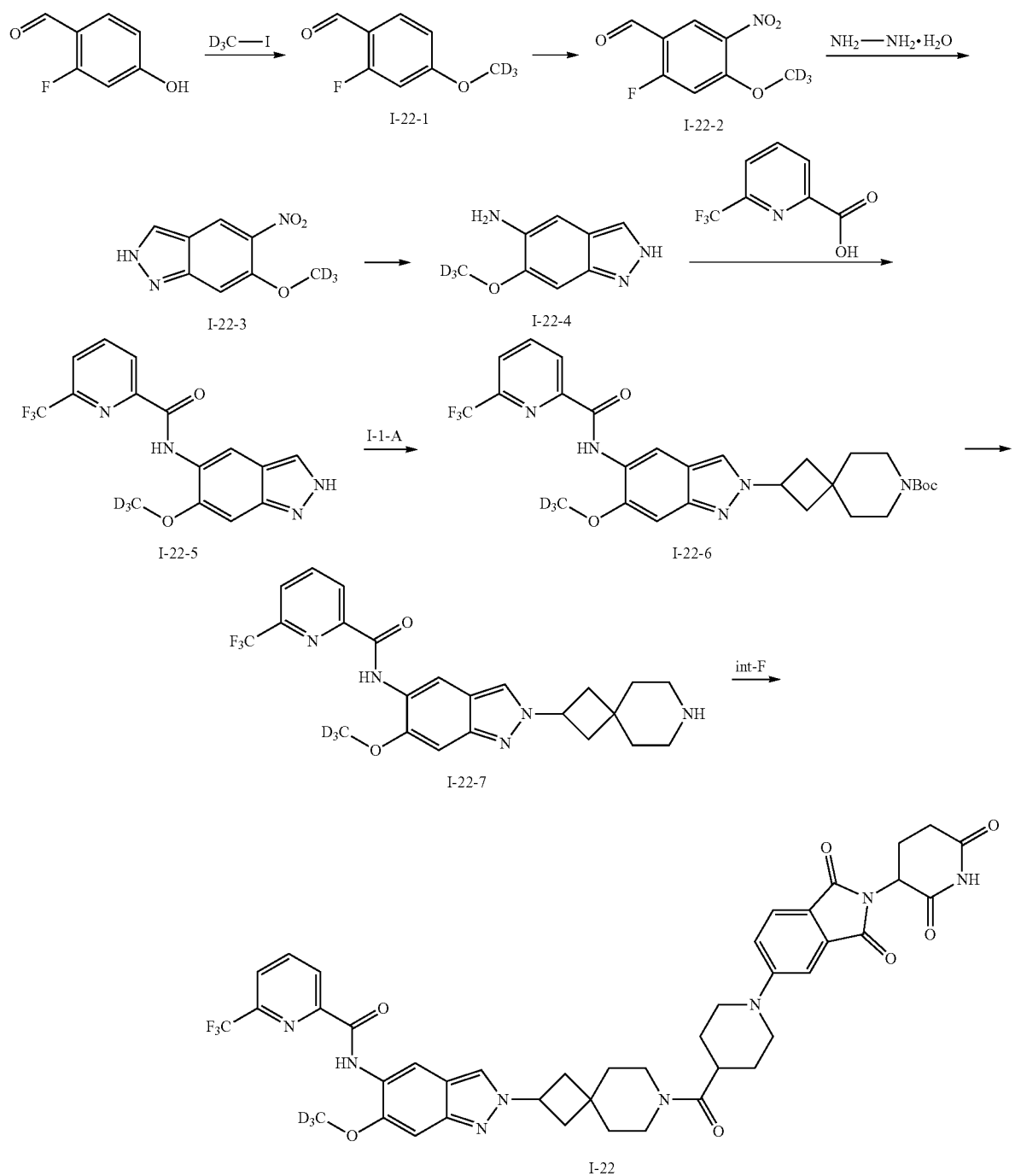

Step 1: Synthesis of (I-22-1)

To a solution of 2-fluoro-4-hydroxybenzaldehyde (25 g, 178.4 mmol), $K_2CO_3$ (49.3 g, 356.9 mmol) in DMF (400 mL) was added $CD_3$-I (31 g, 214.2 mmol) under nitrogen at 0° C., and the mixture was stirred at 25° C. for 16 hours. The mixture was quenched with $NH_4Cl$ solution (saturated, 400 mL) and extracted with ethyl acetate (500 mL×3). The combined organic phases were washed with saturated brine, dried over anhydrous sodium sulfate, filtered, and concentrated under reduced pressure to obtain product I-22-1 as a white solid (27 g, yield 95.7%), MS (ESI) m/z: 158.2 $[M+H]^+_o$ $^1H$ NMR (400 MHz, $CDCl_3$) δ 10.21 (s, 1H), 7.82 (t, J=8.4 Hz, 1H), 6.78 (dd, J=8.8, 2.4 Hz, 1H), 6.64 (dd, J=12.4, 2.4 Hz, 1H).

Step 2: Synthesis of (I-22-2)

To a solution of $KNO_3$ (18 g, 179 mmol) and concentrated $H_2SO_4$ (130 mL) was added I-22-1 (25 g, 163 mmol) in batches at 0° C. After 0.5 hours, the dropwise addition was completed, and the mixture was stirred at 25° C. for 2 hours. The reaction mixture was quenched with ice water, filtered, washed with $H_2O$ and dried under vacuum to obtain product I-22-2 as a yellow solid (30 g, yield 93.2%), MS (ESI) m/z:

203.2 [M+H]⁺ₒ ¹H NMR (400 MHz, CDCl₃) δ 10.22 (s, 1H), 8.46 (d, J=7.2 Hz, 1H), 6.87 (d, J=11.6 Hz, 1H).

Step 3: Synthesis of (I-22-3)

A solution of I-22-2 (27 g, 133.5 mmol), hydrazine hydrate (13.4 g, 267.1 mmol) and DMF (60 mL) was stirred at 140° C. for 2 hours. After cooling to room temperature, the reaction mixture was washed with ice water to obtain product I-22-3 as a yellow solid (30 g, yield 97%), MS (ESI) m/z: 197.2 [M+H]⁺ₒ ¹H NMR (400 MHz, DMSO-d₆) δ 13.36 (s, 1H), 8.41 (s, 11H), 8.20 (s, 1H), 7.21 (s, 1H).

Step 4: Synthesis of (I-22-4)

A mixed solution of I-22-3 (16 g, 81.6 mmol), a solution of wet Pd/C (3 g, 10% purity) in THF (1 L) and DMF (100 mL) was stirred under a hydrogen atmosphere at 25° C. for 16 hours. The reaction system was filtered through diatomaceous earth and washed with THF (1 L). The filtrate was distilled under reduced pressure to obtain product I-22-4 as a brown solid (11.5 g, yield 84.9%), MS (ESI) m/z: 167.2 [M+H]⁺.

Step 5: Synthesis of (I-22-5)

A mixed solution of I-22-4 (23 g, 138 mmol), HATU (56 g, 162 mmol), DIEA (32 g, 277 mmol) and DMF (100 mL) was stirred at 25° C. for 10 min, and then a solution of 6-(trifluoromethyl)picolinic acid (23 g, 135 mmol) in DMF (20 mL) was added at 0° C. The resulting mixture was stirred at 25° C. for 16 h, diluted with H₂O (300 mL) and extracted with ethyl acetate (300 mL×3). The combined organic phases were concentrated under reduced pressure to obtain product I-22-5 as a brown solid (24 g, yield 51.1%), MS (ESI) m/z: 340.1 [M+H]⁺.

Step 6: Synthesis of (I-22-6)

A solution of I-22-5 (24 g, 70.8 mmol), I-1-A (42 g, 106.2 mmol), Cs₂CO₃ (69 g, 212.4 mmol), KI (11.8 g, 70.8 mmol) and DMF (120 mL) was stirred at 90° C. for 16 hours under a nitrogen atmosphere. The mixture was diluted with H₂O (200 mL) and extracted with EtOAc (300 mL×3). The combined organic phases were washed with saturated brine, dried over anhydrous sodium sulfate, filtered and concentrated. The crude product was purified by flash silica gel column chromatography (PE/EtOAc=1/1) to obtain product I-22-6 as a yellow solid (5 g, yield 13%), MS (ESI) m/z: 563.2 [M+H]⁺.

Step 7: Synthesis of (I-22-7)

A solution of I-22-6 (5 g, 8.9 mmol) and HCl-dioxane (1 M, 100 mL) was stirred at 25° C. for 1 hour. Diethyl ether was added to the reaction mixture under stirring. The supernatant was removed after standing and repeated three times to remove the residual HCl in the reaction mixture to obtain the product I-22-7 as a white solid (4 g, yield 97%), MS (ESI) m/z: 463.2 [M+H]⁺.

Step 8: Synthesis of (I-22)

A solution of int-F (2.9 g, 7.5 mmol), DIEA (3.9 g, 30.0 mmol), HATU (3.4 g, 9.0 mmol) and DMF (20 mL) was stirred at 25° C. for 10 min, and then a solution of I-22-7 (3.7 g, 7.5 mmol) in DMF (10 mL) was added at 0° C. The resulting mixture was stirred for 2 hours until the reaction was complete. The mixture was diluted with H₂O (100 mL) and extracted with ethyl acetate (100 mL×3). The combined organic phases were washed with saturated brine (200 mL), dried over anhydrous sodium sulfate, filtered and concentrated under reduced pressure to obtain a crude product, which was purified by reversed phase C18 column chromatography to obtain product I-22 as a yellow solid (2.1 g, yield 32%), MS (ESI) m/z: 830.2 [M+H]⁺ₒ ¹H NMR (400 MHz, DMSO-d₆) δ 11.08 (s, 1H), 10.51 (s, 1H), 8.69 (s, 1H), 8.52-8.33 (m, 3H), 8.22 (d, J=7.6 Hz, 1H), 7.67 (d, J=8.4 Hz, 1H), 7.33 (s, 1H), 7.29-7.17 (m, 2H), 5.231-5.12 (m, 1H), 5.07 (dd, J=12.8, 5.2 Hz, 1H), 4.07 (d, J=13.2 Hz, 2H), 3.58-3.31 (m, 4H), 3.10-3.05 (m, 3H), 2.92-2.84 (m, 1H), 2.61-2.54 (m, 2H), 2.48-2.35 (m, 4H), 2.07-1.96 (m, 1H), 1.77-1.53 (m, 8H).

Example 6: Synthesis of I-23

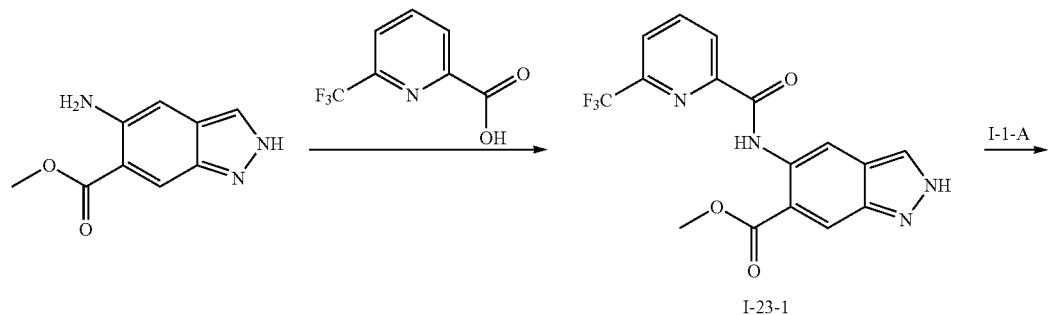

I-23-1

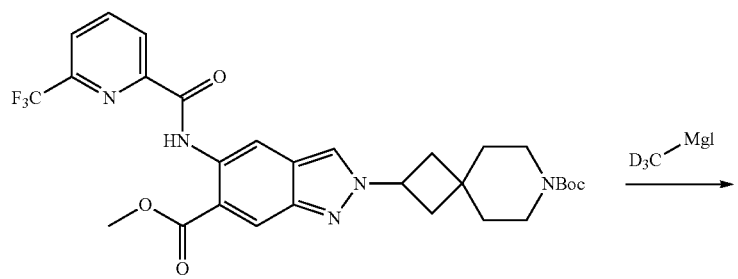

I-23-2

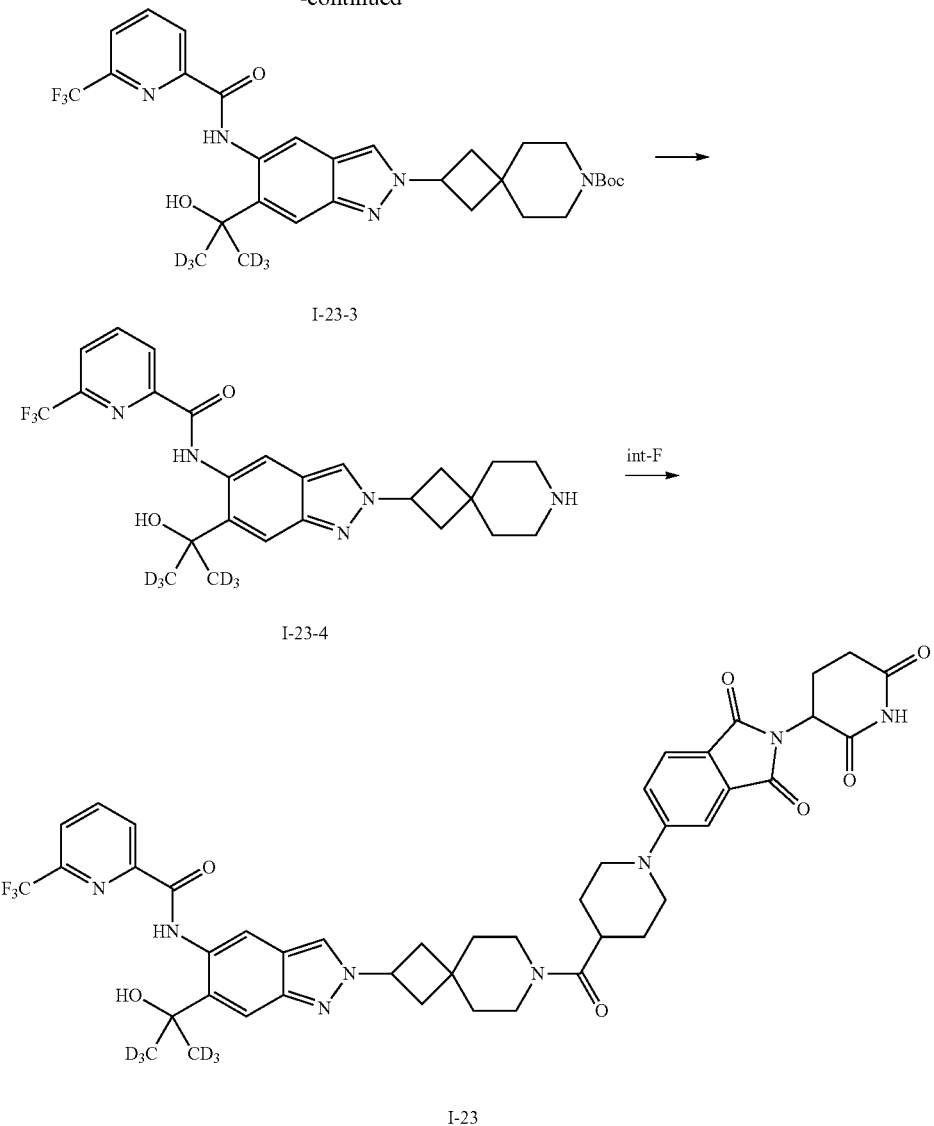

I-23-3

I-23-4

I-23

Step 1: Synthesis of (I-23-1)

5-amino-2H-indazole-6-carboxylic acid methyl ester (5 g, 26 mmol) was dissolved in tetrahydrofuran (50 mL), and the reaction solution was slowly added with DIPEA (27 g, 209 mmol), and then added with T₃P (propyl phosphoric anhydride, 25 g, 78.6 mmol), and then added with 6-(trifluoromethyl)picolinic acid (7.5 g, 39 mmol). After the dropwise dropwise addition was completed, the reaction solution was stirred at 25° C. for 16 hours. Water was added to the reaction system to precipitate the solid, which was filtered, and dried, and the filter cake was filtered under vacuum to obtain the product I-23-1 as a light yellow solid (9.3 g, yield 98%).

Step 2: Synthesis of (I-23-2)

A solution of I-23-1 (5 g, 13.72 mmol), I-1-A (10.86 g, 27.45 mmol), Cs₂CO₃ (13.4 g, 41.2 mmol), KI (2.28 g, 13.72 mmol) and DMF (50 mL) was stirred at 50° C. for 16 hours. The mixture was diluted with H₂O (50 mL) and extracted with EtOAc (150 mL×3). The combined organic phases were washed with saturated brine, dried over anhydrous sodium sulfate, filtered and concentrated. The crude product was purified by flash silica gel column chromatography (PE/EtOAc=1/1) to obtain product I-23-2 as a brown solid (1.0 g, yield 12.3%), MS (ESI) m/z: 588.2 [M+H]⁺.

Step 3: Synthesis of (I-23-3)

To a solution of I-23-2 (850 mg, 1.45 mmol) in THF (40 mL) was added dropwise (methyl-D₃)magnesium iodide (14.5 mL, 14.5 mmol) at 0° C., and the mixture was stirred at 25° C. for 16 hours. The reaction solution was poured into water and extracted with EtOAc (50 mL×3). The combined organic phases were washed with saturated brine, dried over anhydrous sodium sulfate, filtered, and concentrated under reduced pressure. The crude product was purified by silica gel column chromatography (PE/EtOAc=2/1) to obtain product I-23-3 as a yellow solid (100 mg, yield 11.6%), MS (ESI) m/z: 594.4 [M+H]⁺.

Step 4: Synthesis of (I-23-4)

To a solution of I-23-3 (100 mg, 0.17 mmol) in DCM (5 mL) was added dropwise TFA (2 mL) at 0° C., and the mixture was stirred at 25° C. for 2 h. Diethyl ether was added to the reaction mixture under stirring. The supernatant was removed after standing and repeated three times to remove the residual TFA in the reaction solution, and dried under vacuum to obtain product I-23-4 as a yellow solid (80 mg, yield 95.2%), MS (ESI) m/z: 494.3 [M+H]$^+$.

Step 5: Synthesis of (I-23)

To a solution of int-F (80 mg, 0.21 mmol), HATU (92 mg, 0.24 mmol) and DMF (5 mL) were added DIEA (53 mg, 0.42 mmol) and I-23-4 (100 mg, 0.21 mmol), and the mixture was stirred at 25° C. for 16 hours. The mixture was added with water (10 mL) and extracted with EtOAc (30 mL×3). The combined organic phases were washed with saturated brine, dried over anhydrous sodium sulfate, filtered, and concentrated under reduced pressure. The crude product was purified by preparative HPLC to obtain product I-23 as a white solid (24.05 mg, yield 13.9%), MS (ESI) m/z: 861.3 [M+H]$^+_o$ $^1$H NMR (400 MHz, DMSO-d$_6$) δ 12.42 (s, 1H), 11.11 (s, 1H), 8.77 (s, 1H), 8.50 (d, J=7.6 Hz, 1H), 8.46-8.37 (m, 2H), 8.20 (d, J=7.6 Hz, 1H), 7.71 (d, J=8.4 Hz, 1H), 7.65 (s, 1H), 7.37 (s, 1H), 7.29 (d, J=8.4 Hz, 1H), 5.98 (s, 1H), 5.35-5.21 (m, 1H), 5.11 (m, 1H), 4.11 (d, J=11.6 Hz, 2H), 3.61-3.46 (m, 6H), 3.16-3.04 (m, 2H), 3.04-2.96 (m, 1H), 2.95-2.81 (m, 1H), 2.69-2.55 (m, 2H), 2.47-2.36 (m, 2H), 2.10-1.96 (m, 1H). 1.84-1.57 (m, 8H).

Compounds I-24 to I-29, I-31~I-38, I-48, I-51, I-53, I-56 can be prepared by referring to the method of Examples 1, 3, 5 and 6 above. The structure and characterization data are shown in the following table:

| Molecular ID | structure | MS (ESI) m/z: [M + H]+ | 1H NMR |
|---|---|---|---|
| I-24 | (structure I-24) | 839.7 | (500 MHz, DMSO-d6) δ 11.08 (s, 1H), 10.51 (s, 1H), 8.68 (s, 1H), 8.46 (d, J = 8.0 Hz, 1H), 8.40 (t, J = 8.0 Hz, 1H), 8.36 (s, 1H), 8.22 (d, J = 8.0 Hz, 1H), 7.65 (d, J = 8.5 Hz, 1H), 7.32 (s, 1H), 7.24 (d, J = 8.5 Hz, 1H), 7.21 (s, 1H), 5.16-5.09 (m, 1H), 5.06 (dd, J = 12.5, 5.5 Hz, 1H), 3.99 (s, 3H), 3.47 (br, 2H), 3.39 (br, 2H), 2.92-2.84 (m, 1H), 2.65-2.53 (m, 3H), 2.53-2.51 (m, 1H), 2.47-2.29 (m, 4H), 2.07-1.95 (m, 1H), 1.78-1.42 (m, 9H), 1.36-1.24 (m, 2H), 1.24-1.20 (m, 2H). |
| I-25 | (structure I-25) | 827.6 | (500 MHz, DMSO-d6) δ 11.09 (s, 1H), 10.51 (s, 1H), 8.69 (s, 1H), 8.47 (d, J = 7.5 Hz, 1H), 8.41 (t, J = 8.0 Hz, 1H), 8.38 (s, 1H), 8.22 (dd, J = 7.5, 0.5 Hz, 1H), 7.69 (d, J = 8.0 Hz, 1H+), 7.34 (t, J = 8.0 Hz, 2H), 7.22 (s, 1H), 5.22-5.13 (m, 1H), 5.10 (dd, J = 12.5, 5.4 Hz, 1H), 3.99 (s, 3H), 3.78-3.69 (m, 2H), 3.60-3.49 (m, 2H), 3.04-2.95 (m, 2H), 2.93-2.83 (m, 2H), 2.63-2.54 (m, 2H), 2.54-2.52 (m, 1H), 2.49-2.46 (m, 1H), 2.46-2.38 (m, 2H), 2.08-1.98 (m, 1H), 1.87-1.78 (m, 2H), 1.76-1.68 (m, 4H), 1.68-1.57 (m, 2H). |

| Molecular ID | structure | MS (ESI) m/z: [M + H]+ | 1H NMR |
|---|---|---|---|
| I-26 | (I-26) | 867.6 | (500 MHz, DMSO-d6) δ 11.07 (s, 1H), 10.51 (s, 1H), 8.69 (s, 1H), 8.46 (d, J = 7.5 Hz, 1H), 8.41 (t, J = 8.0 Hz, 1H), 8.37 (s, 1H), 8.22 (dd, J = 7.5, 0.8 Hz, 1H), 7.63 (d, J = 8.0 Hz, 1H), 7.21 (s, 1H), 6.79 (d, J = 1.5 Hz, 1H), 6.65 (dd, J = 8.5, 2.0 Hz, 1H), 5.20-5.12 (m, 1H), 5.05 (dd, J = 13.0, 5.5 Hz, 1H), 3.99 (s, 3H), 3.78 (s, 2H), 3.70 (s, 2H), 3.50 (br, 2H), 3.42 (br, 2H), 2.93-2.83 (m, 1H), 2.65-2.55 (m, 2H), 2.54 (s, 2H), 2.49-2.47 (m, 1H), 2.44-2.38 (m, 2H), 2.03-1.98 (m, 1H), 1.96-1.91 (m, 2H), 1.74-1.66 (m, 2H), 1.65-1.55 (m, 6H), 1.47-1.39 (m, 2H). |
| I-27 | (I-27) | 855.6 | (500 MHz, DMSO-d6) δ 11.08 (s, 1H), 10.51 (s, 1H), 8.69 (d, J = 4.5 Hz, 1H), 8.46 (d, J = 7.5 Hz, 1H), 8.41 (t, J = 8.0 Hz, 1H), 8.38 (s, 1H), 8.22 (d, J = 8.0 Hz, 1H), 7.67 (d, J = 8.5 Hz, 1H), 7.33 (s, 1H), 7.25 (dd, J = 8.5, 2.0 Hz, 1H), 7.17 (s, 1H), 5.07 (dd, J = 13.0, 5.5 Hz, 1H), 4.45-4.34 (m, 1H), 4.12-4.02 (m, 2H), 3.99 (d, J = 1.0 Hz, 3H), 3.66-3.45 (m, 4H), 3.15-3.04 (m, 2H), 3.03-2.94 (m, 1H), 2.94-2.84 (m, 1H), 2.63-2.52 (m, 2H), 2.13-2.00 (m, 3H), 1.99-1.91 (m, 2H), 1.91-1.81 (m, 2H), 1.77-1.68 (m, 2H), 1.68-1.51 (m, 4H), 1.46-1.27 (m, 4H). |

| Molecular ID | structure | MS (ESI) m/z: [M + H]+ | 1H NMR |
|---|---|---|---|
| I-28 | I-28 | 813.5 | (500 MHz, DMSO-d6) δ 11.08 (s, 1H), 10.51 (s, 1H), 8.69 (s, 1H), 8.46 (d, J = 7.5 Hz, 1H), 8.42 (d, J = 7.5 Hz, 1H), 8.36 (s, 1H), 8.24-8.19 (m, 1H), 7.67 (d, J = 8.5 Hz, 1H), 7.34 (d, J = 2.0 Hz, 1H), 7.26 (d, J = 8.5 Hz, 1H), 7.18 (s, 1H), 5.20-5.14 (m, 1H), 5.07 (dd, J = 12.5, 5.0 Hz, 1H), 4.14-4.06 (m, 2H), 3.99 (s, 3H), 3.84-3.78 (m, 1H), 3.58 (dd, J = 12.4, 8.5 Hz, 1H), 3.50 (dd, J = 10.9, 4.5 Hz, 1H), 3.30-3.26 (m, 1H), 3.11-3.03 (m, 3H), 2.97-2.92 (m, 1H), 2.90-2.78 (m, 2H), 2.65-2.53 (m, 2H), 2.41-2.33 (m, 2H), 2.17-2.08 (m, 2H), 2.05-1.99 (m, 1H), 1.83-1.73 (m, 2H), 1.68-1.59 (m, 2H). |

| Molecular ID | structure | MS (ESI) m/z: [M + H]+ | 1H NMR |
|---|---|---|---|
| I-29 | 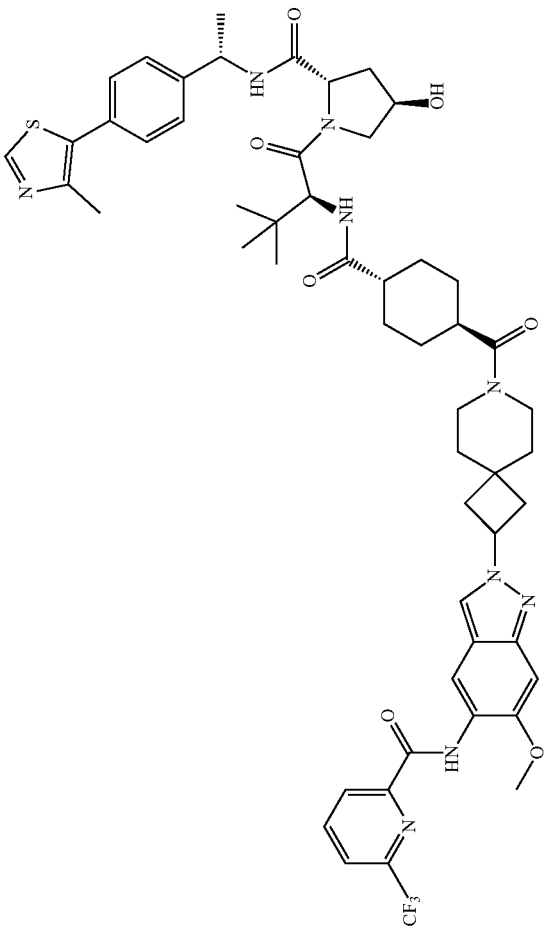 I-29 | 1040.6 | (500 MHz, DMSO-$d_6$) δ 10.53-10.49 (m, 1H), 8.99 (s, 1H), 8.69 (s, 1H), 8.47 (d, J = 7.5 Hz, 1H), 8.41 (d, J = 7.5 Hz, 1H), 8.40-8.38 (m, 1H), 8.37 (s, 1H), 8.22 (d, J = 7.5 Hz, 1H), 7.68 (d, J = 8.0 Hz, 1H), 7.44 (d, J = 8.0 Hz, 2H), 7.38 (d, J = 8.0 Hz, 2H), 7.21 (s, 1H), 5.19-5.13 (m, 1H), 5.13-5.10 (m, 1H), 4.95-4.90 (m, 1H), 4.53-4.49 (m, 1H), 4.46-4.41 (m, 1H), 4.31-4.27 (m, 1H), 3.99 (s, 3H), 3.64-3.55 (m, 2H), 3.52-3.45 (m, 2H), 3.43-3.39 (m, 2H), 2.63-2.57 (m, 1H), 2.49-2.44 (m, 5H), 2.44-2.35 (m, 3H), 2.04-1.99 (m, 1H), 1.82-1.76 (m, 2H), 1.73-1.64 (m, 5H), 1.63-1.55 (m, 2H), 1.51-1.43 (m, 2H), 1.40-1.33 (m, 5H), 0.97-0.90 (m, 9H). |

| Molecular ID | structure | MS (ESI) m/z: [M + H]+ | 1H NMR |
|---|---|---|---|
| I-31 | (structure I-31) | 842.6 | (500 MHz, DMSO-d6) δ 11.11 (s, 1H), 10.51 (s, 1H), 8.69 (s, 1H), 8.46 (d, J = 7.5 Hz, 1H), 8.41 (t, J = 7.5 Hz, 1H), 8.37 (s, 1H), 8.22 (dd, J = 7.5, 1.0 Hz, 1H), 7.81 (d, J = 8.5 Hz, 1H), 7.48 (d, J = 1.5 Hz, 1H), 7.37 (dd, J = 8.1, 1.0 Hz, 1H), 7.21 (s, 1H), 5.25-5.14 (m, 1H), 5.12 (dd, J = 12.5, 5.4 Hz, 1H), 4.72-4.58 (m, 1H), 3.99 (s, 3H), 3.60-3.47 (m, 2H), 3.47-3.38 (m, 2H), 2.96-2.85 (m, 1H), 2.77-2.66 (m, 1H), 2.66-2.53 (m, 2H), 2.49-2.45 (m, 2H), 2.45-2.37 (m, 2H), 2.17-2.08 (m, 2H), 2.08-2.02 (m, 2H), 1.82-1.70 (m, 3H), 1.70-1.56 (m, 5H), 1.56-1.43 (m, 2H). |
| I-32 | (structure I-32) | 865.6 | (500 MHz, DMSO-d) δ 11.08 (s, 1H), 10.51 (s, 1H), 8.68 (s, 1H), 8.46 (d, J = 7.5 Hz, 1H), 8.41 (t, J = 8.0 Hz, 1H), 8.36 (s, 1H), 8.22 (dd, J = 7.5, 1.0 Hz, 1H), 7.69 (d, J = 8.5 Hz, 1H), 7.39 (d, J = 2.0 Hz, 1H), 7.37 (s, 1H), 7.31 (dd, J = 8.5, 2.0 Hz, 1H), 7.21 (s, 1H), 7.17 (s, 1H), 5.17-5.13 (m, 1H), 5.08 (dd, J = 13.0, 5.5 Hz, 1H), 4.38-4.33 (m, 1H), 4.19-4.14 (m, 2H), 3.99 (s, 3H), 3.19-3.14 (m, 2H), 2.88-2.85 (m, 2H), 2.81-2.76 (m, 2H), 2.65-2.60 (m, 1H), 2.59-2.54 (m, 1H), 2.46-2.42 (m, 2H), 2.41-2.37 (m, 2H), 2.05-2.01 (m, 3H), 1.99-1.96 (m, 1H), 1.94-1.89 (m, 2H), 1.81-1.77 (m, 2H), 1.77-1.73 (m, 2H). |

| Molecular ID | structure | MS (ESI) m/z: [M + H]+ | 1H NMR |
|---|---|---|---|
| I-33 | (structure I-33) | 843.5 | (500 MHz, DMSO-d6) δ 11.08 (s, 1H), 10.51 (s, 1H), 8.70-8.67 (m, 1H), 8.46 (d, J = 7.5 Hz, 1H), 8.40 (t, J = 7.5 Hz, 1H), 8.37 (s, 1H), 8.22 (dd, J = 7.5, 1.0 Hz, 1H), 7.66 (d, J = 8.5 Hz, 1H), 7.34 (d, J = 2.0 Hz, 1H), 7.25 (dd, J = 8.5, 2.0 Hz, 1H), 7.21 (s, 1H), 5.71 (s, 1H), 5.18-5.13 (m, 1H), 5.07 (dd, J = 12.5, 5.5 Hz, 1H), 3.99 (s, 3H), 3.81-3.76 (m, 2H), 3.43-3.36 (m, 3H), 3.32-3.28 (m, 1H), 2.92-2.84 (m, 1H), 2.65-2.51 (m, 3H), 2.49-2.45 (m, 2H), 2.44-2.39 (m, 2H), 2.03-1.96 (m, 3H), 1.83-1.72 (m, 3H), 1.72-1.60 (m, 4H). |
| I-34 | (structure I-34) | 845.5 | (500 MHz, DMSO-d6) δ 11.09 (s, 1H), 10.51 (s, 1H), 8.69 (s, 1H), 8.46 (d, J = 7.5 Hz, 1H), 8.40 (t, J = 7.5 Hz, 1H), 8.37 (s, 1H), 8.22 (dd, J = 7.5, 1.0 Hz, 1H), 7.70 (d, J = 8.5 Hz, 1H), 7.41 (d, J = 2.0 Hz, 1H), 7.31 (dd, J = 8.5, 2.0 Hz, 1H), 7.22 (s, 1H), 5.20-5.13 (m, 1H), 5.08 (dd, J = 12.5, 5.0 Hz, 1H), 3.99 (s, 3H), 3.98-3.91 (m, 2H), 3.77-3.61 (m, 2H), 3.57-3.41 (m, 2H), 3.33-3.28 (m, 1H), 2.94-2.85 (m, 1H), 2.65-2.51 (m, 3H), 2.50-2.46 (m, 2H), 2.46-2.39 (m, 2H), 2.24-2.10 (m, 2H), 2.07-1.99 (m, 3H), 1.79-1.63 (m, 4H). |

| Molecular ID | structure | MS (ESI) m/z: [M + H]+ | 1H NMR |
|---|---|---|---|
| I-35 | (I-35 structure) | 863.6 | (500 MHz, DMSO-d6) δ 11.09 (s, 1H), 10.51 (s, 1H), 8.69 (s, 1H), 8.47 (d, J = 7.5 Hz, 1H), 8.41 (t, J = 7.5 Hz, 1H), 8.38 (s, 1H), 8.22 (dd, J = 7.8, 0.8 Hz, 1H), 7.69 (d, J = 8.0 Hz, 1H), 7.45 (s, 1H), 7.38-7.33 (m, 1H), 7.21 (d, J = 2.0 Hz, 1H), 5.20-5.15 (m, 1H), 5.08 (dd, J = 12.8, 5.4 Hz, 1H), 4.38-4.31 (m, 1H), 3.99 (s, 3H), 3.98-3.92 (m, 1H), 3.89-3.67 (m, 3H), 3.61-3.46 (m, 4H), 2.92-2.85 (m, 1H), 2.65-2.59 (m, 1H), 2.58-2.54 (m, 1H), 2.46-2.41 (m, 2H), 2.10-1.96 (m, 3H), 1.87-1.82 (m, 1H), 1.79-1.59 (m, 5H). |
| I-36 | (I-36 structure) | 840.3 | (500 MHz, CDCl3) δ 9.57 (s, 1H), 8.76 (s, 1H), 8.70 (d, J = 4.0 Hz, 1H), 8.41 (s, 1H), 8.04 (s, 1H), 7.88 (s, 1H), 7.86 (s, 1H), 7.82 (s, 1H), 7.69 (d, J = 8.0 Hz, 1H), 7.29 (s, 1H), 7.11 (s, 1H), 7.06 (d, J = 8.5 Hz, 1H), 5.06-4.99 (m, 1H), 4.97-4.91 (m, 1H), 4.07 (s, 3H), 3.98 (d, J = 13.0 Hz, 2H), 3.67-3.45 (m, 4H), 3.07 (t, J = 11.5 Hz, 2H), 2.92-2.78 (m, 3H), 2.73 (s, 3H), 2.58 (d, J = 8.0 Hz, 3H), 2.37-2.32 (m, 1H), 2.17-2.10 (m, 1H), 2.07-2.02 (m, 1H), 1.98-1.92 (m, 2H), 1.88-1.79 (m, 4H), 1.77-1.73 (m, 2H). |

| Molecular ID | structure | MS (ESI) m/z: [M + H]+ | 1H NMR |
|---|---|---|---|
| I-37 | I-37 | 841.5 | (500 MHz, DMSO-d6) δ 11.07 (s, 1H), 10.51 (s, 1H), 8.69 (s, 1H), 8.47 (d, J = 7.5 Hz, 1H), 8.41 (t, J = 7.5 Hz, 1H), 8.37 (s, 1H), 8.22 (d, J = 7.5 Hz, 1H), 7.65 (d, J = 8.5 Hz, 1H), 7.29 (d, J = 1.5 Hz, 1H), 7.24-7.17 (m, 2H), 5.22-5.12 (m, 1H), 5.06 (dd, J = 12.5, 5.5 Hz, 1H), 3.99 (s, 3H), 3.73-3.45 (m, 6H), 2.93-2.83 (m, 1H), 2.66-2.52 (m, 3H), 2.48-2.35 (m, 4H), 2.23-2.13 (m, 2H), 2.08-1.94 (m, 2H), 1.75-1.54 (m, 6H), 1.29 (s, 3H). |
| I-38 | I-38 | 773.5 | (500 MHz, DMSO-d6) δ 11.07 (s, 1H), 10.71 (s, 1H), 8.70 (s, 1H), 8.35 (s, 1H), 8.02-7.93 (m, 2H), 7.67 (d, J = 8.5 Hz, 1H), 7.56 (dd, J = 7.5, 2.0 Hz, 1H), 7.33 (s, 1H), 7.25 (d, J = 9.0 Hz, 1H), 7.19 (s, 1H), 5.19-5.12 (m, 1H), 5.07 (dd, J = 12.5, 5.5 Hz, 1H), 4.07 (d, J = 13.0 Hz, 3H), 4.01 (s, 3H), 3.58-3.38 (m, 4H), 3.06-3.13 (m, 2H), 2.97-3.03 (m, 1H), 2.85-2.92 (m, 1H), 2.63 (s, 3H), 2.60-2.51 (m, 2H), 2.47-2.35 (m, 4H), 2.04-1.99 (m, 1H), 1.76-1.56 (m, 8H). |

| Molecular ID | structure | MS (ESI) m/z: [M + H]+ | 1H NMR |
|---|---|---|---|
| I-48 | I-48 | 841.8 | (500 MHz, DMSO-d6) δ 13.59 (s, 1H), 11.08 (s, 1H), 9.12 (s, 1H), 8.56 (s, 1H), 8.49 (s, 1H), 8.45 (d, J = 7.5 Hz, 1H), 8.37 (t, J = 8.0 Hz, 1H), 8.17 (d, J = 8.0 Hz, 1H), 7.67 (d, J = 8.5 Hz, 1H), 7.33 (s, 1H), 7.25 (d, J = 8.5 Hz, 1H), 5.34-5.24 (m, 1H), 5.07 (dd, J = 12.5, 5.5 Hz, 1H), 4.13-4.02 (m, 2H), 3.61-3.54 (m, 1H), 3.54-3.47 (m, 3H), 3.13-3.06 (m, 2H), 3.04-2.97 (m, 1H), 2.92-2.84 (m, 1H), 2.66-2.59 (m, 1H), 2.59-2.53 (m, 2H), 2.49-2.35 (m, 3H), 2.05-1.98 (m, 1H), 1.82-1.56 (m, 8H). |
| I-51 | I-51 | 827.7 | (500 MHz, DMSO-d6) δ 11.15 (s, 1H), 10.51 (s, 1H), 8.68 (s, 1H), 8.46 (d, J = 7.5 Hz, 1H), 8.41 (d, J = 7.5 Hz, 1H), 8.35 (s, 1H), 8.22 (d, J = 8.0 Hz, 1H), 7.98 (d, J = 7.5 Hz, 1H), 7.92 (s, 1H), 7.90-7.84 (m, 1H), 7.21 (s, 1H), 5.18 (dd, J = 12.8, 5.4 Hz, 1H), 5.14-5.07 (m, 1H), 4.51 (d, J = 12.5 Hz, 1H), 3.99 (s, 3H), 3.48 (d, J = 9.5 Hz, 1H), 3.16-3.01 (m, 1H), 2.95-2.86 (m, 1H), 2.81 (s, 1H), 2.65-2.51 (m, 3H), 2.42-2.30 (m, 6H), 2.11-2.04 (m, 1H), 1.83 (s, 1H), 1.67 (d, J = 20.0 Hz, 4H), 1.47 (d, J = 11.5 Hz, 2H), 1.28-1.21 (m, 1H). |

| Molecular ID | structure | MS (ESI) m/z: [M + H]$^+$ | $^1$H NMR |
|---|---|---|---|
| I-53 | I-53 | 815.6 | (500 MHz, DMSO-$d_6$) δ 11.15 (s, 1H), 10.51 (s, 1H), 8.68 (s, 1H), 8.46 (d, J = 8.0 Hz, 1H), 8.41 (t, J = 8.0 Hz, 1H), 8.35 (s, 1H), 8.22 (d, J = 8.0 Hz, 1H), 7.98 (d, J = 7.5 Hz, 1H), 7.92 (s, 1H), 7.87 (dd, J = 8.0, 1.0 Hz, 1H), 7.21 (s, 1H), 5.18 (dd, J = 13.0, 5.5 Hz, 1H), 5.14-5.07 (m, 1H), 4.55-4.47 (m, 1H), 3.99 (s, 3H), 3.51-3.43 (m, 1H), 3.10-3.01 (m, 1H), 2.95-2.86 (m, 1H), 2.84-2.77 (m, 1H), 2.66-2.52 (m, 4H), 2.47-2.26 (m, 7H), 2.11-2.04 (m, 1H), 1.88-1.80 (m, 1H), 1.74-1.60 (m, 5H), 1.53-1.40 (m, 2H). |
| I-56 | I-56 | 827.5 | (400 MHz, DMSO) δ 11.09 (s, 1H), 10.43 (s, 1H), 8.72 (s, 1H), 8.47 (d, J = 7.5 Hz, 1H), 8.41 (t, J = 7.5 Hz, 1H), 8.22 (d, J = 7.5 Hz, 1H), 8.07 (s, 1H), 7.72 (d, J = 8.5 Hz, 1H), 7.42 (s, 1H), 7.36 (d, J = 2.0 Hz, 1H), 7.26 (dd, J = 8.5, 2.0 Hz, 1H), 5.36-5.26 (m, 1H), 5.08 (dd, J = 12.5, 5.5 Hz, 1H), 4.04 (s, 3H), 3.71-3.49 (m, 10H), 2.92-2.83 (m, 1H), 2.69-2.60 (m, 2H), 2.59-2.54 (m, 1H), 2.43-2.37 (m, 1H), 2.32-2.21 (m, 2H), 2.09-1.97 (m, 2H), 1.85-1.76 (m, 1H), 1.71-1.65 (m, 1H), 1.58-1.49 (m, 4H). |

Example 7: Synthesis of I-30
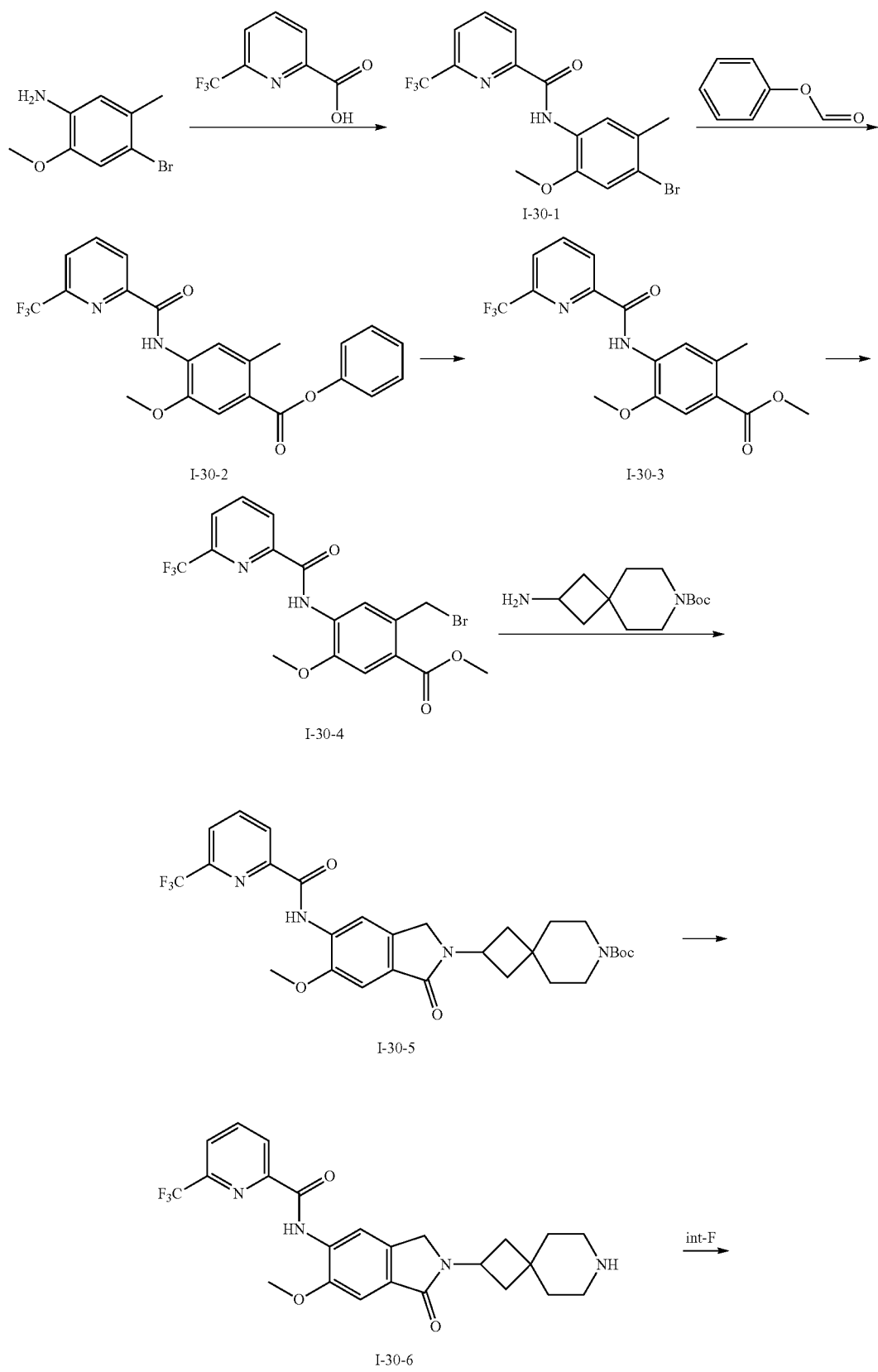

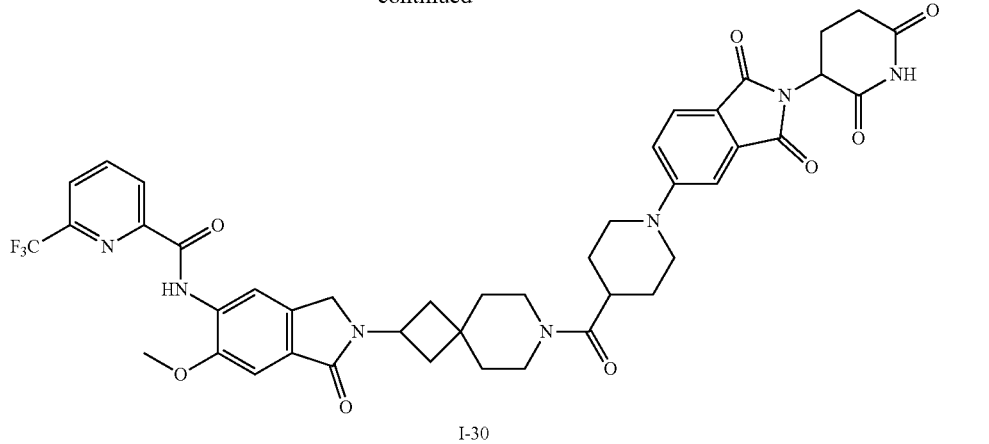

I-30

Step 1: Synthesis of (I-30-1)
Under nitrogen protection, 4-bromo-2-methoxy-5-methyl-aniline (1 g, 4.63 mmol), 6-(trifluoromethyl)pyridine-2-carboxylic acid (1.06 g, 5.55 mmol), DIPEA (1.20 g, 9.26 mmol, 1.61 mL) and anhydrous THF (15 mL) were added to the reaction flask and cooled to 0° C. $T_3P$ (2.95 g, 9.26 mmol) was slowly added dropwise, and the reaction was stirred at 25° C. for 1 hour. $H_2O$ (60 mL) was added to the reaction system. The product was precipitated, filtered, the filter cake was washed with water, and dried under vacuum to obtain the product I-30-1 as white solid (1.77 g, yield 98.16%), MS (ESI) m/z: 389.2 $[M+H]^+$.

Step 2: Synthesis of (I-30-2)
Under nitrogen protection, I-30-1 (1.77 g, 4.54 mmol), phenyl formate (1.1 g, 9.08 mmol), $Pd(OAc)_2$ (palladium acetate, 101 mg, 0.45 mmol), $P(t-Bu)_3 \cdot HBF_4$ (tri-tert-butylphosphine tetrafluoroborate, 516.4 mg, 1.78 mmol), $Et_3N$ (triethylamine, 917.08 mg, 9.08 mmol), and acetonitrile (3 mL) were added into a reaction bottle, and warmed to 80° C. for reaction overnight. The mixture was returned to room temperature, filtered, and the filtrate was concentrated under reduced pressure, added with ethyl acetate to dilute, washed twice with saturated brine, dried over anhydrous sodium sulfate, filtered, and concentrated under reduced pressure to obtain a crude product, which was purified by reverse-phase C18 column chromatography (mobile phase 0-60% water/acetonitrile) to obtain product I-30-2 as a white solid (1.3 g, yield 70%), MS (ESI) m/z: 431.1 $[M+H]^+$.

Step 3: Synthesis of (I-30-3)
I-30-2 (1.3 g, 3.2 mmol), potassium carbonate (1.77 g, 12.8 mmol) and methanol (4 mL) were added to a reaction bottle and reacted at room temperature for 2 hours. Water was added to precipitate a product, which was filtered, and the filter cake was washed with water and vacuum-dried to obtain a crude product. The crude product was purified by reversed-phase C18 column chromatography (mobile phase 0-60% water/acetonitrile) to obtain product I-30-3 as a white solid (900 mg, yield 75%), MS (ESI) m/z: 369.1 $[M+H]^+$.

Step 4: Synthesis of (I-30-4)
Under nitrogen protection, I-30-3 (900 mg, 2.4 mmol), NBS (512.6 mg, 2.88 mmol), AIBN (39 mg, 0.24 mmol) and $CCl_4$ (9 mL) were added into a reaction bottle, warmed to 80° C., and reacted for 5 hours. The reaction solution was returned to room temperature and filtered, and the filtrate was added with $H_2O$ (30 mL), and extracted with EA (25 mL×3). The organic phases were combined, dried over anhydrous $Na_2SO_4$, filtered, and concentrated under reduced pressure to obtain a crude product, which was purified by reverse-phase C18 column chromatography, eluting with (MeCN/H2O+1‰ HCOOH) to obtain the desired product I-30-4 as a white solid (802 mg, yield 76%), MS (ESI) m/z: 447.1 $[M+H]^+$.

Step 5: Synthesis of (I-30-5)
A mixed solution of I-30-4 (300 mg, 670.84 μmol), 2-amino-7-azaspiro[3.5]non-7-carboxylic acid tert-butyl ester (177.35 mg, 737.92 μmol), DIPEA (260.10 mg, 2.01 mmol, 350.53 μL) and ACN (4 mL) was stirred at 25° C. for 3 hours. The reaction solution was added with $H_2O$ (20 mL), and extracted with EA (15 mL×3). The combined organic phases were washed with saturated brine (20 mL), dry over anhydrous $Na_2SO_4$, filtered and concentrated under reduced pressure. The crude product was purified by flash silica gel column chromatography (DCM:MeOH=30:1) to obtain product I-30-5 as a brown solid (135 mg, yield 35.02%), MS (ESI) m/z: 575.3 $[M+H]^+$.

Step 6: Synthesis of (I-30-6)
I-30-5 (135 mg, 234.95 μmol) was dissolved in DCM (3 mL), added with TFA (1.5 mL), and stirred at 25° C. for 2 hours. The resulting mixture was concentrated under reduced pressure to obtain product I-30-6 as a white solid (86 mg, yield 70.32%, TFA salt), MS (ESI) m/z: 475.2 $[M+H]^+$.

Step 7: Synthesis of (I-30)
A mixed solution of I-30-6 (40 mg, 76.85 μmol), int-F (32.58 mg, 84.53 μmol), HATU (35.06 mg, 92.22 μmol), DIPEA (39.73 mg, 307.40 μmol, 53.54 μL) and DMF (2 mL) was stirred at 25° C. for 1 hour. The reaction solution was added with 1120 (25 mL), and extracted with EA (20 mL×3). The combined organic phases were washed with saturated brine (20 mL), dried over anhydrous $Na_2SO_4$, filtered and concentrated under reduced pressure. The crude product was purified by preparative thin layer chromatography (DCM:MeOH=20:1) to obtain product I-30 as a yellow solid (27 mg, yield 40.90%). $^1$H NMR (500 MHz, DMSO-$d_6$) δ 11.08 (s, 1H), 10.58 (s, 1H), 8.67 (s, 1H), 8.48 (d, J=7.5 Hz, 1H), 8.42 (t, J=8.0 Hz, 11H), 8.25 (d, J=7.5 Hz, 1H), 7.66 (d, J=8.5 Hz, 1H), 7.36 (s, 1H), 7.33 (d, J=1.5 Hz, 1H), 7.25 (dd, J=8.5, 2.0 Hz, 1H), 5.07 (dd, J=13.0, 5.5 Hz, 1H), 4.85-4.77 (m, 1H), 4.59 (s, 2H), 4.10-4.03 (m, 2H), 4.02 (s, 3H), 3.57-3.50 (m, 1H), 3.50-3.41 (m, 2H), 3.40-3.36 (m, 1H), 3.13-3.05 (m, 2H), 3.04-2.97 (m, 1H), 2.93-2.84 (m, 1H), 2.66-2.52 (m, 3H), 2.23-2.09 (m, 4H), 2.05-1.98 (m, 1H), 1.74-1.66 (m, 3H), 1.66-1.56 (m, 4H), 1.54-1.49 (m, 1H).

Example 8: Synthesis of I-41

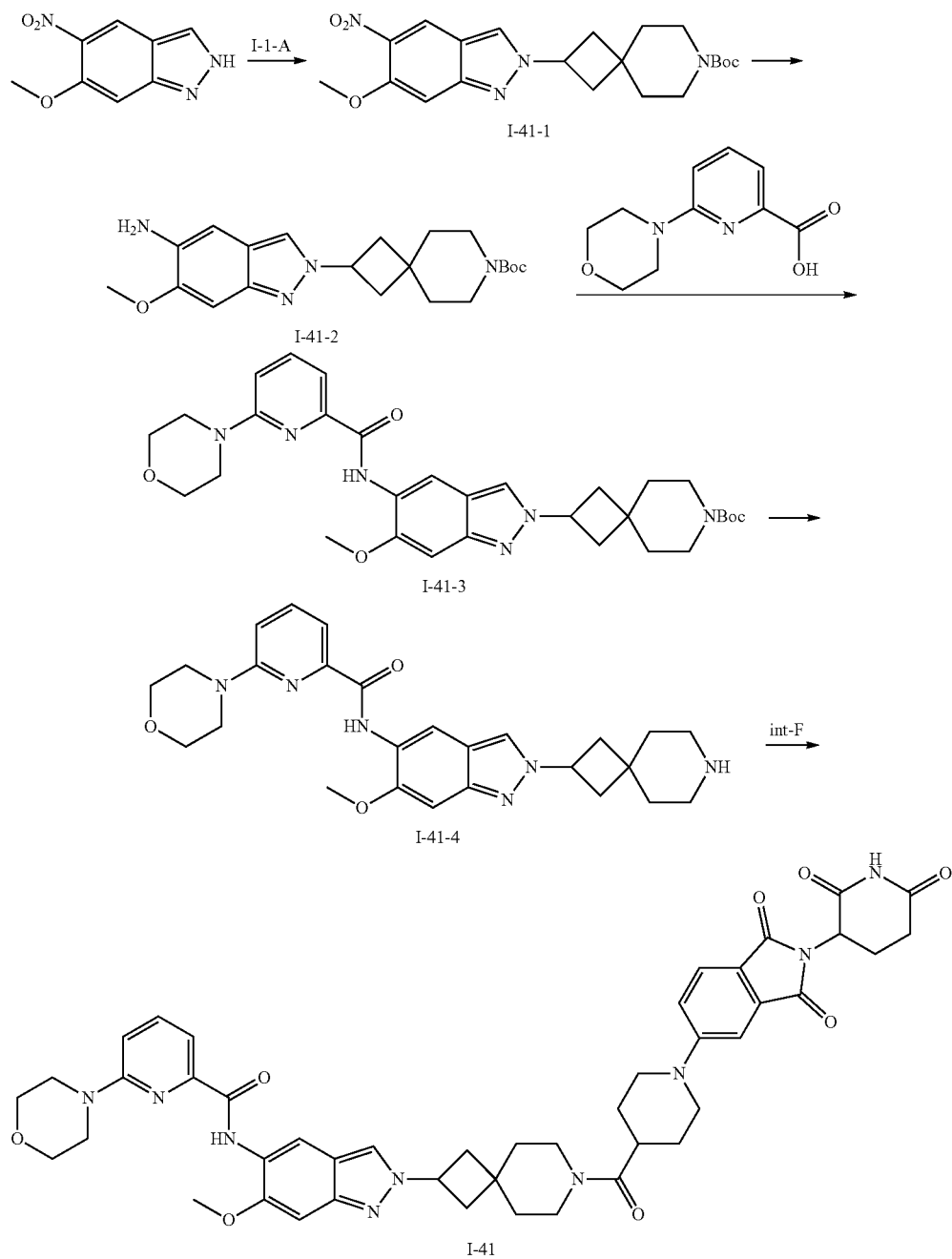

Step 1: Synthesis of (I-41-1)

Under nitrogen protection, a mixture of 6-methoxy-5-nitro-2H-indazole (1.17 g, 6.07 mmol), DMF (12 mL), cesium carbonate (4.94 g, 15.17 mmol) and I-1-A (3 g, 7.59 mmol) was stirred at 90° C. for 3 hours. The reaction mixture was returned to room temperature, added with H₂O (60 mL), and extracted with DCM (35 mL×3). The combined organic phases were washed with saturated brine (50 mL), dried over anhydrous Na₂SO₄, filtered and concentrated under reduced pressure. The crude product was purified by flash silica gel column chromatography (DCM/MeOH=98/2) to obtain product I-41-1 as a white solid (770 mg, yield 24.38%), MS (ESI) m/z: 417.5 [M+H]⁺.

Step 2: Synthesis of (I-41-2)

Under a hydrogen atmosphere, I-41-1 (770 mg, 1.85 mmol) was dissolved in MeOH (7 mL), added with catalyst wet Pd/C (80 mg, 10% purity), and reacted at 25° C. for 4 hours.

The reaction solution was filtered through diatomaceous earth to remove the catalyst, and the filtrate was concentrated under reduced pressure to obtain product II-41-2 as a yellow solid (500 mg, yield 69.97%), MS (ESI) m/z: 387.2 [M+H]⁺.

Step 3: Synthesis of (I-41-3)

A mixed solution of II-41-2 (50 mg, 129.37 μmol), 6-morpholinepyridine-2-carboxylic acid (26.94 mg, 129.37 μmol), HATU (49.19 mg, 129.37 μmol), DIPEA (33.44 mg, 258.74 μmol, 45.07 μL) and DMF (2 mL) was stirred at 25° C. for 2 hours. The reaction solution was added with $H_2O$ (300 mL), and extracted with EA (20 mL×3). The combined organic phases were washed with saturated brine (20 mL), dried over anhydrous $Na_2SO_4$, filtered and concentrated under reduced pressure. The crude product was purified by preparative thin layer chromatography to obtain product II-41-3 as a white solid (64 mg, yield 85.78%), MS (ESI) m/z: 577.5 $[M+H]^+$.

Step 4: Synthesis of (I-41-4)

A mixed solution of I-41-3 (63 mg, 109.25 μmol), TFA (2 mL) and DCM (2 mL) was stirred at 25° C. for 1 hour. The reaction solution was concentrated under reduced pressure to obtain product I-41-4 as a yellow oil (64 mg, crude product, TFA salt), MS (ESI) m/z: 477.3 $[M+H]^+$.

Step 5: Synthesis of (I-41)

A mixed solution of I-41-4 (52 mg, 109.11 μmol), int-F (42.05 mg, 109.11 μmol), HATU (41.49 mg, 109.11 μmol), DIPEA (28.20 mg, 218.23 μmol, 38.01 L) and DMF (2 mL) was stirred at 25° C. for 2 hours. The reaction solution was added with $H_2O$ (300 mL), and extracted with EA (20 mL×3). The combined organic phases were washed with saturated brine, dried over anhydrous sodium sulfate, and purified by preparative thin layer chromatography to obtain the product I-41 as a yellow solid (28 mg, yield 29.80%), MS (ESI) m/z: 844.6 $[M+H]^+_o$ $^1H$ NMR (500 MHz, DMSO-$d_6$) δ 11.08 (s, 1H), 10.79 (s, 1H), 8.64 (s, 1H), 8.33 (s, 1H), 7.84-7.78 (m, 1H), 7.67 (d, J=8.5 Hz, 1H), 7.46 (d, J=7.0 Hz, 1H), 7.33 (s, 1H), 7.25 (d, J=8.5 Hz, 1H), 7.18 (s, 1H), 7.16 (d, J=8.5 Hz, 1H), 5.22-5.12 (m, 11H), 5.07 (dd, J=12.5, 5.5 Hz, 1H), 4.11-4.03 (m, 2H), 3.97 (s, 3H), 3.84-3.78 (m, 4H), 3.69-3.59 (m, 4H), 3.56-3.39 (m, 4H), 3.15-3.05 (m, 2H), 3.04-2.95 (m, 1H), 2.93-2.84 (in, H), 2.68-2.53 (m, 2H), 2.48-2.32 (m, 4H), 2.05-1.99 (m, 1H), 1.75-1.57 (m, 8H).

Compounds I-42, I-44, I-46, I-47, I-49, I-50, I-52, I-54, and I-55 can be prepared by referring to the method of Example 8 above. The structure and characterization data are shown in the following table:

| Molecular ID | structure | MS (ESI) m/z: [M + H]+ | 1H NMR |
|---|---|---|---|
| I-42 | 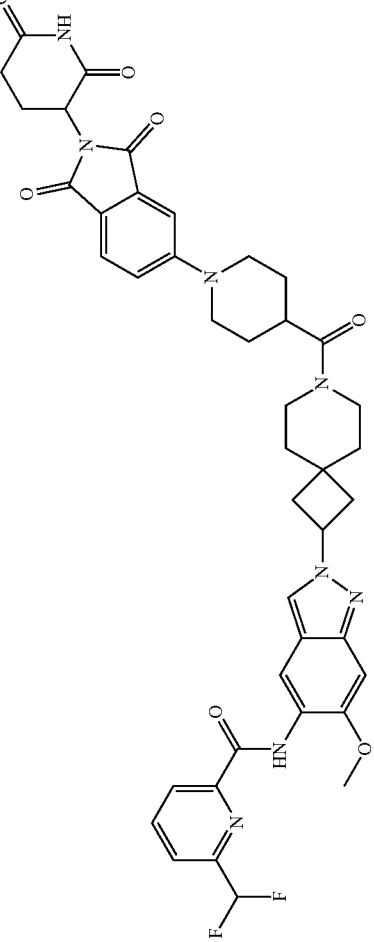 | 809.5 | (500 MHz, DMSO-d6) δ 11.07 (s, 1H), 10.56 (s, 1H), 8.69 (s, 1H), 8.37 (s, 1H), 8.36-8.29 (m, 2H), 8.00 (dd, J = 7.5, 1.0 Hz, 1H), 7.67 (d, J = 8.5 Hz, 1H), 7.33 (s, 1H), 7.27-7.04 (m, 3H), 5.21-5.13 (m, 1H), 5.07 (dd, J = 12.5, 5.5 Hz, 1H), 4.11-4.04 (m, 2H), 4.01 (s, 3H), 3.58-3.39 (m, 4H), 3.14-3.05 (m, 2H), 3.04-2.96 (m, 1H), 2.93-2.84 (m, 1H), 2.65-2.54 (m, 2H), 2.47-2.35 (m, 4H), 2.05-1.98 (m, 1H), 1.77-1.67 (m, 4H), 1.66-1.57 (m, 4H). |
| I-44 | 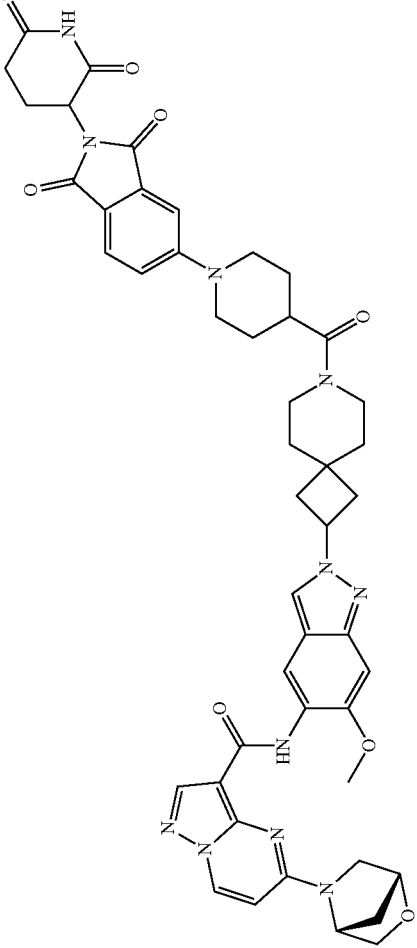 | 896.6 | (500 MHz, DMSO-d6) δ 11.08 (s, 1H), 9.86 (d, J = 21.5 Hz, 1H), 8.79 (d, J = 7.5 Hz, 1H), 8.69 (s, 1H), 8.29 (s, 1H), 8.28 (s, 1H), 7.66 (d, J = 8.5 Hz, 1H), 7.33 (s, 1H), 7.24 (d, J = 7.5 Hz, 1H), 7.17 (d, J = 8.5 Hz, 1H), 6.88-6.46 (m, 1H), 5.46-5.04 (m, 3H), 4.89-4.81 (m, 1H), 4.12-4.02 (m, 2H), 3.94 (s, 3H), 3.87-3.82 (m, 1H), 3.78-3.60 (m, 2H), 3.58-3.53 (m, 1H), 3.52-3.44 (m, 2H), 3.44-3.38 (m, 1H), 3.31-3.27 (m, 1H), 3.14-3.05 (m, 2H), 3.05-2.95 (m, 1H), 2.93-2.83 (m, 1H), 2.65-2.53 (m, 2H), 2.48-2.35 (m, 4H), 2.11-1.98 (m, 3H), 1.80-1.67 (m, 4H), 1.67-1.56 (m, 4H). |

| Molecular ID | structure | MS (ESI) m/z: [M + H]+ | 1H NMR |
|---|---|---|---|
| I-46 | I-46 | 862.5 | (500 MHz, DMSO-d6) δ 11.11 (s, 1H), 10.79 (s, 1H), 8.64 (s, 1H), 8.33 (s, 1H), 7.81 (dd, J = 8.0, 7.0 Hz, 1H), 7.71 (d, J = 11.0 Hz, 1H), 7.46 (d, J = 7.0 Hz, 1H), 7.44 (d, J = 7.5 Hz, 1H), 7.18 (s, 1H), 7.15 (d, J = 8.5 Hz, 1H), 5.20-5.13 (m, 1H), 5.11 (dd, J = 13.0, 5.5 Hz, 1H), 3.97 (s, 3H), 3.83-3.78 (m, 4H), 3.66-3.62 (m, 2H), 3.62-3.58 (m, 4H), 3.55-3.49 (m, 2H), 3.47-3.41 (m, 2H), 3.03-2.97 (m, 2H), 2.93-2.86 (m, 2H), 2.65-2.55 (m, 2H), 2.49-2.45 (m, 2H), 2.44-2.39 (m, 2H), 2.06-2.02 (m, 1H), 1.78-1.71 (m, 5H), 1.69-1.59 (m, 3H). |
| I-47 | I-47 | 798.6 | (500 MHz, DMSO-d6) δ 11.08 (s, 1H), 9.40 (s, 1H), 8.51 (s, 1H), 8.45 (d, J = 3.0 Hz, 1H), 8.35 (s, 1H), 8.09 (s, 1H), 7.98 (s, 1H), 7.86 (s, 1H), 7.67 (d, J = 8.5 Hz, 1H), 7.33 (s, 1H), 7.24 (d, J = 8.5 Hz, 1H), 7.19 (s, 1H), 7.03 (d, J = 2.5 Hz, 1H), 5.20-5.13 (m, 1H), 5.07 (dd, J = 13.0, 5.5 Hz, 1H), 4.07 (d, J = 12.5 Hz, 2H), 3.97 (s, 3H), 3.59-3.39 (m, 4H), 3.15-3.06 (m, 2H), 3.04-2.97 (m, 1H), 2.92-2.84 (m, 1H), 2.62-2.52 (m, 2H), 2.49-2.44 (m, 2H), 2.44-2.38 (m, 2H), 2.04-1.99 (m, 1H), 1.77-1.67 (m, 4H), 1.67-1.57 (m, 4H). |

| Molecular ID | structure | MS (ESI) m/z: [M + H]+ | 1H NMR |
|---|---|---|---|
| I-49 | (structure of I-49) | 897.6 | (500 MHz, DMSO-d6) δ 11.08 (s, 1H), 9.76 (s, 1H), 8.80 (d, J = 7.0 Hz, 1H), 8.67 (s, 1H), 8.29 (s, 2H), 7.66 (d, J = 8.5 Hz, 1H), 7.33 (s, 1H), 7.25 (d, J = 8.5 Hz, 1H), 7.16 (s, 1H), 6.93 (d, J = 8.0 Hz, 1H), 5.21-5.11 (m, 1H), 5.07 (dd, J = 12.5, 5.0 Hz, 1H), 4.10-4.02 (m, 2H), 3.93 (s, 3H), 3.91-3.82 (m, 3H), 3.58-3.39 (m, 4H), 3.16-3.05 (m, 2H), 3.05-2.83 (m, 3H), 2.67-2.52 (m, 4H), 2.46-2.33 (m, 5H), 2.27 (s, 3H), 2.07-1.94 (m, 2H), 1.76-1.56 (m, 8H). |
| I-50 | (structure of I-50) | 862.7 | (500 MHz, DMSO-d6) δ 11.08 (s, 1H), 10.79 (s, 1H), 8.63 (s, 1H), 8.33 (s, 1H), 7.82 (dd, J = 8.5, 7.3 Hz, 1H), 7.70 (d, J = 8.5 Hz, 1H), 7.46 (d, J = 7.0 Hz, 1H), 7.41 (d, J = 2.0 Hz, 1H), 7.31 (dd, J = 8.7, 2.1 Hz, 1H), 7.18 (s, 1H), 7.16 (d, J = 8.5 Hz, 1H), 5.34-5.30 (m, 1H), 5.17-5.13 (m, 1H), 5.08 (dd, J = 13.0, 5.5 Hz, 1H), 3.97 (s, 3H), 3.95-3.92 (m, 1H), 3.82-3.79 (m, 4H), 3.62-3.58 (m, 4H), 2.64-2.56 (m, 2H), 2.45-2.39 (m, 3H), 2.38-2.35 (m, 1H), 2.05-1.96 (m, 6H), 1.78-1.64 (m, 6H), 1.55-1.42 (m, 4H). |

| Molecular ID | structure | MS (ESI) m/z: [M + H]+ | 1H NMR |
|---|---|---|---|
| I-52 | 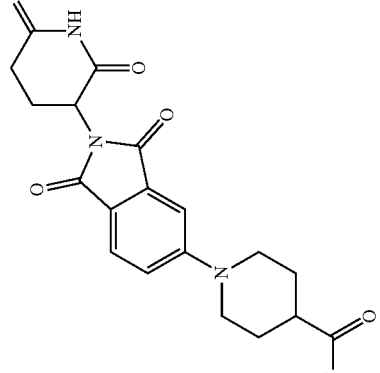 | 856.7 | (500 MHz, DMSO-d6) δ 11.08 (s, 1H), 10.82 (s, 1H), 8.64 (s, 1H), 8.33 (s, 1H), 7.75 (dd, J = 8.0, 7.5 Hz, 1H), 7.67 (d, J = 8.5 Hz, 1H), 7.38 (d, J = 7.0 Hz, 1H), 7.33 (s, 1H) 7.25 (d, J = 8.5 Hz, 1H), 7.17 (s, 1H), 6.86 (d, J = 8.0 Hz, 1H), 5.19-5.11 (m, 1H), 5.07 (dd, J = 12.5, 5.5 Hz, 1H), 4.95 (s, 1H), 4.76 (s, 1H), 4.07 (d, J = 12.0 Hz, 2H), 3.98 (s, 3H), 3.89 (d, J = 7.0 Hz, 1H), 3.74 (d, J = 7.5 Hz, 1H), 3.60 (d, J = 10.0 Hz, 1H), 3.57-3.39 (m, 4H), 3.38-3.35 (m, 1H), 3.14-3.06 (m, 2H), 3.03-2.96 (m, 1H), 2.92-2.85 (m, 1H), 2.65-2.53 (m, 2H), 2.47-2.33 (m, 4H), 2.05-1.94 (m, 3H), 1.78-1.55 (m, 8H). |
| I-54 | 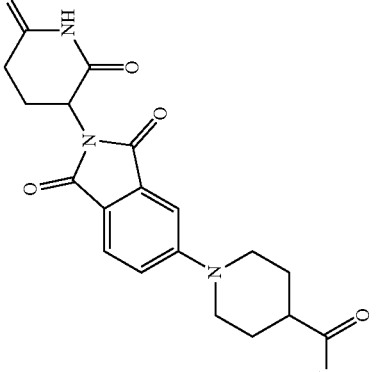 | 834.7 | (500 MHz, DMSO-d6) δ 11.08 (s, 1H), 9.34 (s, 1H), 8.55 (s, 1H), 8.33 (s, 1H), 8.28 (s, 1H), 7.67 (d, J = 8.5 Hz, 1H), 7.33 (s, 1H), 7.25 (d, J = 8.5 Hz, 1H), 7.16 (s, 1H), 5.17-5.12 (m, 1H), 5.07 (dd, J = 13.0, 5.5 Hz, 1H), 4.09-4.05 (m, 2H), 3.96 (s, 3H), 3.75-3.69 (m, 4H), 3.49-3.45 (m, 5H), 3.43-3.38 (m, 2H), 3.15-3.05 (m, 3H), 3.03-2.98 (m, 1H), 2.94-2.83 (m, 2H), 2.44-2.36 (m, 3H), 2.08-1.95 (m, 3H), 1.74-1.67 (m, 4H), 1.65-1.57 (m, 4H). |

| Molecular ID | structure | MS (ESI) m/z: [M + H]+ | 1H NMR |
|---|---|---|---|
| I-55 | 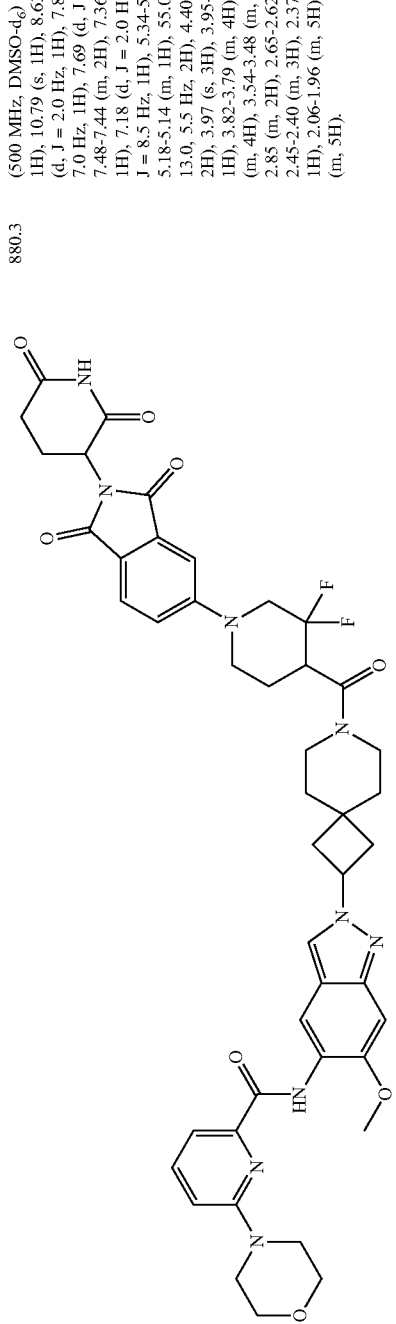<br>I-55 | 880.3 | (500 MHz, DMSO-d6) δ 11.08 (s, 1H), 10.79 (s, 1H), 8.63 (s, 1H), 8.34 (d, J = 2.0 Hz, 1H), 7.82 (dd, J = 8.5, 7.0 Hz, 1H), 7.69 (d, J = 8.5 Hz, 1H), 7.48-7.44 (m, 2H), 7.36-7.34 (m, 1H), 7.18 (d, J = 2.0 Hz, 1H), 7.16 (d, J = 8.5 Hz, 1H), 5.34-5.30 (m, 1H), 5.18-5.14 (m, 1H), 5.08 (dd, J = 13.0, 5.5 Hz, 2H), 4.40-4.30 (m, 2H), 3.97 (s, 3H), 3.95-3.92 (m, 2H), 3.82-3.79 (m, 4H), 3.61-3.58 (m, 4H), 3.54-3.48 (m, 2H), 2.93-2.85 (m, 2H), 2.65-2.62 (m, 1H), 2.45-2.40 (m, 3H), 2.37-2.35 (m, 1H), 2.06-1.96 (m, 5H), 1.75-1.64 (m, 5H). |

Example 9: Synthesis of I-43

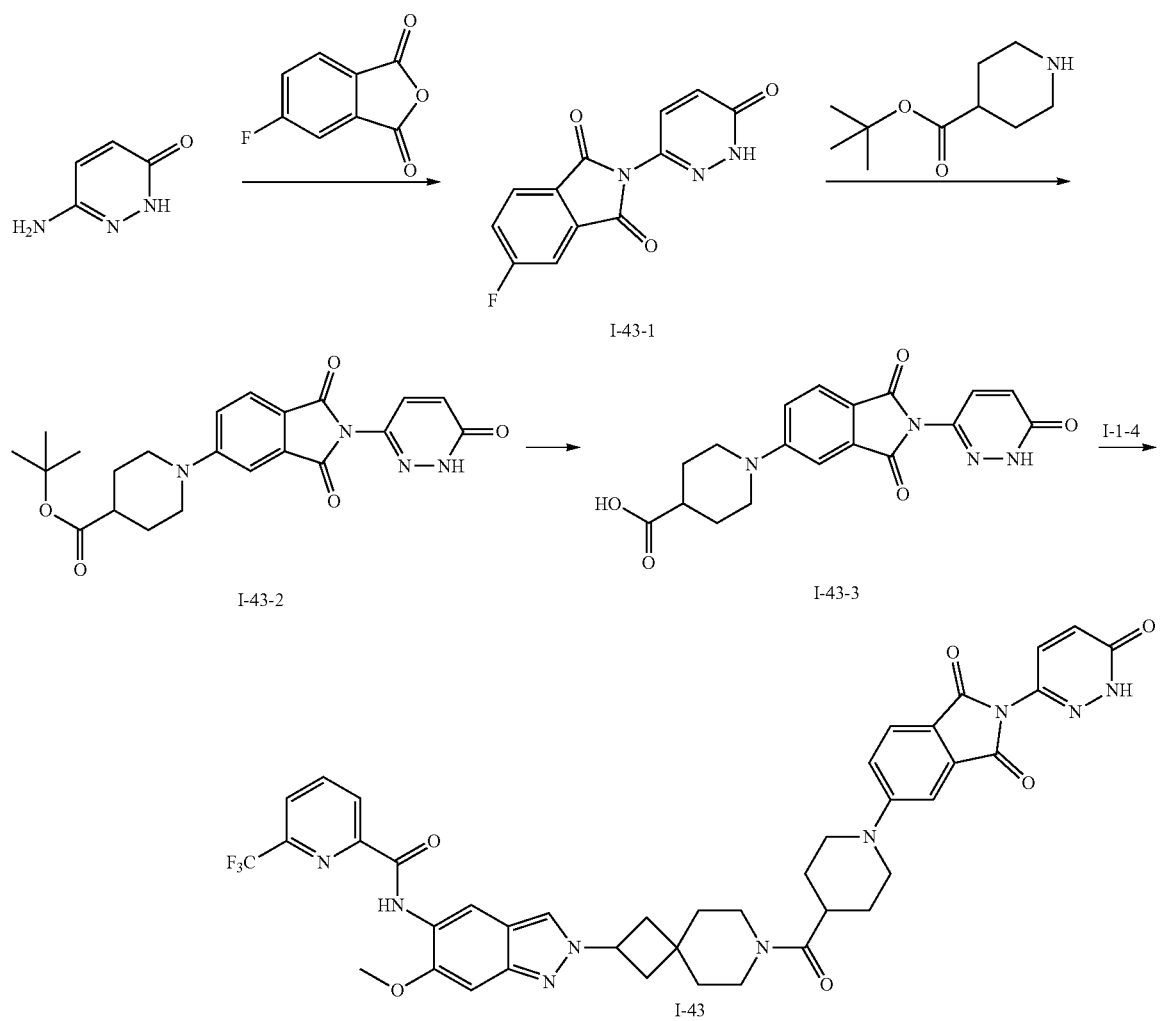

Step 1: Synthesis of (I-43-1)

A mixture of 5-fluoroisobenzofuran-1,3-dione (0.9 g, 8.6 mmol), 6-aminopyridazine-3(2H)-one (1.3 g, 7.8 mmol), NaOAc (1.3 g, 15.5 mmol)) and HOAc (7 mL) was stirred at 80° C. for 16 hours. The mixture was returned to room temperature and concentrated under reduced pressure. The residue was poured into water and stirred. The solid was precipitated, filtered, washed with diethyl ether, and the filter cake was dried under vacuum to obtain the product I-43-1 as a white solid (1.2 g, yield 55%), MS (ESI) m/z: 260.2 [M+H]$^+$.

Step 2: Synthesis of (I-43-2)

To a solution of I-43-1 (1.1 g, 4.4 mmol) in anhydrous DMSO (10.0 mL) was added DIEA (1.14 g, 8.8 mmol) and piperidine-4-carboxylic acid tert-butyl ester (0.82 g, 4.4 mmol), and the mixture was reacted at 90° C. for 2 hours. The mixture was returned to room temperature, diluted with water (100 mL), and extracted with ethyl acetate (80 mL×3). The combined organic phases were washed with saturated brine (50 mL), dried over anhydrous magnesium sulfate, filtered, and concentrated under reduced pressure. The crude product was purified by reverse C18 column chromatography to obtain product I-43-2 as a yellow solid (200 mg, yield 11%), MS (ESI) m/z: 425.3 [M+H]$^+$.

Step 3: Synthesis of (I-43-3)

TFA (1 mL) was added dropwise to a solution of I-43-2 (200 mg, 0.47 mmol) and DCM (5 mL) at 0° C., and the mixture was stirred at 25° C. for 16 hours. Diethyl ether was added to precipitate a solid, the supernatant was removed after standing and repeated three times, and dried under vacuum to obtain product I-43-3 as a yellow solid (180 mg, yield 99%), MS (ESI) m/z: 369.1 [M+H]$^+$.

Step 4: Synthesis of (I-43)

A mixed solution of I-43-3 (60 mg, 0.14 mmol), I-1-4 (52 mg, 0.14 mmol), HCTU (67 mg, 0.16 mmol), TEA (142 mg, 1.4 mmol) and DMF (3 mL) was stirred at 25° C. for 1 hour. The reaction solution was purified by preparative HPLC to obtain the product I-43 as a yellow solid (11.2 mg, yield 10%), MS (ESI) m/z: 810.2 [M+H]$^+$. $^1$H NMR (400 MHz, DMSO-d$_6$) δ 10.51 (s, 1H), 8.69 (s, 1H), 8.47 (d, J=7.5 Hz, 1H), 8.44-8.39 (m, 1H), 8.38 (d, J=1.0 Hz, 1H), 8.22 (dd, J=7.5, 1.0 Hz, 1H), 7.74 (d, J=8.5 Hz, 1H), 7.56 (d, J=9.5 Hz, 1H), 7.40 (d, J=1.5 Hz, 1H), 7.33-7.28 (m, 1H), 7.21 (s, 1H), 7.06 (d, J=9.5 Hz, 1H), 5.21-5.14 (m, 1H), 4.20-4.07 (m, 3H), 3.99 (s, 3H), 3.59-3.38 (m, 4H), 3.13-3.02 (m, 3H), 2.70-2.65 (m, 1H)2.49-2.36 (m, 4H), 1.84-1.49 (m, 8H).

Example 10: Synthesis of I-45
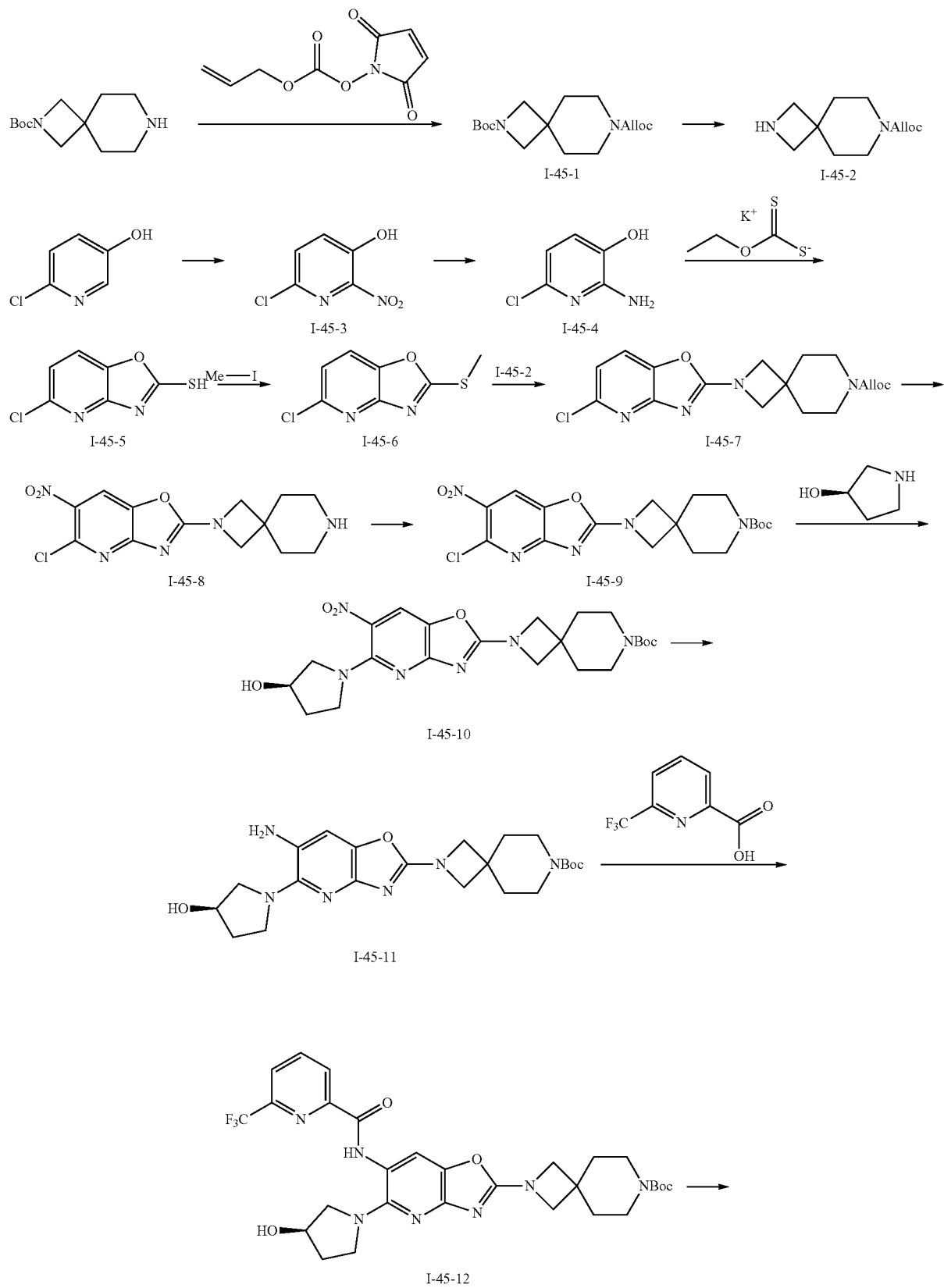

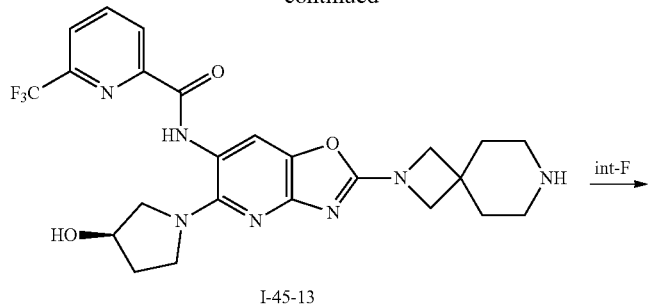

I-45-13

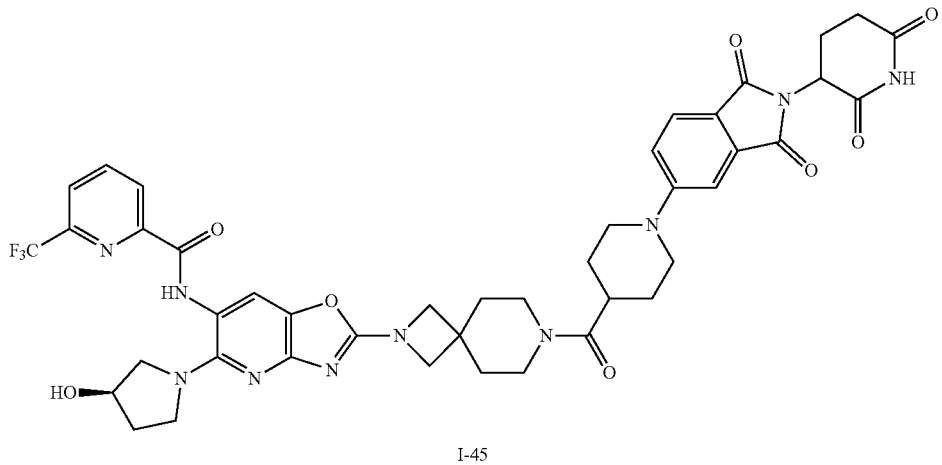

I-45

Step 1: Synthesis of (I-45-1)

To a solution of $K_2CO_3$ (18.35 g, 132.8 mmol) and 2,7-diazaspiro[3.5]nonane-2-carboxylic acid tert-butyl ester (10 g, 44.25 mmol) in acetone/$H_2O$(120/40 mL) was add (2,5-dioxy-2,5-dihydro-1H-pyrrol-1-yl) allyl carbonate (10.6 g, 53.1 mmol) under a nitrogen atmosphere at 0° C., and the solution was stirred at 25° C. for 16 hours. The reaction system was diluted with ethyl acetate (500 mL), washed with 3N HCl, dried over anhydrous sodium sulfate, and concentrated under reduced pressure to obtain a crude product, which was purified by flash silica gel column chromatography to obtain product I-45-1 as a yellow solid (13.0 g, yield 94%), $^1$H NMR (400 MHz, $CDCl_3$) δ 6.00-5.87 (m, 1H), 5.31-5.20 (m, 2H), 4.59-4.57 (m, 2H), 3.65 (s, 4H), 3.46-3.38 (m, 4H), 1.74-1.70 (m, 4H), 1.43 (s, 9H).

Step 2: Synthesis of (I-45-2)

TFA (24 mL) was added to a solution of I-45-1 (12.2 g, 39.0 mmol) in DCM (240 mL) at 0° C., and the reaction was carried out at 25° C. for 2 hours. Diethyl ether was added to precipitate a solid, the supernatant was removed after standing and repeated three times, and dried under vacuum to obtain product I-45-2 as a brown solid (10 g, yield 100%), $^1$H NMR (400 MHz, DMSO-$d_6$) δ 5.97-5.87 (m, 1H), 5.29-5.17 (m, 2H), 4.53-4.51 (m, 2H), 3.73 (t, J=6.4 Hz, 4H), 1.78-1.66 (m, 4H).

Step 3: Synthesis of (I-45-3)

To a solution of $KNO_3$ (31 g, 308 mmol) and concentrated $H_2SO_4$ (250 mL) was added 6-chloropyridin-3-ol (22 g, 170 mmol) in batches at 0° C. After 0.5 hours, the dropwise addition was completed, and the mixture was stirred at 25° C. for 2 hours. The reaction mixture was quenched with ice water, the solid was filtered, washed with $H_2O$, and the filter cake was dried under vacuum to obtain product I-45-3 as a yellow solid (20 g, yield 69%), MS (ESI) m/z: 175.1 [M+H]$^+$, $^1$H NMR (400 MHz, DMSO-$d_6$) δ 11.92 (s, 1H), 7.73 (q, J=8.8 Hz, 2H).

Step 4: Synthesis of (I-45-4)

Under a nitrogen atmosphere, Fe (25.4 g, 453 mmol) was added to a solution of I-45-3 (15 g, 90 mmol) and $NH_4Cl$ (24 g, 453 mmol) in MeOH/$H_2O$ (150 mL/50 mL), and the solution was reacted at 70° C. for 4 hours. The reaction solution was returned to room temperature, added with water (300 mL) to dilute, and extracted with ethyl acetate (200 mL×3). The combined organic phases were washed with saturated brine (300 mL), dried over anhydrous sodium sulfate, filtered, and concentrated under reduced pressure to obtain a crude product, which was purified by silica gel column chromatography (PE/EtOAc=5/1) to obtain product I-45-4 as a yellow solid (5 g, yield 24%), MS (ESI) m/z: 145.0 [M+H]$^+$.

Step 5: Synthesis of (I-45-5)

A mixture of I-45-4 (7 g, 48 mmol) and potassium O-ethyldithiocarbonate (10.8 g, 68 mmol) in pyridine (80 mL) was stirred at 110° C. for 16 hours under a nitrogen atmosphere. The reaction system was returned to room temperature and diluted with ice water (100 mL), acidified with dilute hydrochloric acid (4 M) to pH=3-4 under stirring, and then extracted with ethyl acetate (100 mL×3). The organic phases were combined, washed with saturated brine (300 mL), dried over anhydrous sodium sulfate, filtered, and concentrated under reduced pressure to obtain product I-45-5 as a yellow solid (4 g, yield 45%), MS (ESI) m/z: 186.1 [M+H]$^+$.

Step 6: Synthesis of (I-45-6)

To a solution of I-45-5 (6 g, 32 mmol) and EtOAc (60 mL) were added methyl iodide (9 g, 64 mmol) and $K_2CO_3$ (8.8 g, 64 mmol), and the resulting mixture was sealed and stirred at 25° C. under nitrogen protection for 2 hours. The reaction solution was diluted with H₂O (100 mL) and extracted with EtOAc (100 mL×3). The combined organic layers were washed with saturated brine, dried over anhydrous sodium sulfate, filtered and concentrated under reduced pressure. The crude product was purified by silica gel column chromatography (PE/EtOAc=10/1) to obtain product I-45-6 as a yellow solid (4 g, yield 62.5%), MS (ESI) m/z: 200.9 [M+H]⁺ₒ, ¹H NMR (400 MHz, CDCl₃) δ 7.58 (d, J=8.4 Hz, 1H), 7.14 (d, J=8.4 Hz, 11H), 2.73 (s, 3H).

Step 7: Synthesis of (I-45-7)

Under a nitrogen atmosphere, I-45-6 (4.2 g, 21 mmol), I-45-2 (22 g, 105 mmol), DIEA (13.6 g, 105 mol) and 1,4-dioxane (40 mL) solution was stirred at 110° C. for 16 hours. The reaction solution was diluted with H₂O (200 mL) and extracted with EtOAc (300 mL×3). The combined organic layers were washed with saturated brine, dried over anhydrous sodium sulfate, filtered and concentrated. The crude product was purified by silica gel column chromatography (PE/EtOAc=3/1) to obtain product I-45-7 as a yellow solid (5 g, yield 65%), MS (ESI) m/z: 363.1 [M+H]⁺.

Step 8: Synthesis of (I-45-8)

To a solution of I-45-7 (5 g, 13.7 mmol) and concentrated H₂SO₄ (40 mL) were slowly added concentrated H₂SO₄ (10 mL) and concentrated HNO₄ (10 mL) dropwise under stirring at −30° C. to −20° C. The dropwise addition was complete after 2 hours. The reaction solution was stirred for 20 minutes and then ice water was added to quench the reaction. The solid was filtered, washed with H₂O, and the filter cake was dried under vacuum to obtain the product I-45-8 as a yellow solid (2.2 g, yield 50%), MS (ESI) m/z: 324.1 [M+H]⁺.

Step 9: Synthesis of (I-45-9)

To a solution of I-45-8 (2.2 g, 6.8 mmol), DMAP (0.08 g, 0.6 mmol), TEA (2.06 g, 20.4 mmol) and THF (20 mL) was added di-tert-butyl dicarbonate (2.22 g, 10 mmol) at 0° C. The resulting mixture was stirred for 1 hour until the reaction was complete. The mixture was diluted with H₂O (200 mL) and extracted with EtOAc (200 mL×3). The combined organic layers were washed with saturated brine, dried over anhydrous sodium sulfate, filtered and concentrated under reduced pressure. The crude product was purified by preparative thin layer chromatography (PE/EtOAc=1/1) to obtain product I-45-9 as a yellow solid (600 mg, yield 21%), MS (ESI) m/z: 424.0 [M+H]⁺.

Step 10: Synthesis of (I-45-10)

A mixture of I-45-9 (600 mg, 1.4 mmol), (R)-pyrrolidin-3-ol (699 mg, 5.66 mmol), DIEA (362 mg, 2.8 mmol) and toluene (10 mL) was sealed and stirred under nitrogen protection at 110° C. for 16 hours. The reaction mixture was returned to room temperature, diluted with H₂O (100 mL) and extracted with EtOAc (100 mL×3). The combined organic layers were washed with saturated brine, dried over anhydrous sodium sulfate, filtered and concentrated under reduced pressure. The crude product was purified by preparative thin layer chromatography (PE/EtOAc=1/1) to obtain product I-45-10 as a yellow solid (350 mg, yield 52.6%), MS (ESI) m/z: 475.3 [M+H]⁺.

Step 11: Synthesis of (I-45-11)

To a solution of I-45-10 (350 mg, 0.73 mmol) in MeOH (2 mL) was added wet Pd/C (35 mg, 10% purity) and the solution was stirred under a hydrogen atmosphere at 25° C. for 4 hours. The reaction system was filtered through diatomaceous earth, and the filter cake was washed with EtOAc (30 mL). The filtrate was concentrated under reduced pressure to obtain the product I-45-11 as a green solid (200 mg, yield 61.5%), MS (ESI) m/z: 445.2 [M+H]⁺.

Step 12: Synthesis of (I-45-12) A mixture of 6-(trifluoromethyl)picolinic acid (51.5 mg, 0.27 mmol), I-45-11 (120 mg, 0.27 mmol), HOBT (54.6 mg, 0.4 mmol), EDCI (52 mg, 0.4 mol), DMAP (6.6 mg, 0.05 mmol) and DMF (2 mL) was stirred at 25° C. for 16 h. The reaction solution was diluted with H₂O (50 mL) and extracted with EtOAc (50 mL×3). The combined organic layers were washed with saturated brine, dried over anhydrous sodium sulfate, filtered and concentrated. The crude product was purified by preparative thin layer chromatography (PE/EtOAc=3/1) to obtain product I-45-12 as a yellow solid (50 mg, yield 30%), MS (ESI) m/z: 618.1 [M+H]⁺.

Step 13: Synthesis of (I-45-13)

I-45-12 (50 mg, 0.08 mmol) was added to HCl-dioxane (1 M, 3 mL) at 0° C., and the reaction mixture was stirred at 25° C. for 1 hour. Diethyl ether was added to the reaction mixture under stirring, and the supernatant was removed after standing and repeated three times to obtain the product I-45-13 as a yellow solid (35 mg, yield 85.3%), MS (ESI) m/z: 518.2 [M+H]⁺.

Step 14: Synthesis of (I-45)

A mixed solution of int-F (28.3 mg, 0.073 mmol), TEA (30 mg, 0.294 mmol), I-45-13 (38 mg, 0.073 mmol), HCTU (33.4 mg, 0.080 mmol) and DMF (20 mL) was stirred at 25° C. for 16 hours until the reaction was complete. The reaction mixture was diluted with H₂O (50 mL) and extracted with ethyl acetate (50 mL×3). The combined organic phases were washed with saturated brine (50 mL), dried over anhydrous sodium sulfate, filtered, and concentrated under reduced pressure. The crude product was purified by preparative HPLC to obtain the product I-45 as a yellow solid (23 mg, yield 35%). ¹H NMR (400 MHz, DMSO-d₆) δ 11.07 (s, 1H), 10.17 (s, 1H), 8.51-8.32 (m, 2H),8.19 (dd, J=7.5, 1.0 Hz, 1H), 8.01 (s, 11H), 7.66 (d, J=8.5 Hz, 11H), 7.33 (d, J=1.5 Hz, 1H), 7.24 (dd, J=8.5, 2.0 Hz, 1H), 5.06 (dd, J=13.0, 5.5 Hz, 1H), 4.88-4.81 (m, 11H), 4.29 (s, 1H), 4.08-4.01 (m, 6H), 3.71-3.50 (m, 4H), 3.48-3.33 (m, 4H), 3.08-3.01 (m, 4H), 2.67-2.56 (m, 1H), 2.70-2.53 (m, 2H), 2.07-1.89 (m, 2H), 1.86-1.58 (m, 8H).

Example 11: Synthesis of Compound II-2

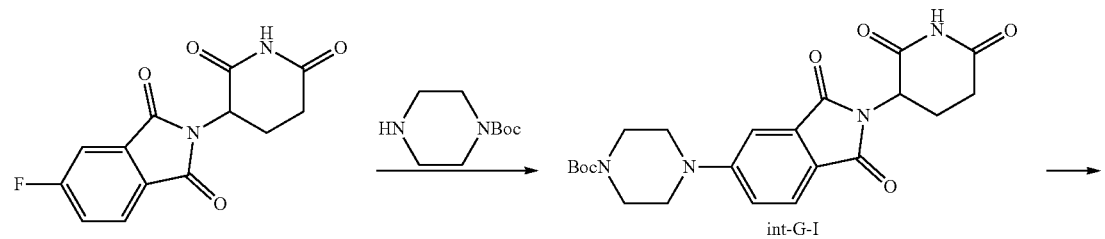

int-G-I

-continued
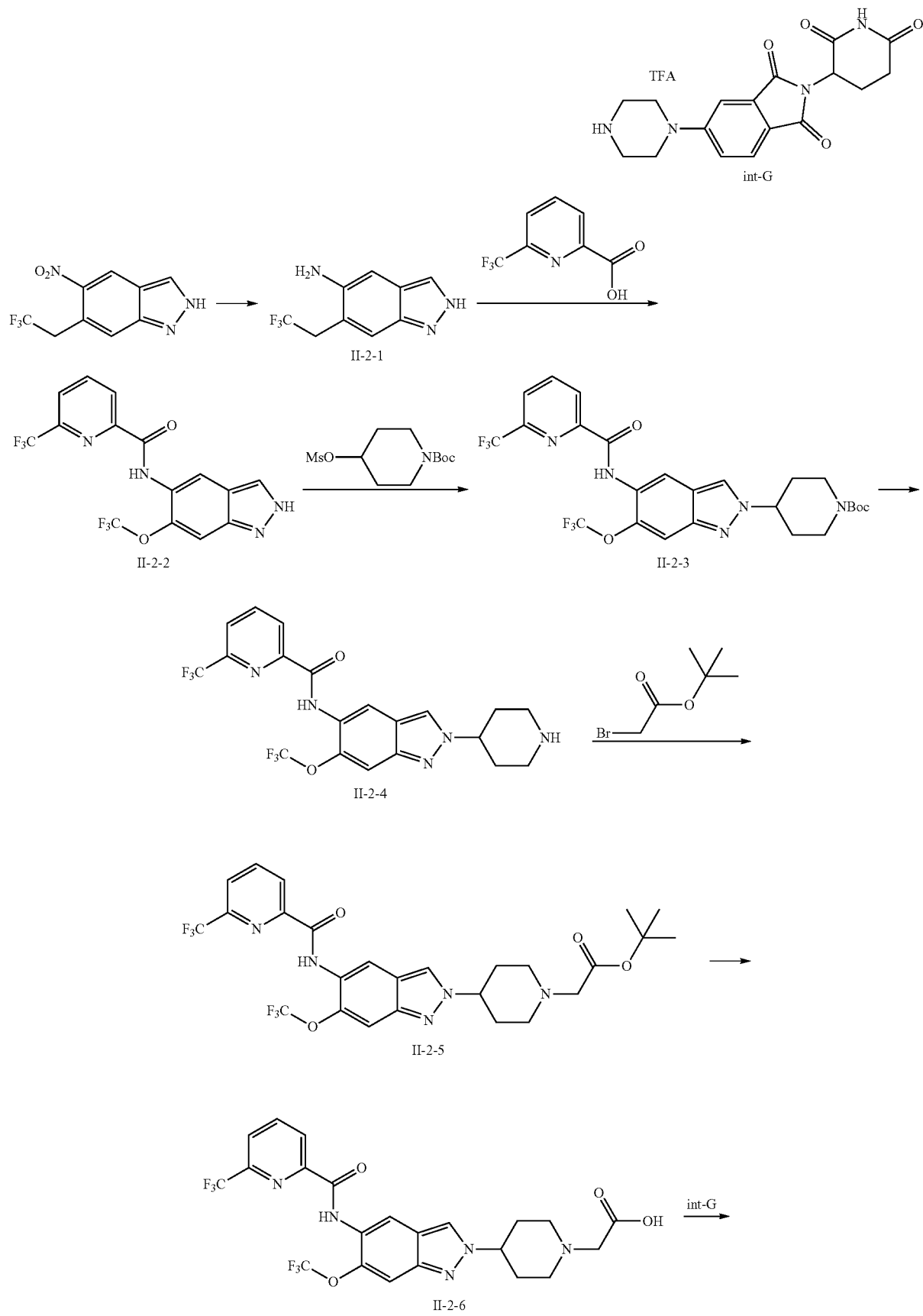

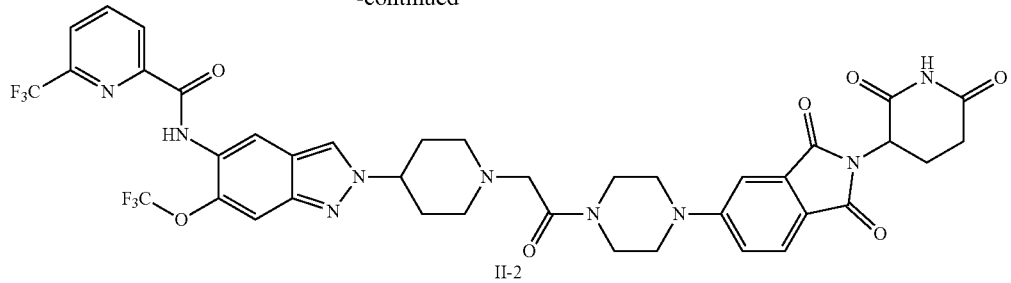

II-2

Step 1: Synthesis of (int-G-1)

A mixed solution of 2-(2,6-dioxo-3-piperidinyl)-5-fluoro-isoindole-1,3-dione (1 g, 3.62 mmol), piperazine-1-carboxylic acid tert-butyl ester (809.14 mg, 4.34 mmol), DIPEA (935.80 mg, 7.24 mmol, 1.26 mL) and DMSO (10 mL) was stirred at 100° C. for 2 hours.

The reaction solution was returned to room temperature, added with water (60 mL) with stirring to precipitate the solid, filtered and dried to obtain the product int-G-1 as a white solid (1.2 g, crude product), MS (ESI) m/z: 443.3 [M+H]$^+$.

Step 2: Synthesis of (int-G)

A mixed solution of int-G-1 (35 mg, 79.10 μmol), TFA (1 mL) and DCM (1 mL) was stirred at 25° C. for 1 hour. The mixture was concentrated under reduced pressure to obtain the product int-G as a yellow solid (25 mg, yield 69.25%, TFA salt), which is directly used in the next step of reaction, MS (ESI) m/z: 343.2 [M+H]$^+$.

Step 3: Synthesis of (II-2-1)

5-nitro-6-(trifluoromethoxy)-2H-indazole (250 mg, 1.01 mmol) was dissolved in MeOH (3 mL), and catalyst wet Pd/C (26.14 mg, 10% purity) was added. The mixed solution was replaced with hydrogen three times under stirring, and kept at the hydrogen environment for 2 hours. The reaction solution was filtered through diatomaceous earth to remove the catalyst, and the filtrate was spin-dried to obtain product I1-2-1 as a brown solid (211 mg, yield 96.05%), MS (ESI) m/z: 218.1 [M+H]$^+$.

Step 4: Synthesis of (II-2-2)

A mixed solution of II-2-1 (320 mg, 1.47 mmol), 6-(trifluoromethyl)pyridine-2-carboxylic acid (309.79 mg, 1.62 mmol), DMF (5 mL), HATU (840.49 mg, 2.21 mmol) and DIPEA (380.91 mg, 2.95 mmol, 513.35 μL) was stirred at 25° C. for 6 hours until the reaction was complete. The reaction solution was added with water (30 mL), and extracted with EA (50 mL×3). The combined organic layers were washed with saturated brine, dried over anhydrous sodium sulfate, filtered and concentrated in vacuo. The crude product was purified by silica gel column chromatography (DCM:MeOH=50:1) to obtain product II-2-2 as a brown solid (295 mg, yield 51.30%), MS (ESI) m/z: 391.2 [M+H]$^+$.

Step 5: Synthesis of (II-2-3)

A mixed solution of II-2-2 (100 mg, 256.25 μmol), tert-butyl 4-methylsulfonyloxypiperidine-1-carboxylate (143.17 mg, 512.51 μmol), NaOH (20.50 mg, 512.51 μmol) and DMF (3 mL) was stirred at 110° C. for 6 hours. The reaction solution was added with water (30 mL), and extracted with EA (50 mL×3). The combined organic layers were washed with brine, dried over sodium sulfate, filtered and concentrated in vacuo. The crude product was purified by silica gel column chromatography (PE:EA=3:1) to obtain product II-2-3 as brown solid (71 mg, yield 48.31%), MS (ESI) m/z: 574.5 [M+H]$^+$.

Step 6: Synthesis of (II-2-4)

II-2-3 (71 mg, 123.80 μmol) was dissolved in DCM (5 mL), and HCl-dioxane solution (4 M, 309.51 μL) was added dropwise to the mixture at 25° C. After the dropwise addition was completed, the reaction system was stirred for 2 hours. The reaction solution was added with water (30 mL), adjusted the pH to neutral with saturated NaHCO$_3$, and then extracted with DCM (20 mL×3). The combined organic layers were washed with saturated brine, dried over anhydrous sodium sulfate, filtered and concentrated in vacuum to obtain product II-2-4 as a white solid (48 mg, yield 81.90%), MS (ESI) m/z: 474.1 [M+H]$^+$.

Step 7: Synthesis of (II-2-5)

A mixture of II-2-4 (48 mg, 101.40 μmol), tert-butyl 2-bromoacetate (23.73 mg, 121.68 μmol), DIPEA (26.21 mg, 202.80 μmol, 35.32 μL) and DMF (2 mL) was stirred at 25° C. for 2 hours. The reaction solution was added with water (20 mL), and extracted with EA (20 mL×3). The combined organic layers were washed with saturated brine, dried over anhydrous sodium sulfate, filtered and concentrated in vacuum. The crude product was purified by silica gel column chromatography (DCM:MeOH=20:1) to obtain product II-2-5 as a white solid (45 mg, yield 75.54%), MS (ESI) m/z: 588.5 [M+H]$^+$.

Step 8: Synthesis of (II-2-6)

A mixed solution of II-2-5 (45 mg, 76.59 μmol), DCM (1.5 mL) and TFA (1.5 mL) was stirred at 25° C. for 2 hours. The mixture was repeatedly concentrated under reduced pressure to remove the solvent to obtain product II-2-6 as a white solid (24 mg, yield 58.96%), MS (ESI) m/z: 532.1 [M+H]$^+$.

Step 9: Synthesis of (II-2)

A mixed solution of II-2-6 (24 mg, 45.16 μmol), int-G (22.67 mg, 49.68 μmol, TFA salt), DMF (2 mL), DIPEA (17.51 mg, 135.49 μmol, 23.60 μL) and HATU (25.76 mg, 67.74 μmol) was stirred at 25° C. for 2 hours. The reaction solution was added with water (20 mL), and extracted with EA (20 mL×3). The combined organic layers were washed with saturated brine, dried over anhydrous sodium sulfate, filtered and concentrated in vacuo. The crude product was purified by preparative thin layer chromatography to obtain product II-2 as a yellow solid (23 mg, yield 58.32%), MS (ESI) m/z: 856.3 [M+H]$^+$. $^1$H NMR (500 MHz, DMSO-d$_6$) δ 11.08 (s, 1H), 10.39 (s, 1H), 8.69 (s, 1H), 8.62 (s, 1H), 8.47 (d, J=7.5 Hz, 1H), 8.42 (t, J=8.0 Hz, 1H), 8.24 (dd, J=7.5, 1.0 Hz, 1H), 7.82 (s, 1H), 7.72 (d, J=8.5 Hz, 1H), 7.39 (d, J=2.0 Hz, 1H), 7.29 (dd, J=8.5, 2.0 Hz, 1H), 5.08 (dd, J=13.0, 5.5 Hz, 1H), 4.57-4.50 (m, 1H), 3.80-3.75 (m, 211), 3.65-3.60 (m, 2H), 3.60-3.55 (m, 2H), 3.52-3.47 (m, 2H), 3.01 (d, J=11.0 Hz, 2H), 2.93-2.84 (m, 1H), 2.66-2.59 (m, 1H), 2.59-2.53 (m, 1H), 2.37-2.24 (m, 3H), 2.17-2.09 (m, 4H), 2.06-1.94 (m, 2H).

Compounds II-4, II-7, II-10, II-12, II-13, II-16, II-17, II-20, and II-21 can be prepared by referring to the method of Examples 2 and 11 above. The structure and characterization data are shown in the following table:

| Molecular ID | structure | MS (ESI) m/z: [M + H]⁺ | ¹H NMR |
|---|---|---|---|
| II-4 | (II-4 structure) | 802.6 | (500 MHz, DMSO-d₆) δ 11.14 (s, 1H), 10.56 (s, 1H), 8.75 (s, 1H), 8.51 (d, J = 7.5 Hz, 1H), 8.48-8.41 (m, 2H), 8.27 (d, J = 7.5, 1.0 Hz, 1H), 7.74 (d, J = 8.5 Hz, 1H), 7.42 (s, 1H), 7.33 (d, J = 8.5, 2.0 Hz, 1H), 7.21 (s, 1H), 5.13 (dd, J = 12.8, 5.4 Hz, 1H), 4.82-4.73 (m, 1H), 4.60-4.53 (m, 1H), 4.34-4.26 (m, 1H), 4.03 (s, 3H), 3.57-3.51 (m, 4H), 3.48-3.46 (m, 1H), 3.37-3.20 (m, 3H), 2.97-2.86 (m, 2H), 2.69-2.65 (m, 4H), 2.64-2.59 (m, 1H), 2.26-2.12 (m, 3H), 2.11-2.05 (m, 1H), 1.99-1.90 (m, 1H). |
| II-7 | (II-7 structure) | 788.6 | (500 MHz, DMSO-d₆) δ 10.95 (s, 1H), 10.50 (s, 1H), 8.69 (s, 1H), 8.46 (d, J = 7.5 Hz, 1H), 8.41 (t, J = 7.5 Hz, 1H), 8.37 (s, 1H), 8.22 (d, J = 7.5 Hz, 1H), 7.56 (d, J = 8.0 Hz, 1H), 7.17 (s, 1H), 7.12 (d, J = 8.5 Hz, 2H), 5.05 (dd, J = 13.0, 5.0 Hz, 1H), 4.44-4.38 (m, 1H), 4.35 (d, J = 16.9 Hz, 1H), 4.23 (d, J = 17.0 Hz, 1H), 3.98 (s, 3H), 3.81-3.72 (m, 2H), 3.66-3.60 (m, 2H), 3.32-3.31 (m, 2H), 3.04-2.97 (m, 2H), 2.95-2.82 (m, 2H), 2.67-2.55 (m, 3H), 2.44-2.35 (m, 2H), 2.32-2.25 (m, 2H), 2.16-2.0 (m, 4H), 2.03-1.92 (m, 2H). |
| II-10 | (II-10 structure) | 816.6 | (500 MHz, DMSO-d₆) δ 11.08 (s, 1H), 10.49 (s, 1H), 8.68 (s, 1H), 8.46 (d, J = 8.0 Hz, 1H), 8.40 (t, J = 8.0 Hz, 1H), 8.35 (d, J = 1.5 Hz, 1H), 8.21 (d, J = 7.5 Hz, 1H), 7.72 (d, J = 8.5 Hz, 1H), 7.40 (d, J = 2.0 Hz, 1H), 7.30 (dd, J = 8.5, 2.0 Hz, 1H), 7.15 (s, 1H), 5.09 (dd, J = 13.0, 5.5 Hz, 1H), 4.42-4.29 (m, 1H), 3.97 (d, J = 2.0 Hz, 3H), 3.89-3.79 (m, 2H), 3.78-3.59 (m, 3H), 3.55-3.41 (m, 2H), 3.01-2.83 (m, 2H), 2.72 (d, J = 11.0 Hz, 1H), 2.67-2.54 (m, 3H), 2.54-2.51 (m, 1H), 2.42-2.32 (m, 1H), 2.21-1.93 (m, 5H), 1.23- |

| Molecular ID | structure | MS (ESI) m/z: [M + H]+ | ¹H NMR |
|---|---|---|---|
| II-12 | 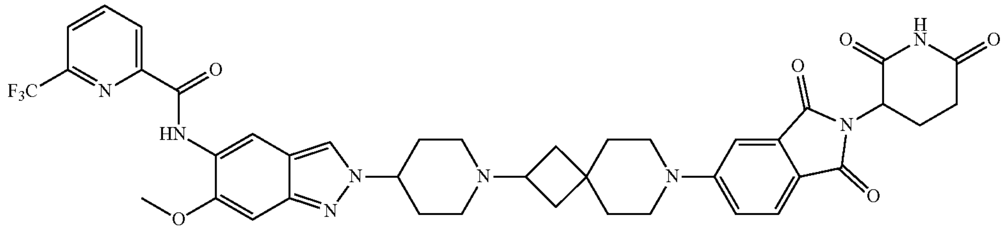 | 799.6 | (500 MHz, DMSO-d₆) δ 11.07 (s, 1H), 10.51 (s, 1H), 8.69 (s, 1H), 8.47 (d, J = 7.5 Hz, 1H), 8.41 (t, J = 8.0 Hz, 1H), 8.38 (s, 1H), 8.22 (d, J = 7.5 Hz, 1H), 7.65 (d, J = 8.5 Hz, 1H), 7.32 (d, J = 2.0 Hz, 1H), 7.25 (dd, J = 8.5, 2.0 Hz, 1H), 7.16 (s, 1H), 5.06 (dd, J = 13.0, 5.5 Hz, 1H), 4.40 (br, 1H), 3.99 (s, 3H), 3.52-3.46 (m, 2H), 3.43-3.37 (m, 2H), 2.98-2.84 (m, 3H), 2.83-2.73 (m, 1H), 2.66-2.56 (m, 2H), 2.14-1.89 (m, 9H), 1.70-1.55 (m, 5H), 1.50-1.43 (m, 1H). |
| II-13 | 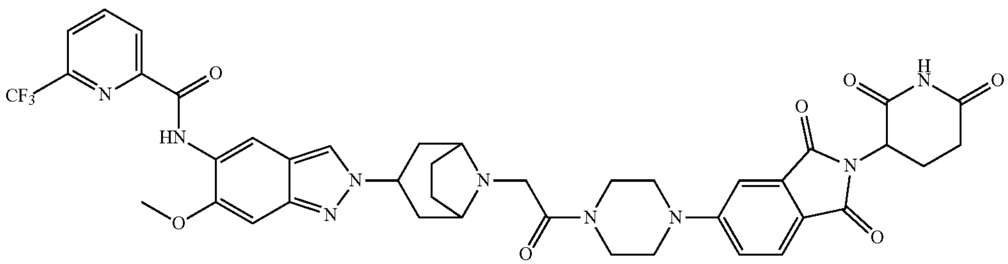 | 828.6 | (500 MHz, CDCl₃) δ 10.62 (s, 1H), 8.73 (s, 1H), 8.42 (d, J = 8.0 Hz, 1H), 8.28 (s, 1H), 8.08-8.01 (m, 1H), 7.93 (s, 1H), 7.78 (d, J = 8.0 Hz, 1H), 7.65 (d, J = 8.0 Hz, 1H), 7.23 (s, 1H), 7.02 (d, J = 8.5 Hz, 1H), 6.99 (s, 1H), 4.89 (dd, J = 12.0, 5.0 Hz, 1H), 4.65-4.58 (m, 2H), 3.95 (s, 3H), 3.85 (br, 2H), 3.75 (br, 2H), 3.52-3.44 (m, 3H), 3.43-3.37 (m, 2H), 3.36-3.25 (m, 2H), 2.86-2.74 (m, 2H), 2.73-2.67 (m, 1H), 2.65-2.56 (m, 3H), 2.10-2.04 (m, 1H), 1.96-1.89 (m, 2H), 1.79-1.72 (m, 2H), 1.68-1.62 (m, 2H). |
| II-16 | 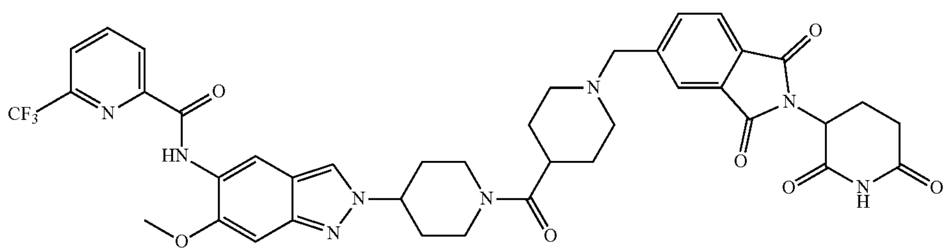 | 801.6 | (500 MHz, DMSO-d₆) δ 11.13 (s, 1H), 10.50 (s, 1H), 8.69 (s, 1H), 8.46 (d, J = 7.5 Hz, 1H), 8.43-8.39 (m, 1H), 8.38 (d, J = 7.5 Hz, 1H), 7.85 (s, 1H), 7.89 (d, J = 7.5 Hz, 1H), 7.16 (s, 1H), 7.82 (d, J = 7.5 Hz, 1H), 7.16 (s, 1H), 5.15 (dd, J = 13.0, 5.5 Hz, 1H), 4.72-4.66 (m, 1H), 4.58-4.52 (m, 1H), 4.13-4.07 (m, 1H), 3.98 (s, 3H), 3.68 (s, 2H), 2.93-2.83 (m, 3H), 2.80-2.74 (m, 1H), 2.70-2.58 (m, 3H), 2.19-2.05 (m, 5H), 2.03-1.94 (m, 2H), 1.91-1.85 (m, 1H), 1.71-1.58 (m, 4H). |

| Molecular ID | structure | MS (ESI) m/z: [M + H]+ | 1H NMR |
|---|---|---|---|
| II-17 | (structure) | 787.5 | (500 MHz, DMSO-d6) δ 11.21 (s, 1H), 10.56 (s, 1H), 8.74 (s, 1H), 8.52 (d, J = 7.5 Hz, 1H), 8.46 (t, J = 8.0 Hz, 1H), 8.42 (s, 1H), 8.27 (d, J = 8.0 Hz, 1H), 8.05 (d, J = 7.5 Hz, 1H), 7.99 (s, 1H), 7.96-7.90 (m, 1H), 7.22 (s, 1H), 5.25 (dd, J = 13.0, 5.5 Hz, 1H), 4.66-4.55 (m, 1H), 4.48-4.37 (m, 1H), 4.04 (s, 3H), 3.18-3.05 (m, 3H), 3.00-2.86 (m, 2H), 2.74-2.65 (m, 2H), 2.63-2.59 (m, 1H), 2.49-2.41 (m, 2H), 2.21-2.08 (m, 5H), 1.99-1.91 (m, 1H), 1.80-1.71 (m, 1H), 1.69-1.44 (m, 3H). |
| II-20 | (structure) | 802.6 | (500 MHz, DMSO-d6) δ 11.11 (s, 1H), 10.50 (s, 1H), 8.68 (s, 1H), 8.46 (d, J = 7.5 Hz, 1H), 8.40 (t, J = 8.0 Hz, 1H), 8.38 (s, 1H), 8.22 (dd, J = 7.5, 1.0 Hz, 1H), 7.74 (dd, J = 8.0, 1.5 Hz, 1H), 7.40 (dd, J = 9.0, 1.5 Hz, 2H), 7.16 (s, 1H), 5.12 (dd, J = 12.5, 5.5 Hz, 1H), 4.44-4.38 (m, 1H), 3.98 (s, 3H), 3.86-3.78 (m, 2H), 3.71-3.63 (m, 2H), 3.32-3.24 (m, 5H), 3.02-2.97 (m, 2H), 2.93-2.85 (m, 5H), 2.66-2.55 (m, 2H), 2.55-2.52 (m, 1H), 2.33-2.26 (m, 2H), 2.15-2.08 (m, 4H), 2.07-2.03 (m, 1H). |

| Molecular ID | structure | MS (ESI) m/z: [M + H]+ | 1H NMR |
|---|---|---|---|
| II-21 | II-21 | 799.6 | (500 MHz, DMSO-d6) δ 11.07 (s, 1H), 10.50 (s, 1H), 8.68 (s, 1H), 8.47 (d, J = 7.5 Hz, 1H), 8.41 (t, J = 8.0 Hz, 1H), 8.37 (s, 1H), 8.22 (d, J = 7.5 Hz, 1H), 7.66 (d, J = 8.5 Hz, 1H), 7.34 (d, J = 2.0 Hz, 1H), 7.29-7.24 (m, 1H), 7.16 (s, 1H), 5.06 (dd, J = 13.0, 5.5 Hz, 1H), 4.40 (br, 1H), 3.99 (s, 3H), 3.52-3.46 (m, 2H), 3.43-3.37 (m, 2H), 2.98-2.84 (m, 3H), 2.83-2.73 (m, 1H), 2.66-2.56 (m, 2H), 2.14-1.89 (m, 9H), 1.70-1.55 (m, 5H), 1.50-1.43 (m, 1H) |

Example 12: Synthesis of I-57 and I-58

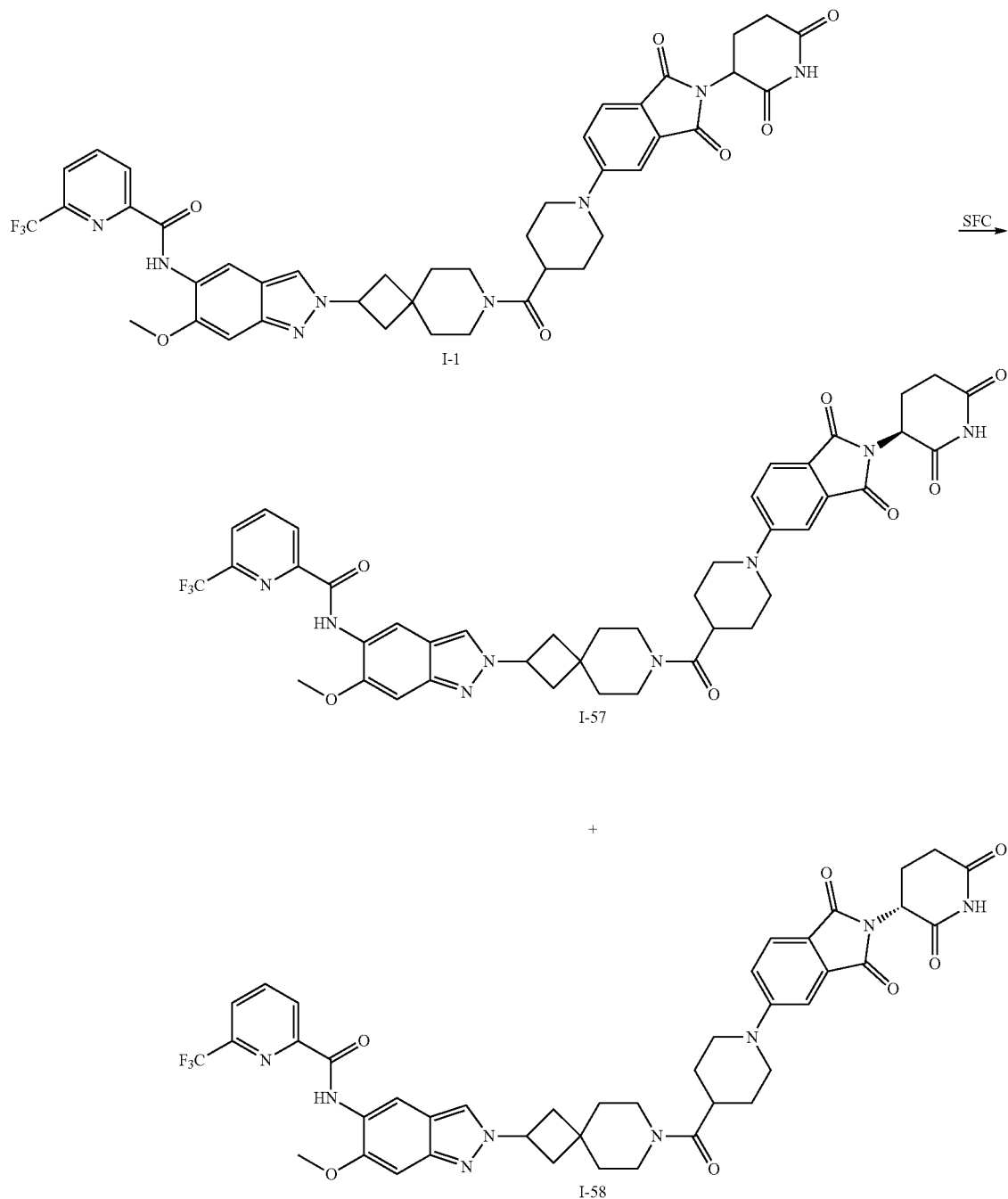

I-1 (100 mg) was chiral resolved by SFC (supercritical fluid chromatography) to obtain I-57 as a yellow solid (47 mg) and I-58 as a yellow solid (44 mg).

I-57 or I-58: Chiral HPLC: Optical purity (ee value)= 100%, RT=2.262 min. MS (ESI) m/z: 827.8 [M+H]$^+_o$, $^1$H NMR (500 MHz, DMSO-d$_6$) δ 11.09 (s, 1H), 10.51 (s, 1H), 8.69 (s, 11H), 8.46 (d, J=8.0 Hz, 11H), 8.41 (t, J=8.0 Hz, 1H), 8.38 (s, 11H), 8.22 (d, J=8.0 Hz, 11H), 7.67 (d, J=8.5 Hz, 1H), 7.34 (s, 11H), 7.25 (d, J=8.5 Hz, 11H), 7.22 (s, 1H), 5.24-5.12 (m, 11H), 5.07 (dd, J=13.0, 5.0 Hz, 1H), 4.07 (d, J=12.5 Hz, 2H), 3.99 (s, 3H), 3.60-3.38 (m, 4H), 3.13-3.07 (m, 2H), 3.04-2.97 (m, 1H), 2.92-2.84 (m, 1H), 2.66-2.52 (m, 2H), 2.49-2.36 (m, 4H), 2.04-1.98 (m, 1H), 1.75-1.67 (m, 4H), 1.66-1.56 (m, 4H).

I-57 or I-58: Chiral HPLC: Optical purity (ee value)= 99.64%, RT=3.319 min. MS (ESI) m/z: 827.8 [M+H]$^+_o$, $^1$H NMR (500 MHz, DMSO-d$_6$) δ 11.10 (s, 1H), 10.51 (s, 1H), 8.69 (s, 11H), 8.46 (d, J=8.0 Hz, 1H), 8.41 (t, J=8.0 Hz, 1H), 8.38 (s, 1H), 8.22 (d, J=8.0 Hz, 1H), 7.67 (d, J=8.5 Hz, 1H), 7.34 (s, 1H), 7.25 (d, J=8.5 Hz, 11H), 7.22 (s, 1H), 5.24-5.13 (m, 1H), 5.07 (dd, J=13.0, 5.0 Hz, 1H), 4.07 (d, J=12.5 Hz, 2H), 3.99 (s, 3H), 3.59-3.39 (m, 4H), 3.13-3.07 (m, 2H), 3.04-2.97 (m, 1H), 2.92-2.83 (m, 11H), 2.66-2.52 (m, 2H), 2.49-2.36 (m, 4H), 2.04-1.98 (m, 1H), 1.75-1.56 (m, 8H).

The conditions for SFC resolation are as follows:
Instrument: SFC-150 (Waters)
Column: IH 25×250 mm, 10 um (Daicel)
Column temperature: 35° C.
Mobile phase: $CO_2$/(MeOH:MeCN=1:1)=50/50
Flow rate: 120 mL/min
Back pressure: 100 bar
Detection wavelength: 214 nm
Cycle time: 8.2 minutes
Sample solution: 100 mg of sample dissolved in 25 mL of methanol/dichloromethane
Injection volume: 4.0 mL Example 13: Synthesis of I-59 and I-60

I-59 or I-60: Chiral HPLC: Optical purity (ee value)= 99.64%, RT=12.068 min. MS (ESI) m/z: 841.9 $[M+H]^+_o$ $^1$H NMR (500 MHz, DMSO-$d_6$) δ 11.07 (s, 1H), 10.51 (s, 1H), 8.69 (s, 1H), 8.46 (d, J=8.0 Hz, 1H), 8.41 (t, J=8.0 Hz, 1H), 8.38 (s, 1H), 8.22 (d, J=8.0 Hz, 1H), 7.55 (d, J=8.0 Hz, 1H), 7.22 (s, 1H), 7.03 (d, J=7.0 Hz, 1H), 6.99 (s, 1H), 6.88 (d, J=8.0 Hz, 1H), 5.20-5.14 (m, 1H), 5.03 (dd, J=13.0, 5.5 Hz, 1H), 3.99 (s, 3H), 3.54-3.37 (m, 5H), 2.91-2.83 (m, 1H), 2.68-2.51 (m, 3H), 2.47-2.35 (m, 3H), 2.04-1.95 (m, 3H), 1.74-1.52 (m, 8H), 1.34-1.22 (m, 3H).

I-59 or I-60: Chiral HPLC: Optical purity (ee value)= 97.76%, RT=14.283 min$_o$ MS (ESI) m/z: 841.9 $[M+H]^+_o$ $^1$H NMR (500 MHz, DMSO-$d_6$) δ 11.07 (s, 1H), 10.51 (s, 1H), 8.69 (s, 11H), 8.46 (d, J=8.0 Hz, 1H), 8.41 (t, J=8.0 Hz, 1H), 8.38 (s, 1H), 8.22 (d, J=8.0 Hz, 1H), 7.55 (d, J=8.0 Hz, 1H), 7.22 (s, 1H), 7.04 (d, J=7.0 Hz, 1H), 6.99 (s, 1H), 6.88 (d, J=8.0 Hz, 1H), 5.20-5.14 (m, 1H), 5.03 (dd, J=13.0, 5.5 Hz, 1H), 3.99 (s, 3H), 3.52-3.37 (m, 5H), 2.91-2.83 (m, 1H), 2.68-2.51 (m, 3H), 2.47-2.35 (m, 3H), 2.04-1.95 (m, 3H), 1.75-1.53 (m, 8H), 1.32-1.25 (m, 3H).

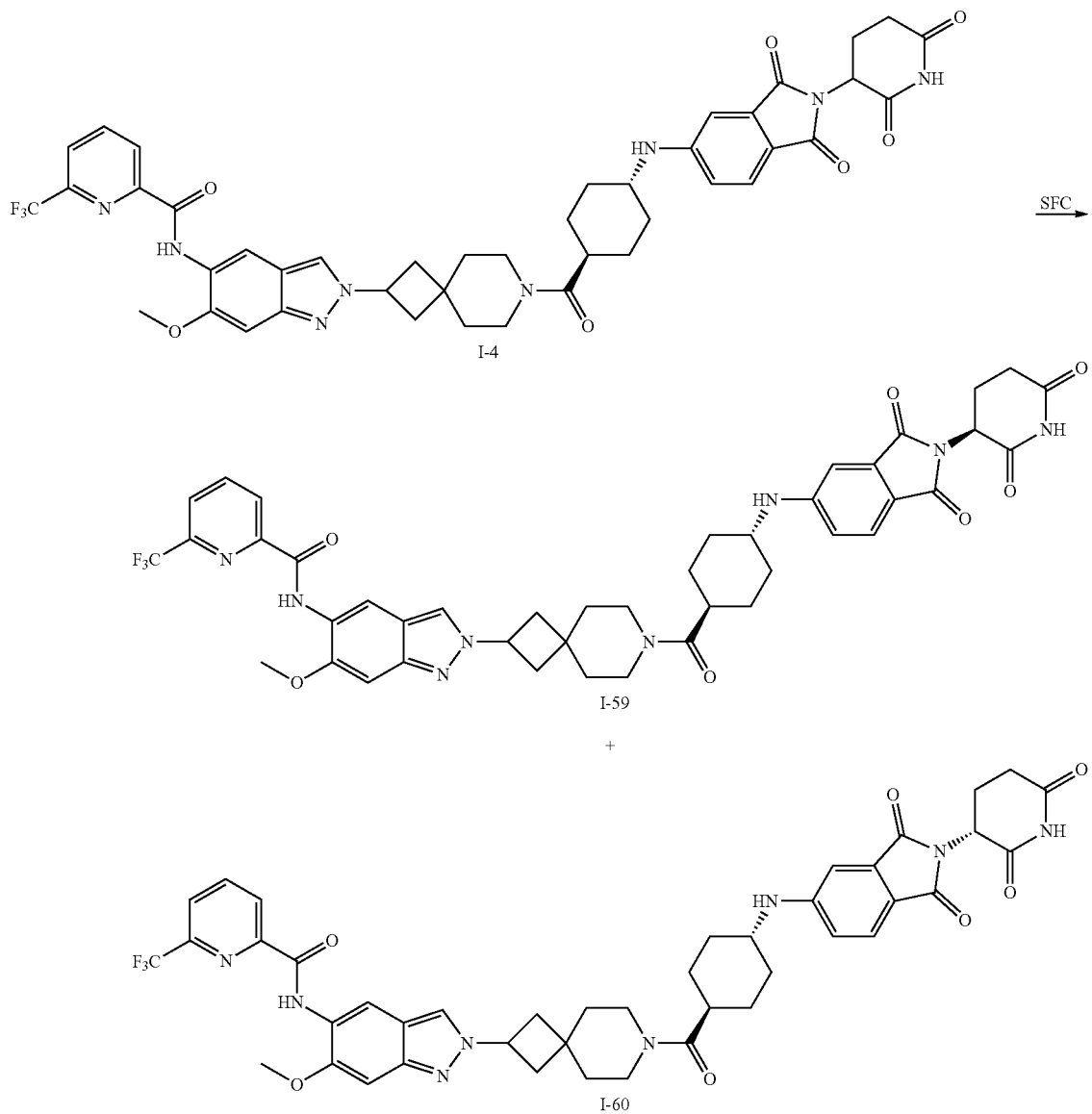

I-4 (50 mg) was chiral resolved by SFC to obtain I-59 as a yellow solid (17.4 mg) and I-60 as a yellow solid (15.9 mg).

The conditions for SFC resolvation are as follows:
Instrument: Gilson-281
Column: IC 25×250 mm, 10 um (Daicel)
Mobile phase: HEX(0.1% DEA):EtOH(0.1% DEA)=50:50
Flow rate: 50 mL/min
Single needle running time: 30 minutes
Injection volume: 3 mL
Sample solution: 50 mg of sample dissolved in 35 mL methanol Example 14: Synthesis of I-61 and I-62

I-8 (100 mg) was chiral resolved by SFC to obtain I-61 as a yellow solid (40.6 mg) and I-62 as a yellow solid (41.2 mg).

I-61 or I-62: Chiral HPLC: Optical purity (ee value)= 100%, RT=1.759 min. MS (ESI) m/z: 845.8 [M+H]$^+_o$. $^1$H NMR (500 MHz, DMSO-d$_6$) δ 11.12 (s, 1H), 10.51 (s, 1H), 8.69 (s, 1H), 8.46 (d, J=8.0 Hz, 1H), 8.41 (t, J=8.0 Hz, 1H), 8.38 (s, 1H), 8.22 (d, J=8.0 Hz, 11H), 7.71 (d, J=11.0 Hz, 1H), 7.44 (d, J=7.0 Hz, 1H), 7.22 (s, 1H), 5.21-5.15 (m, 11H), 5.11 (dd, J=13.0, 5.5 Hz, 1H), 3.99 (s, 3H), 3.64 (d, J=11.5 Hz, 2H), 3.58-3.39 (m, 4H), 3.05-2.97 (m, 2H),

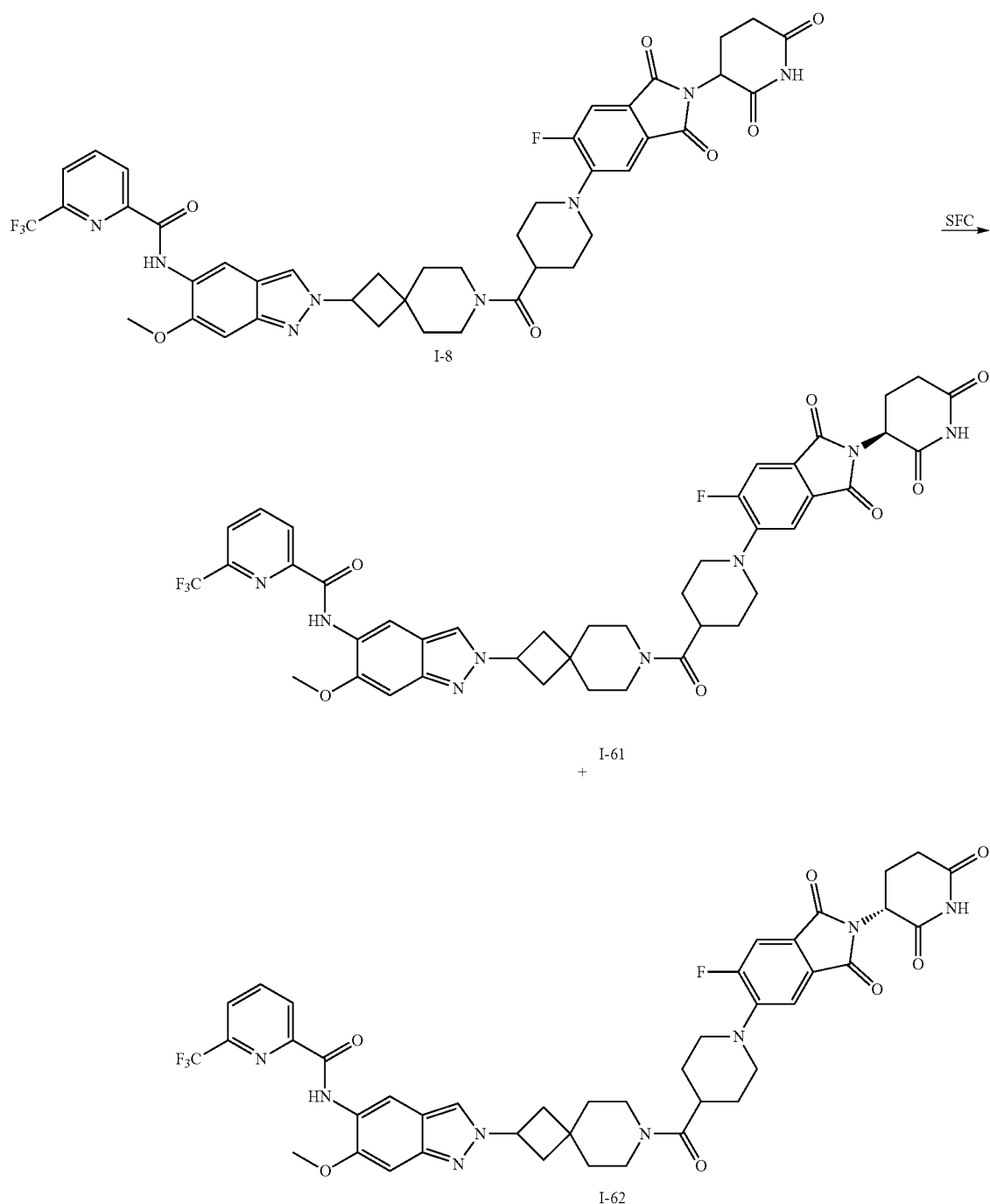

2.94-2.86 (m, 2H), 2.64-2.53 (m, 2H), 2.49-2.36 (m, 4H), 2.10-2.01 (m, 1H), 1.79-1.57 (m, 8H).

I-61 or I-62: Chiral HPLC: Optical purity (ee value)= 99.74%, RT=2.520 min. MS (ESI) m/z: 845.8 [M+H]$^+$. $^1$H NMR (500 MHz, DMSO-$d_6$) δ 11.12 (s, 11H), 10.51 (s, 1H), 8.69 (s, 1H), 8.46 (d, J=8.0 Hz, 1H), 8.41 (t, J=8.0 Hz, 1H), 8.38 (s, 1H), 8.23 (d, J=8.0 Hz, 1H), 7.71 (d, J=11.0 Hz, 1H), 7.44 (d, J=7.0 Hz, 1H), 7.22 (s, 1H), 5.21-5.15 (m, 1H), 5.11 (dd, J=13.0, 5.5 Hz, 1H), 3.99 (s, 3H), 3.64 (d, J=11.5 Hz, 2H), 3.57-3.39 (m, 4H), 3.05-2.97 (m, 2H), 2.94-2.85 (m, 2H), 2.64-2.52 (m, 2H), 2.49-2.36 (m, 4H), 2.10-2.02 (m, 1H), 1.79-1.57 (m, 8H).

The conditions for SFC resolvation are as follows:
Instrument: SFC-150 (Waters)
Column: IH 25×250 mm, 10 um (Daicel)
Column temperature: 35° C.
Mobile phase: $CO_2$/(MeOH:MeCN=1:1)=50/50
Flow rate: 120 mL/min
Back pressure: 100 bar
Detection wavelength: 214 nm
Cycle time: 6.15 minutes
Sample solution: 100 mg of sample dissolved in 18 mL of methanol
Injection volume: 4.0 mL Example 15: Synthesis of I-63 and I-64

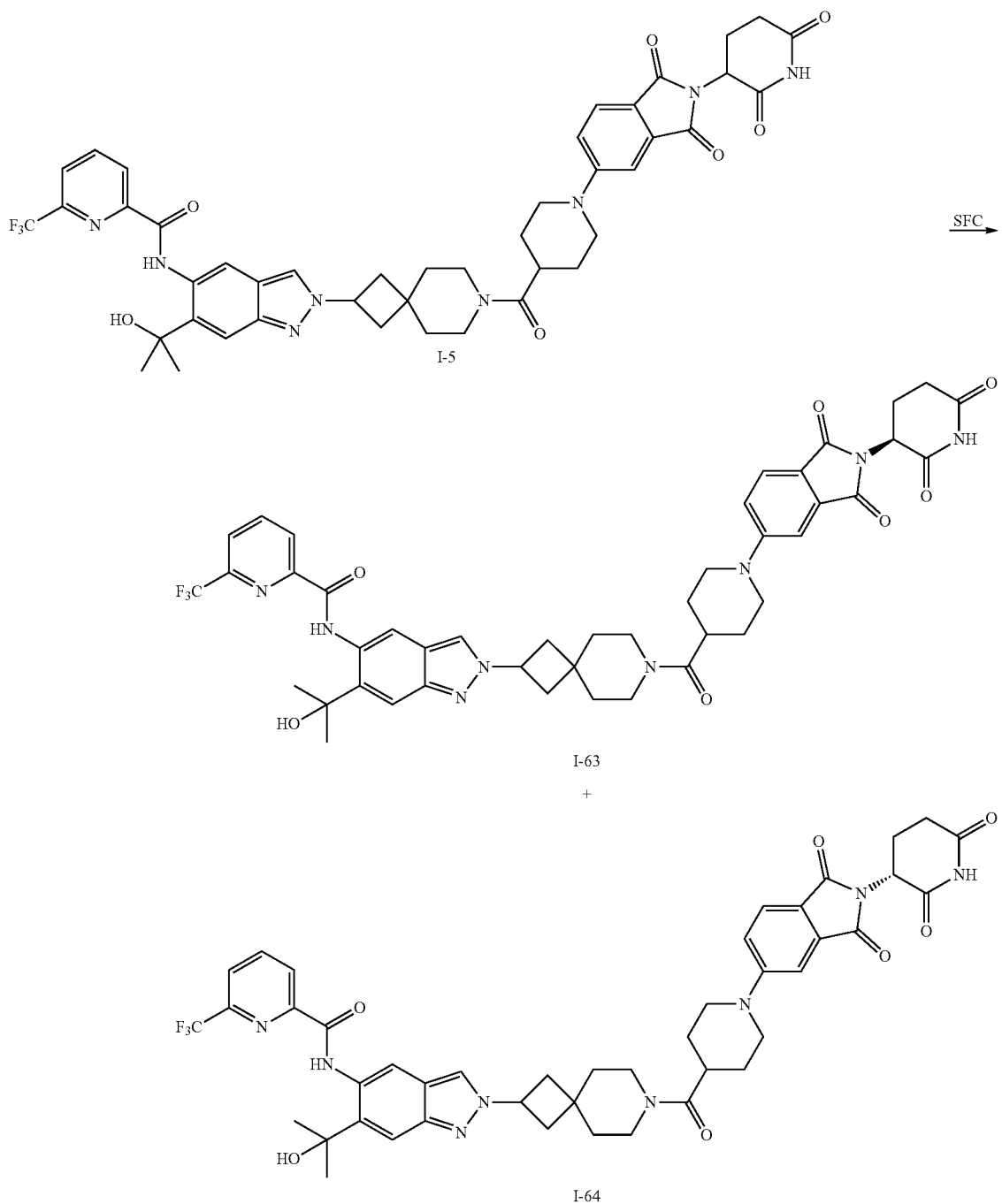

I-5 (20 mg) was chiral resolved by SFC to obtain I-63 as a yellow solid (5.7 mg) and I-64 as a yellow solid (3.9 mg).

I-63 or I-64: Chiral HPLC: Optical purity (ee value)= 100%, RT=1.299 min. MS (ESI) m/z: 855.9 [M+H]$^+$.

I-63 or I-64: Chiral HPLC: Optical purity (ee value)= 99.98%, RT=1.936 min. MS (ESI) m/z: 855.9 [M+H]$^+$.

The conditions for SFC resolution are as follows:
Instrument: SFC-150 (Waters)
Column: AS 25×250 mm, 10 um (Daicel)
Column temperature: 35° C.

Mobile phase: $CO_2$/[MeOH(0.2% $NH_3$(7M in MeOH):MeCN=1:1]=40/60
Flow rate: 100 mL/min
Back pressure: 100 bar
Detection wavelength: 214 nm
Cycle time: 7.1 minutes
Sample solution: 20 mg of sample dissolved in 35 mL of methanol
Injection volume: 4.9 mL Example 16: Synthesis of I-65 and I-66

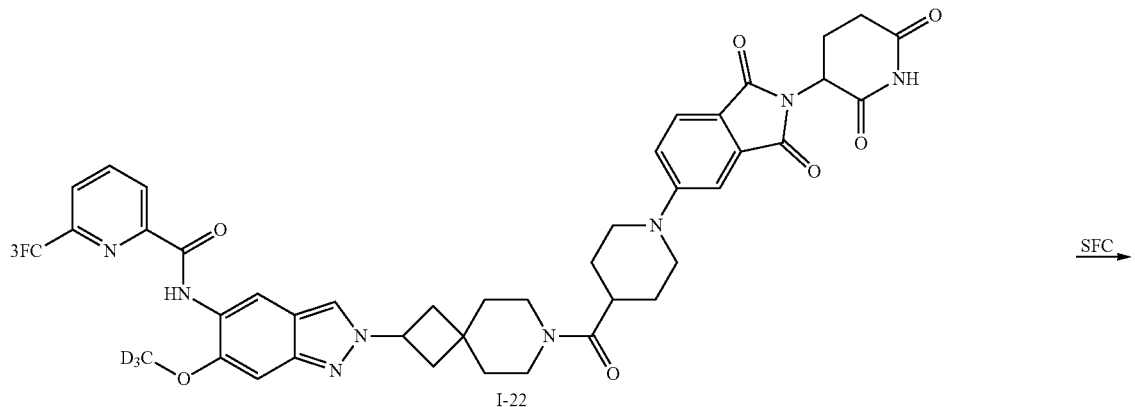

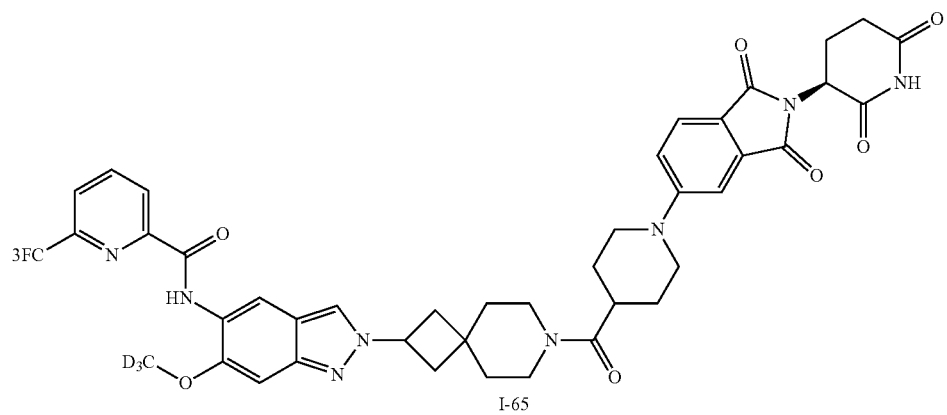

+

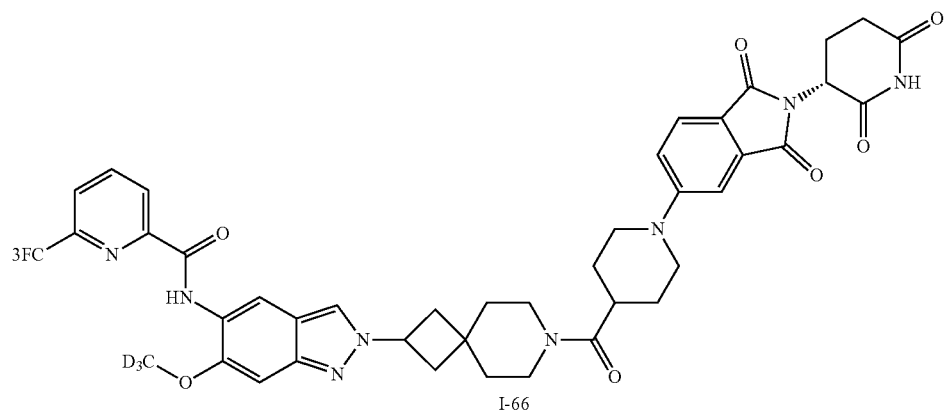

I-22 (100 mg) was chiral resolved by SFC to obtain I-65 as a yellow solid (48.2 mg) and I-66 as a yellow solid (46.6 mg).

I-65 or I-66: Chiral HPLC: Optical purity (ee value)= 100%, RT=2.309 min. MS (ESI) m/z: 830.8 $[M+H]^+_o$ $^1H$ NMR (400 MHz, DMSO-$d_6$) δ 11.09 (s, 1H), 10.51 (s, 1H), 8.69 (s, 1H), 8.47-8.38 (m, 3H), 8.22 (d, J=7.6 Hz, 1H), 7.67 (d, J=8.4 Hz, 1H), 7.34 (s, 1H), 7.26-7.21 (m, 2H), 5.21-5.15 (m, 1H), 5.07 (dd, J=12.8, 5.2 Hz, 1H), 4.07 (d, J=13.2 Hz, 2H), 3.56-3.38 (m, 4H), 3.10-2.97 (m, 3H), 2.92-2.84 (m, 1H), 2.64-2.54 (m, 2H), 2.48-2.36 (m, 4H), 2.07-1.96 (m, 1H), 1.77-1.53 (m, 8H).

I-65 or I-66: Chiral HPLC: Optical purity (ee value)= 99.70%, RT=3.384 min. MS (ESI) m/z: 830.8 $[M+H]^+_o$ $^1H$ NMR (400 MHz, DMSO-$d_6$) δ 11.09 (s, 1H), 10.51 (s, 1H), 8.69 (s, 1H), 8.47-8.38 (m, 3H), 8.22 (d, J=7.6 Hz, 1H), 7.67 (d, J=8.4 Hz, 1H), 7.34 (s, 1H), 7.26-7.21 (m, 2H), 5.20-5.15 (m, 1H), 5.07 (dd, J=12.8, 5.2 Hz, 1H), 4.07 (d, J=13.2 Hz, 2H), 3.56-3.41 (m, 4H), 3.10-2.97 (m, 3H), 2.92-2.85 (m, 1H), 2.64-2.51 (m, 2H), 2.48-2.36 (m, 4H), 2.04-1.99 (m, 1H), 1.75-1.53 (m, 8H).

The conditions for SFC resolution are as follows:
Instrument: SFC-150 (Waters)
Column: IH 25×250 mm, 10 um (Daicel)
Column temperature: 35° C.
Mobile phase: $CO_2$/[MeOH:MeCN=1:1]=50/50
Flow rate: 120 mL/min
Back pressure: 100 bar
Detection wavelength: 214 nm
Cycle time: 8.65 minutes
Sample solution: 100 mg of sample dissolved in 35 mL of methanol
Injection volume: 4.8 mL

APPLICATION EXAMPLES

1. Evaluation of Inhibitory Effects of Compounds on Kinase Activity

Based on an experimental method of fluorescence microfluidic mobility detection, an $IC_{50}$ value of competitive binding of kinase IRAK4 to ATP by the compounds was determined. The initial detection concentration of the compounds was 10 μM, diluted 4-fold gradient down to 0.38 nM, and tested in duplicate. Among them, commercial staurosporine was the standard control substance in this experiment.

1.1 Reagents and Materials Information is as Follows:

1.2 Experimental Operation Method

1) IRAK4 kinase was dissolved in kinase buffer (50 mM HEPES pH 7.5, 10 mM $MgCl_2$, 2 mM DTT and 0.01% Brij-35) to a final concentration of 6 nM.

2) The substrate peptide FAM-P8 and ATP were dissolved in the above kinase buffer. The final concentrations of the IRAK4 substrate peptide FAM-P8 and ATP were 3 μM and 10 μM respectively.

3) Dilution of the compounds: the compound was first diluted to 50 μM, and then diluted down with a 4-fold gradient of DMSO. The solution without the compound and kinase is used as a blank control, corresponding to the "minimum value" shown below; and the solution without the compound but with kinase, adenosine 5'-triphosphate disodium salt hydrate, DMSO and buffer is used as a positive control, corresponding to the "maximum value" shown below.

4) Kinase reaction and termination: 10 μL of kinase buffer was added to a 384-well plate containing 5 μL of the compound to be tested, and incubated at room temperature for 10 minutes. Another 10 μL of buffer containing the substrate peptide and adenosine 5'-triphosphate disodium salt hydrate was added to the 384-well plate. After incubation at 28° C. for one hour, 25 μL stop solution (100 mM HEPES pH 7.5, 50 mM EDTA, 0.2% Coating Reagent #3 and 0.015% Brij-35) was added to each well to terminate the reaction.

5) Data reading: the CaliperEZ Reader II instrument was used to read the conversion rate data. Conditions: downstream voltage −500V, upstream voltage −2250V, base pressure −0.5 PSI, and screening pressure −1.2 PSI.

6) Data calculation: the conversion rate data was copied from CaliperEZ Reader II and converted into inhibition rate data. The calculation formula is as follows:

Inhibition percentage (%) = (maximum value − conversion rate)/
(maximum value − minimum value) ∗ 100%

$IC_{50}$ values were fitted using XLFit excel add-in version 5.4.0.8,

Fitting formula: Y=Bottom+(Top−Bottom)/(1+($IC_{50}$/X)^HillSlope)

Kinase activity data are shown in Table 1 or 2

| Name | Supplier | No. |
|---|---|---|
| kinase IRAK4 | Carna | 09-145 |
| substrate peptide FAM-P8 | GL Biochem | 112396 |
| Adenosine 5'-triphosphate disodium salt hydrate | Merck | A7699-1G |
| Dimethyl Sulfoxide (DMSO) | Merck | D2650 |
| Ethylene Diamine Tetraacetic Acid (EDTA) | Merck | E5134 |
| Staurosporine | Selleckchem | S1421 |
| 4-(2-hydroxyethyl)-1-piperazine ethanesulfonic acid (HEPES) | Gibco | 15630-080 |
| Polyethylene oxide lauroyl ether (Brij-35 solution) | Merck | 9002-92-0 |
| 1,4-dimercaptothreitol (DDT) | Merck | D0632-20G |
| 0.2% Coating Reagent #3 | Platinum Elmer | 760050 |
| 96-well plate | Corning | 3365 |
| 384-well plate | Corning | 3573 |

TABLE 1

| No. | IRAK4 IC$_{50}$ (nM) |
|---|---|
| I-1 | ++++ |
| I-2 | ++++ |
| I-3 | ++++ |
| I-4 | ++++ |
| I-8 | ++++ |
| I-13 | ++++ |
| II-1 | ++++ |
| II-4 | ++++ |
| II-5 | ++++ |
| II-6 | ++++ |
| II-10 | ++++ |
| II-12 | ++++ |
| II-13 | ++++ |
| II-16 | ++++ |
| II-17 | ++++ |

TABLE 2

| No. | IRAK4 IC$_{50}$ (nM) | No. | IRAK4 IC$_{50}$ (nM) | No. | IRAK4 IC$_{50}$ (nM) |
|---|---|---|---|---|---|
| II-1 | 16.4 | II-2 | 34 | II-4 | 20 |
| II-5 | 11 | II-6 | 8.2 | II-7 | 3.57 |
| II-10 | 7.45 | II-12 | 14.24 | II-13 | 10.52 |
| II-16 | 14 | II-17 | 11 | II-20 | 5.5 |
| I-1 | 26 | I-2 | 11 | I-3 | 16 |
| I-4 | 36.6 | I-5 | 11.35 | I-7 | 8.1 |
| I-8 | 25.87 | I-9 | 32.9 | I-10 | 24 |
| I-12F | 57.6 | I-13 | 4.81 | I-14 | 16.6 |
| I-16 | 11.55 | I-17 | 31 | I-19 | 8.1 |
| I-20 | 23.6 | I-22 | 25 | I-23 | 10.2 |
| I-24 | 17.43 | I-25 | 20.4 | I-26 | 30 |
| I-27 | 42 | I-28 | 12.5 | I-29 | 74 |
| I-30 | 24 | I-31 | 34 | I-32 | 34.8 |
| I-33 | 26.5 | I-34 | 39.7 | I-35 | 33.4 |
| I-36 | 12.4 | I-37 | 29.9 | I-38 | 14.1 |
|  |  |  |  | I-41 | 49.8 |
| I-42 | 10.2 | I-43 | 20.7 | I-44 | 17 |
| I-45 | 39.1 | I-46 | 17.7 | I-47 | 9.17 |
| I-48 | 19.2 | I-49 | 13.4 | I-50 | 70.7 |
| I-51 | 5.33 | I-52 | 13.3 | I-53 | 138 |
| I-54 | 11.6 | I-55 | 34.3 | I-56 | 1955 |
| I-57 | 32.4 | I-58 | 35.1 | I-59 | 27.3 |
| I-60 | 40.5 | I-61 | 31.4 | I-62 | 19.0 |
| I-63 | 32.1 | I-64 | 22.7 | I-65 | 26.3 |
| I-66 | 25.3 |  |  |  |  |

IRAK4 assay: IC$_{50}$ <100 nM: ++++; ≥100 nM, <1 μM: +++; ≥1 μM, <10 μM: ++; ≥10 μM: +

2. LPS Stimulates THP-1 to Release Cytokines
2.1 Experimental Materials

| Name | Supplier | No. |
|---|---|---|
| THP-1 | ATCC | TIB-202 |
| Dulbecco's Phosphate Buffer (DPBS) | Biosera | LM-S2041/500 |
| RPMI1640 medium | Thermo Fisher | 11875119 |
| Fetal Calf Serum (FBS) | Biological Industries | 04-002-1A |
| Penicillin-Streptomycin Solution (P/S) | Invitrogen | 15140122 |
| β-Mercaptoethanol | Merck | M3148 |
| Dimethylsulfoxide (DMSO) | Sigma | D2650 |
| lipopolysaccharide (LPS) | Thermo Fisher | tlrl-pb5lps |
| 96-well cell culture plate | Corning | 3799 |
| Human TNF-α Duoset ELISA Kit | R&D | DY210 |

2. Detection of PROTAC-Induced IRAK4 Protein Degradation in TH-1

2.1 Based on the experimental method of Western Blot, specific antibodies were used to stain the THP-1 cell samples treated by gel electrophoresis, and the degrading activity of the compounds on the IRAK4 protein in THP-1 cells was determined by analyzing the position and depth of staining. The concentrations of compound for the detection included 0 μM, 0.3 μM, 1 μM and 3 μM, and the cells were treated by the compound for 8 hours, 16 hours, 24 hours, and 48 hours. Glyceraldehyde-3-phosphate dehydrogenase (GAPDH) is an internal reference protein in this experiment.

2.2 Cells, Reagents and Materials Information is as Follows:

| Name | Supplier | No. |
|---|---|---|
| THP-1 cell | ATCC | TIB-202 |
| RPMI 1640 medium | Gibco | 22400-089 |
| Fetal Calf Serum, FBS | ExCell Bio | FSP500 |
| Penicillin-Streptomycin Solution (P/S) | HyClone | SV30010 |
| Pierce™ BCA Protein Assay Kit | Thermo Fisher | 23227 |
| RIPA lysate | Merck | R0278 |
| Protease inhibitor (complete Tablets EDTA-free, EASYpack) | Roche | 4693132001 |
| Phosphatase Inhibitor Cocktail 2 | Merck | P5726 |
| Phosphatase Inhibitor Cocktail 3 | Merck | P0044-5ML |
| Dimethylsulfoxide, DMSO | Merck | D2650 |
| NuPAGE™ MOPS SDS electrophoresis buffer (20×) | Invitrogen | NP0001 |
| Pierce™ 20× TBS Tween™ 20 buffer | Thermo Fisher | 28360 |
| NuPAGE™ 4-12% Bis-Tris, 1.5 mm, Mini protein gel, 15 wells | Invitrogen | NP0336BOX |
| 1,4-dimercaptothreitol (DDT) | Invitrogen | P2325 |
| Bovine Serum Albumin (BSA) | Merck | B2064-100G |
| Difco™ skim milk | BD Biosciences | 232100 |
| IBlot™ 2 transfer membrane set, nitrocellulose, regular size | Invitrogen | IB23001 |
| NuPAGE® LDS sample buffer (4×) | Invitrogen | NP0007 |
| PageRuler Prestained Protein Ladder | Thermo Fisher | 26616 |
| SuperSignal™ West Femto Maximum Sensitivity Substrate | Thermo Fisher | 34095 |

-continued

| Name | Supplier | No. |
|---|---|---|
| Anti-IRAK4 antibody | Abcam | ab5985 |
| Anti-Glyceraldehyde-3-Phosphate Dehydrogenase Antibody, clone 6C5 (GAPDH) | Merck | MAB374 |
| Goat Anti-Rabbit IgG H&L (HRP) | Abcam | ab205718 |
| Goat Anti-Mouse IgG H&L (HRP) | Abcam | ab205719 |

2.3 Device

| Name of device | Supplier | No. |
|---|---|---|
| Cell counter | Count start | IC1000 |
| Multi-Mode Microplate Reader | Molecular Device | Molecular Device Flexstation III |
| Life technologies iBlot2 Gel Transfer Device | IB 21001 | 31252173 |
| Image Quant LAS 4000 | 399699 | Image Quant LAS 4010 |

2.4 Method for Preparing the Reagents
  Electrophoresis buffer: 50 mL MOPS SDS Running Buffer (20×) and 50 mL 20×TBS Tween-20 buffer were diluted with deionized water to 1 L as the electrophoresis buffer;
  5% skim milk (w/v): 2.5 g skim milk was diluted with 50 mL 1×TBS Tween-20 buffer to prepare 5% skim milk;
  5% BSA (w/v): 2.5 g BSA was diluted with 50 mL 1×TBS Tween-20 buffer to prepare 5% BSA;
  Anti-IRAK4 antibody was diluted with 5% BSA at 1:1000 into a primary antibody working solution;
  Goat Anti-Rabbit IgG H&L (HRP) was diluted with 5% BSA at 1:2000 into a second antibody working solution; and
  Goat Anti-Mouse IgG H&L (HRP) was diluted with 5% BSA at 1:2000 into a second antibody working solution.

THP-1 cells were plated in a 6-well plate at a density of $1.5\times10^6$ cells per ml and incubated for 2 hours in a cell culture incubator under 37° C. and 5% $CO_2$. The compound was diluted with DMSO to 0.6 mM, 0.2 mM and 0.06 mM respectively. 10 μL of compound solution was added to the corresponding wells, and continued to incubate in the incubator for 16 hours, 24 hours and 48 hours respectively. The compound-treated THP-1 cells in the well were collected, added with 120 μL of RIPA lysate containing protease inhibitor, Phosphatase Inhibitor Cocktail 2 and Phosphatase Inhibitor Cocktail 3, lysed on wet ice for 30 minutes, and then the cells lysate was centrifuged at a high speed and a low temperature for 5 minutes to collect the supernatant. The protein concentration of the cell sample was determined according to the instructions in the Pierce™ BCA Protein Assay Kit.

The concentration of the sample was adjusted to be consistent using lysis buffer and NuPAGE® LDS sample buffer containing 1M DTT. The samples were heated at 95° C. for 5 minutes and centrifuged at a low temperature and at a high speed. 20 μL of the prepared protein sample and 4 μL of PageRuler Prestained Protein Ladder were added into the gel well for running at 80V voltage for 0.5 hours, then the voltage was adjusted to 120V for further running for 1.5 hours. The gel was removed and the proteins in the gel were transferred onto the IBlot™ 2 transfer membrane set at 20V. After successful transfer, bands at 65 kDa-40 kDa and 40 kDa-30 kDa were cut respectively. The membranes were blocked with 5% skim milk for 1 hour at room temperature.

The membranes were washed three times with 1× concentration of TBST, then incubated with IRAK4 antibody working solution overnight at 4° C. The IRAK4 antibody working solution was discarded, and the membranes were washed three times with 1× concentration of TBST, and incubated with Goat Anti-Rabbit IgG H&L (HRP) working solution and Goat Anti-Mouse IgG H&L (HRP) working solution at room temperature. After 1 hour of incubation, the antibody working solution was discarded and the membranes were washed three times with 1× concentration of TBST. According to the instructions of the kit SuperSignal™ West Femto Maximum Sensitivity Substrate, the reagents in the kit were mixed in equal volume proportions to prepare a luminescent liquid mixture. The membranes were incubated for 1 minute, then removed for exposure.

The results of Western blotting 24 hours after administration of the compounds with a concentration of 1 μM were shown in Table 3:

TABLE 3

| No. | IRAK4 degradation rate 24 hours after administration of the compounds with a concentration of 1 μM |
|---|---|
| I-1 | 75~100% |
| I-2 | 75~100% |
| I-3 | 75~100% |
| II-1 | 75~100% |
| II-4 | 50~75% |
| II-5 | 75~100% |
| II-6 | 75~100% |
| II-16 | <25% |
| II-17 | <25% |

The concentrations that degraded 50% of IRAK4 by Western blotting 24 hours after administration were shown in Table 4:

TABLE 4

| No. | IRAK4 $DC_{50}$ (nM) | No. | IRAK4 $DC_{50}$ (nM) | No. | IRAK4 $DC_{50}$ (nM) |
|---|---|---|---|---|---|
| II-1 | 4.33 | II-2 | 32.77 | II-4 | 12.4 |
| II-5 | 6.15 | II-6 | 9.99 | II-7 | 2.2 |
| II-10 | 5.98 | II-12 | 20.49 | II-13 | 478.5 |

TABLE 4-continued

| No. | IRAK4 DC$_{50}$ (nM) | No. | IRAK4 DC$_{50}$ (nM) | No. | IRAK4 DC$_{50}$ (nM) |
|---|---|---|---|---|---|
| II-16 | 32.92 | II-17 | >1000 | II-20 | 14.06 |
| I-1 | 4.02 | I-2 | 4.41 | I-3 | 3.64 |
| I-4 | 2.06 | I-5 | 3.6 | I-7 | 3.6 |
| I-8 | 8.20 | I-9 | 12 | I-10 | 5.07 |
| I-12F | 1.08 | I-13 | 15.75 | I-14 | 12.61 |
| I-16 | 9.9 | I-17 | 25.9 | I-19 | 1.78 |
| I-20 | 11.2 | I-22 | 6.6 | I-23 | 7.2 |
| I-24 | 15.3 | I-25 | >1000 | I-26 | 44.6 |
| I-27 | 6.9 | I-28 | 8.3 | I-29 | 16.32 |
| I-30 | 26.21 | I-31 | 47.28 | I-32 | 33.8 |
| I-33 | 8.05 | I-34 | 22.72 | I-35 | 7.86 |
| I-36 | 1.16 | I-37 | 20.67 | I-38 | 2.61 |
|  |  |  |  | I-41 | 4.42 |
| I-42 | 1.20 | I-43 | >1000 | I-44 | 1.16 |
| I-45 | >1000 | I-46 | 9.15 | I-47 | 5.53 |
| I-48 | >1000 | I-49 | 9.79 | I-50 | 21.6 |
| I-51 | 148.9 | I-52 | 3.9 | I-53 | >1000 |
| I-54 | 6.2 | I-55 | 14.6 |  |  |
| I-57 | 12.15 | I-58 | 2.67 | I-59 | 8.05 |
| I-60 | 2.75 | I-61 | 7.62 | I-62 | 3.26 |
| I-63 | 2.41 | I-64 | 2.32 | I-65 | 3.71 |
| I-66 | 3.14 |  |  |  |  |

What claimed is:

1. A compound of formula I-1, a pharmaceutically acceptable salt or an isotope compound thereof:

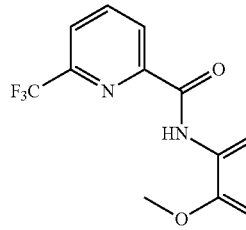

2. The compound as claimed in claim 1, the pharmaceutically acceptable salt or the isotope compound thereof, characterized in that

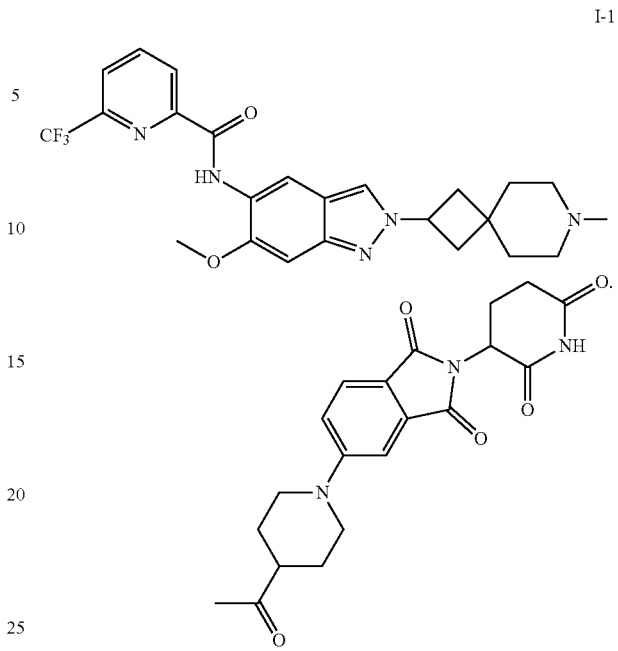

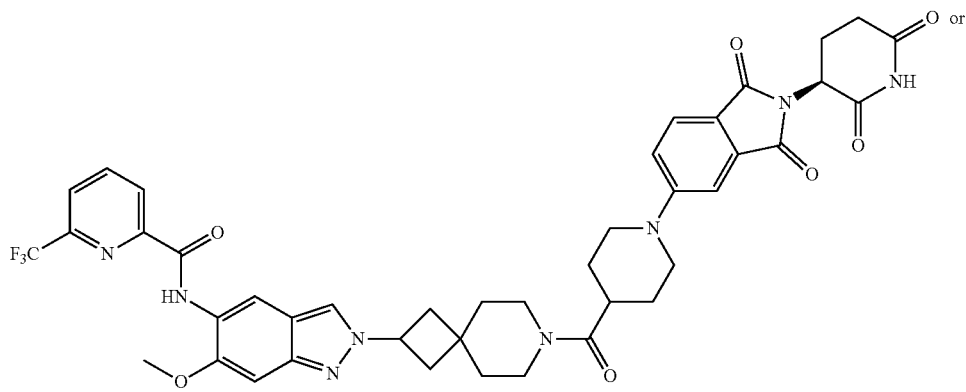

is

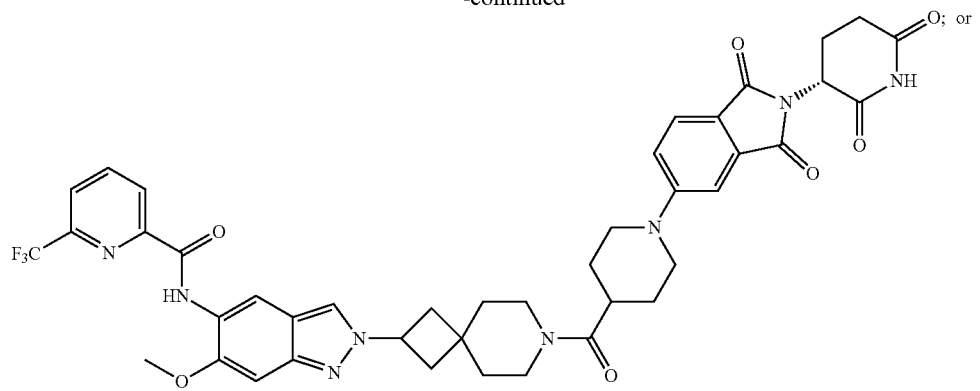

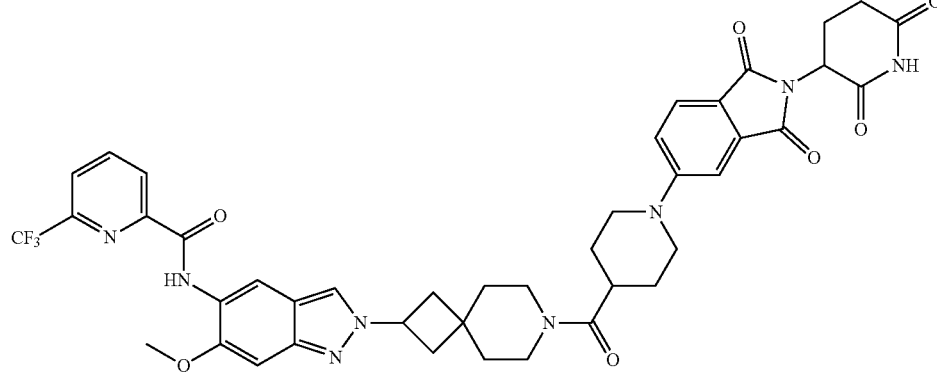

is a compound with a retention time of 2.262 min or 3.319 min under the following conditions: chromatographic column: IH 25×250 mm, 10 um (Daicel); mobile phase: $CO_2$/(MeOH:MeCN=1:1)=50/50; flow rate: 120 mL/min.

3. A pharmaceutical composition comprising substance Z and pharmaceutical excipients, wherein the substance Z is a compound of formula I-1 as claimed in claim 1, a pharmaceutically acceptable salt or an isotope compound thereof, or the substance Z is a compound as claimed in claim 2, a pharmaceutically acceptable salt or an isotope compound thereof.

* * * * *

UNITED STATES PATENT AND TRADEMARK OFFICE
CERTIFICATE OF CORRECTION

| | | |
|---|---|---|
| PATENT NO. | : 12,343,343 B2 | Page 1 of 1 |
| APPLICATION NO. | : 18/651214 | |
| DATED | : July 1, 2025 | |
| INVENTOR(S) | : Jason Shaoyun Xiang et al. | |

It is certified that error appears in the above-identified patent and that said Letters Patent is hereby corrected as shown below:

On the Title Page

In item (30) the Foreign Application Priority Data, please insert:
-- (30) Foreign Application Priority Data
Jun. 15, 2022 (CN)    202210675599.3
Dec. 16, 2022 (CN)    202211627919.4
Jun 5, 2023 (CN)      202310658843.X --

Signed and Sealed this
Twenty-third Day of September, 2025

John A. Squires
*Director of the United States Patent and Trademark Office*